United States Patent [19]
Ohmoto et al.

[11] Patent Number: 5,710,153
[45] Date of Patent: Jan. 20, 1998

[54] TETRAZOLE COMPOUND

[75] Inventors: Kazuyuki Ohmoto; Makoto Tanaka; Tohru Miyazaki; Hiroyuki Ohno, all of Osaka, Japan

[73] Assignee: Ono Phramaceutical Co., Ltd., Osaka, Japan

[21] Appl. No.: 712,393

[22] Filed: Sep. 11, 1996

[30] Foreign Application Priority Data

Sep. 12, 1995 [JP] Japan ..................... 7-259277

[51] Int. Cl.⁶ ..................... A61K 31/535; C07D 413/06
[52] U.S. Cl. ..................... 514/236.2; 514/255; 514/326; 514/340; 514/381; 514/382; 544/132; 544/366; 546/210; 546/268.4; 548/253
[58] Field of Search ..................... 548/253, 514/381, 514/382, 326, 340, 236.2, 255; 546/210, 268.4

[56] References Cited

U.S. PATENT DOCUMENTS 5,434,248  7/1995  Chapman et al. ..................... 530/330

FOREIGN PATENT DOCUMENTS

0618223A2  10/1994  European Pat. Off. .
0644198A1  3/1995  European Pat. Off. .
9309135  5/1993  WIPO .

OTHER PUBLICATIONS

Dinarello & Woff, "The Role of Interleukin–1 Disease", *The N.E. J. Med.*, 328:2:106–113, (1993).

Campion et al., "Dose–Range and Dose–Frequency Study of Recombinant Human Interleukin–1 Receptor Antagonist in Patients with Rheumatoid Arthritis", *Arthr. & Rheumatism*, 39:7:1092–1101, (1996).

Mjalli et al., "Inhibition of Interleukin–1β Converting Enzyme by N–Acyl–Aspartyl Aryloxymethyl Ketones", *Bioorg. & Medicinal Chem. Ltrs.*, 5:13:1409–1414, (1995).

*Primary Examiner*—Joseph McKane
*Attorney, Agent, or Firm*—Sughrue, Mion, Zinn, Macpeak & Seas, PLLC

[57] ABSTRACT

A tetrazole derivatives of formula (I)

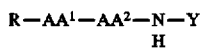

a non-toxic salt thereof, an acid addition salt thereof or a hydrate thereof which has an inhibitory effect on interleukin-1β converting enzyme (ICE).

12 Claims, No Drawings

TETRAZOLE COMPOUND

FIELD OF THE INVENTION

This invention relates to tetrazole compounds. More particularly, this invention relates to:

(1) tetrazole compounds having interleukin-1β converting enzyme inhibitory activity of the following formula (I):

wherein all of the symbols have the same meanings as described hereinafter, or a non-toxic salt thereof, an acid addition salt thereof or a hydrate thereof;

(2) processes for the preparation thereof; and (3) pharmaceutical agents containing such derivative as an active ingredient.

BACKGROUND OF THE INVENTION

Interleukin 1 (IL-1) is a key cytokine that directly or indirectly participates in the regulation of, for example, the immune system, hemopoietic system and neuroendocrine system, and thus, has a crucial physiological role. There are two types of IL-1, which have different isoelectric points (IL-1α: pI=5, IL-1β:pI=7). Both of these are produced as a precursor having molecular weight of 31 Kd. The IL-1β precursor does not bind to the IL receptor nor exerts a biological function. The IL-1β converting enzyme (ICE) cleaves the precursor protein between Asp 116 and Ala 117 and converts into an active IL-1β mature form having a molecular weight of 17 Kd. Following the cleavage, IL-1β is secreted, binds to the receptor and triggers various biological activities (Ref. The New England Journal of Medicine, 328, 106 (1993)).

The inhibition of ICE enzymatic activity leads to prevention of conversion of the IL-1β precursor into the mature form and hence results in blockage of IL-1 biological activity. There are many possible target diseases for ICE inhibitors, for example, prevention and/or treatment of insulin dependent diabetes (type I), autoimmune diseases, including multiple sclerosis, immune diseases, such as acute or delayed type hypersensitivity, infectious diseases, infection complications, septic shock, acute or chronic inflammatory diseases, such as arthritis, colitis, glomelular nephritis, hepatitis, pancreatitis, reperfusion injury, cholangeitis, encephalitis, endocarditis, myocarditis and vasculitis, neural diseases, such as Alzheimer's disease and Parkinson's disease, bone or cartilage-resorption diseases, Crohn's disease, osteo arthritis etc.

It is believed that ICE and/or ICE-like cystein proteases play important roles in cell death by apoptosis. Therefore it is possible that an ICE inhibitor may be used in the prevention and/or treatment of diseases resulting from apoptosis disorders, such as infection, reduction or enhancement of immune or central nervous system function, neoplasm etc. Diseases associated with apoptosis disorders are as follows; AIDS, ARC (AIDS related complex), adult T cell leukemia, hairy cell (pilocytic) leukemia, myelosis, respiratory dysfunction, arthropathy, HIV or HTLV-I related diseases, such as uveitis, virus related diseases, such as hepatitis C, neoplasm, diffuse collagen diseases, such as systemic lupus erythematosis or rheumatoid arthritis, autoimmune diseases, such as ulcerative colitis, Sjogren's syndrome, primary biliary cirrhosis, idiopathic thrombocytopnic purpura, autoimmonohaemolytic anemia, severe myasthenia, insulin dependent (type I) diabetes, osteodysplasia syndrome, periodic thrombocytopenia, aplastic anemia, idiopathic thrombocytopenia, various diseases which accompany thrombocytopenia, such as disseminated intravascular coagulation, hepatic diseases, including hepatitis (type C, A, B, or F virus borne or drug mediated) and hepatic cirrhosis, Alzheimer's disease, dementia, such as Alzheimer type senile dementia, cerebral vascular disturbance, neurodegenerative diseases, adult dyspnea syndrome, infection, hyperplasia of the prostate, myoma of the uterus, asthma bronchiole, arteriosclerosis, various kinds of congenital teratoma, nephritis, senile cataract, chronic fatigue syndrome, myodystrophy, peripheral nervous disturbance, and so on (Ref. The New England Journal of Medicine, 328, 106–113 (1993), Arthritis & Rheumatism, 39, 1092 (1996)).

Compounds having an inhibitory activity on IL-1β converting enzyme (ICE) are known. The sequence of the ICE cleavage site of pre-IL-1β (Tyr-Val-His-Asp) has high affinity with ICE. Substrate analog inhibitors which are chemically modified and based on the above substrate sequence, for example, a compound of formula (X):

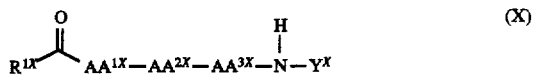

wherein $Y^X$ is

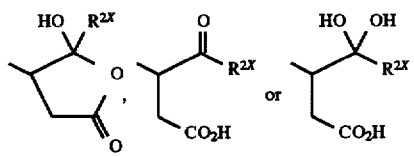

$R^{1X}$ is (a) a substituted C1–12 alkyl (in which a substituent is hydrogen, hydroxy etc.) or (b) an aryl C1–6 alkyl (in which aryl is phenyl, naphthyl, pyridyl, furyl, thienyl, thiazolyl, isothiazolyl, imidazolyl, benzoimidazolyl, pyrazinyl, pyrimidyl, quinolyl, isoquinolyl, benzofuryl, benzothienyl, pyrazolyl, indolyl, purinyl or isooxazolyl), wherein the aryl can be mono-substituted or di-substituted (in which a substituent is a C1–6 alkyl, halogen, hydroxyl, C1–6 alkylcarbonyl etc.);

$R^{2X}$ is (a) hydrogen (b) 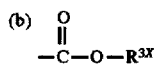

(c) 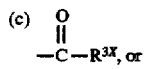

(d) 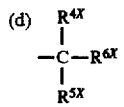

(in which $R^{3X}$ is (1) a substituted C1–12 alkyl (in which a substituent is hydrogen, hydroxy etc.), or (2) an aryl C1–6 alkyl or substituted aryl C1–6 alkyl, as hereinbefore defined (in which an aryl may be mono-substituted or di-substituted by C1–6 alkyl, halogen, hydroxyl, C1–6 alkylcarbonyl etc.);

$R^{4X}$ and $R^{5X}$ are each hydrogen, hydroxyl etc.; and $R^{6X}$ is
(1) hydrogen,
(2) a substituted C1–6 alkyl (in which a substituent is hydrogen, hydroxyl etc.),
(3) an aryl C1–6 alkyl (in which alkyl is substituted by hydrogen, oxo, C1–3 alkyl etc., aryl has the same meaning as hereinbefore defined, said aryl is mono-substituted or di-substituted, said substituent is C1–6 alkyl, halogen, hydroxyl, C1–6 alkylcarbonyl etc.),
(4) a $C_{1-6}$ alkylaminocarbonylC1–6 alkyl or C1–6 alkylcarbonylaminoC1–6 alkyl,
(5) an arylaminocarbonylC1–6 alkyl or arylcarbonylaminoC1–6 alkyl (in which aryl has the same meaning as hereinbefore defined, said aryl is mono-substituted or di-substituted, said substituent is C1–6 alkyl, halogen, hydroxyl, C1–6 alkylcarbonyl etc.) or
(6) an aryl C1–6 alkylaminocarbonyl C1–6 alkyl or aryl C1–6 alkylcarbonylamino C1–6 alkyl (in which aryl has the same meaning as hereinbefore defined, said aryl is mono-substituted or di-substituted, said substituent is C1–6 alkyl, halogen, hydroxyl, C1–6 alkylcarbonyl etc.) etc.;

$AA^{1X}$ is a bond etc.;
$AA^{2X}$ is a bond or

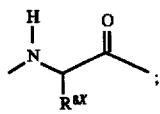

and $AA^{3X}$ is a bond or

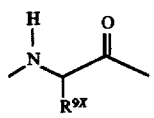

(wherein $R^{8X}$ and $R^{9X}$ is
(a) hydrogen,
(b) a substituted C1–6 alkyl (in which a substituent is hydrogen, hydroxyl etc.) or
(c) an aryl C1–6 alkyl (in which aryl has the same meaning as hereinbefore defined, said aryl is mono-substituted or di-substituted, said substituent is C1–6 alkyl, halogen, hydroxyl, C1–6 alkylcarbonyl, etc.))
(with the proviso that, definitions not related are omitted) are disclosed as having an inhibitory activity on ICE (see EP 519748).

The compounds of formula (Y):

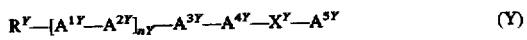      (Y)

wherein $R^Y$ is hydrogen, an amino protecting group or benzyloxy, which may be optionally substituted by a ring;

nY is 0 or 1;
$A^{1Y}$ is Val, Leu, Ala, Ile or trimethylsilyl-Ala;
$A^{2Y}$ is Phe or Tyr;
$A^{3Y}$ is Val, Leu, Ala, Ile, trimethylsilyl-Ala or a divalent radical group:

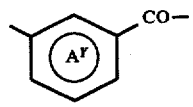

(in which ring $A^Y$ may be optionally substituted by hydroxy or C1–4 alkoxy);
$A^{4Y}$ is a bond or

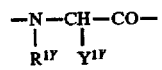

(in which $R^{1Y}$ is hydrogen or C1–4 alkyl, and
$Y^{1Y}$ a residue bonded to the α-carbon atom of an optionally protected α-amino acid);
wherein $A^{3Y}$ and $A^{4Y}$ together may form:

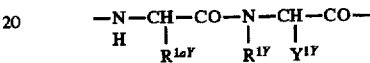

(wherein $Y^{1Y}$ has the same meaning as hereinbefore defined, and $R^{1Y}$ and
$R^{1aY}$ are combined to form —$(CH_2)_{mY}$— (in which mY is 2, 3, 4 or 5));
$X^Y$ is a divalent radical group:

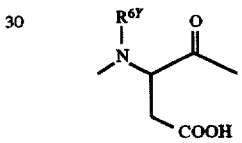

wherein $R^{6Y}$ is hydrogen or C1–4 alkyl); and
$A^{5Y}$ is hydrogen, $CF_3$, —$Z^{1Y}$—$Z^{2Y}$—$Y^{2Y}$ (in which $Z^{1Y}$ and $Z^{2Y}$ is each, independently, a bond or an α-amino acid residue and $Y^{2Y}$ is $NH_2$, C1–4 alkylamino, di-(C1–4 alkyl)amino or hetero ring bonded to the $Z^{2Y}$ nitrogen), —$CH_2$—$X^{1Y}$—$Y^{3Y}$ (in which $X^{1Y}$ is O or S and $Y^{3Y}$ is heteroaryl) or —$CH_2$—$Y^{3Y}$ wherein $Y^{3Y}$ is as previously defined)
(with the proviso that, definitions not related are omitted) have an inhibitory activity on IL-1β release (see WO 93/09135).

Further, it is disclosed that compounds of formula (Z):

      (Z)

wherein $R^Z$ is an amino or hydroxy protecting group or benzyloxy which may be optionally substituted by a ring;
$A^{1Z}$ is an α-hydroxy acid, amino acid residue or thiocarbonyl analogue, each with an optionally protected side chain, or

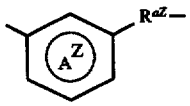

(in which ring $A^Z$ may be optionally substituted by hydroxy or C1–4 alkoxy and $R^{aZ}$ is CO or CS);
$A^{2Z}$ is an α-hydroxy acid, —NH—$CHR^{3Z}$—CO— (in which $R^{3Z}$ is an optionally protected side chain of an α-amino acid);

$X^Z$ is

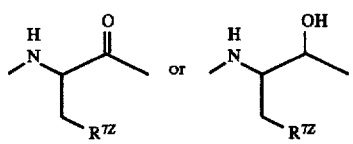

(in which $R^{7Z}$ is —$CO_2H$, —CONHOH or a bioisosteric group); and $A^{3Z}$ is —$CH_2$—$X^{1Z}$—CO—$Y^{1Z}$, —$CH_2$—O—$Y^{2Z}$ or —$CH_2$—S—$Y^{3Z}$ (in which $X^{1Z}$ is O or S, $Y^{1Z}$ is an aliphatic ring, optionally substituted with aryl, diphenylmethyl, optionally substituted by a ring, piperidino or optionally substituted mono, di or tricyclic heteroaryl. $Y^{2Z}$ is an aliphatic ring, diphenylmethyl, optionally substituted by a ring, or optionally substituted di or tricyclic heteroaryl etc. and $Y^{3Z}$ is an aliphatic ring, tri-(C1–4 alkyl)methylcarbonyl, di-(C1–4 alkyl) aminothiocarbonyl, 4-nitrophenyl, 2,6-dichloro-benzoyl, 2,3,6-trichloro-4-pyridyl, 5-membered heterocyclic ring containing a nitrogen atom or optionally substituted di or tricyclic heteroaryl, etc.) etc.; and $A^{1Z}$ and $A^{2Z}$ may form

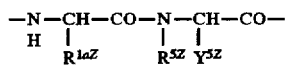

(in which $R^{1aZ}$ and $R^{5Z}$ together make form C2–5 alkylene or C2–5 alkenylene and $Y^{5Z}$ is an optionally protected side chain of an α-amino acid, etc.) (with the proviso that, definitions not related are omitted) have an inhibitory activity on IL-1β release (see EP 618223).

Furthermore, it is disclosed that compounds of formula (W):

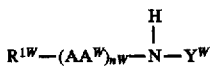

wherein nW is 0–4;
$Y^W$ is

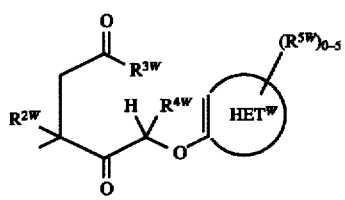

wherein when $R^{3W}$ is O, $Y^W$ is

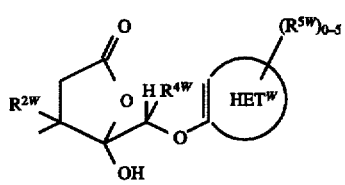

(in which $R^{2W}$ is hydrogen or deuterium;
$R^{3W}$ is O, OH, $OR^{6W}$, $NR^{6W}OR^{7W}$ or $NR^{6W}R^{7W}$;
$R^{6W}$ and $R^{7W}$ each, independently, is hydrogen, alkyl, aralkyl, heteroaralkyl, aryl or heteroaryl;

$R^{4W}$ is hydrogen or alkyl;
$R^{5W}$ is hydrogen, alkyl, alkenyl, aryl, heteroaryl, aralkyl, heteroaralkyl, halogen, haloalkyl, nitro or cyano,
$HET^W$ is heteroaryl);
$AA^W$ is

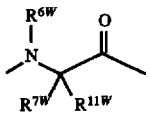

(in which $R^{6W}$ and $R^{7W}$ have the same meaning as hereinbefore defined and $R^{11W}$ is $(CR^{6W}R^{7W})_{0-6}$—$R^{12W}$ (wherein $R^{12W}$ is aryl, heteroaryl or optionally selected from hereinbefore described $R^{5W}$)) or an amino acid; and $R^{1W}$ is $R^{12W}$—CO— or $R^{12W}SO_2$— (wherein $R^{12W}$ has the same meaning as hereinbefore defined)

(with the proviso that, definitions not related are omitted) have an inhibitory activity on IL-1β converting enzyme (see CA 2125021).

SUMMARY OF THE INVENTION

Energetic investigations have been carried out to discover new compounds having inhibitory activity on IL-1β converting enzyme. As a result, the present inventors have achieved that goal by a tetrazole compound of formula (I):

TABLE 57

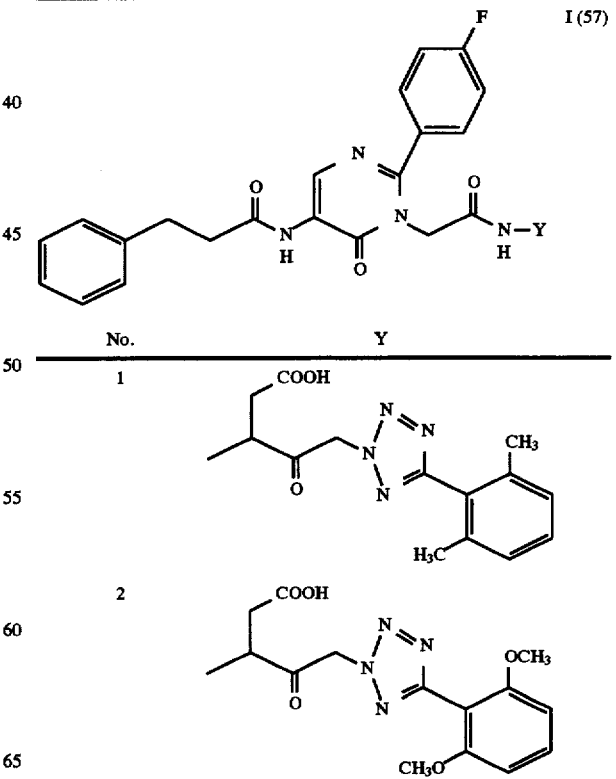

TABLE 57-continued

I(57)

| No. | Y |
|-----|---|
| 3 | (3-methyl-4-oxo-pentanoic acid with tetrazole linked to phenyl-pyrrole) |
| 4 | (3-methyl-4-oxo-pentanoic acid with tetrazole linked to pyrrole) |
| 5 | (3-methyl-4-oxo-pentanoic acid with tetrazole linked to cyclohexyl-phenyl-pyrrole) |
| 6 | (3-methyl-4-oxo-pentanoic acid with tetrazole linked to 2,6-dimethylphenyl) |
| 7 | (3-methyl-4-oxo-pentanoic acid with tetrazole linked to 2,6-dimethoxyphenyl) |

TABLE 57-continued

I(57)

| No. | Y |
|-----|---|
| 8 | (3-methyl-4-oxo-pentanoic acid with tetrazole linked to phenyl-pyrrole) |
| 9 | (3-methyl-4-oxo-pentanoic acid with tetrazole linked to pyrrole) |
| 10 | (3-methyl-4-oxo-pentanoic acid with tetrazole linked to phenyl-pyrrole) | wherein R is a hydrogen atom, $$R^1 \overset{O}{-}\!\!\!- \quad \text{or} \quad R^1 \overset{(O)_m}{-}\!\!\!S\!\!-,$$

$R^1$ is
1) C1–8 alkyl,
2) C1–8 alkoxy,
3) C1–8 alkylamino,
4) C1–8 alkylthio,
5) Cyc¹ (in which Cyc¹ is a carbocyclic ring or hetero ring, and Cyc¹ may be substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, —OR², —NR²R³, —SR², —COOR² or —COR², wherein R² and R³ each, independently, is a hydrogen atom, C1–4 alkyl, phenyl or C1–4 alkyl substituted by phenyl) or p2 6) C1–8 alkyl, C1–8 alkoxy, C1–8 alkylamino or C1–8 alkylthio substituted by Cyc¹, m is 0–2, (with the proviso that,
(1) when m is 0, R¹ is C1–8 alkyl or C1–8 alkoxy, each optionally substituted by Cyc¹, and
(2) when m is 1, R¹ is C1–8 alkyl, C1–8 alkoxy or C1–8 alkylamino, each optionally substituted by Cyc¹), AA¹ is
1) a bond or 2) 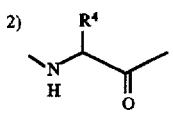

(in which R⁴ is
(1) a hydrogen atom,
(2) C1–8 alkyl,
(3) Cyc² (in which Cyc² is a carbocyclic ring or hetero ring, and Cyc² may be substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, —OR⁵, —NR⁵R⁶, —SR⁵, —COOR⁵ or —COR⁵, wherein R⁵ and R⁶ each, independently, is a hydrogen atom, C1–4 alkyl, phenyl or C1–4 alkyl substituted by phenyl) or
(4) C1–8 alkyl substituted by a substituent selected from —OR⁷, —NR⁷R⁸, —SR⁷, —COOR⁷, —COR⁷, —CONH₂, —NR⁷—CO—NR⁷R⁸, guanidino or Cyc² (in which R⁷ and R⁸ each, independently, is a hydrogen atom, C1–4 alkyl, phenyl or C1–4 alkyl substituted by phenyl), AA² is
1) a bond or 2) 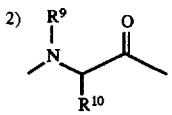

(in which R⁹ and R¹⁰ each, independently, is
(1) a hydrogen atom,
(2) C1–8 alkyl,
(3) Cyc³ (in which Cyc³ is a carbocyclic ring or hetero ring, and Cyc³ may be substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, —OR¹¹, —NR¹¹R¹², —SR¹¹, —COOR¹¹ or —COR¹¹, wherein R¹¹ and R¹² each, independently, is a hydrogen atom, C1–4 alkyl, phenyl or C1–4 alkyl substituted by phenyl),
(4) C1–8 alkyl substituted by a substituent selected from —OR¹³, —NR¹³R¹⁴, —SR¹³, —COOR¹³, —COR¹³, —CONH₂, —NR¹³—CO—NR¹³R¹⁴, guanidino or Cyc³ (in which R¹³ and R¹⁴ each, independently, is a hydrogen atom, C1–4 alkyl, phenyl or C1–4 alkyl substituted by phenyl) or
(5) R⁹ and R¹⁰, together, is a C1–6 alkylene or C2–6 alkenylene), AA¹ and AA², together, may have the formula:

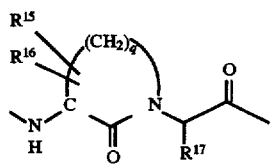

in which R¹⁵ and R¹⁶ each, independently, is a hydrogen atom, C1–4 alkyl, phenyl or C1–4 alkyl substituted by phenyl (with the proviso that, C1–4 alkyl or phenyl may be substituted by C1–4 alkyl, C1–4 alkoxy, a halogen atom, trifluoromethyl or phenyl), R¹⁷ is
(1) a hydrogen atom,
(2) C1–8 alkyl,
(3) Cyc³ (in which Cyc³ has the same meaning as hereinbefore defined) or
(4) C1–8 alkyl substituted by a substituent selected from —OR¹³, —NR¹³R¹⁴, —SR¹³, —COOR¹³, —COR¹³, —CONH₂, —NR¹³—CO—NR¹³R¹⁴, guanidino or Cyc³ (in which R¹³ and R¹⁴ have the same meaning as hereinbefore defined), q is 2–12, with the proviso that, a carbon atom in —(CH₂)_q— may be replaced by an oxygen atom, sulfur atom or —NR¹⁸— (in which R¹⁸ is a hydrogen atom, C1–4 alkyl, phenyl or C1–4 alkyl substituted by phenyl), or two hydrogen atom at ortho positions are replaced by a double bond and Y is

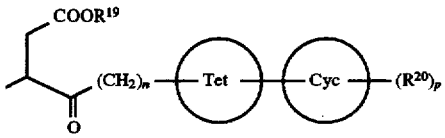

in which R¹⁹ is a hydrogen atom, C1–8 alkyl, phenyl or C1–4 alkyl substituted by phenyl, n is 1–4,

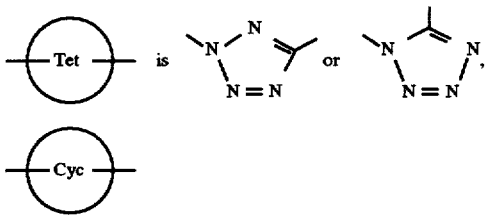

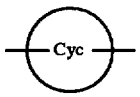

is a carbocyclic ring or hetero ring,
with the proviso that,

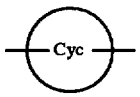

is bonded directly to the carbon atom on a tetrazole ring,
R²⁰ is
1) a hydrogen atom,
2) C1–4 alkyl,
3) a halogen atom, 4) nitro,
5) trifluoromethyl,
6) nitrile,
7) —$OR^{22}$,
8) —$NR^{22}R^{23}$,
9) —$SR^{22}$,
10) $Cyc^4$ (in which $Cyc^4$ is a carbocyclic ring or hetero ring, and $Cyc^4$ may be substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, —$OR^{24}$, —$NR^{24}R^{25}$, —$SR^{24}$, —$COOR^{24}$ or —$COR^{24}$ (in which $R^{24}$ and $R^{25}$ each, independently, is a hydrogen atom, C1–4 alkyl, phenyl or C1–4 alkyl substituted by phenyl)),
11) —$COOR^{26}$ or
12) —$COR^{27}$, $R^{22}$ and $R^{23}$ each, independently, is a hydrogen atom, C1–4 alkyl, phenyl or C1–4 alkyl substituted by phenyl, $R^{26}$ is a hydrogen atom, C1–4 alkyl, trihalomethyl, C1–4 alkyl substituted by trihalomethyl, $Cyc^4$ ($Cyc^4$ has the same meaning as hereinbefore defined), C1–4 alkyl substituted by $Cyc^4$, $R^{27}$ is
(1) a hydrogen atom,
(2) C1–4 alkyl,
(3) —$NR^{28}R^{29}$,
(4) phenyl,
(5) C1–4 alkyl substituted by phenyl, (6) 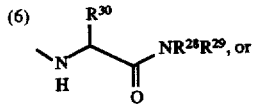

(7) 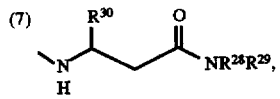

wherein $R^{28}$ and $R^{29}$ each, independently, is a hydrogen atom, C1–4 alkyl, phenyl or C1–4 alkyl substituted by phenyl, or $R^{28}$ and $R^{29}$, together, is a hetero ring, $R^{30}$ is a hydrogen atom, C1–8 alkyl, $Cyc^2$ (in which $Cyc^2$ has the same meaning as hereinbefore defined) or C1–8 alkyl substituted by a substituent selected from —$OR^7$, —$NR^7R^8$, —$SR^7$, —$COOR^7$, —$COR^7$, —$CONH_2$, —$NR^7$—CO—$NR^7R^8$, guanidino or $Cyc^2$ (in which $Cyc^2$, $R^7$ and $R^8$ have the same meaning as hereinbefore defined), or $R^{30}$ and one of $R^{28}$ or $R^{29}$, together, is —$(CH_2)_q$— (in which —$(CH_2)_q$— has the same meaning as hereinbefore defined) and p is 1–5;

or a non-toxic salt thereof, an acid addition salt thereof or a hydrate thereof, (2) processes for the preparation thereof and
(3) pharmaceutical agents containing such a derivative as an active ingredient.

Comparison

The tetrazole compounds of the present invention are newly synthesized and therefore, are quite novel.

To summarize, in the compound of formula (X) known in the art (EP 519748), $R^{6X}$ of $Y^X$ can represent aryl C1–6 alkyl. But, the aryl group does not include a tetrazole. On the other hand, in the compound of the present invention, Y essentially is the tetrazole group. Therefore, it can be said that the compounds of the present invention have a chemical structure quite different from the compounds of formula (X). A representative example of formula (X) is compound (X-1).

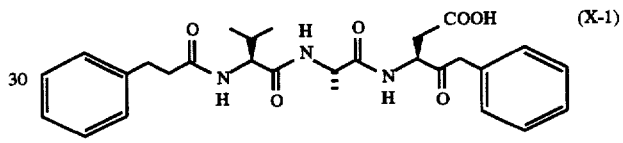

In the compound of formula (Y) of WO93/09135, $Y^{3Y}$ of $A^{5Y}$ can be a heteroaryl group. Further, exemplification of the heteroaryl group includes a tetrazole group. But, no substituents of the heteroaryl group are disclosed in detail in WO93/09135. On the other hand, a compound of the present invention has a ring essentially as substituents of the tetrazole of Y. It can be invention has a ring essentially as substituents of the tetrazole of Y. It can be said that the compounds of the present invention have a chemical structure quite different from the compounds of formula (Y). Representative examples of formula (Y) are compounds (Y-1) and (Y-2).

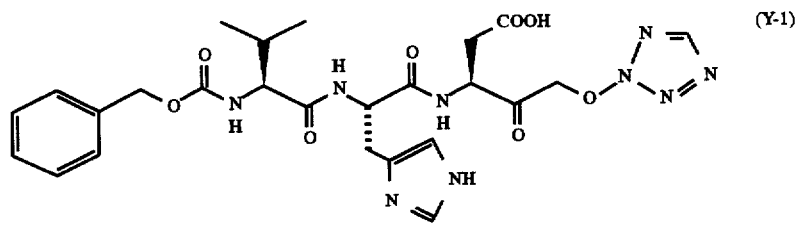

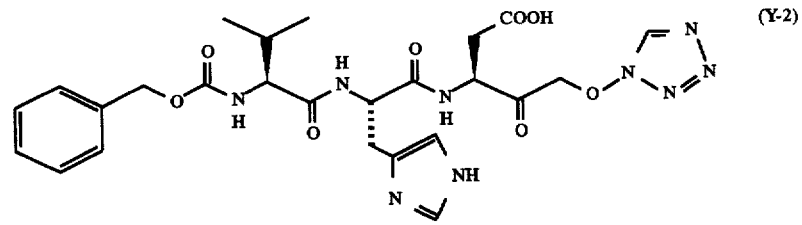

Further, in a compound of formula (Z), EP 618223, $Y^{3Z}$ of $A^{3Z}$ can represent a heteroaryl group. Further, exemplification of the heteroaryl group includes a tetrazole. But, only C1–4 alkyl is disclosed as substituents of the heteroaryl group. On the other hand, a compound of the present invention has a ring as a substituent of the tetrazole of Y. Therefore, it can be said that the compounds of the present invention have a chemical structure quite different from the compounds of formula (Z). Furthermore, in the compounds of formula (Z), $Y^{3Z}$ as a heteroaryl group is essentially bonded to a hetero atom (oxygen or sulfur atom). On the other hand, in the present invention, the tetrazole group of Y is bonded to a carbon atom. Thus, for another reason, compounds of formula (I) of the present invention have a chemical structure quite different from a compound of formula (Z). A representative example of a compound of formula (Z) is compound (Z-1).

alkyl substituted by a group selected from $-OR^7$, $-NR^7R^8$, $-SR^7$, $-COOR^7$, $-COR^7$, $-CONH_2$, $-NR^7-CO-NR^7R^8$, guanidino and $Cyc^2$ and C1–8 alkyl substituted by a group selected from $-OR^{13}$, $-NR^{13}R^{14}$, $-SR^{13}$, $-COOR^{13}$, $-COR^{13}$, $-CONH_2$, $-NR^{13}-CO-NR^{13}R^{14}$, guanidino and $Cyc^3$ means methyl, ethyl, propyl, butyl, pentyl, hexyl, heptyl, octyl and an isomer thereof.

In formula (I), C1–8 alkoxy represented by $R^1$ and C1–8 alkoxy substituted by $Cyc^1$ means methoxy, ethoxy, propoxy, butoxy, pentyloxy, hexyloxy, heptyloxy, octyloxy and an isomer thereof.

In formula (I), C1–4 alkyl represented by a substituent of $Cyc^1$, substituent of $Cyc^2$, substituent of $Cyc^3$, substituent of $Cyc^4$, substituent of $R^{15}$ and $R^{16}$, $R^2$, $R^3$, $R^5$, $R^6$, $R^7$, $R^8$, $R^{11}$, $R^{12}$, $R^{13}$, $R^{14}$, $R^{15}$, $R^{16}$, $R^{18}$, $R^{20}$, $R^{22}$, $R^{23}$, $R^{24}$, $R^{25}$, $R^{26}$,

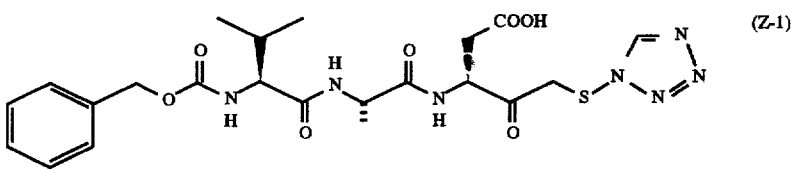

Furthermore, in the compounds of formula (W) of CA 2125021, $HET^W$ of $Y^W$ can be a heteroaryl group. Further, exemplification of the heteroaryl group includes a tetrazole group. But, there are no preparative examples of compounds in which a heteroaryl group is a tetrazole. Additionally, in the compound of formula (W), $HET^W$ as a heteroaryl is bonded to a hetero atom (oxygen atom). On the other hand, in the present invention, the tetrazole group Y is bonded to a carbon atom. Thus, compounds of formula (I) of the present invention have a chemical structure quite different from compound of formula (W). A representative compound of formula (W) is compound (W-1).

$R^{27}$, $R^{28}$ and $R^{29}$ means methyl, ethyl, propyl, butyl and an isomer thereof.

In formula (I), C1–4 alkoxy represented by a substituent of $R^{15}$ and $R^{16}$ means methoxy, ethoxy, propoxy, butoxy and an isomer thereof.

In formula (I), C1–8 alkylamino represented by $R^1$ and C1–8 alkylamino substituted by $Cyc^1$ each means methyl, ethyl, propyl, butyl, pentyl, hexyl, heptyl, octyl and an isomer thereof, which are substituted by an amino group.

In formula (I), C1–8 alkylthio represented by $R^1$ and C1–8 alkylthio substituted by $Cyc^1$ each means thiomethyl,

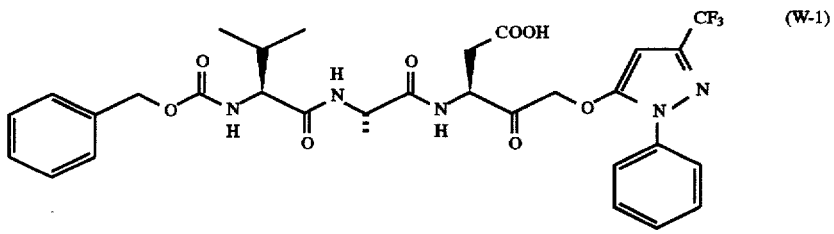

Therefore, the compounds of the present invention have a chemical structure quite different from the compounds of formulae (X), (Y), (Z) and (W) known in the art. The instant compounds are novel and not previously described.

Preparative examples of tetrazole derivatives are provided in the compounds of formulae (Y-1), (Y-2) and (Z-1); however, the tetrazole group therein is bonded to hetero atom. Therefore, the synthesis of compounds in which a tetrazole is bonded to a carbon atom as provided herein is not previously described.

Therefore, the present inventors have found that tetrazole compounds of formula (I) have an inhibitory activity on IL-1β converting enzyme even if a hetero atom dose not exist between a ketone group and a ring. That observation is quite unexpected from what is known in the art, and has been confirmed from experiments by the present inventors for the first time.

DETAILED DESCRIPTION OF THE INVENTION

In formula (I), C1–8 alkyl represented by $R^1$, $R^4$, $R^9$, $R^{10}$, $R^{17}$, $R^{19}$, and $R^+$, C1–8 alkyl substituted by $Cyc^1$, C1–8 thioethyl, thiopropyl, thiobutyl, thiopentyl, thiohexyl, thioheptyl, thiooctyl and an isomer thereof.

In formula (I), trihalomethyl represented by $R^{26}$ means trifluoromethyl, trichloromethyl, tribromomethyl and tri-iodomethyl group.

In formula (I), C1–4 alkyl substituted by trihalomethyl represented by $R^{26}$ means methyl, ethyl, propyl, butyl and the isomer thereof, which are substituted by a trifluoromethyl, trichloromethyl, tribromomethyl and tri-iodomethyl group.

In formula (I), C1–4 alkyl substituted by phenyl represented by substituent of $Cyc^1$, substituent of $Cyc^2$, substituent of $Cyc^3$, substituent of $Cyc^4$, $R^2$, $R^3$, $R^5$, $R^6$, $R^7$, $R^8$, $R^{11}$, $R^{12}$, $R^{13}$, $R^{14}$, $R^{15}$, $R^{16}$, $R^{18}$, $R^{19}$, $R^{22}$, $R^{23}$, $R^{24}$, $R^{25}$, $R^{27}$, $R^{28}$ and $R^{29}$ means methyl, ethyl, propyl, butyl and the isomer thereof, which are substituted by a phenyl group.

In formula (I), a halogen atom represented by a substituent of $Cyc^1$, substituent of $Cyc^2$, substituent of $Cyc^3$, substituent of $Cyc^4$, substituent of $R^{15}$ and $R^{16}$, and $R^{20}$ means fluorine, chlorine, bromine and iodide.

In formula (I), C1–6 alkylene represented by $R^9$ and $R^{10}$, taken together, means methylene, ethylene, trimethylene, tetramethylene, pentamethylene, hexamethylene and an isomer thereof.

In formula (I), C2–6 alkenylene represented by $R^9$ and $R^{10}$, taken together, means vinylene, propenylene, butenylene, pentenylene, hexenylene, butadienylene, pentadienylene, hexadienylene, hexatrienylene and an isomer thereof.

In formula (I), a carbocyclic ring represented by $Cyc^1$, $Cyc^2$, $Cyc^3$, $Cyc^4$ and

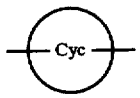

means a 3–10 membered mono-cyclic or bi-cyclic carbocyclic ring. For example, a 3–10 membered mono-cyclic or bi-cyclic carbocyclic ring include cyclopropyl, cyclobutyl, cyclopentyl, cyclohexyl, cycloheptyl, cyclopentadiene, benzene, pentalene, benzocyclobutene, indene, 2,3-dihydroindene, naphthalene, tetrahydronaphthalene, azulene ring etc.

In formula (I), a hetero ring represented by $Cyc^1$, $Cyc^2$, $Cyc^3$, $Cyc^4$ and

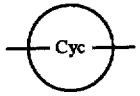

means a 5–15 membered mono-cyclic or bi-cyclic hetero ring containing one or two nitrogen atoms, one oxygen atom or a sulfur atom. For example, a 5–15 membered mono-cyclic or bi-cyclic hetero ring containing one or two nitrogen atoms, one oxygen atom or a sulfur atom includes pyrrole, imidazole, pyrazole, pyridine, pyrazine, pyrimidine, pyridazine, azepine, diazepine, furan, pyran, oxepine, oxazepine, thiophene, thiaine (thiopyran), thiepine, oxazole, isooxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, pyrroline, pyrrolidine, imidazoline, imidazolidine, pyrazoline, pyrazolidine, piperidine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisooxazole, tetrahydroisooxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole ring etc.

In formula (I), a hetero ring represented by $R^{28}$ and $R^{29}$, taken together, means a 5–7 membered mono-cyclic hetero ring containing one or two nitrogen atoms. For example, a 5–7 membered mono-Cyclic hetero ring containing one or two nitrogen atoms includes pyrrolidine, imidazolidine, pyrazolidine, piperidine, piperazine, tetrahydropyrimidine, tetrahydropyridazine ring etc.

In formula (I),

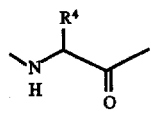

represented by $AA^1$ may be an a-amino acid residue. For example, glycine, alanine, serine, threonine, cystine, valine, methionine, leucine, isoleucine, phenylalanine, tyrosine, tryptophan, aspartic acid, glutamic acid, arginine, glutamine, lysine, histidine, proline etc.

In formula (I),

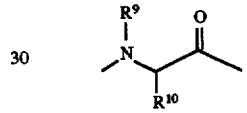

represented by $AA^2$ may be an α-amino acid residue. For example, glycine, alanine, serine, threonine, cystine, valine, methionine, leucine, isoleucine, phenylalanine, tyrosine, tryptophan, aspartic acid, glutamic acid, arginine, glutamine, lysine, histidine, proline etc.

Throughout the specification, including claims, it may be easily understood by those skilled in the art, that all isomers are included in the present invention. For example, the alkyl, alkoxy and alkylene groups include straight-chain and also branched-chain ones. Accordingly, all isomers produced by the existence of asymmetric carbon atoms are included in the present invention when branched-chain alkyl, alkoxy, alkylene, etc. exist.

In the present invention, non-toxic salts includes all such salts. For example, the following salt, acid addition salt or hydrate, etc.

The compounds of formula (I) of the present invention may be converted into a corresponding non-toxic salt by methods known per se. Non toxic and water-soluble salts are preferable. Suitable salts, for example, are salts of an alkaline metal (potassium, sodium etc.), salts of an alkaline earth metal (calcium, magnesium etc.), ammonium salts and salts of pharmaceutically-acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine etc.).

The compounds of formula (I) of the present invention may be converted into a corresponding acid addition salt by methods known per se. Non toxic and water-soluble salts are preferable. Suitable acid addition salts include salts of inorganic acids such as hydrochloric acid, hydrobromic acid, sulfuric acid, phosphoric acid and nitric acid, and salts with organic acids such as acetic acid, trifluoroacetic acid, lactic acid, tartaric acid, oxalic acid, fumaric acid, maleic acid, benzenesulfonic acid, toluenesulfonic acid, isethionic acid, glucuronic acid and gluconic acid.

The compounds of formula (I) or salts thereof of the present invention may be converted into a corresponding hydrate by methods known per se.

Preferred compounds of the present invention are as follows: tetrazole derivative of formula I (1)

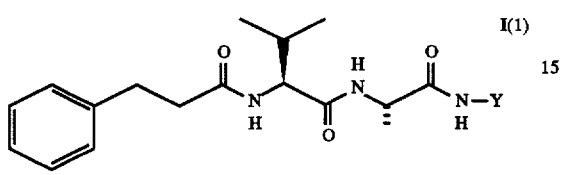

I(1)

(wherein Y has the same meaning as hereinbefore defined), the compound of formula I (2)

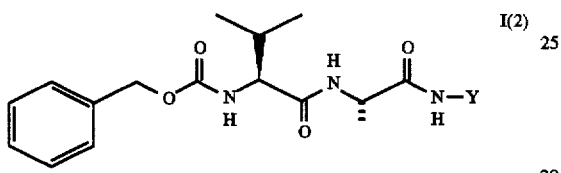

I(2)

(wherein Y has the same meaning as hereinbefore defined), the compound of formula I (3)

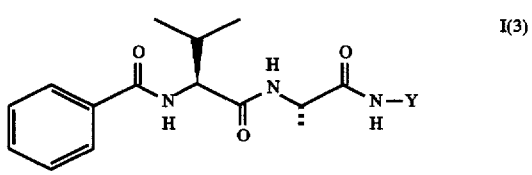

I(3)

(wherein Y has the same meaning as hereinbefore defined), the compound of formula I (4)

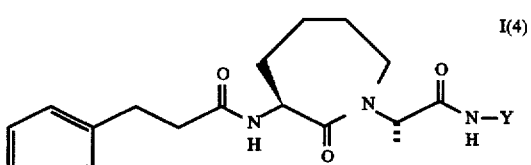

I(4)

(wherein Y has the same meaning as hereinbefore defined), the compound of formula I (5)

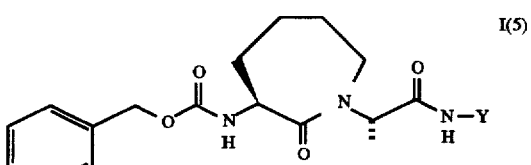

I(5)

(wherein Y has the same meaning as hereinbefore defined), the compound of formula I (6)

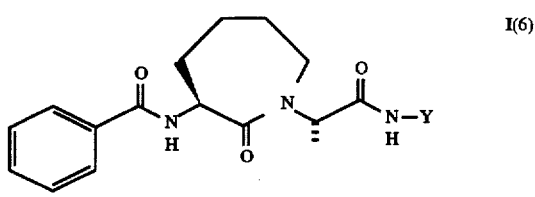

I(6)

(wherein Y has the same meaning as hereinbefore defined), the compound of formula I (7)

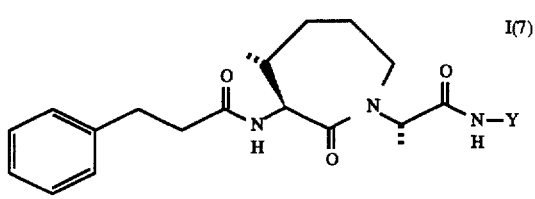

I(7)

(wherein Y has the same meaning as hereinbefore defined), the compound of formula I (8)

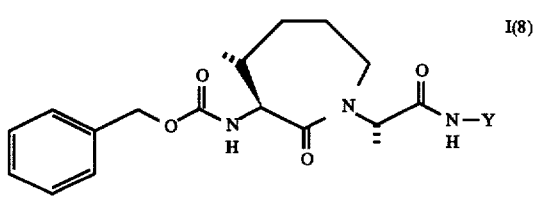

I(8)

(wherein Y has the same meaning as hereinbefore defined), the compound of formula I (9)

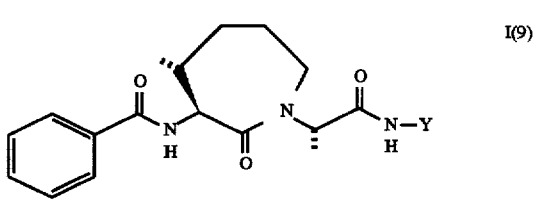

I(9)

(wherein Y has the same meaning as hereinbefore defined), the compound of formula I (10)

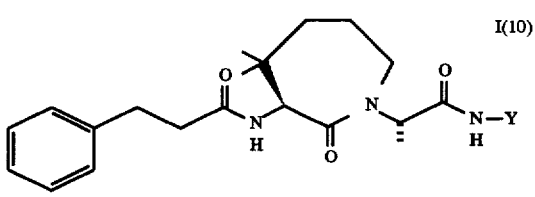

I(10)

(wherein Y has the same meaning as hereinbefore defined), the compound of formula I (11)

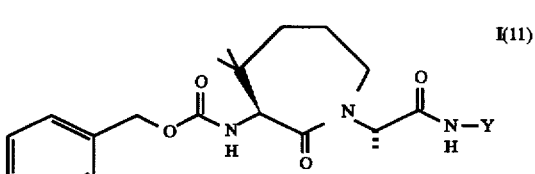

I(11)

(wherein Y has the same meaning as hereinbefore defined), the compound of formula I (12)

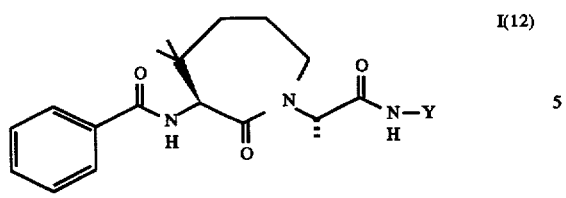

(wherein Y has the same meaning as hereinbefore defined), the compound of formula I (13)

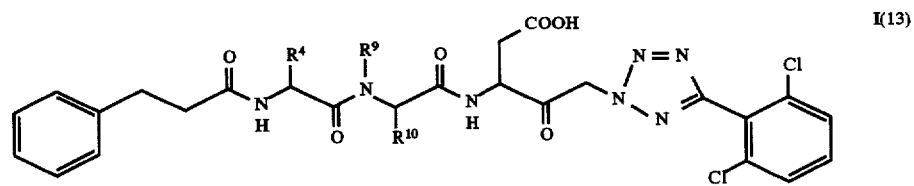

(wherein $R^4$, $R^9$ and $R^{10}$ have the same meaning as hereinbefore defined), the compound of formula I (14)

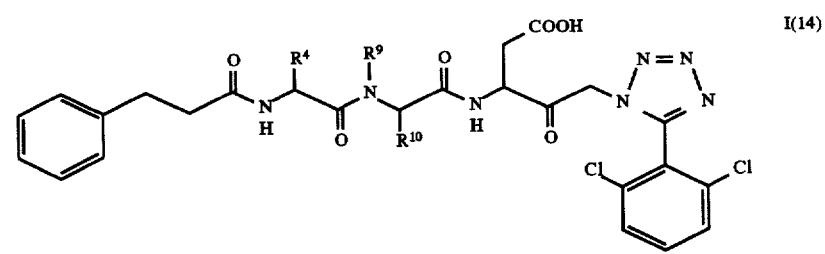

(wherein $R^4$, $R^9$ and $R^{10}$ have the same meaning as hereinbefore defined), the compound of formula I (15)

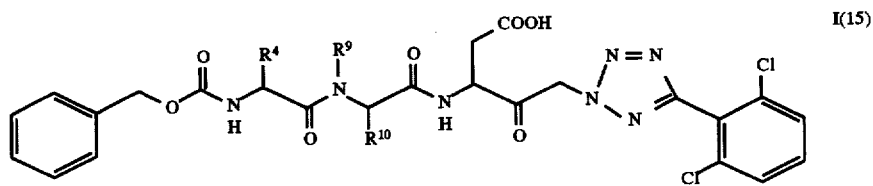

(wherein $R^4$ $R^9$ and $R^{10}$ have the same meaning as hereinbefore defined), the compound of formula I (16)

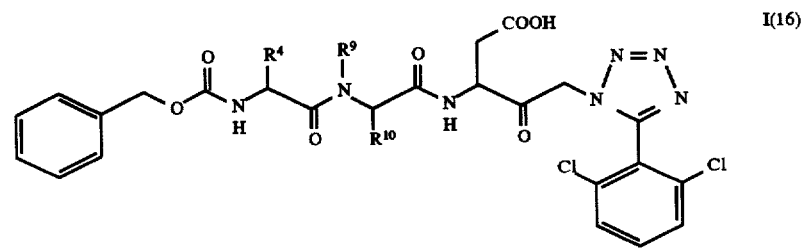

(wherein $R^4$, $R^9$ and $R^{10}$ have the same meaning as hereinbefore defined), the compound of formula I (17)

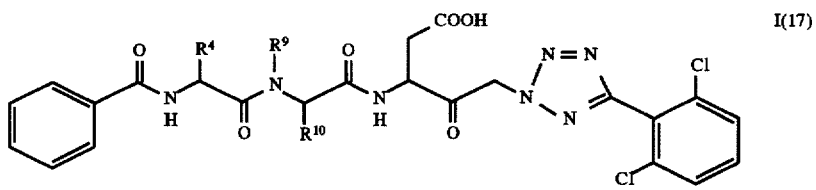

I(17)

(wherein $R^4$, $R^9$ and $R^{10}$ have the same meaning as hereinbefore defined), the compound of formula I (18)

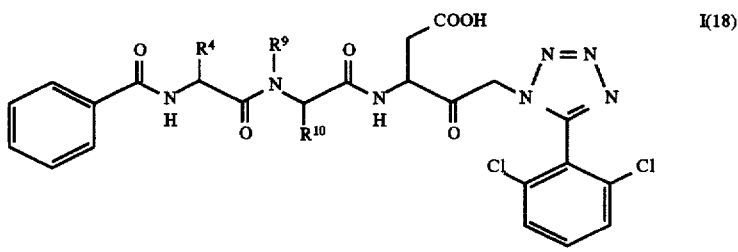

I(18)

(wherein $R^4$, $R^9$ and $R^{10}$ have the same meaning as hereinbefore defined), the compound of formula I (19)

(wherein $R^{15}$, $R^{16}$, $R^{17}$ and $-(CH_2)_q-$ have the same meaning as hereinbefore defined), the compound of formula I (22)

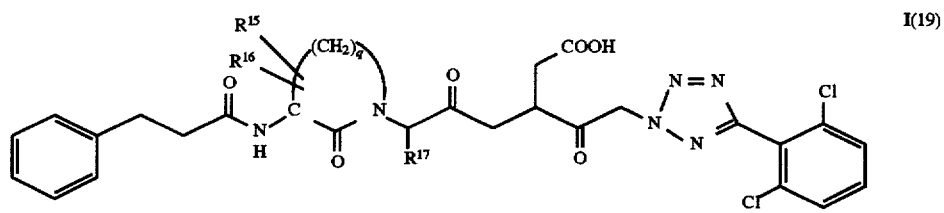

I(19)

(wherein $R^{15}$, $R^{16}$, $R^{17}$ and $-(CH_2)_q-$ have the same meaning as hereinbefore defined), the compound of formula I (20)

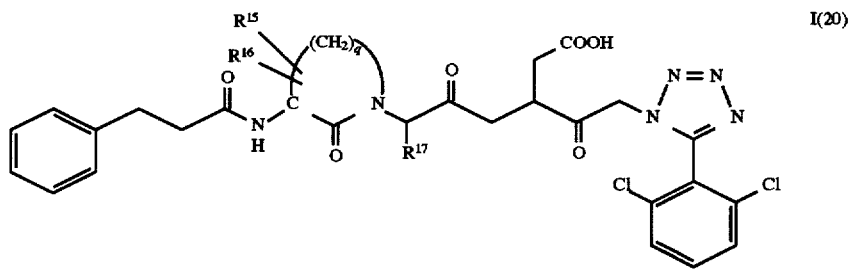

I(20)

(wherein $R^{15}$, $R^{16}$, $R^{17}$ and $-(CH_2)_q-$ have the same meaning as hereinbefore defined), the compound of formula I (21)

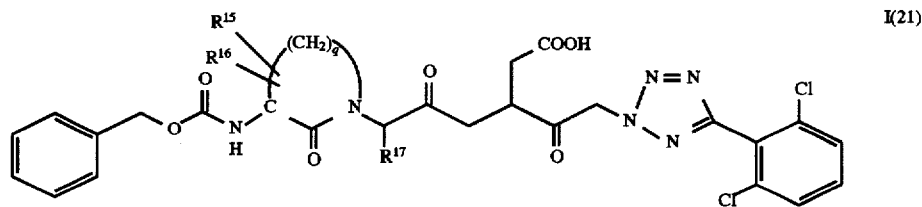

I(21)

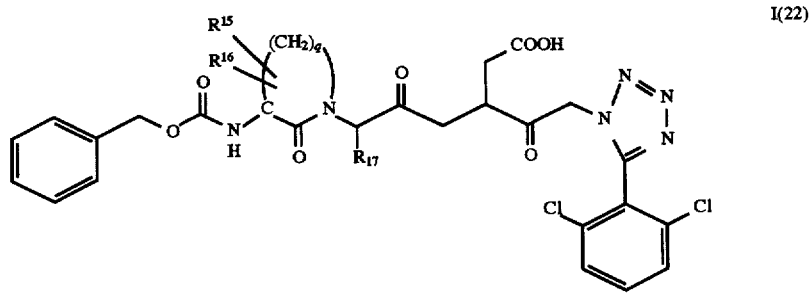

I(22)

(wherein $R^{15}$, $R^{16}$, $R^{17}$ and —$(CH_2)_q$— have the same meaning as hereinbefore defined), the compound of formula I (23)

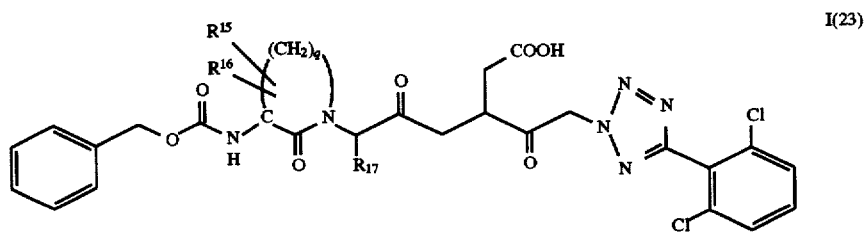

I(23)

(wherein $R^{15}$, $R^{16}$, $R^{17}$ and —$(CH_2)_q$— have the same meaning as hereinbefore defined), the compound of formula I (24)

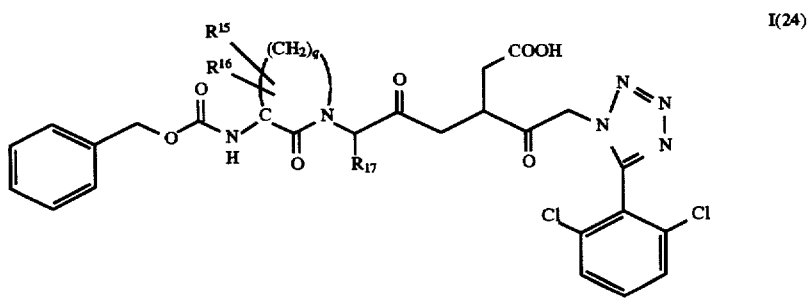

I(24)

(wherein $R^{15}$, $R^{16}$, $R^{17}$ and —$(CH_2)_q$— have the same meaning as hereinbefore defined), the compound of formula I (25)

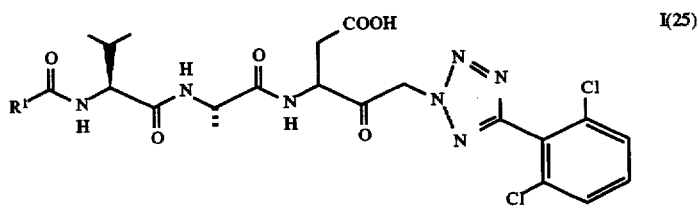

I(25)

(wherein $R^1$ has the same meaning as hereinbefore defined), the compound of formula I(26)

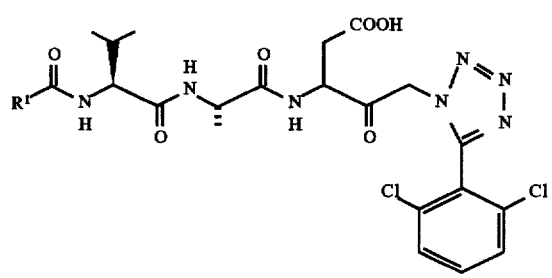

I(26)

(wherein R¹ has the same meaning as hereinbefore defined), the compound of formula I (27)

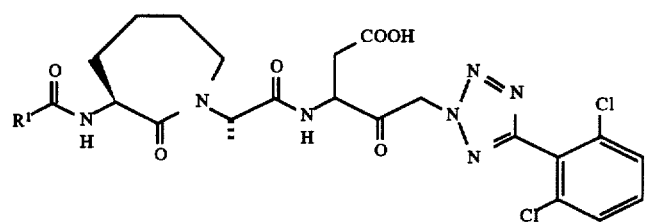

I(27)

(wherein R¹ has the same meaning as hereinbefore defined), the compound of formula I(28)

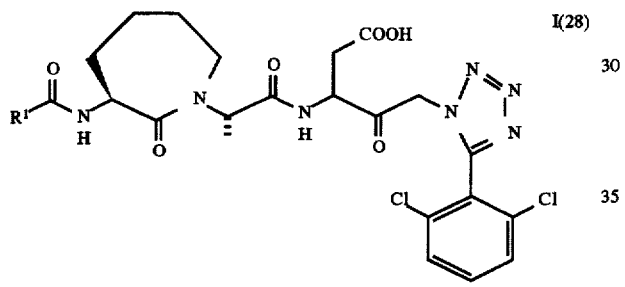

I(28)

(wherein R¹ has the same meaning as hereinbefore defined), the compound of formula I (29)

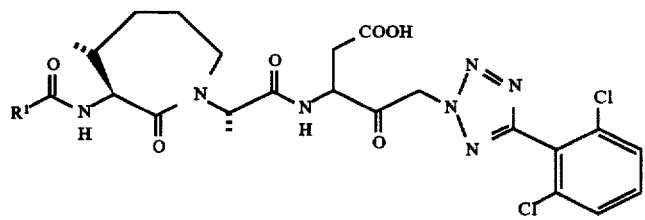

I(29)

(wherein R¹ has the same meaning as hereinbefore defined), the compound of formula I (30)

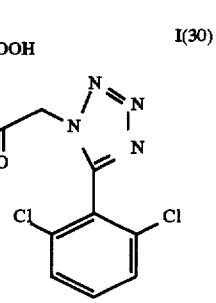

I(30)

(wherein R¹ has the same meaning as hereinbefore defined), the compound of formula I (31)

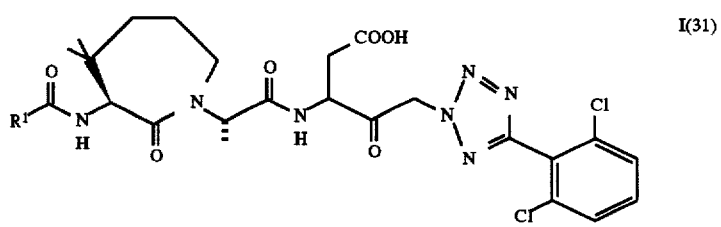

I(31)

(wherein R¹ has the same meaning as hereinbefore defined), the compound of formula I (32)

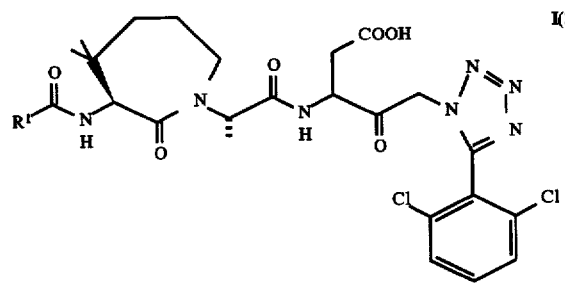

(wherein R¹ has the same meaning as hereinbefore defined), the compound of formula I (33)

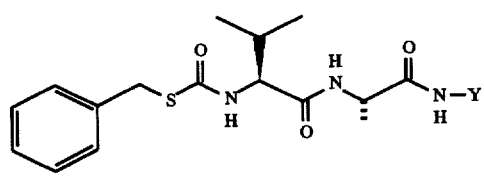

(wherein Y has the same meaning as hereinbefore defined), the compound of formula I(34)

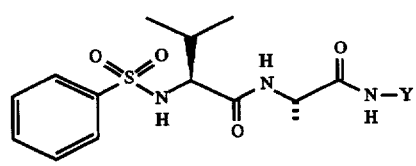

(wherein Y has the same meaning as hereinbefore defined), the compound of formula I (35)

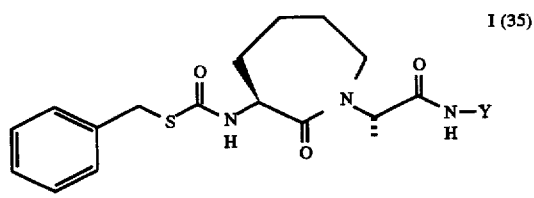

(wherein Y has the same meaning as hereinbefore defined), the compound of formula I(36)

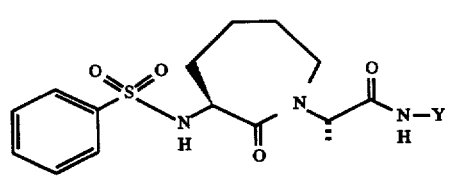

(wherein Y has the same meaning as hereinbefore defined), the compound of formula I (37)

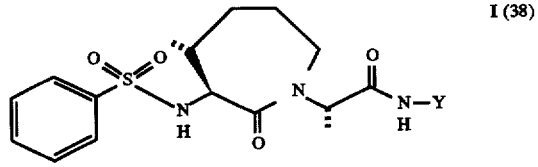

(wherein Y has the same meaning as hereinbefore defined), the compound of formula I (38)

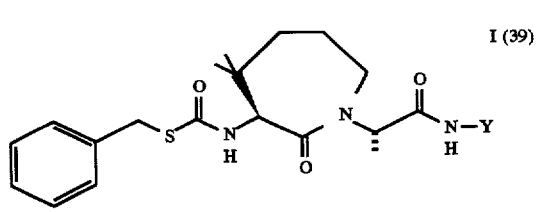

(wherein Y has the same meaning as hereinbefore defined), the compound of formula I (39)

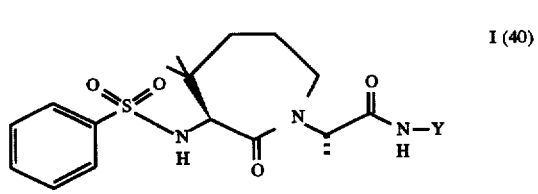

(wherein Y has the same meaning as hereinbefore defined), the compound of formula I (40)

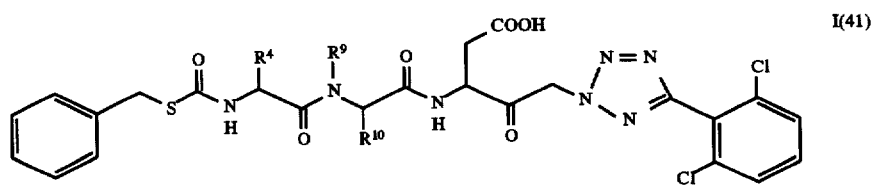

(wherein Y has the same meaning as hereinbefore defined), the compound of formula I (41)

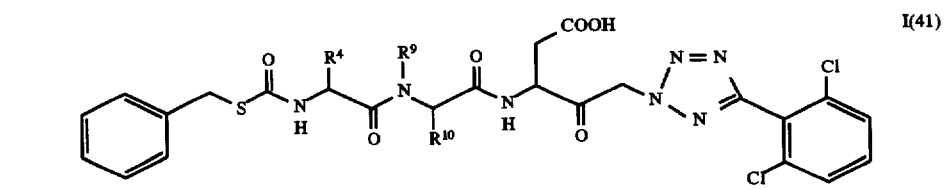

(wherein $R^4$, $R^9$, and $R^{10}$ have the same meaning as hereinbefore defined), the compound of formula I (42)

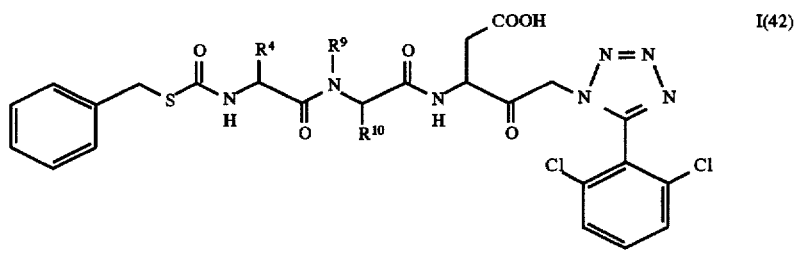

I(42)

(wherein R⁴, R⁹, and R¹⁰ have the same meaning as hereinbefore defined), the compound of formula I (43)

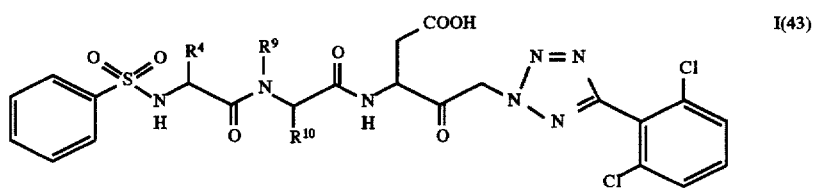

I(43)

(wherein R⁴, R⁹, and R¹⁰ have the same meaning as hereinbefore defined), the compound of formula I (44)

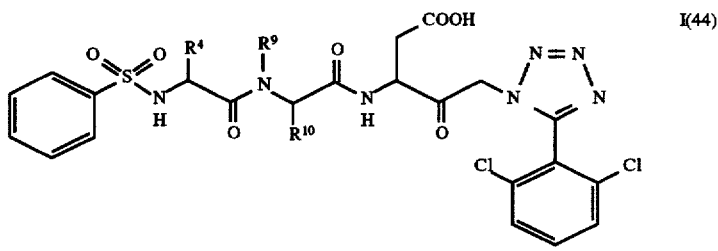

I(44)

(wherein R⁴, R⁹, and R¹⁰ have the same meaning as hereinbefore defined), the compound of formula I (45)

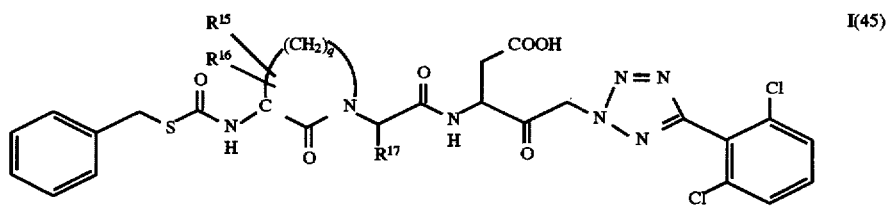

I(45)

(wherein R¹⁵, R¹⁶, R¹⁷ and —(CH₂)$_q$— have the same meaning as hereinbefore defined), the compound of formula I (46)

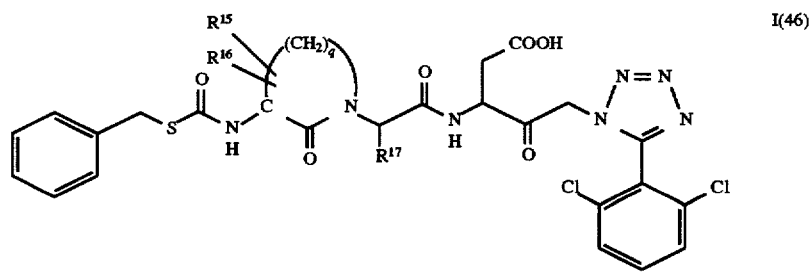

I(46)

(wherein R¹⁵, R¹⁶, R¹⁷ and —(CH₂)$_q$— have the same meaning as hereinbefore defined), the compound of formula I (47)

I(47)

(wherein R¹⁵, R¹⁶, R¹⁷ and —(CH₂)_q— have the same meaning as hereinbefore defined), the compound of formula I (48)

I(48)

(wherein R¹⁵, R¹⁶, R¹⁷ and —(CH₂)_q— have the same meaning as hereinbefore defined), the compound of formula I (49)

I(49)

(wherein Y has the same meaning as hereinbefore defined), the compound of formula I (50)

I(50)

(wherein Y has the same meaning as hereinbefore defined), the compound of formula I (51)

I(51)

(wherein Y has the same meaning as hereinbefore defined), the compound of formula I (52)

I(52)

(wherein Y has the same meaning as hereinbefore defined), the compound of formula I (53)

I(53)

(wherein Y has the same meaning as hereinbefore defined), the compound of formula I (54)

I(54)

(wherein Y has the same meaning as hereinbefore defined), the compound of formula I (55)

I(55)

(wherein Y has the same meaning as hereinbefore defined), the compound of formula I (56)

I(56)

(wherein Y has the same meaning as hereinbefore defined), the compound of formula I (57)

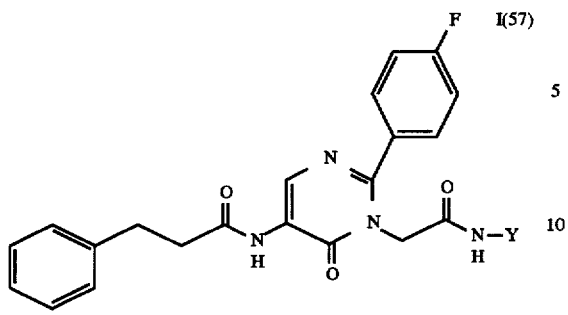

(wherein Y has the same meaning as hereinbefore defined), the compound of formula I (58)

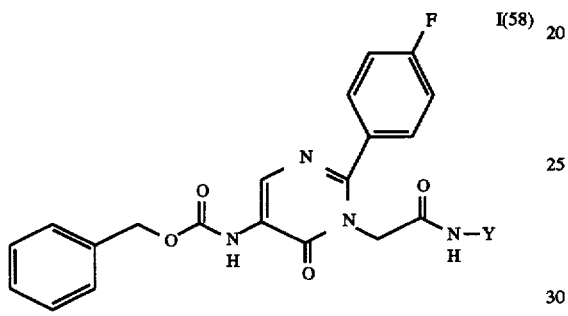

(wherein Y has the same meaning as hereinbefore defined), the compound of formula I (59)

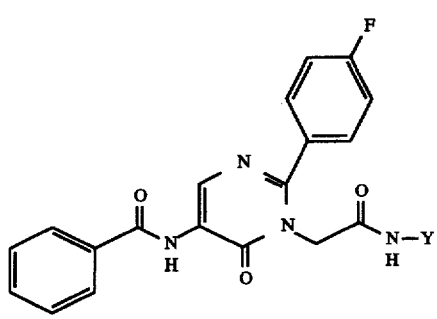

(wherein Y has the same meaning as hereinbefore defined), the compound of formula I (60)

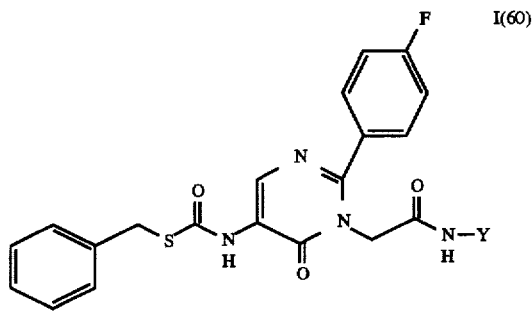

(wherein Y has the same meaning as hereinbefore defined), the compound of formula I (61)

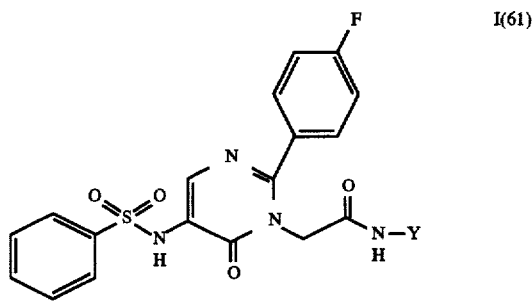

(wherein Y has the same meaning as hereinbefore defined), the compound of formula I (62)

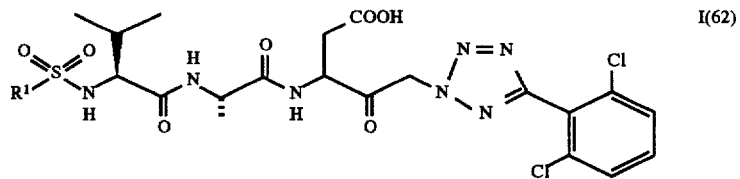

(wherein $R^1$ has the same meaning as hereinbefore defined), the compound of formula I (63)

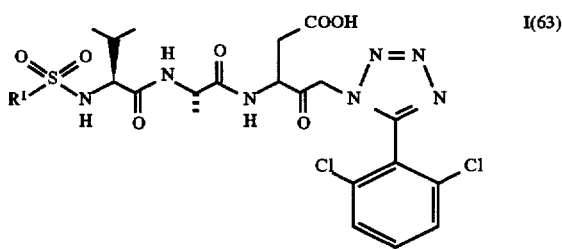

(wherein $R^1$ has the same meaning as hereinbefore defined), the compound of formula I (64)

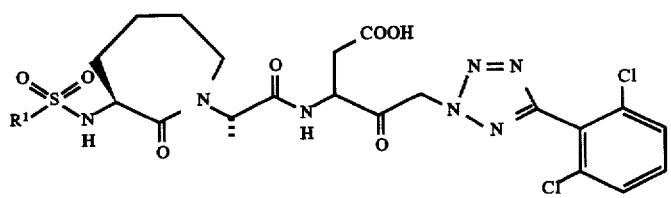

I(64)

(wherein R¹ has the same meaning as hereinbefore defined), the compound of formula I (65)

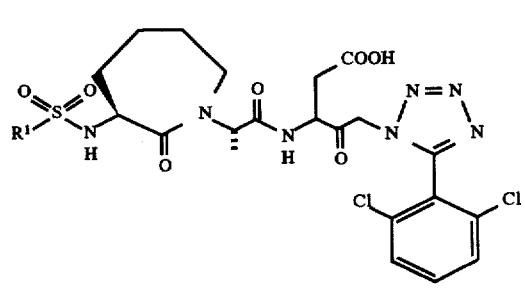

I(65)

(wherein R¹ has the same meaning as hereinbefore defined), the compound of formula I (66)

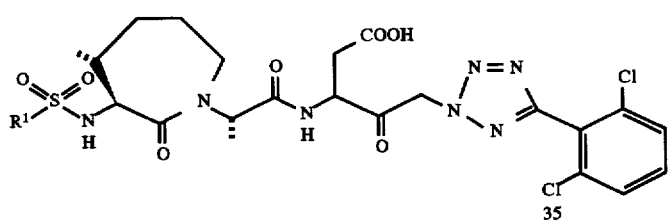

I(66)

(wherein R¹ has the same meaning as hereinbefore defined), the compound of formula I (67)

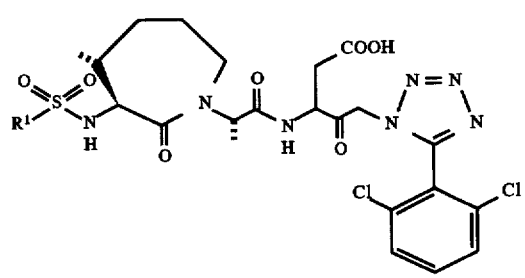

I(67)

(wherein R¹ has the same meaning as hereinbefore defined), the compound of formula I (68)

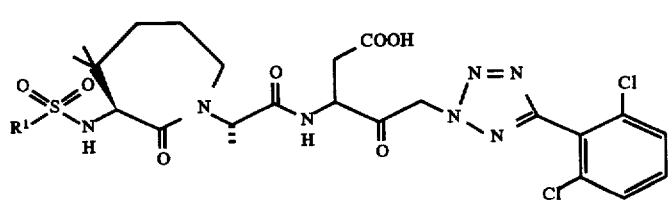

I(68)

(wherein R¹ has the same meaning as hereinbefore defined), the compound of formula I (69)

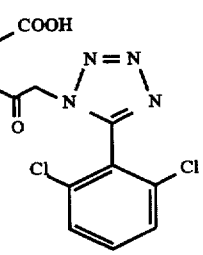

I(69)

(wherein R¹ has the same meaning as hereinbefore defined), the compound of formula I (70)

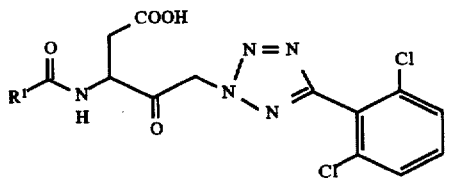

I(70)

(wherein R¹ has the same meaning as hereinbefore defined), the compound of formula I (71)

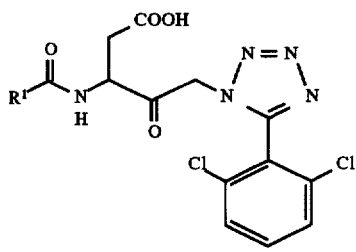

(wherein R¹ has the same meaning as hereinbefore defined), the compound of formula I (72)

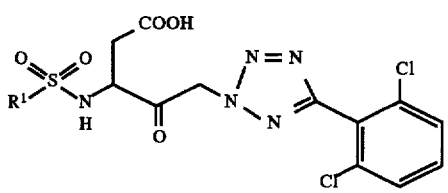

(wherein R¹ has the same meaning as hereinbefore defined), the compound of formula I (73)

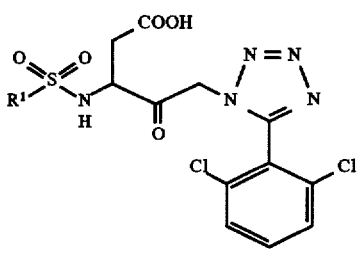

(wherein R¹ has the same meaning as hereinbefore defined), the compound of formula I (74)

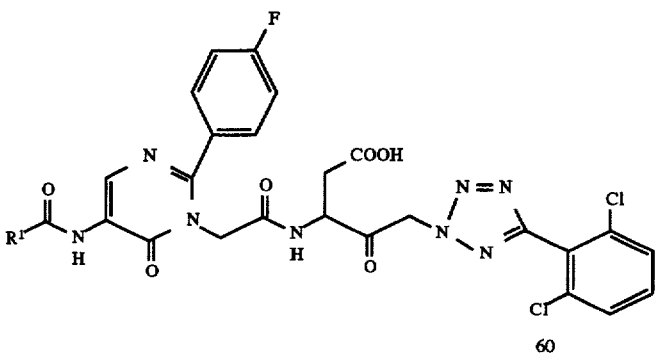

(wherein R¹ has the same meaning as hereinbefore defined), the compound of formula I (75)

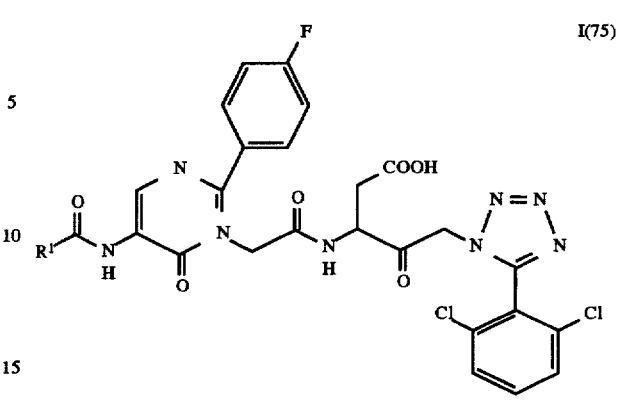

(wherein R¹ has the same meaning as hereinbefore defined), the compound of formula I (76)

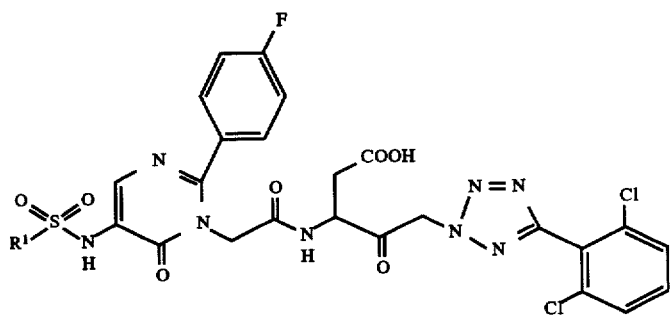
(wherein R¹ has the same meaning as hereinbefore defined) and the compound of formula I (77)
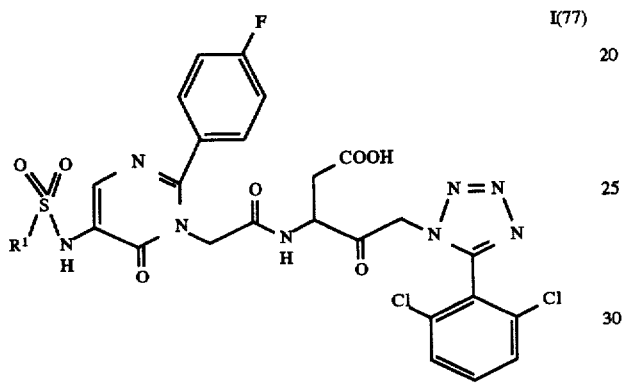
(wherein R¹ has the same meaning as hereinbefore defined), or a non-toxic salt thereof, an acid addition salt thereof or a hydrate thereof.
Examples of representative compounds of formula (I) of the present invention are listed in Table 1–77.
TABLE 1

TABLE 1-continued
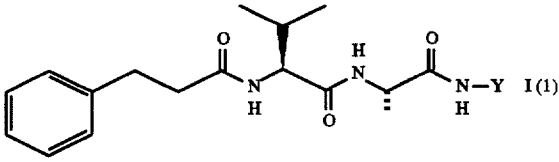
| No. | Y | No. | Y |
|---|---|---|---|
| 3 | 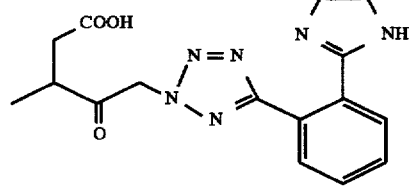 | 8 | 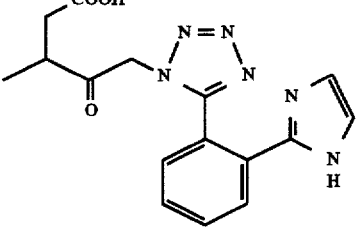 |
| 4 | 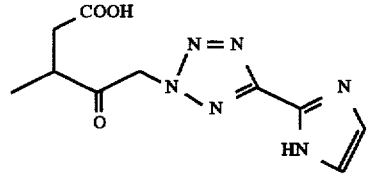 | 9 | 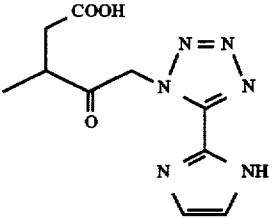 |
| 5 | 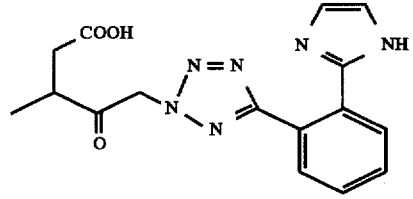 | 10 | 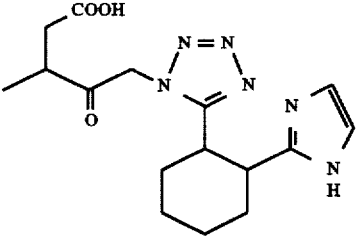 |
TABLE 2
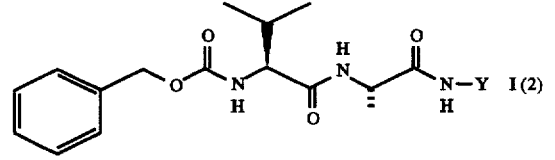
| No. | Y | No. | Y |
|---|---|---|---|
| 1 | 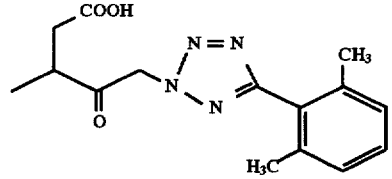 | 6 | 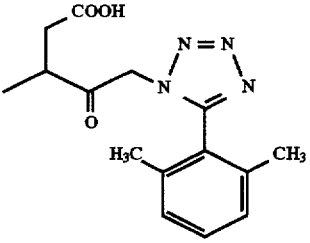 |

TABLE 2-continued
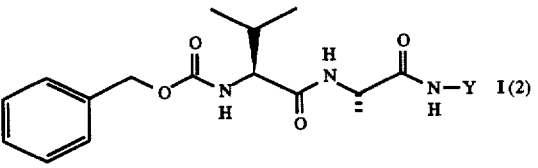
| No. | Y | No. | Y |
|---|---|---|---|
| 2 | 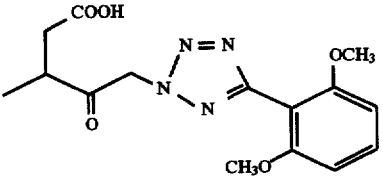 | 7 | 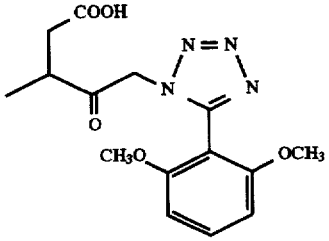 |
| 3 | 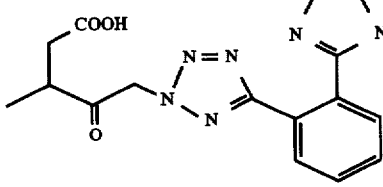 | 8 | 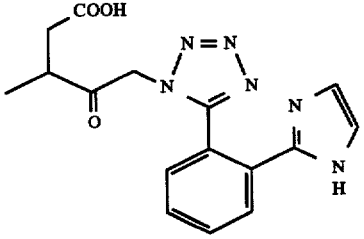 |
| 4 | 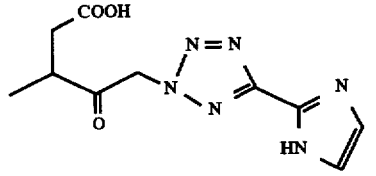 | 9 | 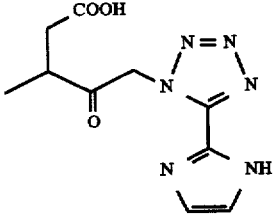 |
| 5 | 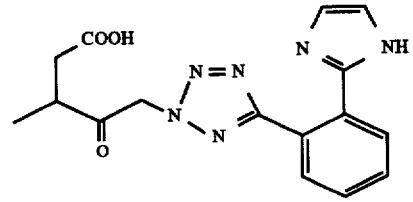 | 10 | 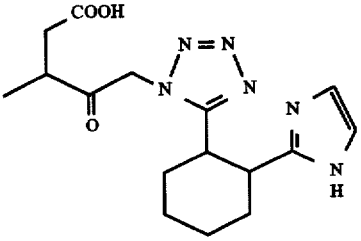 |

TABLE 3
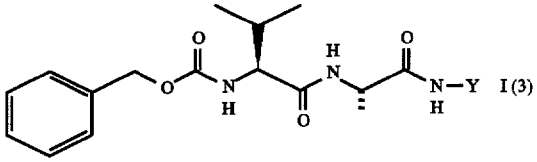
| No. | Y | No. | Y |
|---|---|---|---|
| 1 | 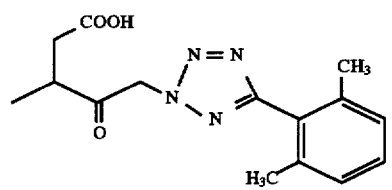 | 6 | 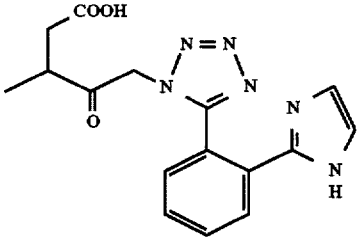 |
| 2 | 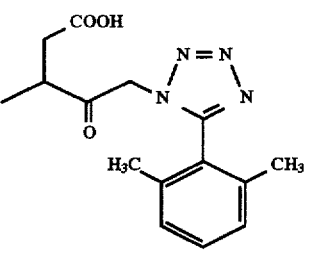 | 7 | 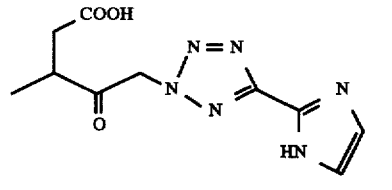 |
| 3 | 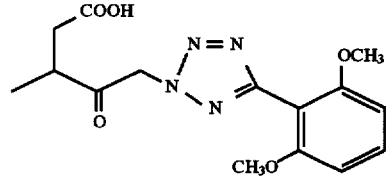 | 8 | 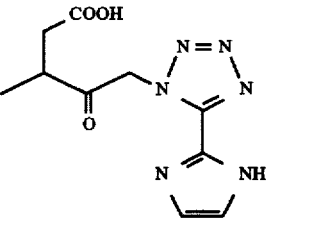 |
| 4 | 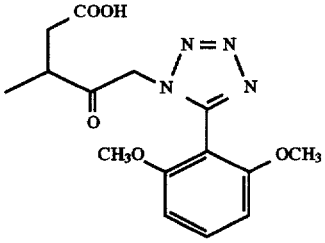 | 9 | 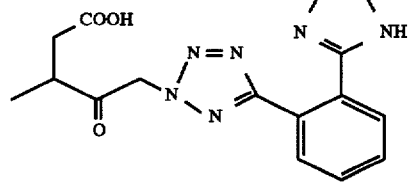 |
| 5 | 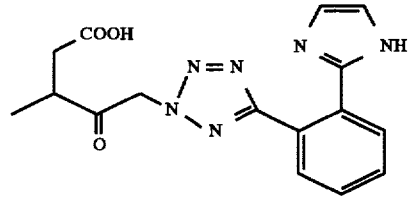 | 10 | 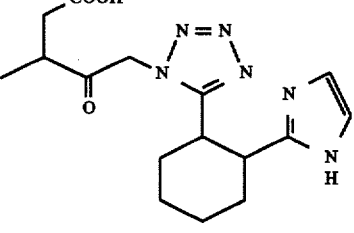 |

TABLE 4
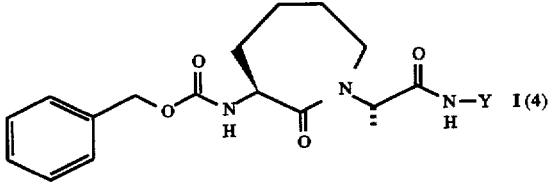
| No. | Y | No. | Y |
|---|---|---|---|
| 1 | 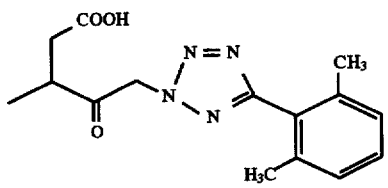 | 6 | 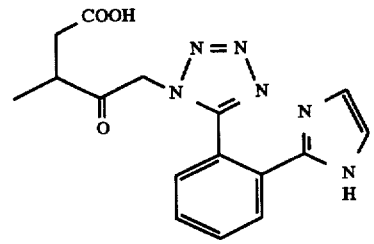 |
| 2 | 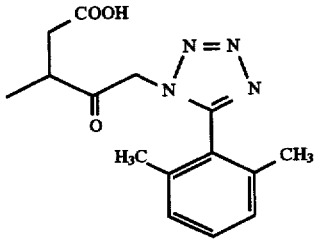 | 7 | 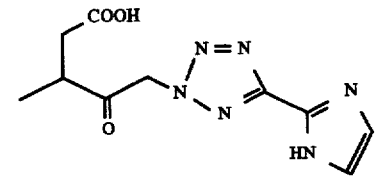 |
| 3 | 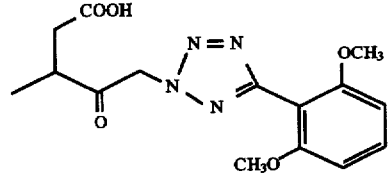 | 8 | 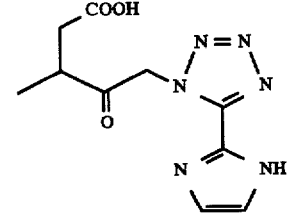 |
| 4 | 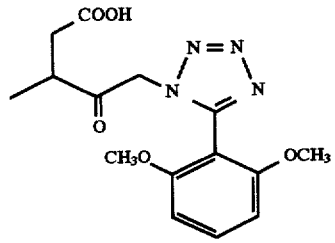 | 9 | 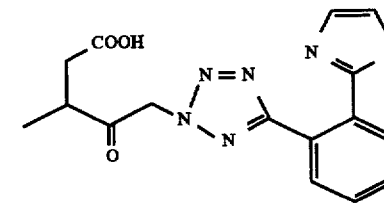 |
| 5 | 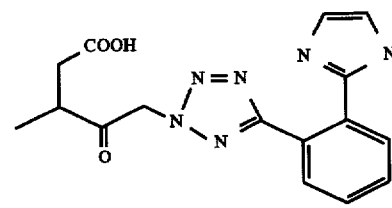 | 10 | 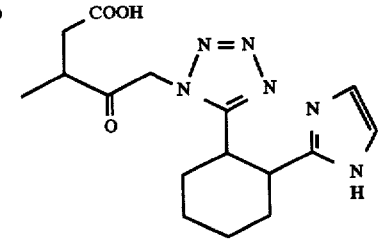 |

TABLE 5
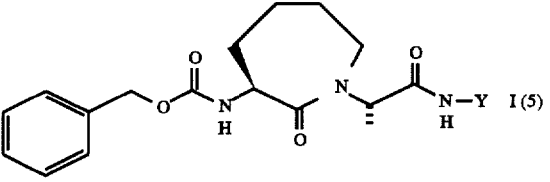
| No. | Y | No. | Y |
|---|---|---|---|
| 1 | 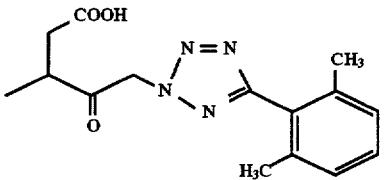 | 6 | 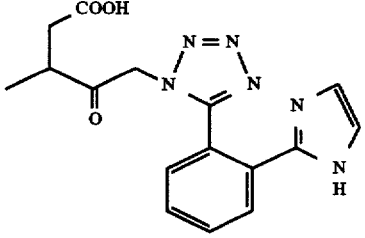 |
| 2 | 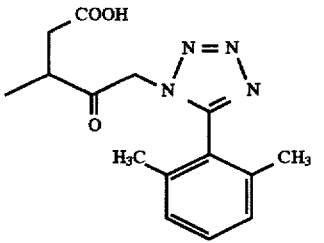 | 7 | 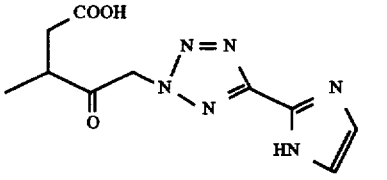 |
| 3 | 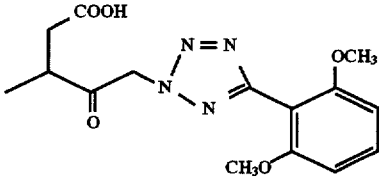 | 8 | 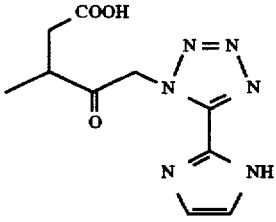 |
| 4 | 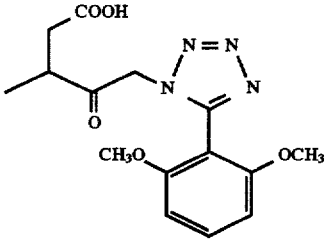 | 9 | 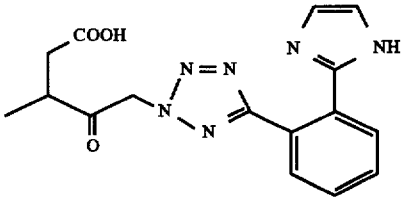 |
| 5 | 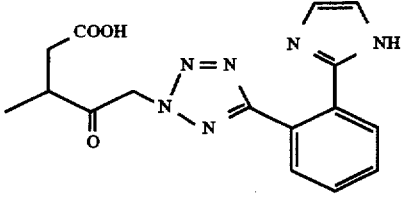 | 10 | 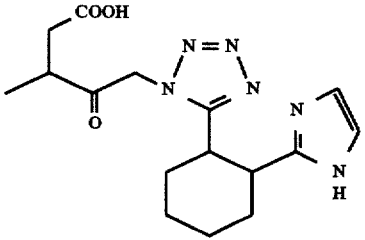 |

TABLE 6

(Structure I(6): benzoyl-NH-[chiral C in 7-membered lactam ring with N]-C(=O)-N(CH₃ chiral)-C(=O)-NH-Y)

| No. | Y | No. | Y |
|-----|---|-----|---|
| 1 | COOH-CH₂-CH(CH₃)-C(=O)-CH₂-[2H-tetrazol-2-yl]-5-(2,6-dimethylphenyl) | 6 | COOH-CH₂-CH(CH₃)-C(=O)-CH₂-[1H-tetrazol-1-yl]-5-(2,6-dimethylphenyl) |
| 2 | COOH-CH₂-CH(CH₃)-C(=O)-CH₂-[2H-tetrazol-2-yl]-5-(2,6-dimethoxyphenyl) | 7 | COOH-CH₂-CH(CH₃)-C(=O)-CH₂-[1H-tetrazol-1-yl]-5-(2,6-dimethoxyphenyl) |
| 3 | COOH-CH₂-CH(CH₃)-C(=O)-CH₂-[2H-tetrazol-2-yl]-5-[2-(1H-imidazol-2-yl)phenyl] | 8 | COOH-CH₂-CH(CH₃)-C(=O)-CH₂-[1H-tetrazol-1-yl]-5-[2-(1H-imidazol-2-yl)phenyl] |
| 4 | COOH-CH₂-CH(CH₃)-C(=O)-CH₂-[2H-tetrazol-2-yl]-5-(1H-imidazol-2-yl) | 9 | COOH-CH₂-CH(CH₃)-C(=O)-CH₂-[1H-tetrazol-1-yl]-5-(1H-imidazol-2-yl) |
| 5 | COOH-CH₂-CH(CH₃)-C(=O)-CH₂-[2H-tetrazol-2-yl]-5-[2-(1H-imidazol-2-yl)phenyl] | 10 | COOH-CH₂-CH(CH₃)-C(=O)-CH₂-[1H-tetrazol-1-yl]-5-[2-(1H-pyrrol-2-yl)cyclohexyl] |

TABLE 7
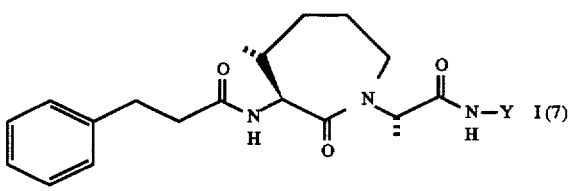
| No. | Y | No. | Y |
|---|---|---|---|
| 1 | 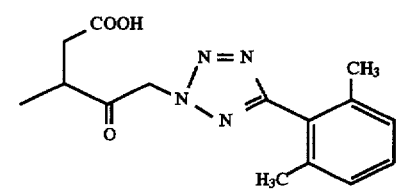 | 6 | 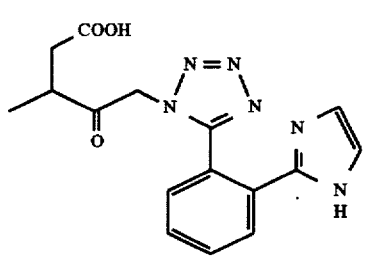 |
| 2 | 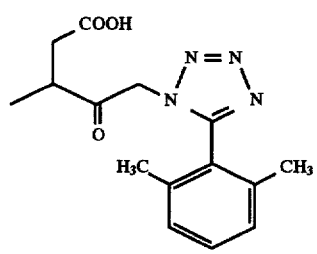 | 7 | 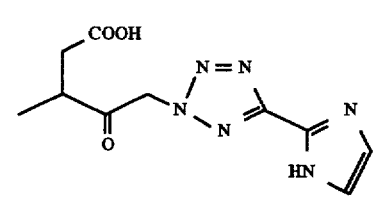 |
| 3 | 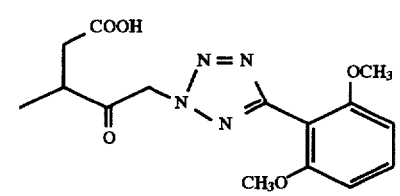 | 8 | 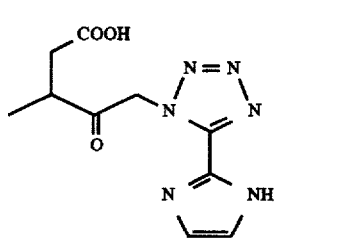 |
| 4 | 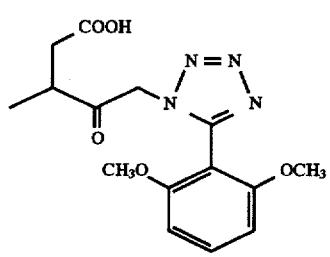 | 9 | 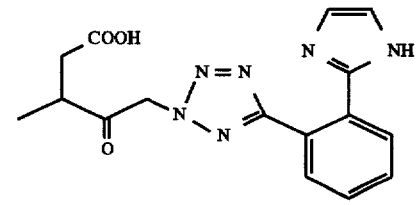 |
| 5 | 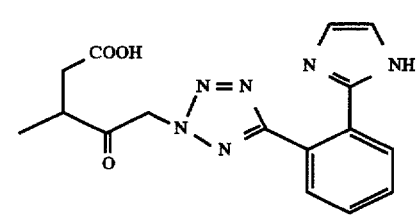 | 10 | 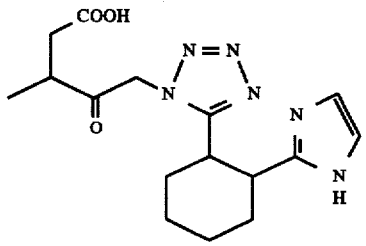 |

TABLE 8
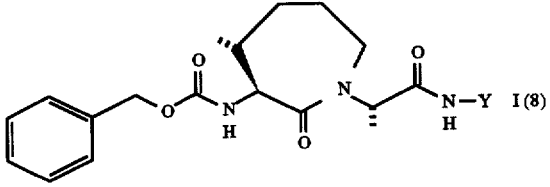
| No. | Y | No. | Y |
|---|---|---|---|
| 1 | 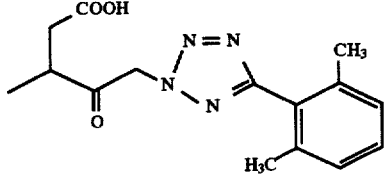 | 6 | 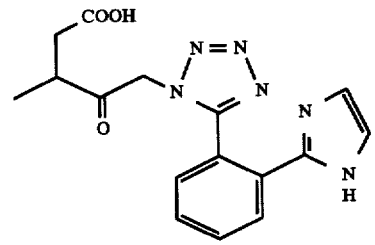 |
| 2 | 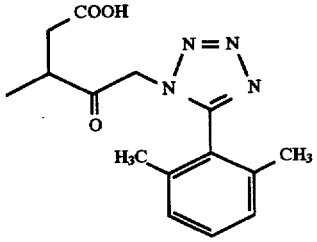 | 7 | 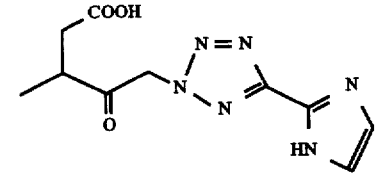 |
| 3 | 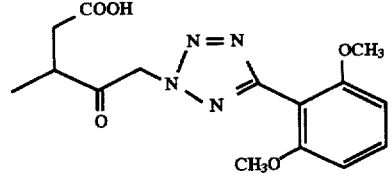 | 8 | 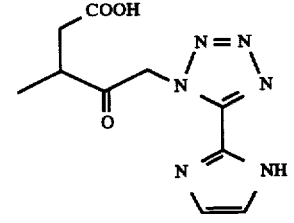 |
| 4 | 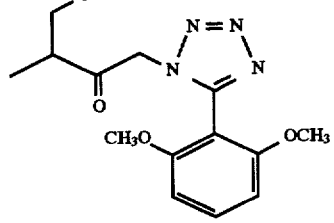 | 9 | 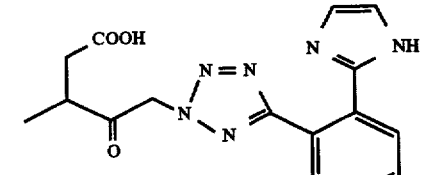 |
| 5 | 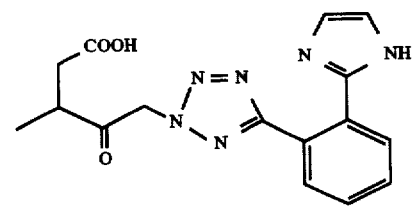 | 10 | 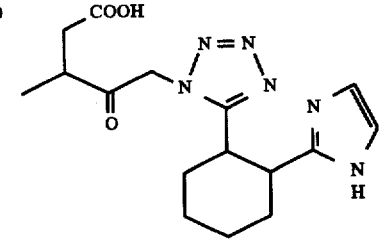 |

TABLE 9

[Structure I(9): Benzamide-substituted azepanone with N-Y amide sidechain]

| No. | Y | No. | Y |
|-----|---|-----|---|
| 1 | 3-methyl-4-oxo-5-[2-(2,6-dimethylphenyl)-2H-tetrazol-2-yl]pentanoic acid moiety | 6 | 3-methyl-4-oxo-5-[5-(2,6-dimethylphenyl)-1H-tetrazol-1-yl]pentanoic acid moiety |
| 2 | 3-methyl-4-oxo-5-[2-(2,6-dimethoxyphenyl)-2H-tetrazol-2-yl]pentanoic acid moiety | 7 | 3-methyl-4-oxo-5-[5-(2,6-dimethoxyphenyl)-1H-tetrazol-1-yl]pentanoic acid moiety |
| 3 | 3-methyl-4-oxo-5-[2-(2-(1H-imidazol-2-yl)phenyl)-2H-tetrazol-2-yl]pentanoic acid moiety | 8 | 3-methyl-4-oxo-5-[5-(2-(1H-imidazol-2-yl)phenyl)-1H-tetrazol-1-yl]pentanoic acid moiety |
| 4 | 3-methyl-4-oxo-5-[2-(1H-imidazol-2-yl)-2H-tetrazol-2-yl]pentanoic acid moiety | 9 | 3-methyl-4-oxo-5-[5-(1H-imidazol-2-yl)-1H-tetrazol-1-yl]pentanoic acid moiety |
| 5 | 3-methyl-4-oxo-5-[2-(2-(1H-imidazol-2-yl)phenyl)-2H-tetrazol-2-yl]pentanoic acid moiety | 10 | 3-methyl-4-oxo-5-[5-(2-(1H-imidazol-2-yl)cyclohexyl)-1H-tetrazol-1-yl]pentanoic acid moiety |

TABLE 10
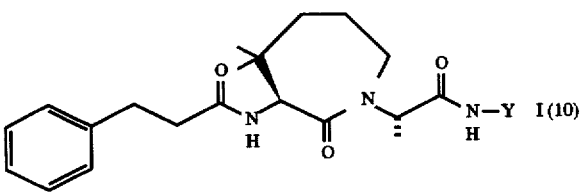
| No. | Y | No. | Y |
|---|---|---|---|
| 1 | 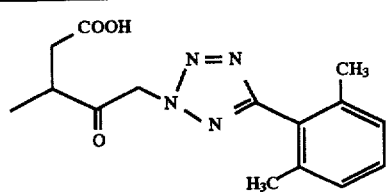 | 6 | 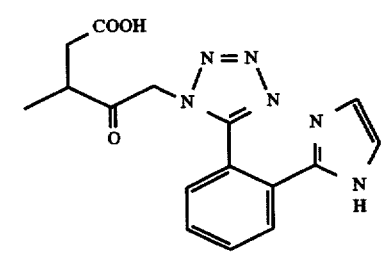 |
| 2 | 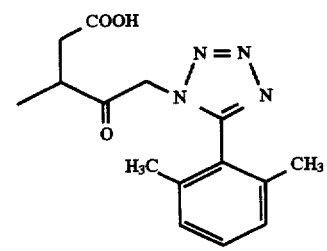 | 7 | 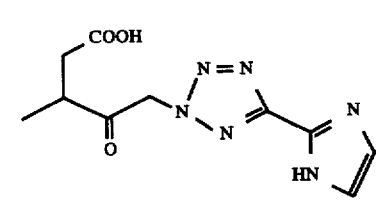 |
| 3 | 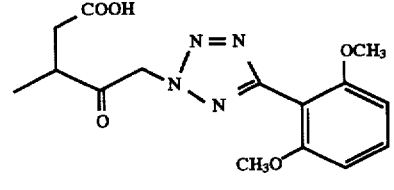 | 8 | 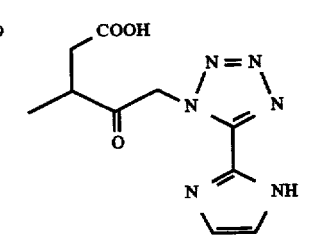 |
| 4 | 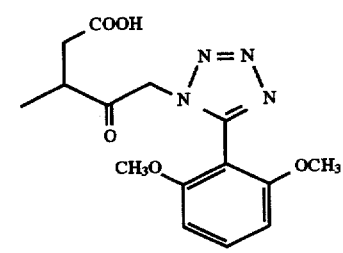 | 9 | 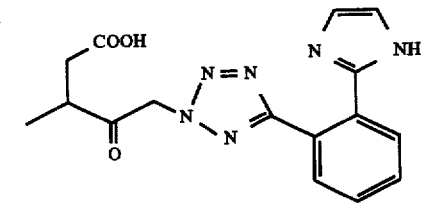 |
| 5 | 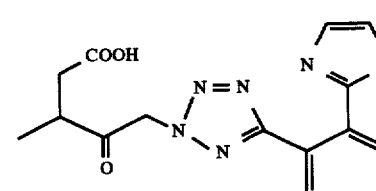 | 10 | 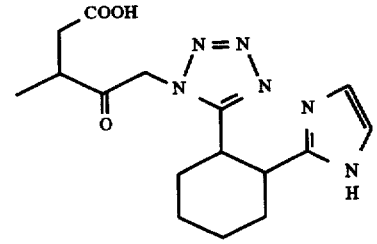 |

TABLE 11

TABLE 12

TABLE 13
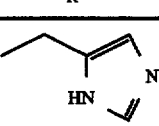
I(13)
| No. | R⁴ | R⁹ | R¹⁰ |
|---|---|---|---|
| 1 | i-Pr | H | (4-ethyl-imidazole) |
| 2 | i-Pr | H | —CH₂—OH |
| 3 | i-Pr | H | (benzyl) |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | (4-hydroxybenzyl-ethyl) | H | Me |
| 10 | (4-ethyl-imidazole) | H | Me |
| 11 | (butyl-guanidine) | H | Me |
| 12 | (butyl-SMe) | H | Me |
TABLE 14
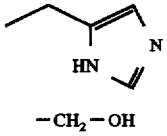
I(14)
| No. | R⁴ | R⁹ | R¹⁰ |
|---|---|---|---|
| 1 | i-Pr | H | (4-ethyl-imidazole) |
| 2 | i-Pr | H | —CH₂—OH |

TABLE 14-continued

I(14) [structure: phenyl-CH2CH2-C(=O)-NH-CHR4-C(=O)-NR9-CHR10-C(=O)-NH-CH(CH2COOH)-C(=O)-CH2-tetrazole-(2,6-dichlorophenyl)]

| No. | R⁴ | R⁹ | R¹⁰ |
|---|---|---|---|
| 3 | i-Pr | H | CH2CH2-phenyl |
| 4 | i-Pr | Me | Me |
| 5 | i-Pr | —(CH2)3— | |
| 6 | i-Pr | —CH2CH=CHCH2— | |
| 7 | Me | H | Me |
| 8 | i-Bu | H | Me |
| 9 | CH2CH2-(4-hydroxyphenyl) | H | Me |
| 10 | CH2-(imidazolyl) | H | Me |
| 11 | (CH2)3-NH-C(=NH)-NH2 | H | Me |
| 12 | (CH2)2-S-CH3 | H | Me |

TABLE 15

I(15) [structure: benzyl-O-C(=O)-NH-CHR4-C(=O)-NR9-CHR10-C(=O)-NH-CH(CH2COOH)-C(=O)-CH2-tetrazole-(2,6-dichlorophenyl)]

| No. | R⁴ | R⁹ | R¹⁰ |
|---|---|---|---|
| 1 | i-Pr | H | CH2-(imidazolyl) |
| 2 | i-Pr | H | —CH2—OH |
| 3 | i-Pr | H | CH2CH2-phenyl |
| 4 | i-Pr | Me | Me |
| 5 | i-Pr | —(CH2)3— | |
| 6 | i-Pr | —CH2CH=CHCH2— | |
| 7 | Me | H | Me |

TABLE 15-continued
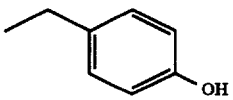
I(15)
| No. | R⁴ | R⁹ | R¹⁰ |
|---|---|---|---|
| 8 | i-Bu | H | Me |
| 9 | 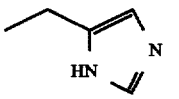 | H | Me |
| 10 | 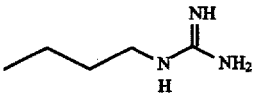 | H | Me |
| 11 | 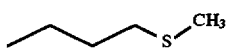 | H | Me |
| 12 | 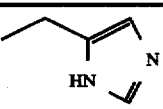 | H | Me |
TABLE 16
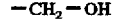
I(16)
| No. | R⁴ | R⁹ | R¹⁰ |
|---|---|---|---|
| 1 | i-Pr | H | 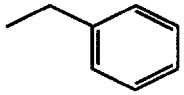 |
| 2 | i-Pr | H | —CH₂—OH |
| 3 | i-Pr | H |  |
| 4 | i-Pr | Me | Me |
| 5 | i-Pr | | —(CH₂)₃— |
| 6 | i-Pr | | —CH₂CH=CHCH₂— |
| 7 | Me | H | Me |
| 8 | i-Bu | H | Me |
| 9 |  | H | Me |

TABLE 16-continued

I(16): [Structure: benzyloxycarbonyl-NH-CH(R⁴)-C(O)-N(R⁹)-CH(R¹⁰)-C(O)-NH-CH(CH₂COOH)-C(O)-CH₂-tetrazole-(2,6-dichlorophenyl)]

| No. | R⁴ | R⁹ | R¹⁰ |
|---|---|---|---|
| 10 | 4-ethyl-imidazole (HN-CH=N-C(Et)=) | H | Me |
| 11 | -(CH₂)₃-NH-C(=NH)-NH₂ | H | Me |
| 12 | -(CH₂)₃-S-CH₃ | H | Me |

TABLE 17

I(17): [Structure: benzoyl-NH-CH(R⁴)-C(O)-N(R⁹)-CH(R¹⁰)-C(O)-NH-CH(CH₂COOH)-C(O)-CH₂-tetrazole-(2,6-dichlorophenyl)]

| No. | R⁴ | R⁹ | R¹⁰ |
|---|---|---|---|
| 1 | i-Pr | H | 4-ethyl-imidazole |
| 2 | i-Pr | H | —CH₂—OH |
| 3 | i-Pr | H | —CH₂—C₆H₅ |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | 4-hydroxybenzyl | H | Me |
| 10 | 4-ethyl-imidazole | H | Me |
| 11 | -(CH₂)₃-NH-C(=NH)-NH₂ | H | Me |

TABLE 17-continued

I(17)

[Structure: benzoyl-NH-CH(R⁴)-C(O)-N(R⁹)-CH(R¹⁰)-C(O)-NH-CH(CH₂COOH)-C(O)-CH₂-tetrazole-(2,6-dichlorophenyl)]

| No. | R⁴ | R⁹ | R¹⁰ |
|---|---|---|---|
| 12 | CH₃CH₂CH₂CH₂-S-CH₃ | H | Me |

TABLE 18

I(18)

[Structure: benzoyl-NH-CH(R⁴)-C(O)-N(R⁹)-CH(R¹⁰)-C(O)-NH-CH(CH₂COOH)-C(O)-CH₂-tetrazole-(2,6-dichlorophenyl)]

| No. | R⁴ | R⁹ | R¹⁰ |
|---|---|---|---|
| 1 | i-Pr | H | CH₂CH(imidazole) |
| 2 | i-Pr | H | —CH₂—OH |
| 3 | i-Pr | H | CH₂-phenyl |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | CH₂-(4-hydroxyphenyl) | H | Me |
| 10 | CH₂CH(imidazole) | H | Me |
| 11 | CH₃CH₂CH₂CH₂-NH-C(=NH)NH₂ | H | Me |
| 12 | CH₃CH₂CH₂CH₂-S-CH₃ | H | Me |

TABLE 19
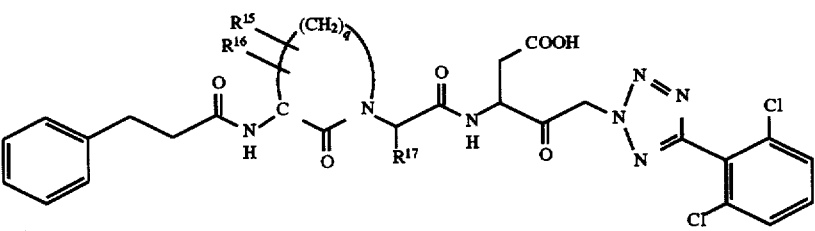

TABLE 20
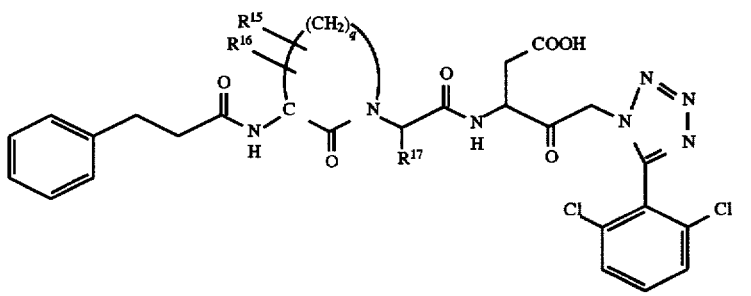
| No. | | $R^{17}$ | No. | | $R^{17}$ |
|---|---|---|---|---|---|
| 1 | 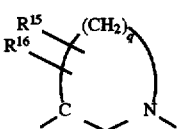 | Me | 7 | 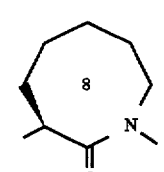 | Me |
| 2 | 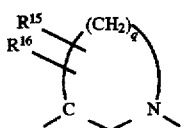 | Me | 8 | 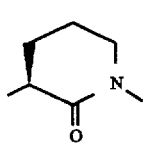 | Me |
| 3 | 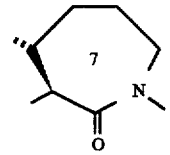 | Me | 9 | 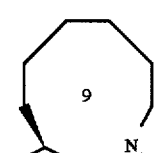 | Me |
| 4 | 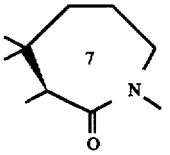 | Me | 10 | 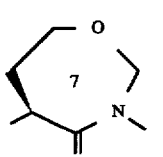 | Me |
| 5 | 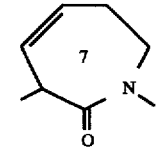 | Me | 11 | 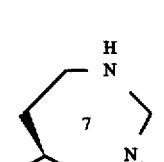 | Me |

TABLE 20-continued

I (20)

TABLE 21

I (21)

TABLE 21-continued

I(21)

| No. | [structure] | R¹⁷ | No. | [structure] | R¹⁷ |
|---|---|---|---|---|---|
| 3 | 8-membered ring | Me | 9 | 6-membered ring | Me |
| 4 | 9-membered ring | Me | 10 | 7-membered ring with O | Me |
| 5 | 7-membered ring with NH | Me | 11 | 7-membered ring with S | Me |
| 6 | 7-membered ring with S | Me | 12 | 7-membered ring with S | Me |

TABLE 22
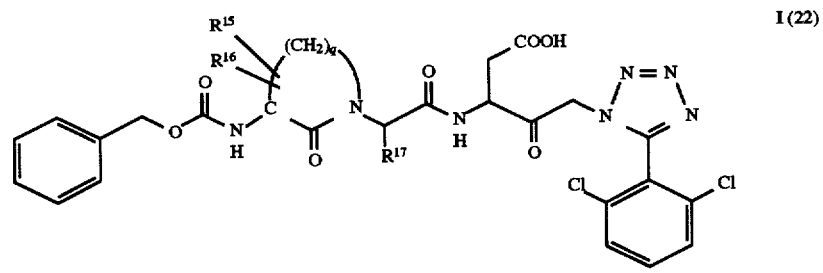
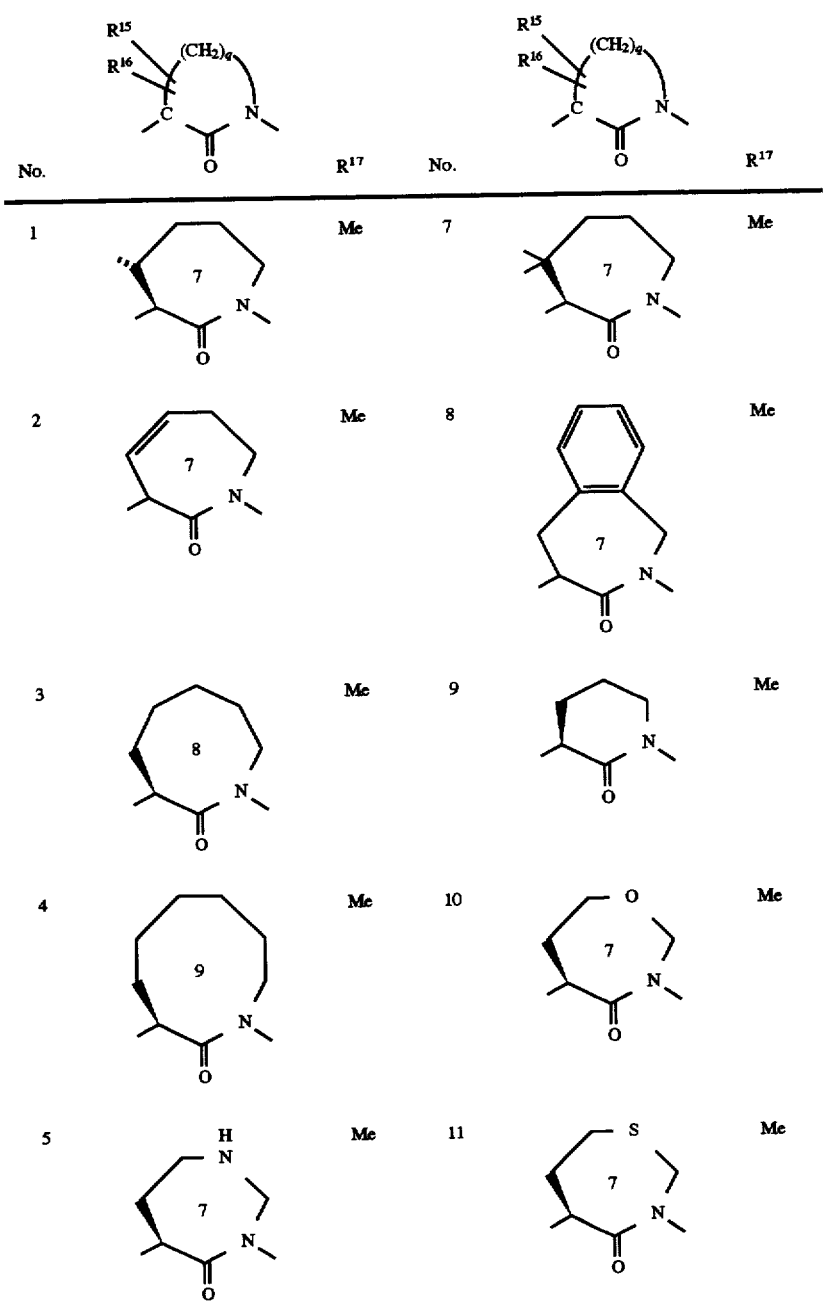

TABLE 22-continued
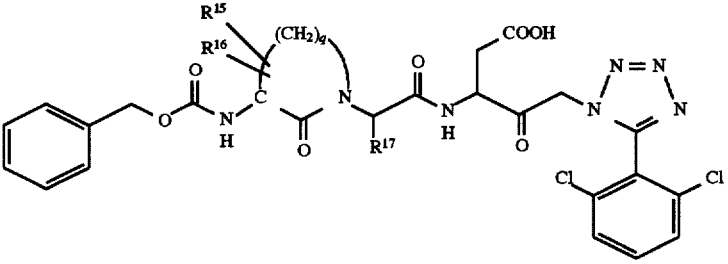

TABLE 23-continued

| No. | (ring structure) | R¹⁷ | No. | (ring structure) | R¹⁷ |
|---|---|---|---|---|---|
| 3 | 8-membered lactam ring | Me | 9 | 6-membered lactam ring | Me |
| 4 | 9-membered lactam ring | Me | 10 | 7-membered morpholinone (O) ring | Me |
| 5 | 7-membered ring with NH | Me | 11 | 7-membered ring with S | Me |
| 6 | 7-membered ring with S | Me | 12 | 7-membered ring with S (gem-dimethyl) | Me |

TABLE 24
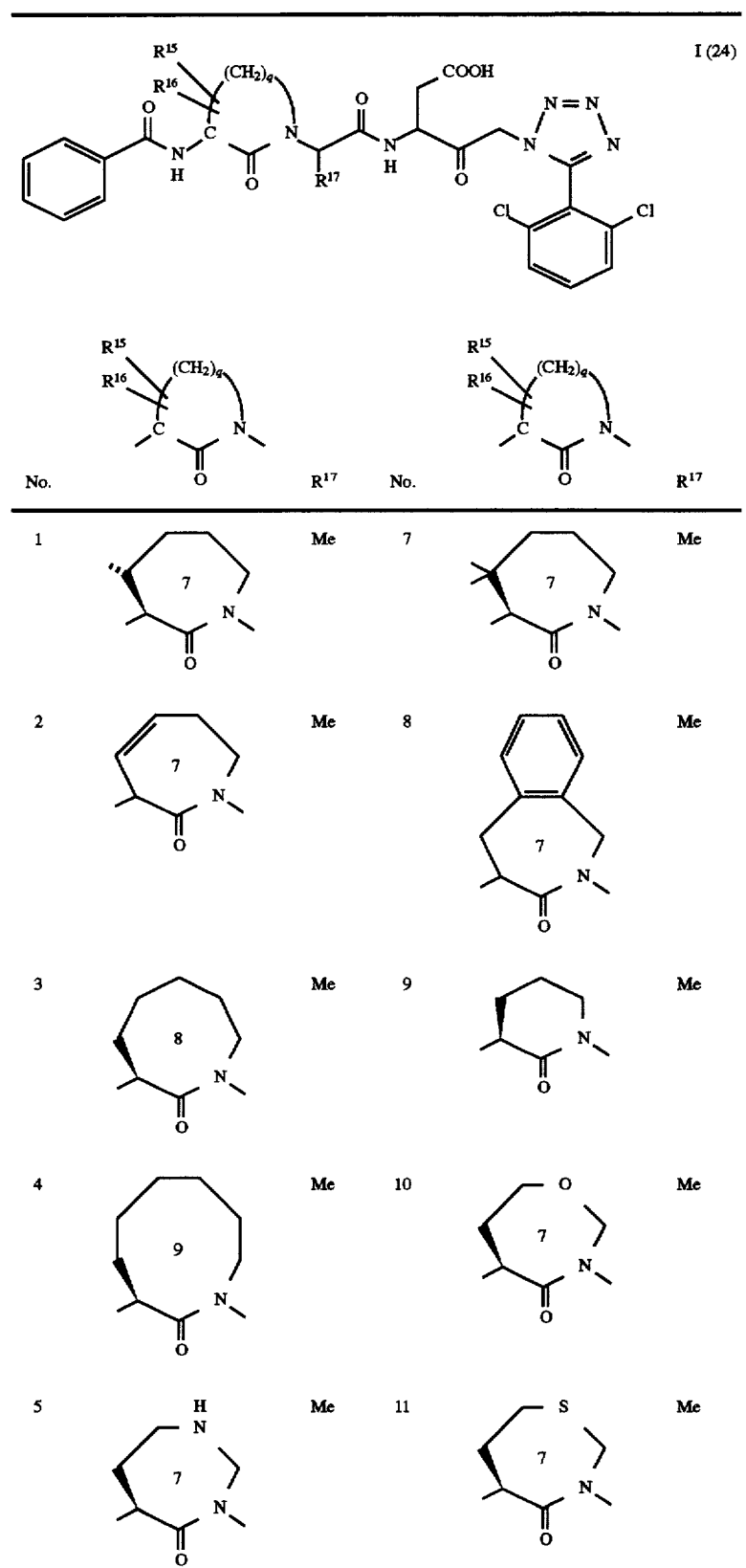

TABLE 24-continued

I(24)

| No. | (R15,R16,(CH2)q,C,N ring structure) | R17 | No. | (R15,R16,(CH2)q,C,N ring structure) | R17 |
|---|---|---|---|---|---|
| 6 | S-containing ring (7) | Me | 12 | S-containing ring (7) | Me |

TABLE 25

I(25)

| No. | R¹ | No. | R¹ |
|---|---|---|---|
| 1 | Me | 10 | 3-HO-phenyl |
| 2 | 2-biphenyl | 11 | 2-(1H-tetrazol-5-yl)phenyl |
| 3 | 3-(CH₃OOC)-phenyl | 12 | 3-(HOOC)-phenyl |
| 4 | 2-Cl-phenyl | 13 | 2-(OCH₃)-phenyl |

TABLE 25-continued
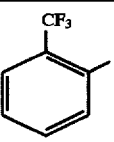 I (25)
| No. | R¹ | No. | R¹ |
|---|---|---|---|
| 5 | 2-(trifluoromethyl)phenyl | 14 | cyclohexyl |
| 6 | 2-naphthyl | 15 | 3-quinolinyl |
| 7 | 1,2,3,4-tetrahydroquinolin-3-yl | 16 | 2-pyridyl |
| 8 | 2-thienyl | 17 | 2-furyl |
| 9 | imidazolyl | 18 | tert-butoxy |
TABLE 26
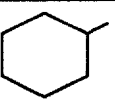 I (26)
TABLE 26-continued
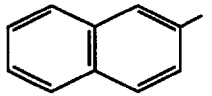 I (26)
| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |

TABLE 26-continued
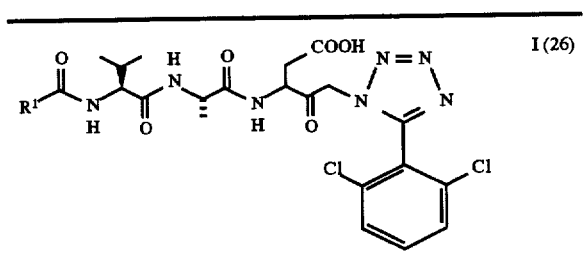
I (26)
| No. | R¹ | No. | R¹ | No. | R¹ | No. | R¹ |
|---|---|---|---|---|---|---|---|
| 5 | 2-CF₃-phenyl | 14 | cyclohexyl | 8 | 2-thienyl | 17 | 2-furyl |
| 6 | 2-naphthyl | 15 | 3-quinolinyl | 9 | imidazolyl | 18 | tert-butoxymethyl |
| 7 | 1,2,3,4-tetrahydroquinolin-3-yl | 16 | 2-pyridyl | | | | |
TABLE 27
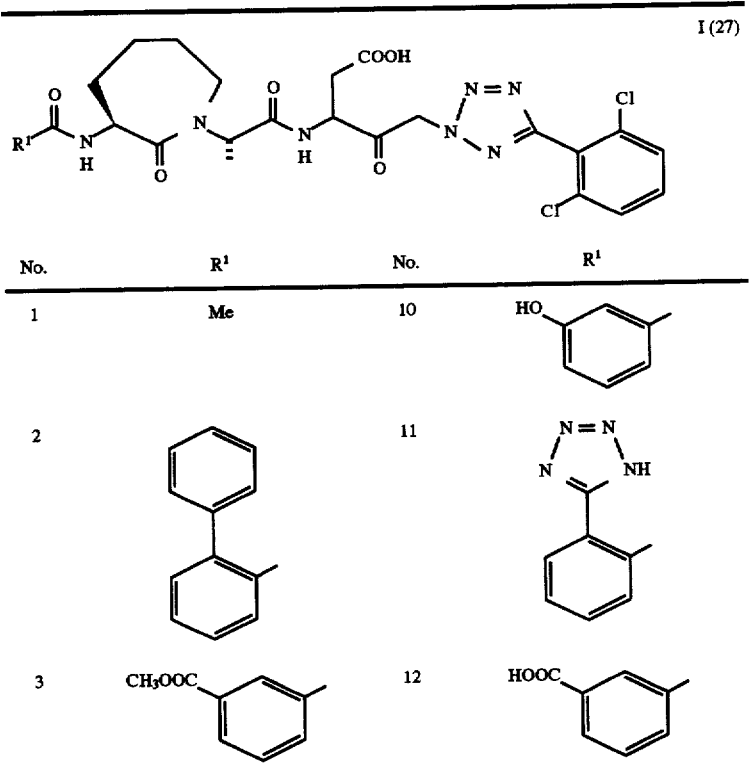
I (27)
| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-carboxyphenyl |

TABLE 27-continued

I(27)

| No. | R¹ | No. | R¹ |
|---|---|---|---|
| 4 | 2-Cl-phenyl | 13 | 2-OCH₃-phenyl |
| 5 | 2-CF₃-phenyl | 14 | cyclohexyl |
| 6 | 2-naphthyl | 15 | 3-quinolinyl |
| 7 | 1,2,3,4-tetrahydroquinolin-3-yl | 16 | 2-pyridyl |
| 8 | 2-thienyl | 17 | 2-furyl |
| 9 | imidazol-4-yl | 18 | tert-butoxy |

TABLE 28

I(28)

| No. | R¹ | No. | R¹ |
|---|---|---|---|
| 1 | Me | 10 | 3-HO-phenyl |

TABLE 28-continued
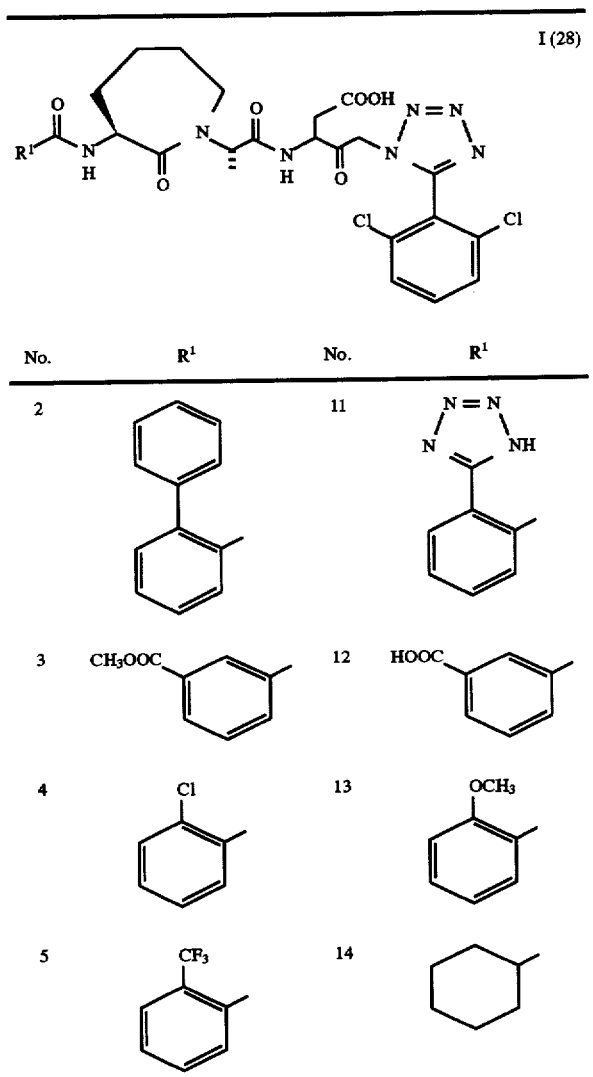
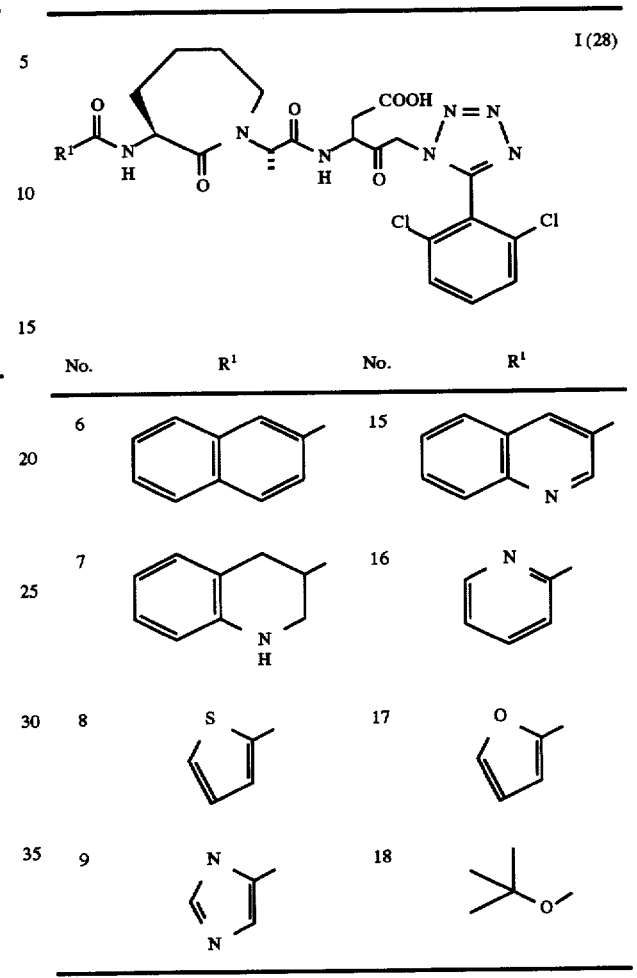
TABLE 29
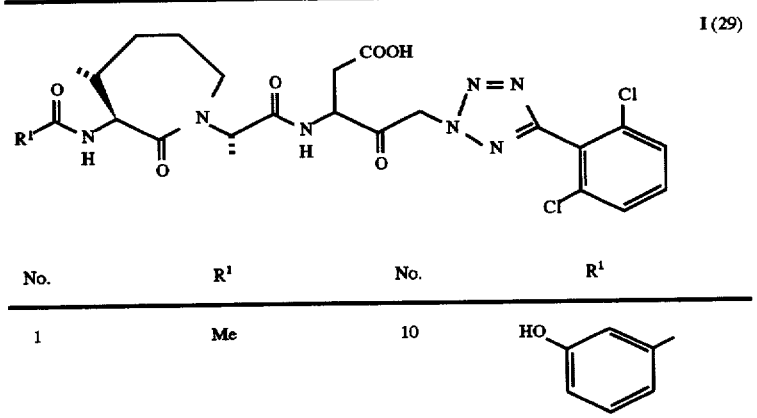

TABLE 29-continued
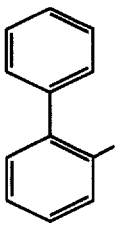
I (29)
| No. | R¹ | No. | R¹ |
|---|---|---|---|
| 2 | 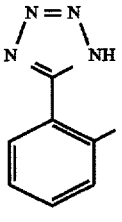 | 11 | 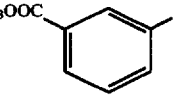 |
| 3 | 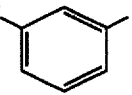 | 12 | 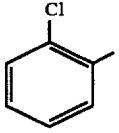 |
| 4 | 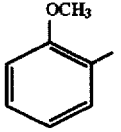 | 13 | 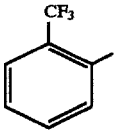 |
| 5 | 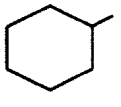 | 14 | 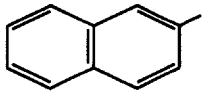 |
| 6 | 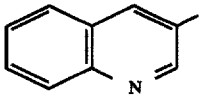 | 15 | 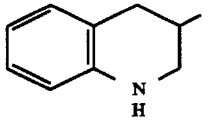 |
| 7 | 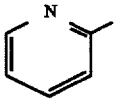 | 16 |  |
| 8 |  | 17 |  |
| 9 | 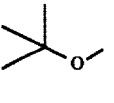 | 18 | |

TABLE 30
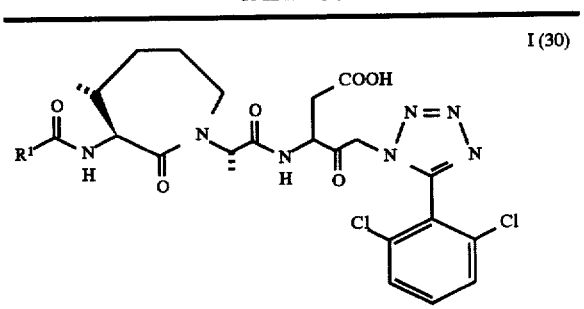
I (30)
| No. | R¹ | No. | R¹ |
|---|---|---|---|
| 1 | Me | 10 | HO-C₆H₄- (m-hydroxyphenyl) |
| 2 | biphenyl (2-phenylphenyl) | 11 | 2-(1H-tetrazol-5-yl)phenyl |
| 3 | m-CH₃OOC-C₆H₄- | 12 | m-HOOC-C₆H₄- |
| 4 | o-Cl-C₆H₄- | 13 | o-CH₃O-C₆H₄- |
TABLE 30-continued
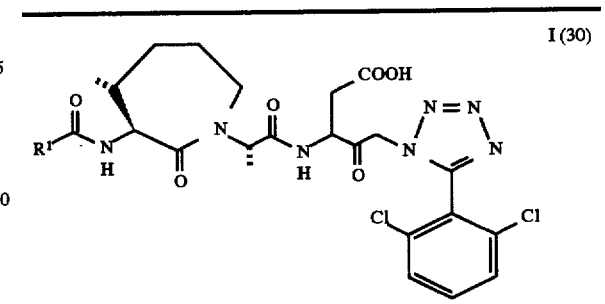
I (30)
| No. | R¹ | No. | R¹ |
|---|---|---|---|
| 5 | o-CF₃-C₆H₄- | 14 | cyclohexyl |
| 6 | 2-naphthyl | 15 | quinolin-3-yl |
| 7 | 1,2,3,4-tetrahydroquinolin-3-yl | 16 | pyridin-2-yl |
| 8 | thien-2-yl | 17 | furan-2-yl |
| 9 | imidazol-4-yl | 18 | t-BuO-CH₂- |
TABLE 31
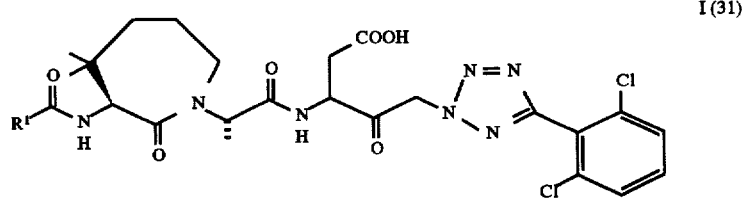
I (31)
| No. | R¹ | No. | R¹ |
|---|---|---|---|
| 1 | Me | 10 | m-HO-C₆H₄- |

TABLE 31-continued

I(31)

[Structure: R¹-C(=O)-NH-[azepanone with gem-dimethyl]-N-CH(CH₃)-C(=O)-NH-CH(CH₂COOH)-C(=O)-CH₂-N(tetrazole)-N=N, tetrazole-C connected to 2,6-dichlorophenyl]

| No. | R¹ | No. | R¹ |
|---|---|---|---|
| 2 | 2-biphenyl | 11 | 2-(1H-tetrazol-5-yl)phenyl |
| 3 | 3-(methoxycarbonyl)phenyl (CH₃OOC-) | 12 | 3-carboxyphenyl (HOOC-) |
| 4 | 2-chlorophenyl (Cl) | 13 | 2-methoxyphenyl (OCH₃) |
| 5 | 2-(trifluoromethyl)phenyl (CF₃) | 14 | cyclohexyl |
| 6 | 2-naphthyl | 15 | quinolin-3-yl |
| 7 | 1,2,3,4-tetrahydroquinolin-3-yl (NH) | 16 | pyridin-2-yl |
| 8 | 2-thienyl (S) | 17 | 2-furyl (O) |
| 9 | pyrimidin-5-yl (N,N) | 18 | tert-butoxy (t-Bu-O-) |

TABLE 32
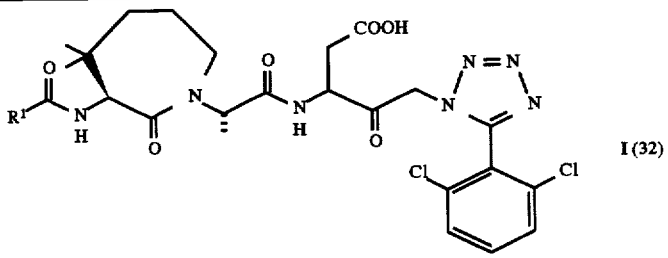
I (32)
| No. | R¹ | No. | R¹ |
|---|---|---|---|
| 1 | Me | 10 | 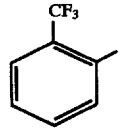 |
| 2 | 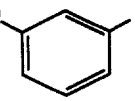 | 11 | 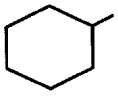 |
| 3 | 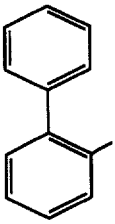 | 12 | 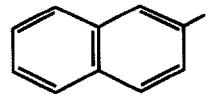 |
| 4 | 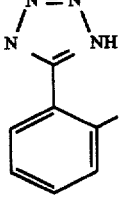 | 13 | 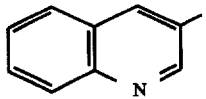 |
| 5 | 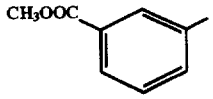 | 14 | 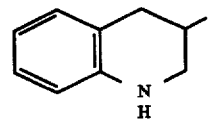 |
| 6 | 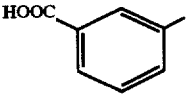 | 15 | 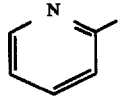 |
| 7 | 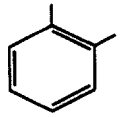 | 16 | 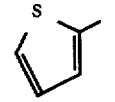 |
| 8 | 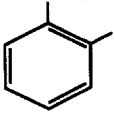 | 17 | 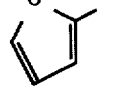 |
| 9 | 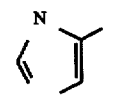 | 18 | 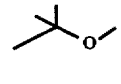 |

TABLE 33
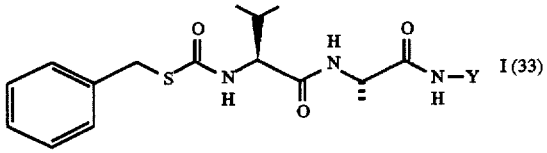 I(33)
| No. | Y | No. | Y |
|---|---|---|---|
| 1 | 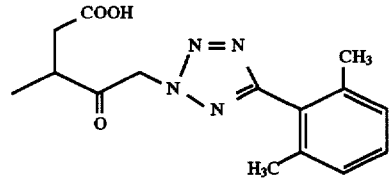 | 6 | 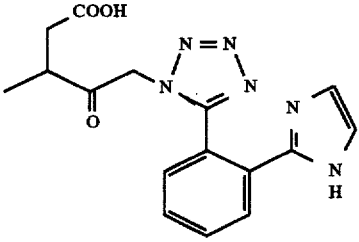 |
| 2 | 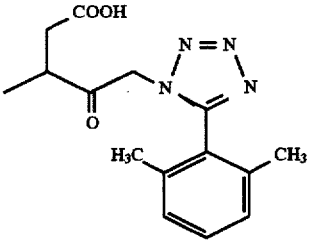 | 7 | 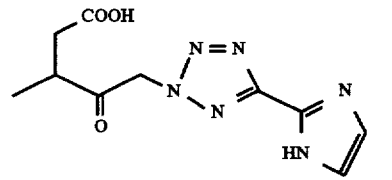 |
| 3 | 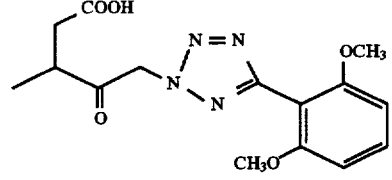 | 8 | 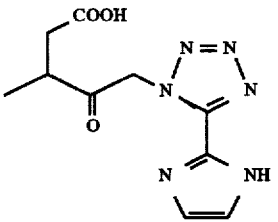 |
| 4 | 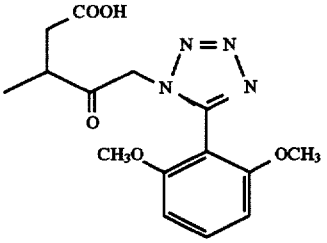 | 9 | 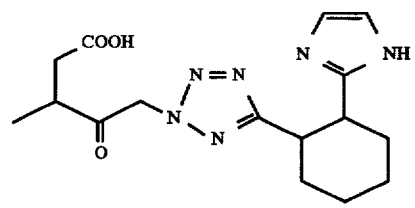 |
| 5 | 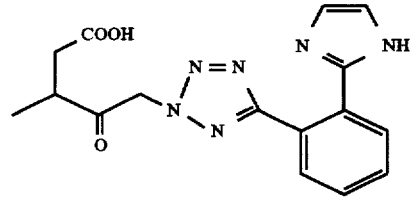 | 10 | 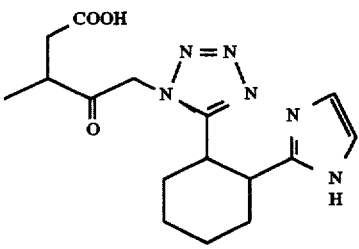 |

TABLE 34

TABLE 35

[Structure I(35): benzyl-S-C(=O)-NH-[azepanone]-N-CH(CH3)-C(=O)-NH-Y]

| No. | Y | No. | Y |
|---|---|---|---|
| 1 | 3-methyl-4-oxo-5-[2-(2,6-dimethylphenyl)tetrazol-2-yl]pentanoic acid moiety | 6 | 3-methyl-4-oxo-5-[5-(2,6-dimethylphenyl)tetrazol-1-yl]pentanoic acid moiety |
| 2 | 3-methyl-4-oxo-5-[2-(2,6-dimethoxyphenyl)tetrazol-2-yl]pentanoic acid moiety | 7 | 3-methyl-4-oxo-5-[5-(2,6-dimethoxyphenyl)tetrazol-1-yl]pentanoic acid moiety |
| 3 | 3-methyl-4-oxo-5-[2-(2-(imidazol-2-yl)phenyl)tetrazol-2-yl]pentanoic acid moiety | 8 | 3-methyl-4-oxo-5-[5-(2-(imidazol-2-yl)phenyl)tetrazol-1-yl]pentanoic acid moiety |
| 4 | 3-methyl-4-oxo-5-[5-(imidazol-2-yl)tetrazol-2-yl]pentanoic acid moiety | 9 | 3-methyl-4-oxo-5-[5-(imidazol-2-yl)tetrazol-1-yl]pentanoic acid moiety |
| 5 | 3-methyl-4-oxo-5-[2-(2-(imidazol-2-yl)cyclohexyl)tetrazol-2-yl]pentanoic acid moiety | 10 | 3-methyl-4-oxo-5-[5-(2-(imidazol-2-yl)cyclohexyl)tetrazol-1-yl]pentanoic acid moiety |

TABLE 36

I(36)

| No. | Y | No. | Y |
|-----|---|-----|---|
| 1 | tetrazole-CH2-C(O)-CH(CH3)-CH2-COOH with 2,6-dimethylphenyl on tetrazole (2N) | 6 | tetrazole-CH2-C(O)-CH(CH3)-CH2-COOH with 2,6-dimethylphenyl on tetrazole (1N) |
| 2 | as above with 2,6-dimethoxyphenyl (2N-tetrazole) | 7 | as above with 2,6-dimethoxyphenyl (1N-tetrazole) |
| 3 | as above with 2-(imidazol-2-yl)phenyl (2N-tetrazole) | 8 | as above with 2-(imidazol-2-yl)phenyl (1N-tetrazole) |
| 4 | as above with imidazol-2-yl (2N-tetrazole) | 9 | as above with imidazol-2-yl (1N-tetrazole) |
| 5 | as above with 2-(imidazol-2-yl)cyclohexyl (2N-tetrazole) | 10 | as above with 2-(imidazol-2-yl)cyclohexyl (1N-tetrazole) |

TABLE 37
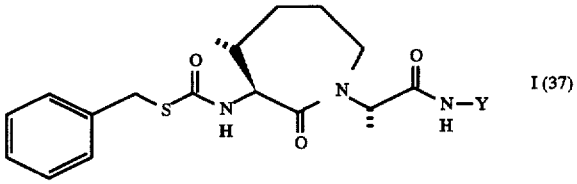
I(37)
| No. | Y | No. | Y |
|---|---|---|---|
| 1 | 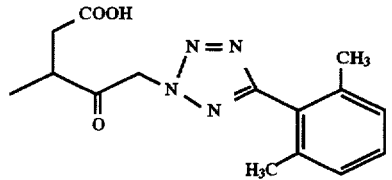 | 6 | 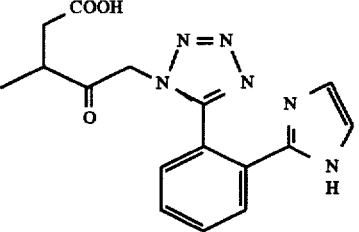 |
| 2 | 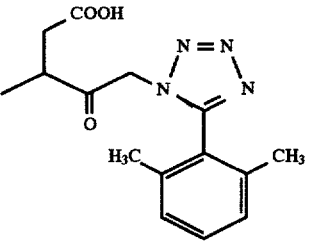 | 7 | 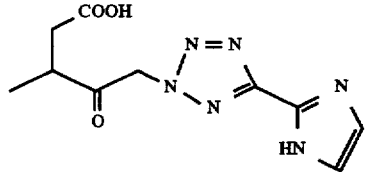 |
| 3 | 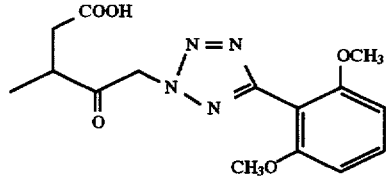 | 8 | 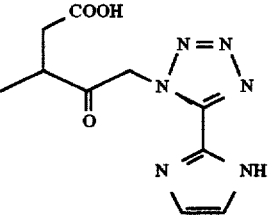 |
| 4 | 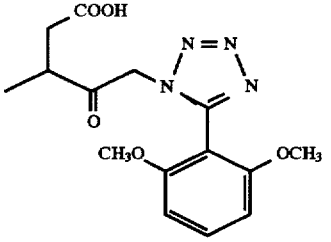 | 9 | 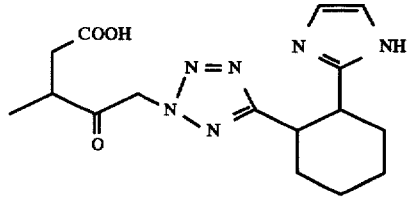 |
| 5 | 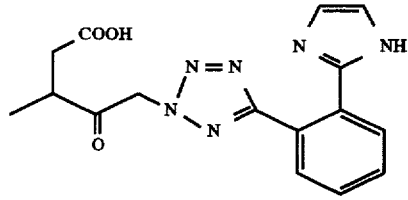 | 10 | 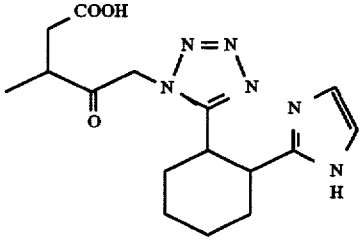 |

TABLE 38
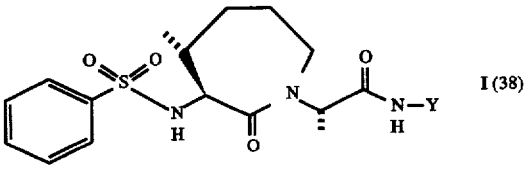
| No. | Y | No. | Y |
|---|---|---|---|
| 1 | 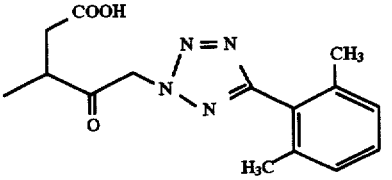 | 6 | 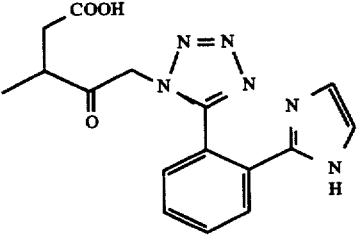 |
| 2 | 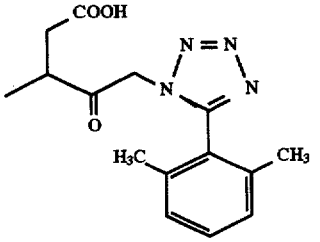 | 7 | 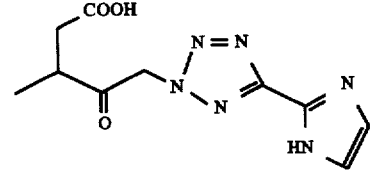 |
| 3 | 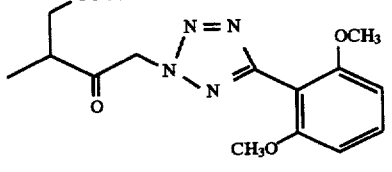 | 8 | 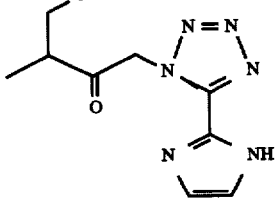 |
| 4 | 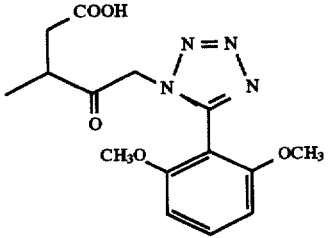 | 9 | 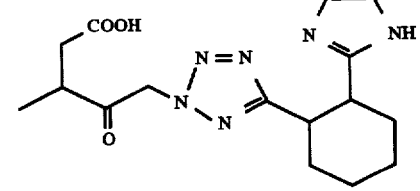 |
| 5 | 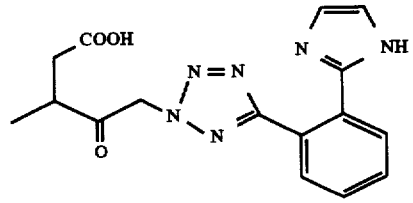 | 10 | 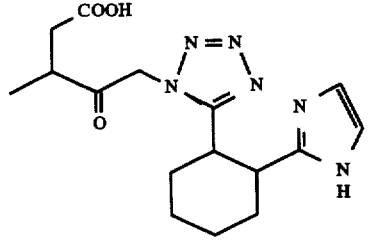 |

TABLE 39

TABLE 40
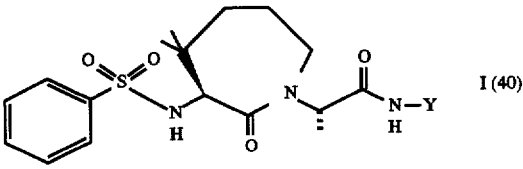
I (40)
| No. | Y | No. | Y |
|---|---|---|---|
| 1 | 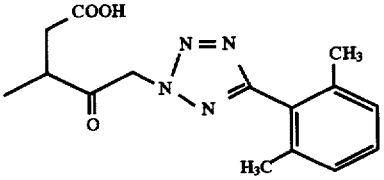 | 6 | 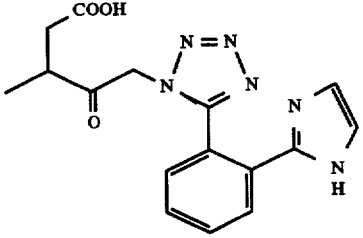 |
| 2 | 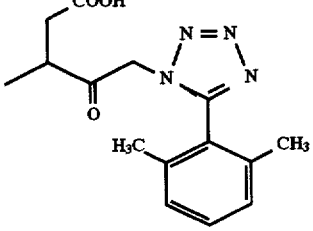 | 7 | 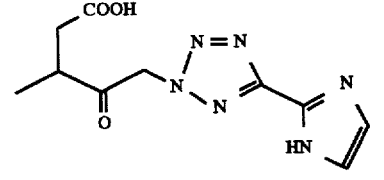 |
| 3 | 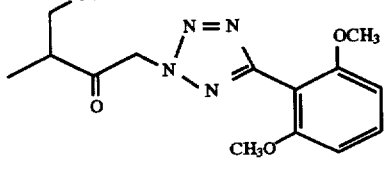 | 8 | 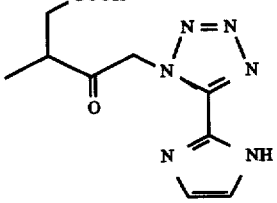 |
| 4 | 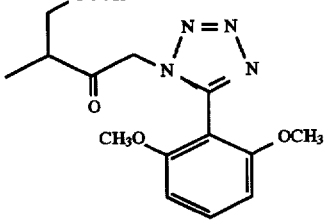 | 9 | 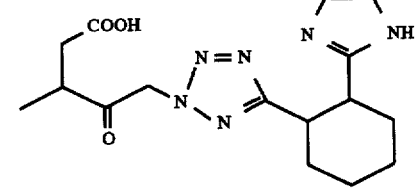 |
| 5 | 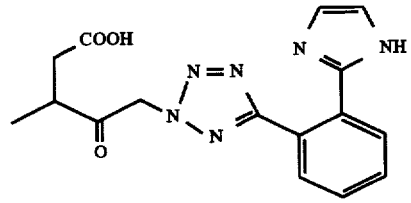 | 10 | 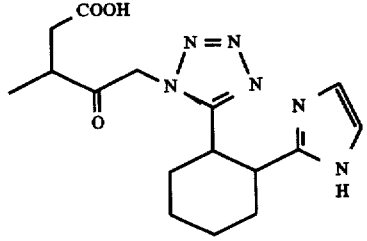 |

TABLE 41
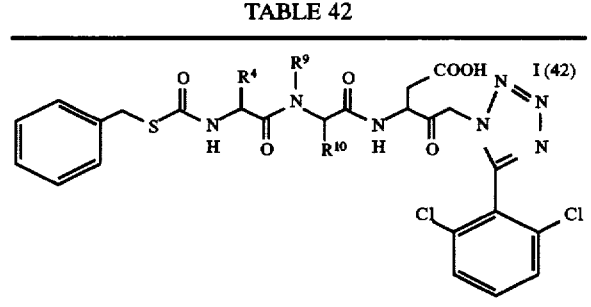
I(41)
| No. | R⁴ | R⁹ | R¹⁰ |
|---|---|---|---|
| 1 | i-Pr | H | (ethyl-imidazole group) |
| 2 | i-Pr | H | —CH₂—OH |
| 3 | i-Pr | H | (benzyl group) |
| 4 | i-Pr | Me | Me |
| 5 | i-Pr | —(CH₂)₃— | |
| 6 | i-Pr | —CH₂CH=CHCH₂— | |
| 7 | Me | H | Me |
| 8 | i-Bu | H | Me |
| 9 | (4-hydroxybenzyl group) | H | Me |
| 10 | (ethyl-imidazole group) | H | Me |
| 11 | (butyl guanidine group) | H | Me |
| 12 | (butyl-S-CH₃ group) | H | Me |
TABLE 42
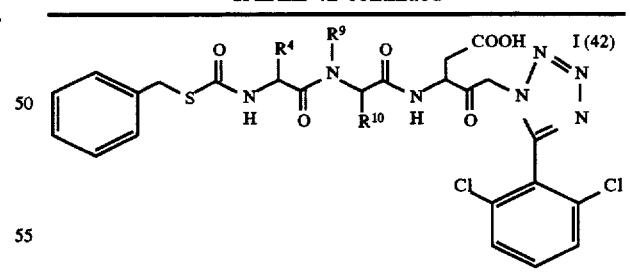
I(42)
| No. | R⁴ | R⁹ | R¹⁰ |
|---|---|---|---|
| 1 | i-Pr | H | (ethyl-imidazole group) |
| 2 | i-Pr | H | —CH₂—OH |
| 3 | i-Pr | H | (benzyl group) |
| 4 | i-Pr | Me | Me |
| 5 | i-Pr | —(CH₂)₃— | |
| 6 | i-Pr | —CH₂CH=CHCH₂— | |
| 7 | Me | H | Me |

TABLE 42-continued

Structure I(42): benzyl-S-C(=O)-NH-CHR⁴-C(=O)-N(R⁹)-CHR¹⁰-C(=O)-NH-CH(COOH)-CH₂-C(=O)-N(tetrazole with 2,6-dichlorophenyl)

| No. | R⁴ | R⁹ | R¹⁰ |
|---|---|---|---|
| 8 | i-Bu | H | Me |
| 9 | -CH₂-C₆H₄-OH (4-hydroxybenzyl) | H | Me |
| 10 | -CH₂-(imidazol-4-yl) | H | Me |
| 11 | -(CH₂)₃-NH-C(=NH)-NH₂ | H | Me |
| 12 | -(CH₂)₂-S-CH₃ | H | Me |

TABLE 43

Structure I(43): PhSO₂-NH-CHR⁴-C(=O)-N(R⁹)-CHR¹⁰-C(=O)-NH-CH(COOH)-CH₂-C(=O)-N(tetrazole with 2,6-dichlorophenyl)

| No. | R⁴ | R⁹ | R¹⁰ |
|---|---|---|---|
| 1 | i-Pr | H | -CH₂-(imidazol-4-yl) |
| 2 | i-Pr | H | -CH₂-OH |
| 3 | i-Pr | H | -CH₂-C₆H₅ |
| 4 | i-Pr | Me | Me |
| 5 | i-Pr | -(CH₂)₃- | |
| 6 | i-Pr | -CH₂CH=CHCH₂- | |
| 7 | Me | H | Me |
| 8 | i-Bu | H | Me |
| 9 | -CH₂-C₆H₄-OH (4-hydroxybenzyl) | H | Me |

TABLE 43-continued

| No. | R⁴ | R⁹ | R¹⁰ |
|---|---|---|---|
| 10 | -CH₂-(imidazol-4-yl) | H | Me |
| 11 | -(CH₂)₃-NH-C(=NH)-NH₂ | H | Me |
| 12 | -(CH₂)₂-S-CH₃ | H | Me |

TABLE 44

Structure I(44): PhSO₂-NH-CHR⁴-C(=O)-N(R⁹)-CHR¹⁰-C(=O)-NH-CH(COOH)-CH₂-C(=O)-N(tetrazole with 2,6-dichlorophenyl)

| No. | R⁴ | R⁹ | R¹⁰ |
|---|---|---|---|
| 1 | i-Pr | H | -CH₂-(imidazol-4-yl) |
| 2 | i-Pr | H | -CH₂-OH |
| 3 | i-Pr | H | -CH₂-C₆H₅ |
| 4 | i-Pr | Me | Me |
| 5 | i-Pr | -(CH₂)₃- | |
| 6 | i-Pr | -CH₂CH=CHCH₂- | |
| 7 | Me | H | Me |
| 8 | i-Bu | H | Me |
| 9 | -CH₂-C₆H₄-OH (4-hydroxybenzyl) | H | Me |
| 10 | -CH₂-(imidazol-4-yl) | H | Me |
| 11 | -(CH₂)₃-NH-C(=NH)-NH₂ | H | Me |

TABLE 44-continued
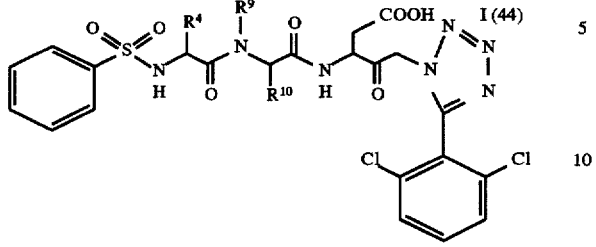
| No. | R⁴ | R⁹ | R¹⁰ |
|---|---|---|---|
| 12 | 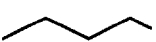 | H | Me |
TABLE 45
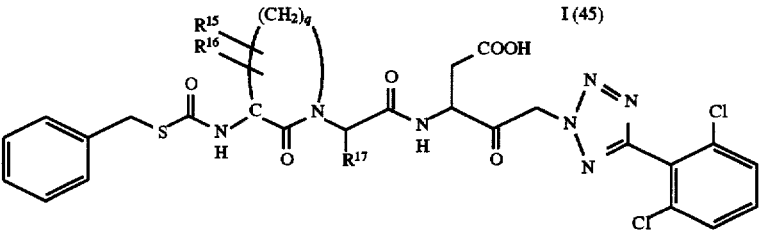
| No. | 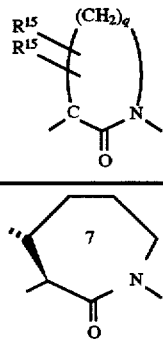 | R¹⁷ |
|---|---|---|
| 1 | 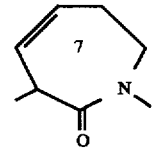 7 | Me |
| 2 | 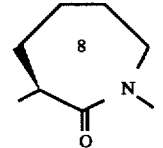 7 | Me |
| 3 | 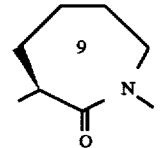 8 | Me |
| 4 | (9-membered ring) 9 | Me |

TABLE 45-continued
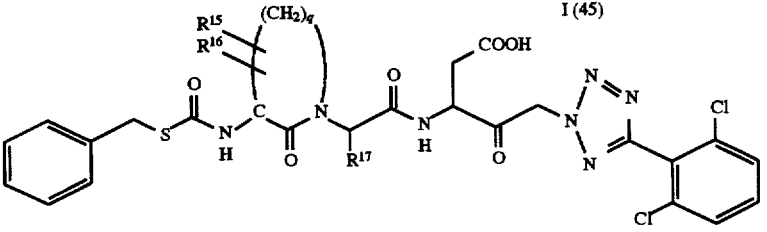
| No. | | R¹⁷ |
|---|---|---|
| 5 | 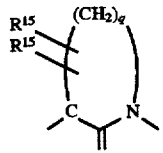 | Me |
| 6 | 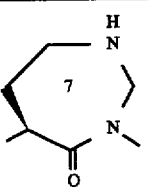 | Me |
| 7 | 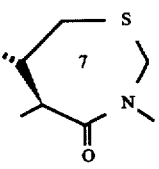 | Me |
| 8 | 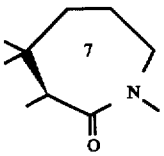 | Me |
| 9 | 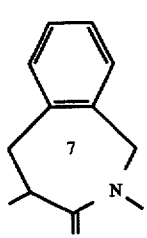 | Me |
| 10 | 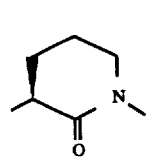 | Me |

TABLE 45-continued
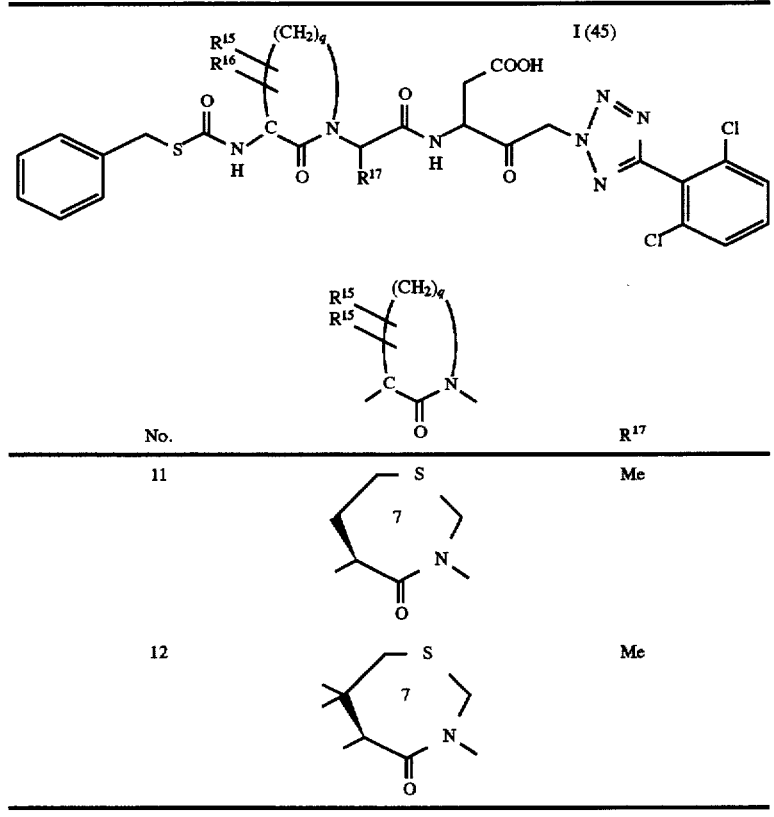
| No. | | R¹⁷ |
|---|---|---|
| 11 | | Me |
| 12 | | Me |
TABLE 46
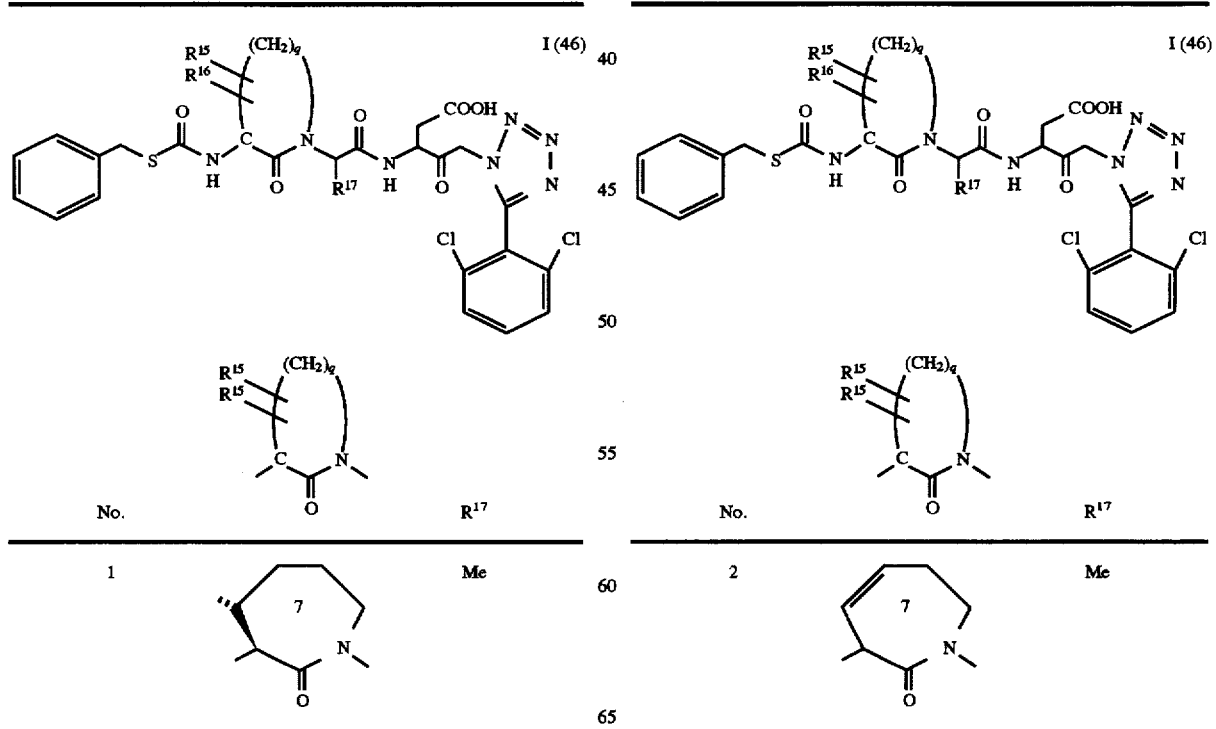
| No. | | R¹⁷ |
|---|---|---|
| 1 | | Me |
| 2 | | Me |

TABLE 46-continued
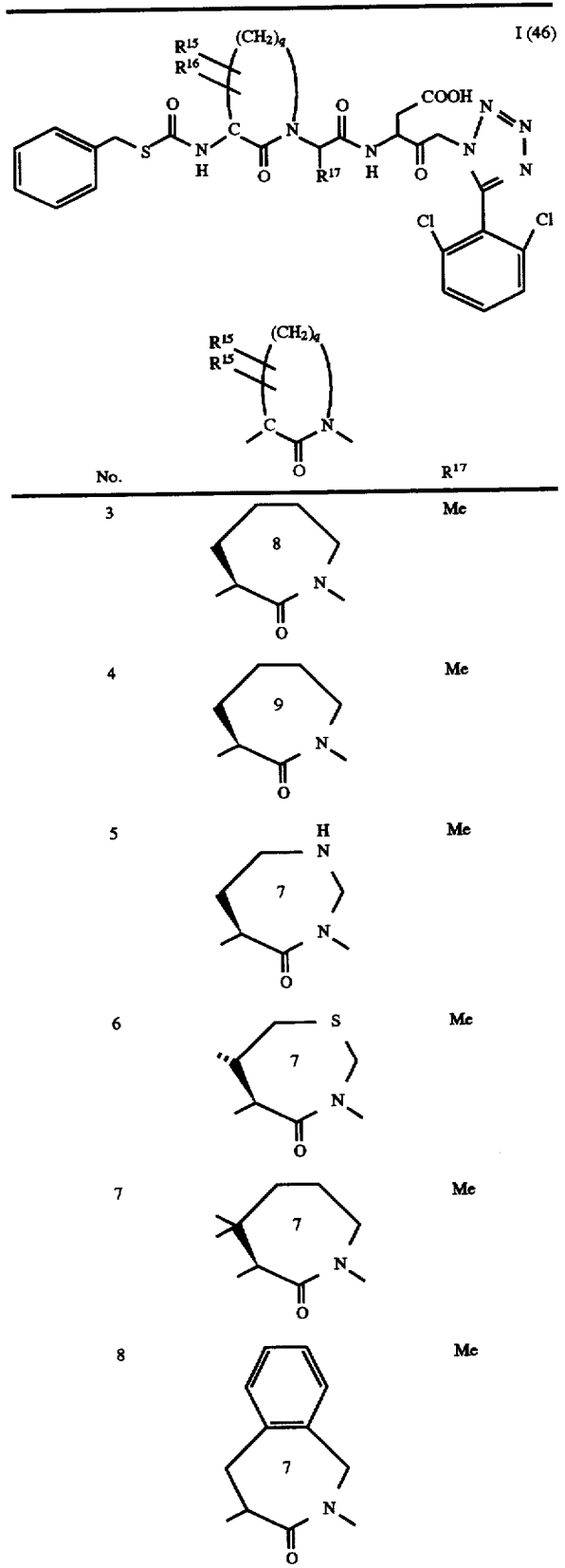
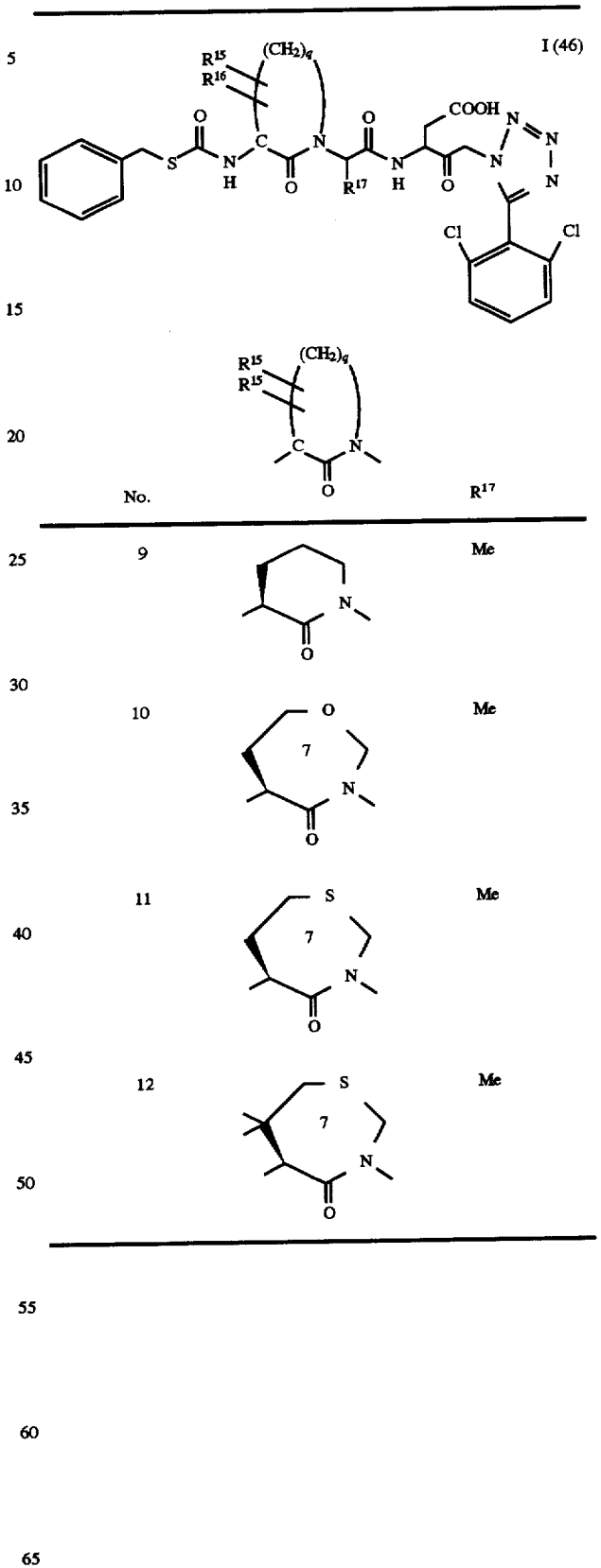

TABLE 47
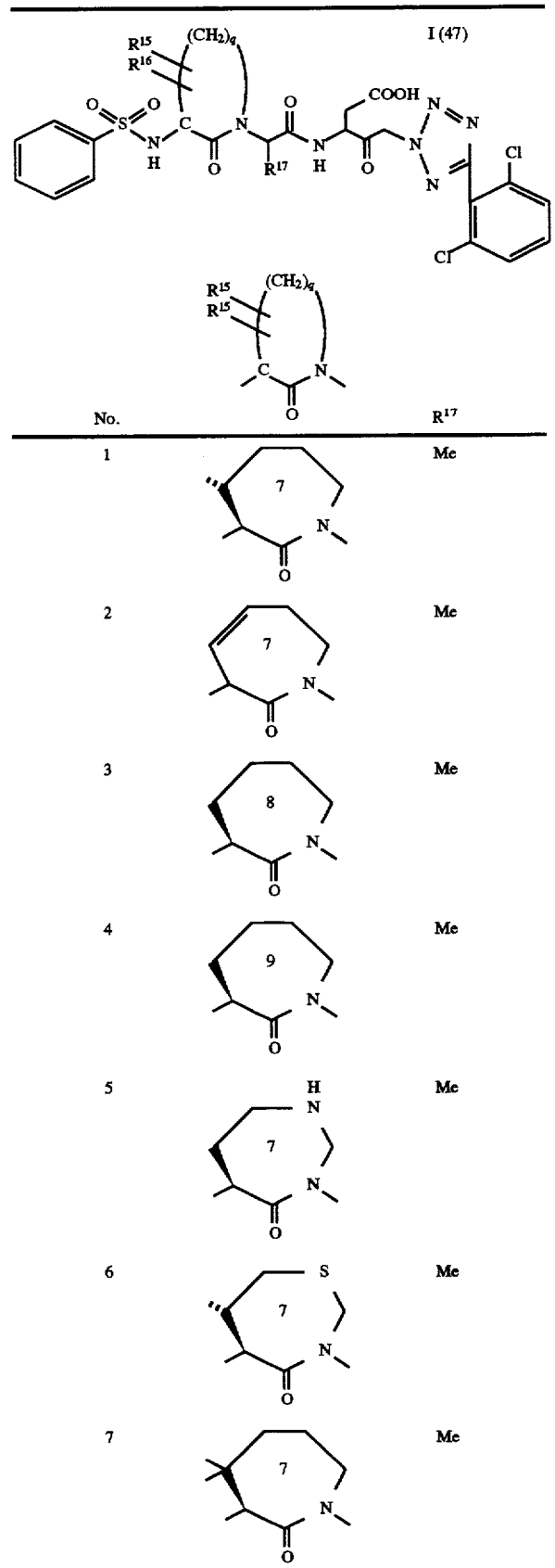
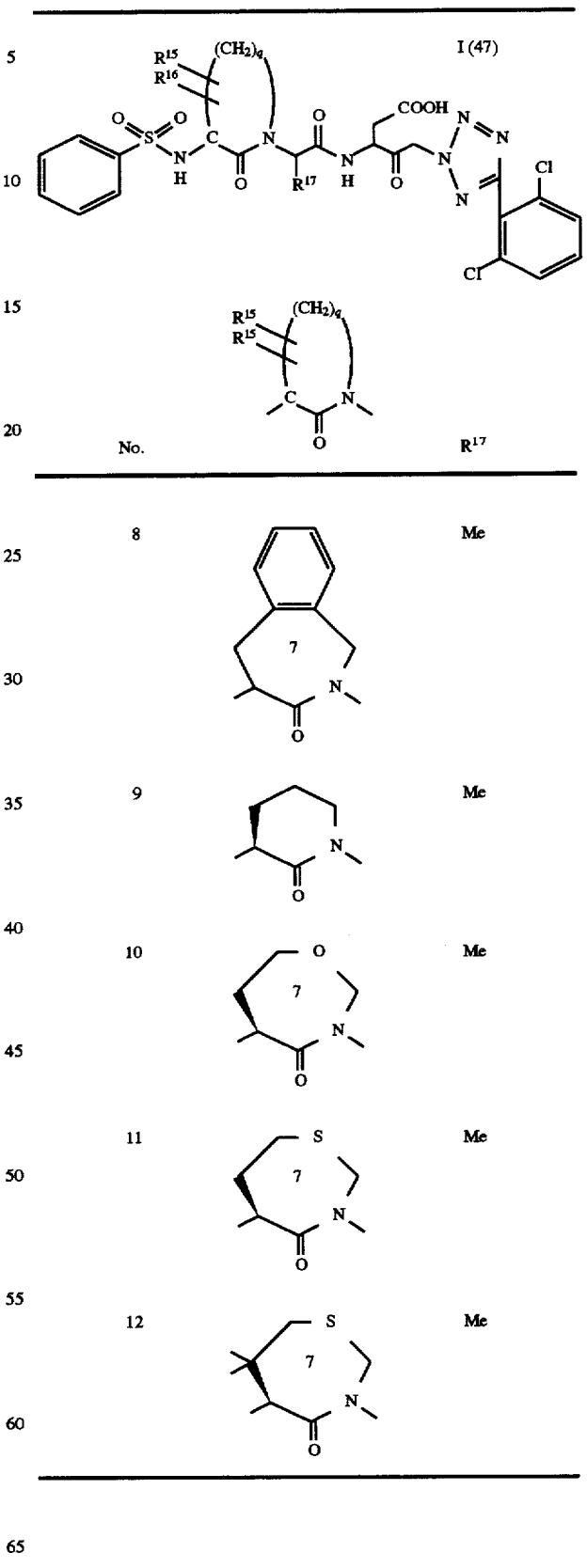

TABLE 48
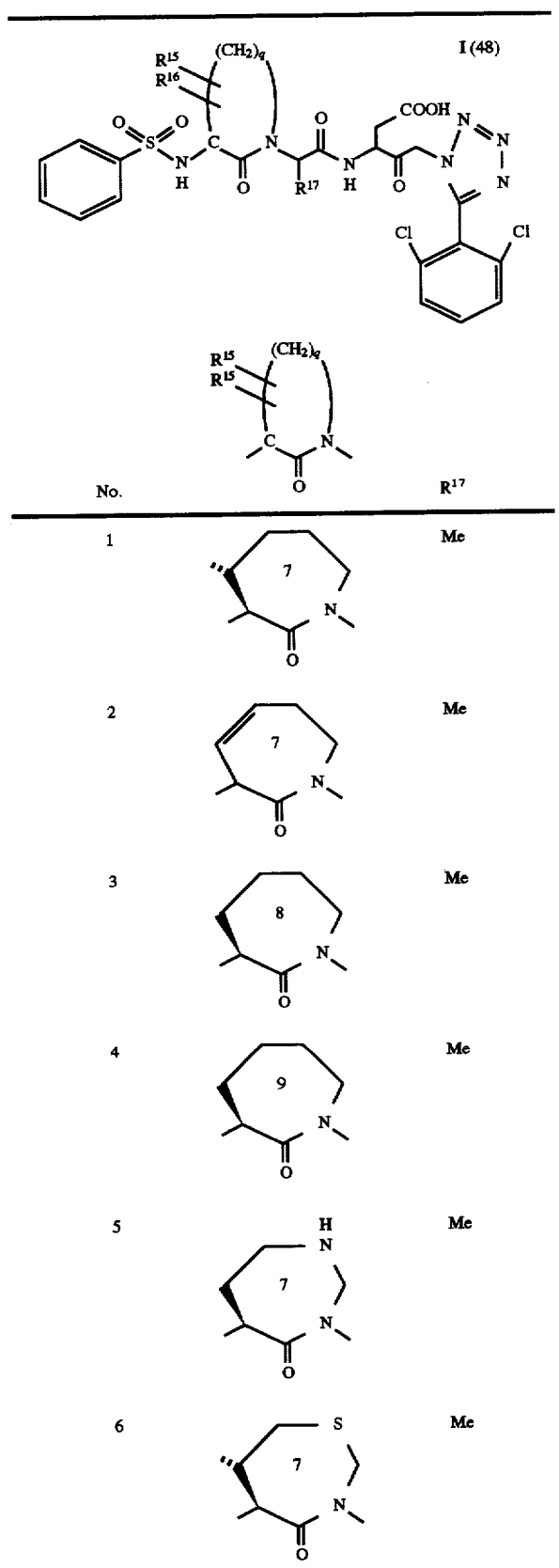
TABLE 48-continued
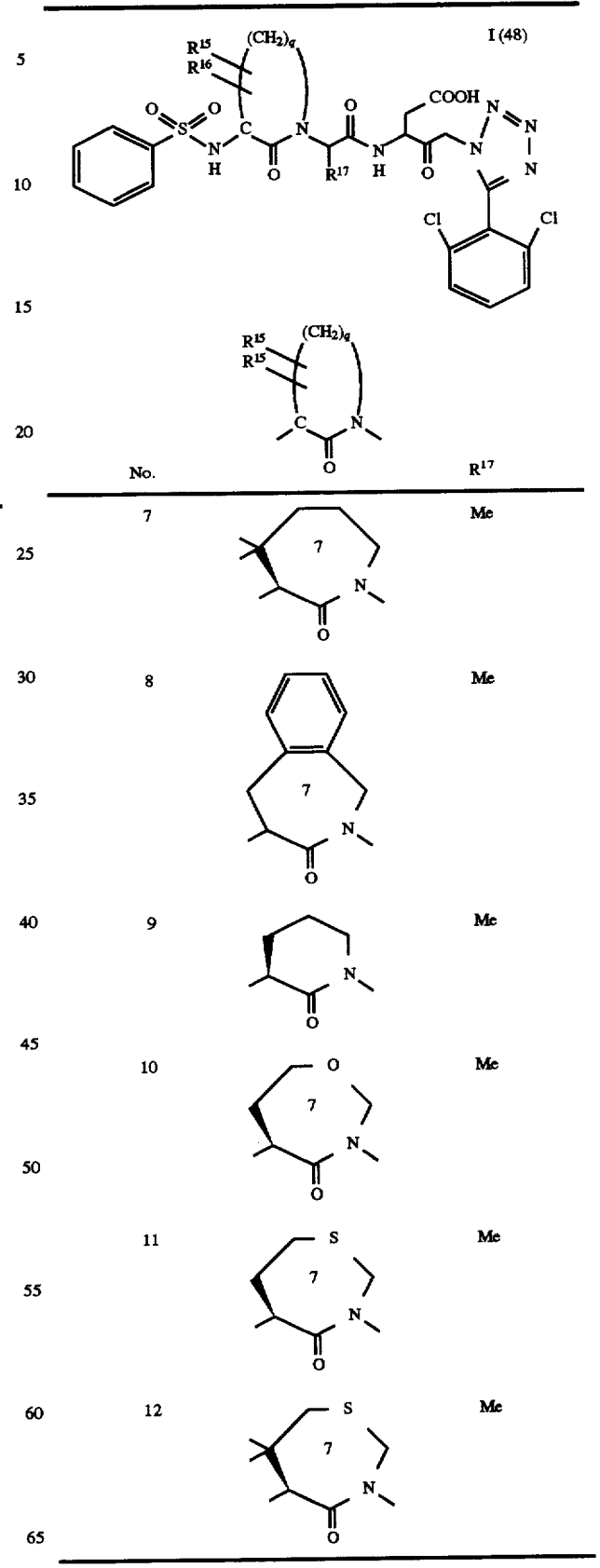

TABLE 49
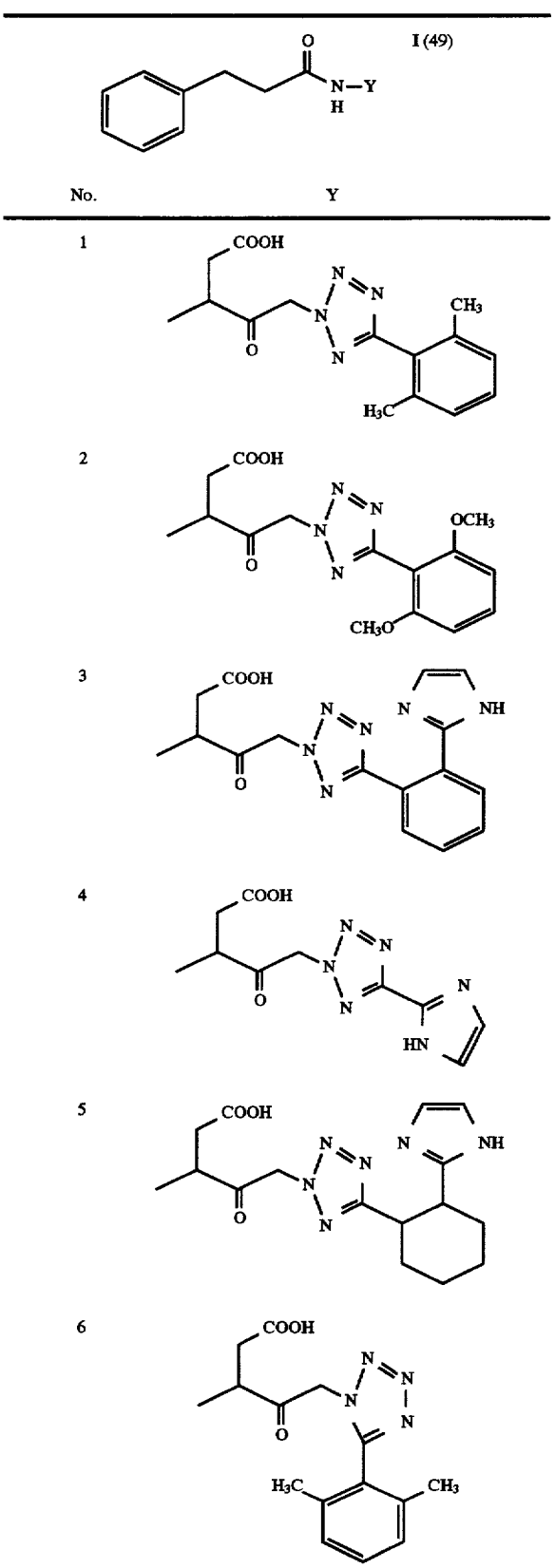
TABLE 49-continued
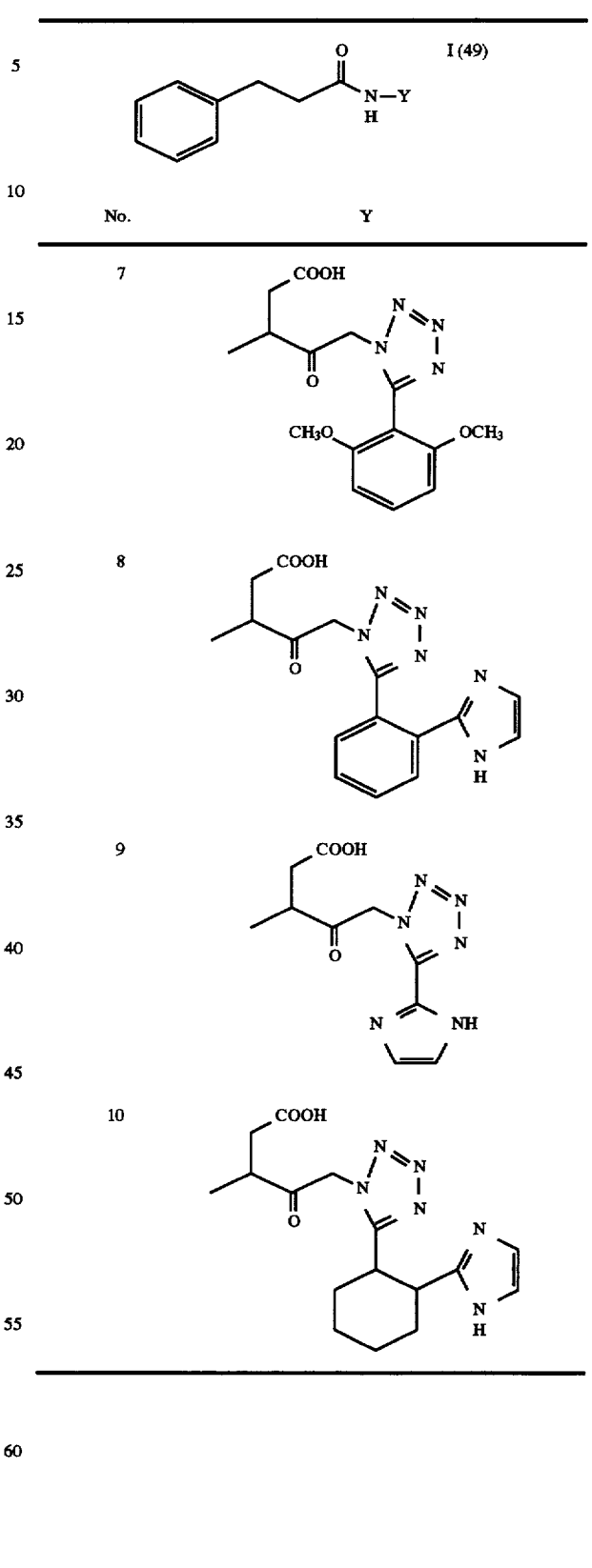

TABLE 50

Structure I(50): benzyl-O-C(=O)-N(H)-Y

| No. | Y |
|---|---|
| 1 | 3-methyl-4-oxo-5-[5-(2,6-dimethylphenyl)tetrazol-2-yl]pentanoic acid moiety |
| 2 | 3-methyl-4-oxo-5-[5-(2,6-dimethoxyphenyl)tetrazol-2-yl]pentanoic acid moiety |
| 3 | 3-methyl-4-oxo-5-[5-(2-(imidazol-2-yl)phenyl)tetrazol-2-yl]pentanoic acid moiety |
| 4 | 3-methyl-4-oxo-5-[5-(imidazol-2-yl)tetrazol-2-yl]pentanoic acid moiety |
| 5 | 3-methyl-4-oxo-5-[5-(2-(imidazol-2-yl)cyclohexyl)tetrazol-2-yl]pentanoic acid moiety |
| 6 | 3-methyl-4-oxo-5-[5-(2,6-dimethylphenyl)tetrazol-1-yl]pentanoic acid moiety |
| 7 | 3-methyl-4-oxo-5-[5-(2,6-dimethoxyphenyl)tetrazol-1-yl]pentanoic acid moiety |
| 8 | 3-methyl-4-oxo-5-[5-(2-(imidazol-2-yl)phenyl)tetrazol-1-yl]pentanoic acid moiety |
| 9 | 3-methyl-4-oxo-5-[5-(imidazol-2-yl)tetrazol-1-yl]pentanoic acid moiety |
| 10 | 3-methyl-4-oxo-5-[5-(2-(imidazol-2-yl)cyclohexyl)tetrazol-1-yl]pentanoic acid moiety |

TABLE 51

I(51)
[benzamide structure: Ph-C(=O)-N(H)-Y]

| No. | Y |
|---|---|
| 1 | 3-methyl-4-oxo-5-[5-(2,6-dimethylphenyl)tetrazol-2-yl]pentanoic acid |
| 2 | 3-methyl-4-oxo-5-[5-(2,6-dimethoxyphenyl)tetrazol-2-yl]pentanoic acid |
| 3 | 3-methyl-4-oxo-5-[5-(2-(1H-imidazol-2-yl)phenyl)tetrazol-2-yl]pentanoic acid |
| 4 | 3-methyl-4-oxo-5-[5-(1H-imidazol-2-yl)tetrazol-2-yl]pentanoic acid |
| 5 | 3-methyl-4-oxo-5-[5-(2-(1H-imidazol-2-yl)cyclohexyl)tetrazol-2-yl]pentanoic acid |
| 6 | 3-methyl-4-oxo-5-[5-(2,6-dimethylphenyl)tetrazol-1-yl]pentanoic acid |

TABLE 51-continued

I(51)
[benzamide structure: Ph-C(=O)-N(H)-Y]

| No. | Y |
|---|---|
| 7 | 3-methyl-4-oxo-5-[5-(2,6-dimethoxyphenyl)tetrazol-1-yl]pentanoic acid |
| 8 | 3-methyl-4-oxo-5-[5-(2-(1H-imidazol-2-yl)phenyl)tetrazol-1-yl]pentanoic acid |
| 9 | 3-methyl-4-oxo-5-[5-(1H-imidazol-2-yl)tetrazol-1-yl]pentanoic acid |
| 10 | 3-methyl-4-oxo-5-[5-(2-(1H-imidazol-2-yl)cyclohexyl)tetrazol-1-yl]pentanoic acid |

TABLE 52
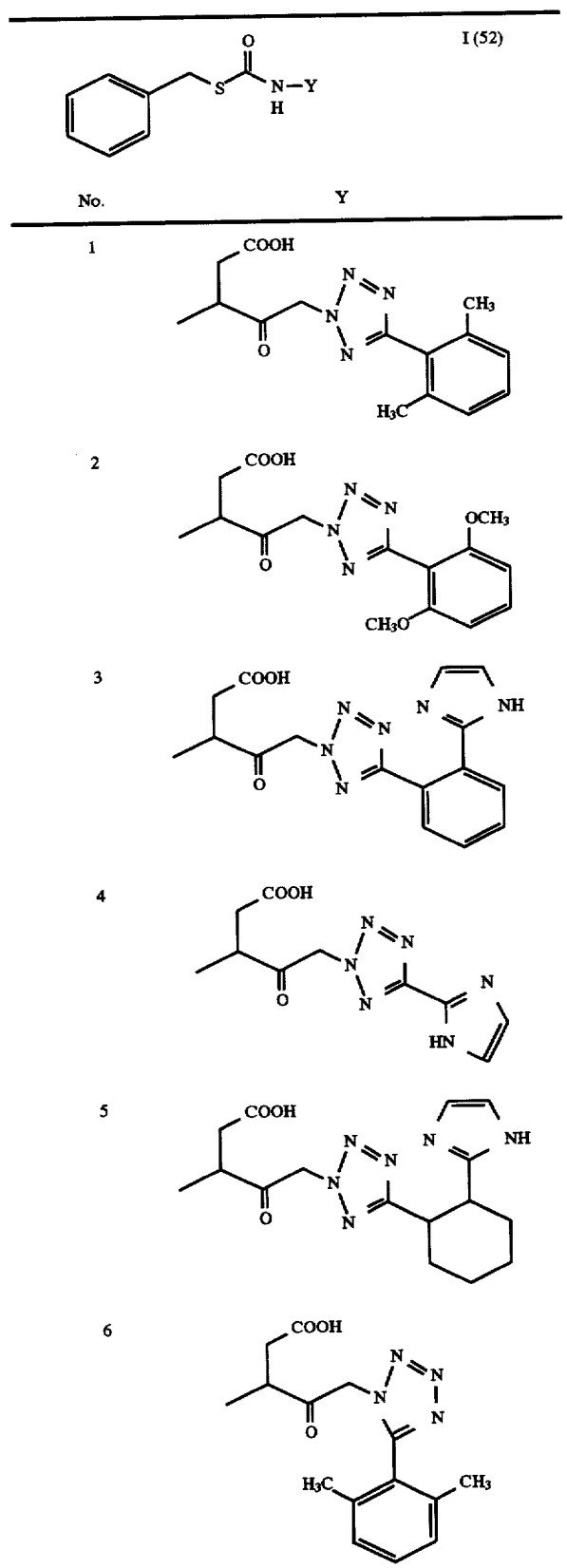
TABLE 52-continued
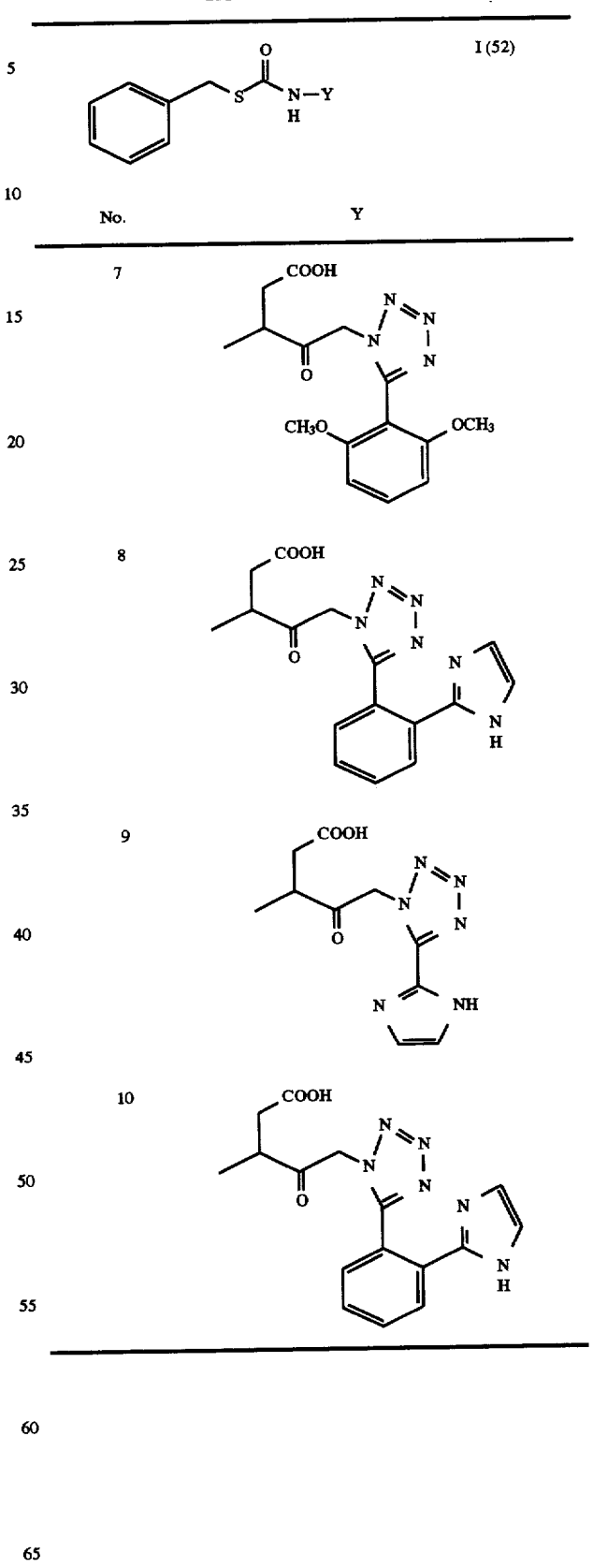

TABLE 53

| | I(53) |
|---|---|
| No. | Y |
| 1 | (3-methyl-4-oxo-5-(5-(2,6-dimethylphenyl)-2H-tetrazol-2-yl)pentanoic acid) |
| 2 | (3-methyl-4-oxo-5-(5-(2,6-dimethoxyphenyl)-2H-tetrazol-2-yl)pentanoic acid) |
| 3 | (3-methyl-4-oxo-5-(5-(2-(1H-imidazol-2-yl)phenyl)-2H-tetrazol-2-yl)pentanoic acid) |
| 4 | (3-methyl-4-oxo-5-(5-(1H-imidazol-2-yl)-2H-tetrazol-2-yl)pentanoic acid) |
| 5 | (3-methyl-4-oxo-5-(5-(2-(1H-imidazol-2-yl)cyclohexyl)-2H-tetrazol-2-yl)pentanoic acid) |
| 6 | (3-methyl-4-oxo-5-(5-(2,6-dimethylphenyl)-1H-tetrazol-1-yl)pentanoic acid) |

TABLE 53-continued

| | I(53) |
|---|---|
| No. | Y |
| 7 | (3-methyl-4-oxo-5-(5-(2,6-dimethoxyphenyl)-1H-tetrazol-1-yl)pentanoic acid) |
| 8 | (3-methyl-4-oxo-5-(5-(2-(1H-imidazol-2-yl)phenyl)-1H-tetrazol-1-yl)pentanoic acid) |
| 9 | (3-methyl-4-oxo-5-(5-(1H-imidazol-2-yl)-1H-tetrazol-1-yl)pentanoic acid) |
| 10 | (3-methyl-4-oxo-5-(5-(2-(1H-imidazol-2-yl)phenyl)-1H-tetrazol-1-yl)pentanoic acid) |

TABLE 54

[Structure: Ph-(CH2)3-C(=O)-N(H)-Y] I(54)

| No. | Y |
|---|---|
| 1 | 3-methyl-4-oxo-5-[5-(2,6-dimethylphenyl)tetrazol-2-yl]pentanoic acid moiety (COOH-CH2-CH(CH3)-C(=O)-CH2-N(tetrazole-2-yl)-5-(2,6-dimethylphenyl)) |
| 2 | 3-methyl-4-oxo-5-[5-(2,6-dimethoxyphenyl)tetrazol-2-yl]pentanoic acid moiety |
| 3 | 3-methyl-4-oxo-5-[5-(2-(imidazol-2-yl)phenyl)tetrazol-2-yl]pentanoic acid moiety |
| 4 | 3-methyl-4-oxo-5-[5-(imidazol-2-yl)tetrazol-2-yl]pentanoic acid moiety |
| 5 | 3-methyl-4-oxo-5-[5-(2-(imidazol-2-yl)cyclohexyl)tetrazol-2-yl]pentanoic acid moiety |
| 6 | 3-methyl-4-oxo-5-[5-(2,6-dimethylphenyl)tetrazol-1-yl]pentanoic acid moiety |

TABLE 54-continued

[Structure: Ph-(CH2)3-C(=O)-N(H)-Y] I(54)

| No. | Y |
|---|---|
| 7 | 3-methyl-4-oxo-5-[5-(2,6-dimethoxyphenyl)tetrazol-1-yl]pentanoic acid moiety |
| 8 | 3-methyl-4-oxo-5-[5-(2-(imidazol-2-yl)phenyl)tetrazol-1-yl]pentanoic acid moiety |
| 9 | 3-methyl-4-oxo-5-[5-(imidazol-2-yl)tetrazol-1-yl]pentanoic acid moiety |
| 10 | 3-methyl-4-oxo-5-[5-(2-(imidazol-2-yl)phenyl)tetrazol-1-yl]pentanoic acid moiety |

TABLE 55

| No. | Y |
|---|---|
| 1 | 2-(2,6-dimethylphenyl)tetrazol-2-yl derivative with 3-methyl-4-oxopentanoic acid chain |
| 2 | 2-(2,6-dimethoxyphenyl)tetrazol-2-yl derivative with 3-methyl-4-oxopentanoic acid chain |
| 3 | 5-[2-(1H-imidazol-2-yl)phenyl]tetrazol-2-yl derivative |
| 4 | 5-(1H-pyrrol-2-yl)tetrazol-2-yl derivative |
| 5 | 5-[2-(1H-pyrrol-2-yl)cyclohexyl]tetrazol-2-yl derivative |
| 6 | 5-(2,6-dimethylphenyl)tetrazol-1-yl derivative |
| 7 | 5-(2,6-dimethoxyphenyl)tetrazol-1-yl derivative |
| 8 | 5-[2-(1H-imidazol-2-yl)phenyl]tetrazol-1-yl derivative |
| 9 | 5-(1H-imidazol-2-yl)tetrazol-1-yl derivative |
| 10 | 5-[2-(1H-pyrrol-2-yl)phenyl]tetrazol-1-yl derivative |

TABLE 56

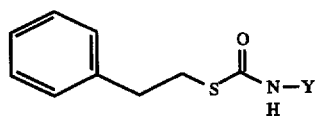 I(56)

| No. | Y |
|---|---|
| 1 | 3-methyl-4-oxo-5-[5-(2,6-dimethylphenyl)tetrazol-2-yl]pentanoic acid moiety |
| 2 | 3-methyl-4-oxo-5-[5-(2,6-dimethoxyphenyl)tetrazol-2-yl]pentanoic acid moiety |
| 3 | 3-methyl-4-oxo-5-[5-(2-(imidazol-2-yl)phenyl)tetrazol-2-yl]pentanoic acid moiety |
| 4 | 3-methyl-4-oxo-5-[5-(imidazol-2-yl)tetrazol-2-yl]pentanoic acid moiety |
| 5 | 3-methyl-4-oxo-5-[5-(2-(imidazol-2-yl)cyclohexyl)tetrazol-2-yl]pentanoic acid moiety |
| 6 | 3-methyl-4-oxo-5-[5-(2,6-dimethylphenyl)tetrazol-1-yl]pentanoic acid moiety |

TABLE 56-continued

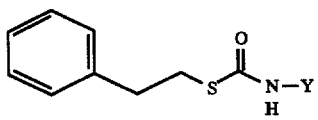 I(56)

| No. | Y |
|---|---|
| 7 | 3-methyl-4-oxo-5-[5-(2,6-dimethoxyphenyl)tetrazol-1-yl]pentanoic acid moiety |
| 8 | 3-methyl-4-oxo-5-[5-(2-(imidazol-2-yl)phenyl)tetrazol-1-yl]pentanoic acid moiety |
| 9 | 3-methyl-4-oxo-5-[5-(imidazol-2-yl)tetrazol-1-yl]pentanoic acid moiety |
| 10 | 3-methyl-4-oxo-5-[5-(2-(imidazol-2-yl)phenyl)tetrazol-1-yl]pentanoic acid moiety |

TABLE 57
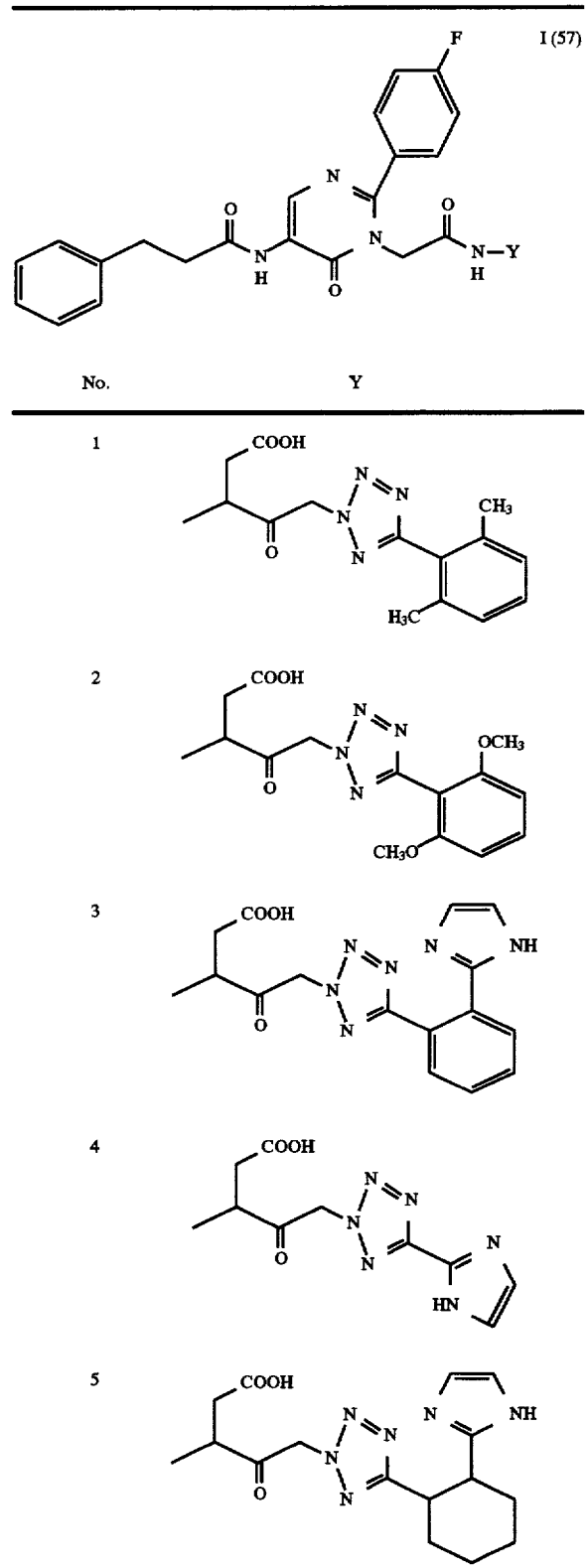
TABLE 57-continued
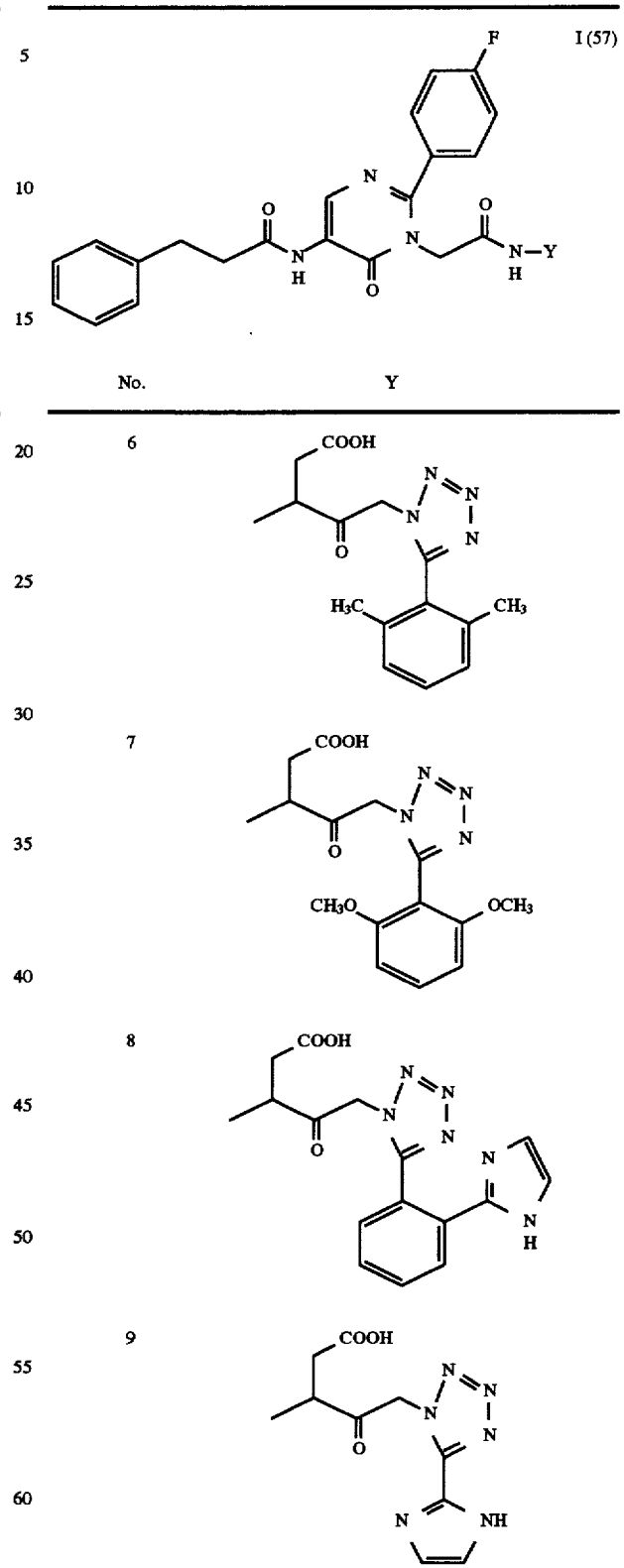

TABLE 57-continued
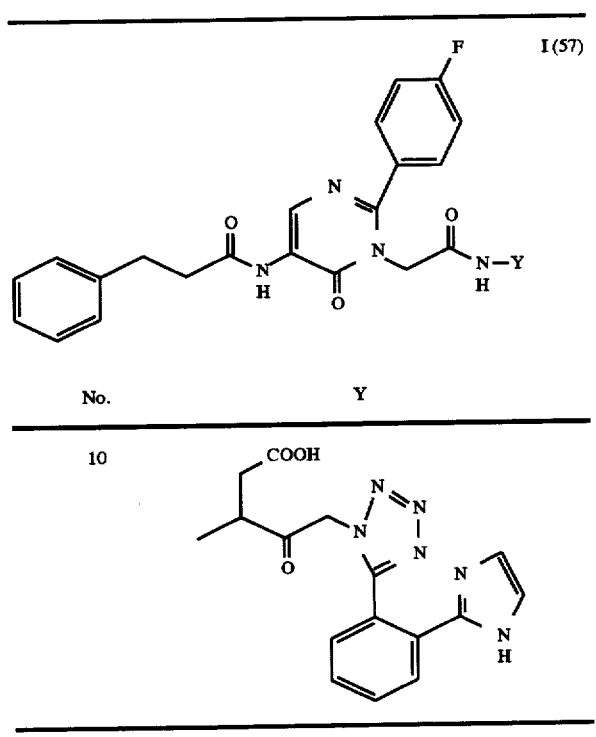
| No. | Y |
|---|---|
| 10 | (structure shown) |
TABLE 58
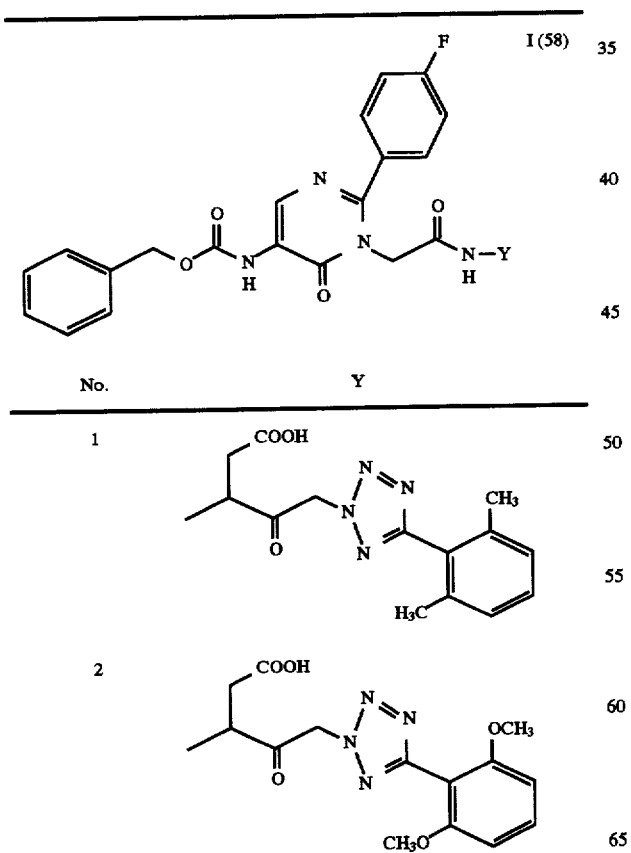
| No. | Y |
|---|---|
| 1 | (structure shown) |
| 2 | (structure shown) |
TABLE 58-continued
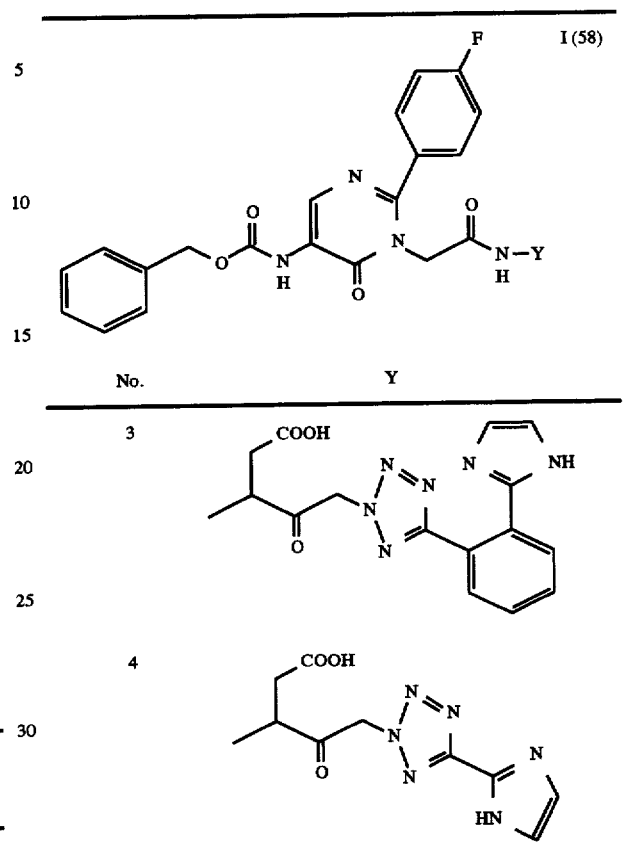
| No. | Y |
|---|---|
| 3 | (structure shown) |
| 4 | (structure shown) |
| 5 | (structure shown) |
| 6 | (structure shown) |
| 7 | (structure shown) |
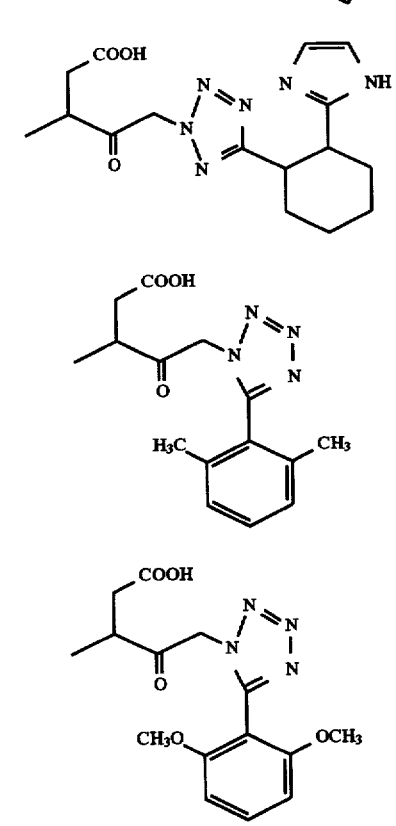

TABLE 58-continued
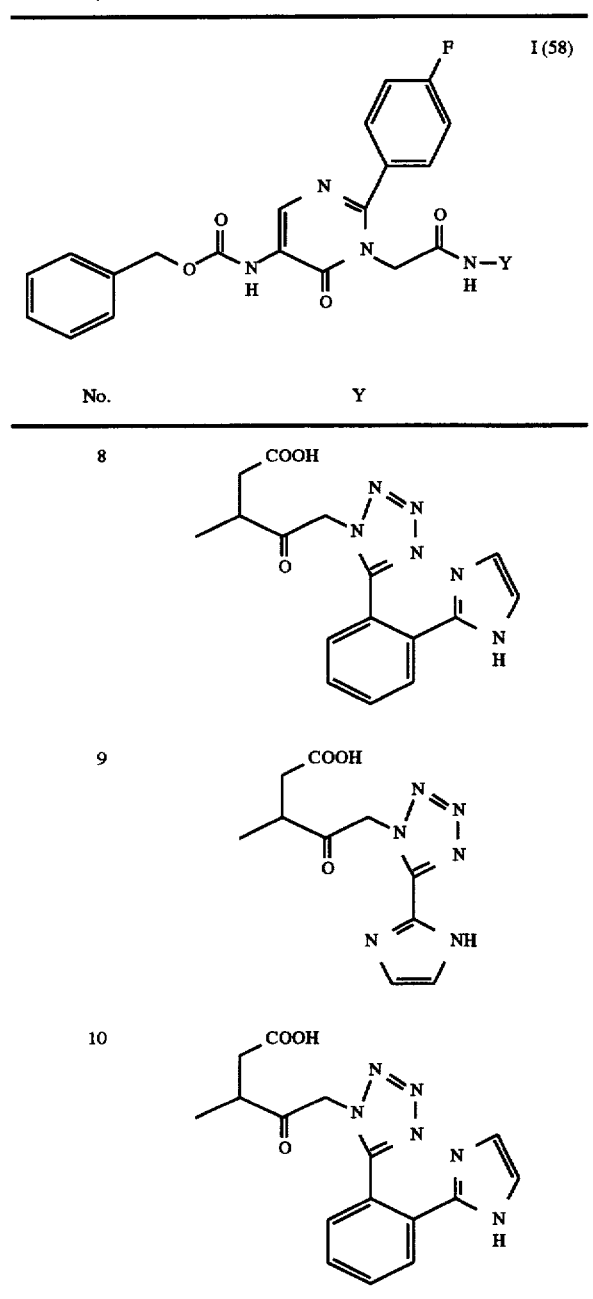
| No. | Y |
|---|---|
| 8 | |
| 9 | |
| 10 | |
TABLE 59
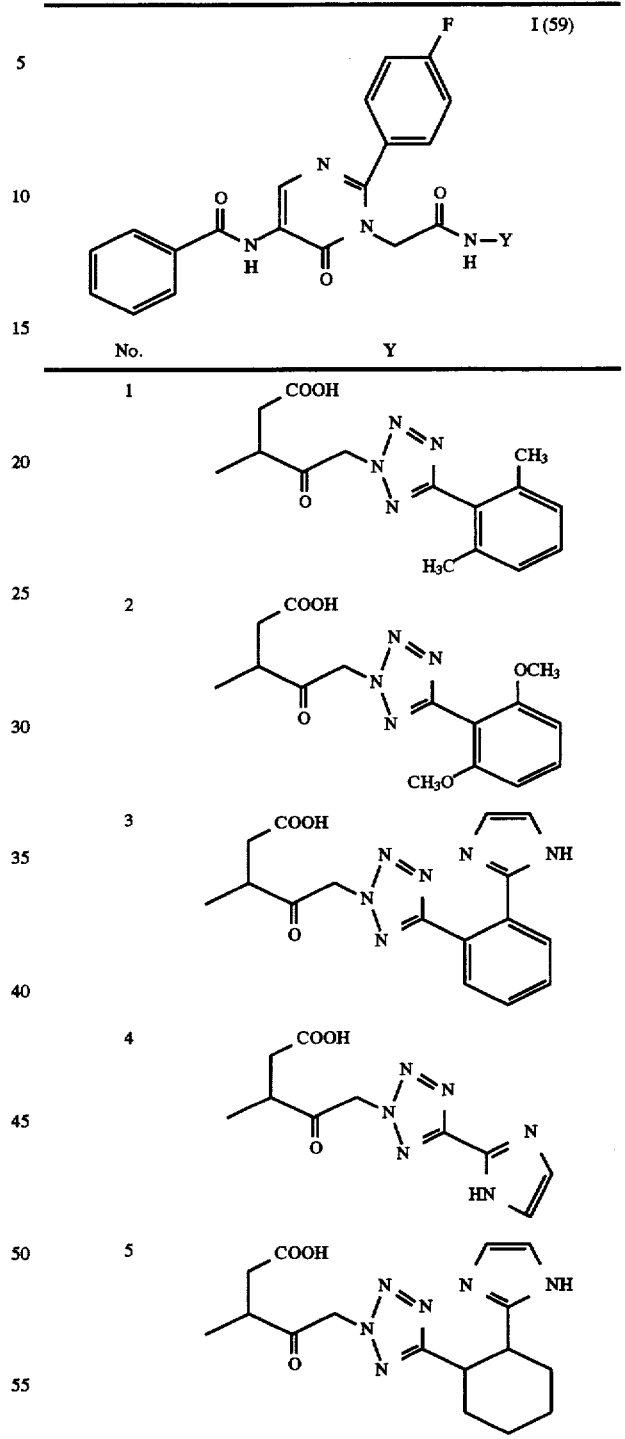
| No. | Y |
|---|---|
| 1 | |
| 2 | |
| 3 | |
| 4 | |
| 5 | |

TABLE 59-continued
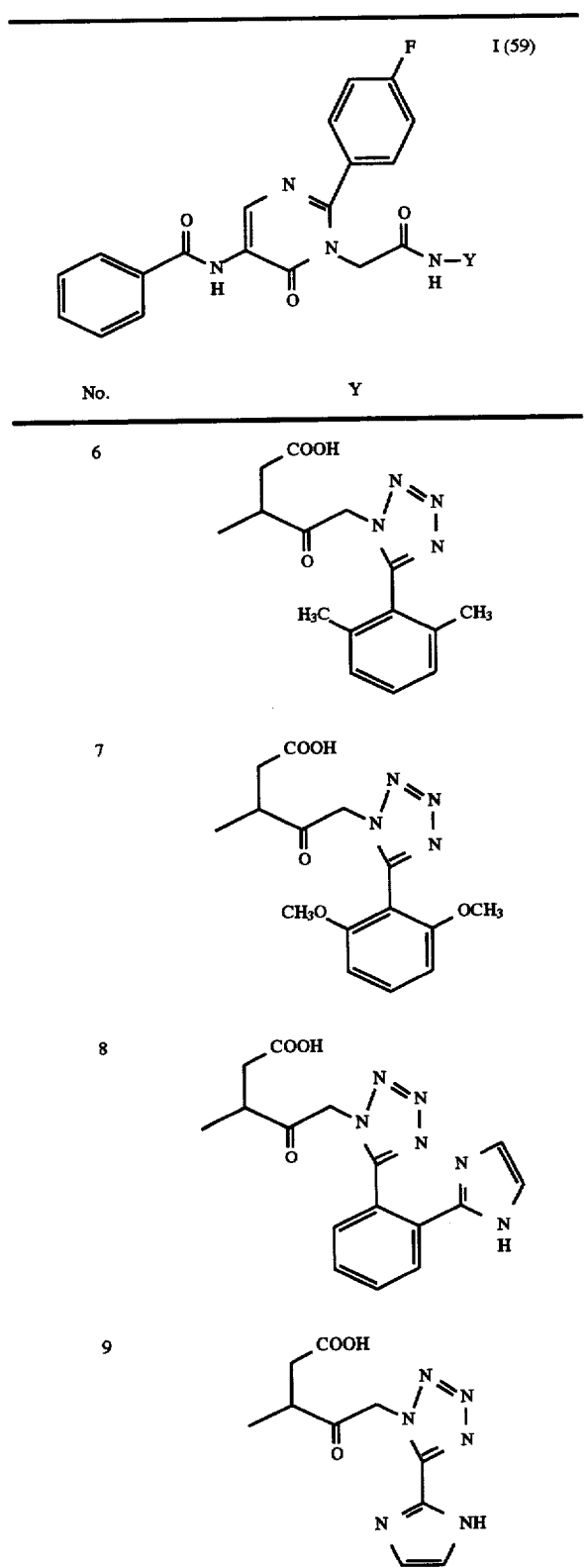
TABLE 59-continued
TABLE 60
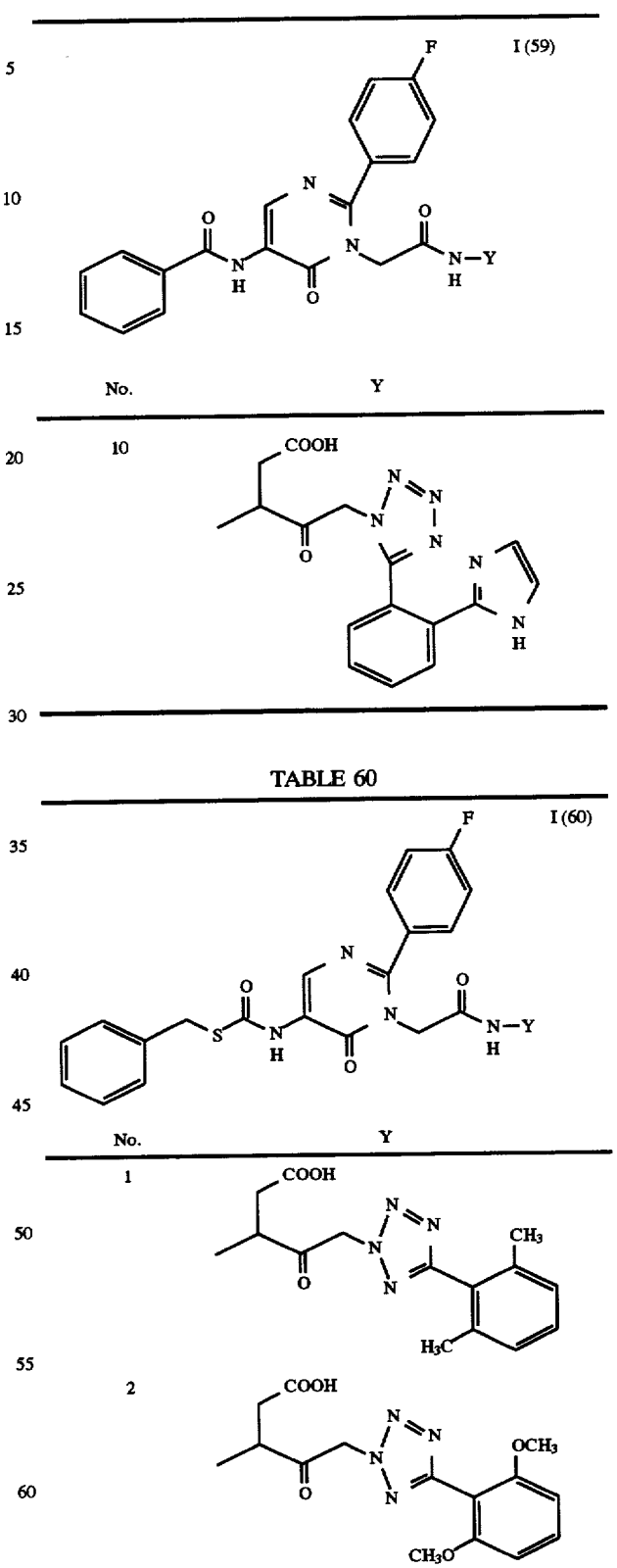

TABLE 60-continued
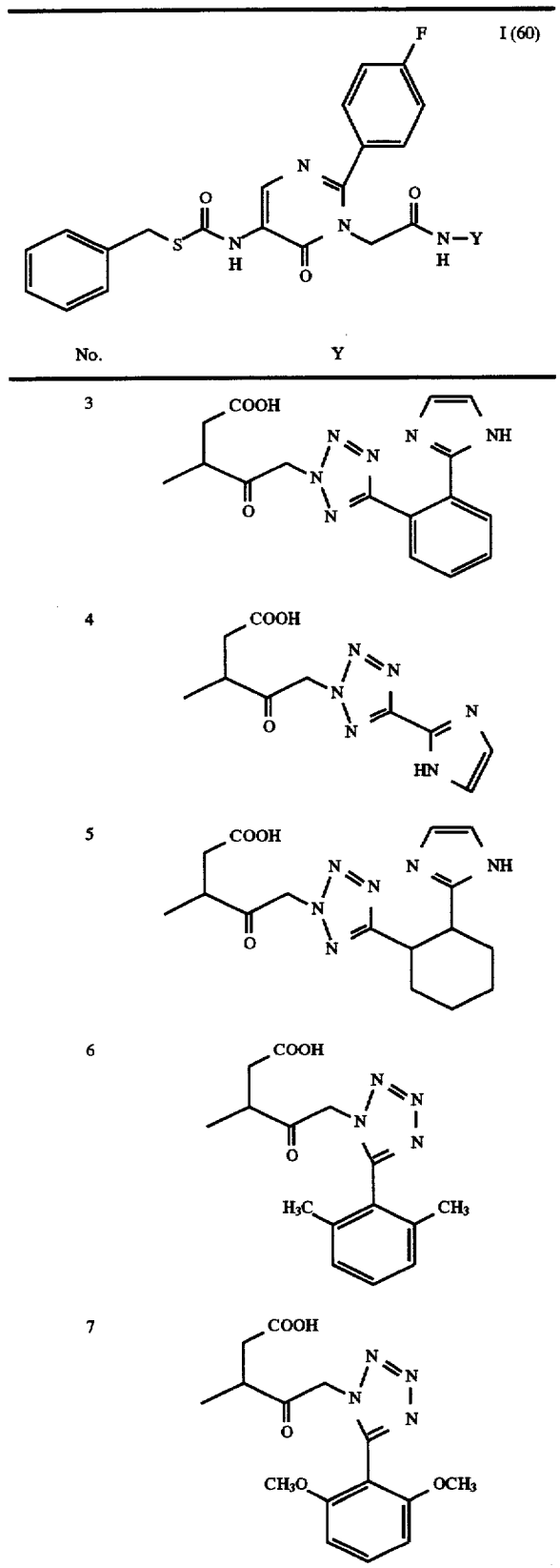
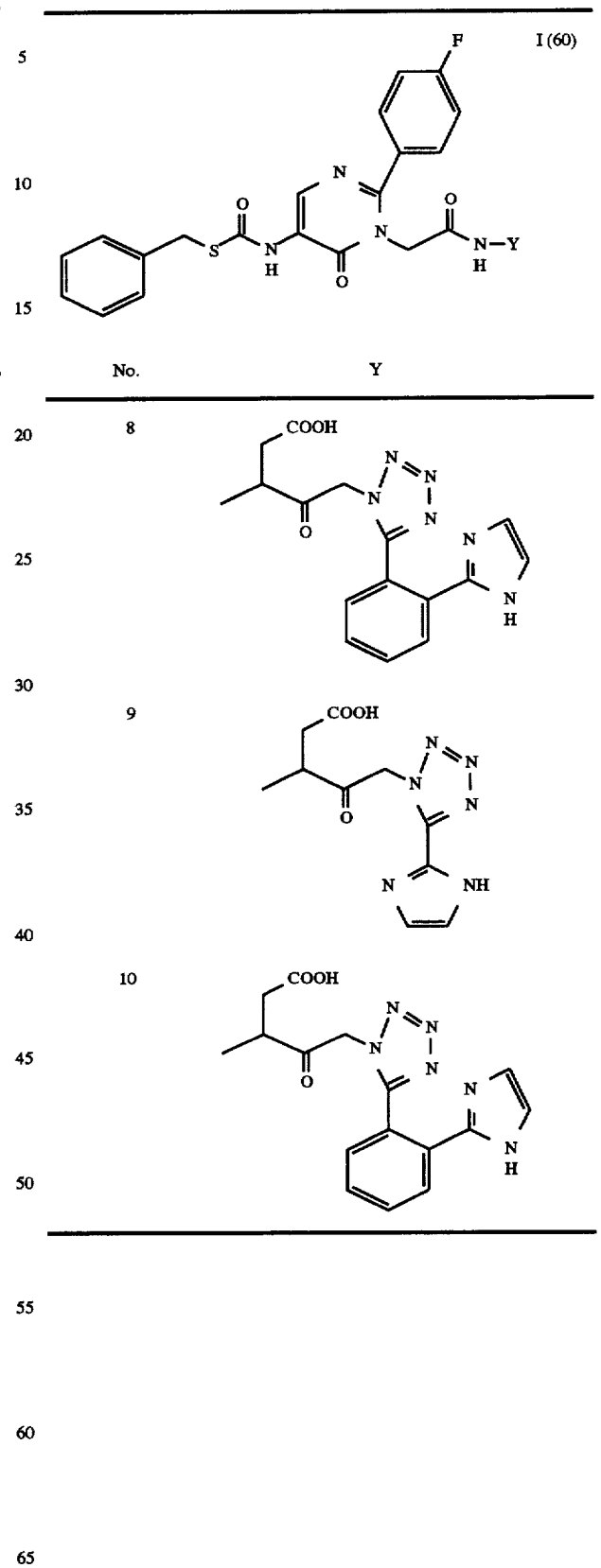

TABLE 61

No. | Y
--- | ---
1 | 3-methyl-4-oxo-5-[5-(2,6-dimethylphenyl)tetrazol-2-yl]pentanoic acid moiety with COOH
2 | 3-methyl-4-oxo-5-[5-(2,6-dimethoxyphenyl)tetrazol-2-yl]pentanoic acid moiety with COOH
3 | 3-methyl-4-oxo-5-[5-(2-(imidazol-2-yl)phenyl)tetrazol-2-yl]pentanoic acid moiety with COOH
4 | 3-methyl-4-oxo-5-[5-(imidazol-2-yl)tetrazol-2-yl]pentanoic acid moiety with COOH
5 | 3-methyl-4-oxo-5-[5-(2-(imidazol-2-yl)cyclohexyl)tetrazol-2-yl]pentanoic acid moiety with COOH TABLE 61-continued No. | Y
--- | ---
6 | 3-methyl-4-oxo-5-[5-(2,6-dimethylphenyl)tetrazol-1-yl]pentanoic acid moiety with COOH
7 | 3-methyl-4-oxo-5-[5-(2,6-dimethoxyphenyl)tetrazol-1-yl]pentanoic acid moiety with COOH
8 | 3-methyl-4-oxo-5-[5-(2-(imidazol-2-yl)phenyl)tetrazol-1-yl]pentanoic acid moiety with COOH
9 | 3-methyl-4-oxo-5-[5-(imidazol-2-yl)tetrazol-1-yl]pentanoic acid moiety with COOH

TABLE 61-continued

I (61)

| No. | Y |
|---|---|
| 10 | (3-methyl-4-carboxy-substituted ketone with CH₂ linked to N of tetrazole bearing 2-(1H-imidazol-2-yl)phenyl group) |

TABLE 62

I (62)

| No. | R¹ | No. | R¹ |
|---|---|---|---|
| 1 | Me | 10 | 3-HO-C₆H₄- |
| 2 | 2-biphenyl | 11 | 2-(1H-tetrazol-5-yl)phenyl |
| 3 | 3-(CH₃OOC)-C₆H₄- | 12 | 3-(HOOC)-C₆H₄- |
| 4 | 2-Cl-C₆H₄- | 13 | 2-(OCH₃)-C₆H₄- |

TABLE 62-continued
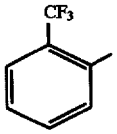
| No. | R¹ | No. | R¹ |
|---|---|---|---|
| 5 |  | 14 | 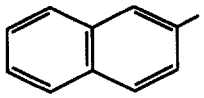 |
| 6 | 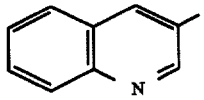 | 15 | 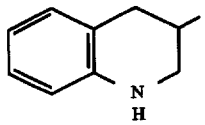 |
| 7 |  | 16 | 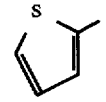 |
| 8 |  | 17 | 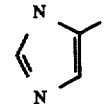 |
| 9 |  | 18 | 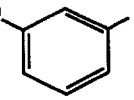 |
TABLE 63
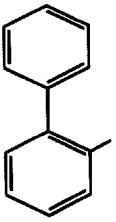
| No. | R¹ | No. | R¹ |
|---|---|---|---|
| 1 | Me | 10 | 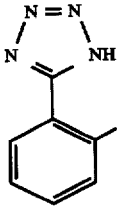 |
| 2 | 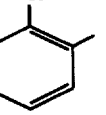 | 11 | 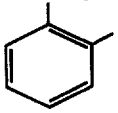 |
TABLE 63-continued
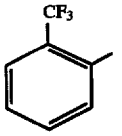
| No. | R¹ | No. | R¹ |
|---|---|---|---|
| 3 | CH₃OOC— (phenyl) | 12 | HOOC— (phenyl) |
| 4 | Cl-phenyl | 13 | OCH₃-phenyl |
| 5 | CF₃-phenyl | 14 | 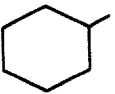 |

TABLE 63-continued
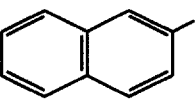
I (63)
| No. | R¹ | No. | R¹ |
|---|---|---|---|
| 6 | 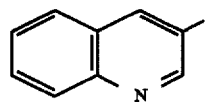 | 15 | 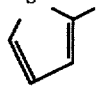 |
| 7 | 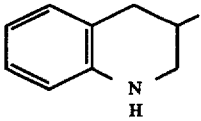 | 16 | 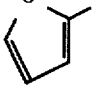 |
TABLE 63-continued
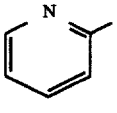
I (63)
| No. | R¹ | No. | R¹ |
|---|---|---|---|
| 8 | 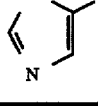 | 17 | 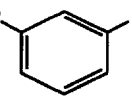 |
| 9 | 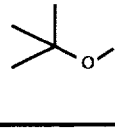 | 18 | 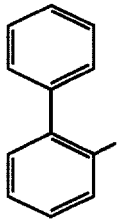 |
TABLE 64
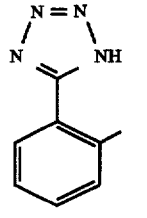
I (64)
| No. | R¹ | No. | R¹ |
|---|---|---|---|
| 1 | Me | 10 | 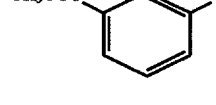 |
| 2 | 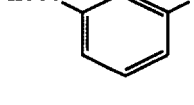 | 11 | 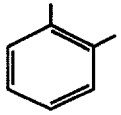 |
| 3 | 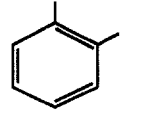 | 12 | HOOC— (phenyl) |
| 4 | Cl— (phenyl) | 13 | OCH₃— (phenyl) |

TABLE 64-continued
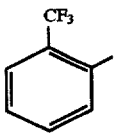
I (64)
| No. | R¹ | No. | R¹ |
|---|---|---|---|
| 5 | 2-CF₃-phenyl | 14 | cyclohexyl |
| 6 | 2-naphthyl | 15 | 3-quinolinyl |
| 7 | 3-(1,2,3,4-tetrahydroquinolinyl) | 16 | 2-pyridyl |
| 8 | 2-thienyl | 17 | 2-furyl |
| 9 | 5-imidazolyl | 18 | t-butoxymethyl |
TABLE 65
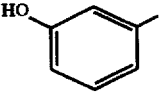
I (65)
| No. | R¹ | No. | R¹ |
|---|---|---|---|
| 1 | Me | 10 | 3-hydroxyphenyl |
TABLE 65-continued
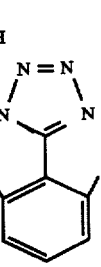
I (65)
| No. | R¹ | No. | R¹ |
|---|---|---|---|
| 2 | 2-biphenyl | 11 | 2-(1H-tetrazol-5-yl)phenyl |

TABLE 65-continued

I (65)

[Structure: sulfonamide-azepanone-peptide with dichlorophenyl tetrazole, R¹ substituent]

| No. | R¹ | No. | R¹ |
|---|---|---|---|
| 3 | CH₃OOC—(3-substituted phenyl) | 12 | HOOC—(3-substituted phenyl) |
| 4 | 2-Cl-phenyl | 13 | 2-OCH₃-phenyl |
| 5 | 2-CF₃-phenyl | 14 | cyclohexyl |
| 6 | 2-naphthyl | 15 | 3-quinolinyl |
| 7 | 1,2,3,4-tetrahydroquinolin-3-yl | 16 | 2-pyridyl |

TABLE 65-continued

I (65)

[Structure: sulfonamide-azepanone-peptide with dichlorophenyl tetrazole, R¹ substituent]

| No. | R¹ | No. | R¹ |
|---|---|---|---|
| 8 | 2-thienyl | 17 | 2-furyl |
| 9 | imidazol-4-yl | 18 | t-BuO-CH₂- (OC(CH₃)₃) |

TABLE 66

I (66)

[Structure with triazole linker and 2,6-dichlorophenyl]

| No. | R¹ | No. | R¹ |
|---|---|---|---|
| 1 | Me | 10 | 3-HO-phenyl |

TABLE 66-continued

I (66)

[Structure: macrocyclic sulfonamide compound with R¹-SO₂-NH- group attached to a 7-membered ring containing N, with side chain containing amide linkages, COOH group, tetrazine ring, and 2,6-dichlorophenyl group]

| No. | R¹ | No. | R¹ |
|---|---|---|---|
| 2 | 2-biphenyl | 11 | 2-(1H-tetrazol-5-yl)phenyl |
| 3 | 3-(methoxycarbonyl)phenyl (CH₃OOC-) | 12 | 3-carboxyphenyl (HOOC-) |
| 4 | 2-chlorophenyl | 13 | 2-methoxyphenyl (OCH₃) |
| 5 | 2-(trifluoromethyl)phenyl (CF₃) | 14 | cyclohexyl |
| 6 | 2-naphthyl | 15 | 3-quinolinyl |
| 7 | 1,2,3,4-tetrahydroquinolin-3-yl | 16 | 2-pyridyl |
| 8 | 2-thienyl | 17 | 2-furyl |
| 9 | pyrazinyl | 18 | tert-butoxymethyl |

TABLE 67

I (67)

| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |
| 5 | 2-(trifluoromethyl)phenyl | 14 | cyclohexyl |

TABLE 67-continued

I (67)

| No. | R¹ | No. | R¹ |
|---|---|---|---|
| 6 | 2-naphthyl | 15 | quinolin-3-yl |
| 7 | 1,2,3,4-tetrahydroquinolin-3-yl | 16 | pyridin-2-yl |
| 8 | thiophen-2-yl | 17 | furan-2-yl |
| 9 | imidazol-4-yl | 18 | tert-butoxy |

TABLE 68

I (68)

| No. | R¹ | No. | R¹ |
|---|---|---|---|
| 1 | Me | 10 | 3-hydroxyphenyl |

TABLE 68-continued

I(68)

[Structure of compound I(68) with R¹-SO₂-NH group attached to a bicyclic lactam system connected via amide linkages to a chain bearing COOH and a tetrazole linked to 2,6-dichlorophenyl]

| No. | R¹ | No. | R¹ |
|---|---|---|---|
| 2 | 2-biphenyl | 11 | 2-(1H-tetrazol-5-yl)phenyl |
| 3 | 3-(methoxycarbonyl)phenyl (CH₃OOC-) | 12 | 3-carboxyphenyl (HOOC-) |
| 4 | 2-chlorophenyl | 13 | 2-methoxyphenyl (OCH₃) |
| 5 | 2-(trifluoromethyl)phenyl (CF₃) | 14 | cyclohexyl |
| 6 | 2-naphthyl | 15 | 3-quinolinyl |
| 7 | 1,2,3,4-tetrahydroquinolin-3-yl | 16 | 2-pyridyl |
| 8 | 2-thienyl | 17 | 2-furyl |
| 9 | imidazolyl (N,N) | 18 | tert-butoxymethyl |

TABLE 69

I (69)

| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |
| 5 | 2-(trifluoromethyl)phenyl | 14 | cyclohexyl |
| 6 | 2-naphthyl | 15 | 3-quinolyl |
| 7 | 1,2,3,4-tetrahydroquinolin-3-yl | 16 | 2-pyridyl |
| 8 | 2-thienyl | 17 | 2-furyl |
| 9 | pyrimidin-5-yl | 18 | tert-butoxymethyl |

TABLE 70

I (70)

| No. | R¹ | No. | R¹ |
|---|---|---|---|
| 1 | Me | 10 | 3-hydroxyphenyl |
| 2 | 2-biphenyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |
| 5 | 2-(trifluoromethyl)phenyl | 14 | cyclohexyl |
| 6 | 2-naphthyl | 15 | 3-quinolyl |
| 7 | 1,2,3,4-tetrahydroquinolin-3-yl | 16 | 2-pyridyl |
| 8 | 2-thienyl | 17 | 2-furyl |
| 9 | pyrimidin-5-yl | 18 | tert-butoxymethyl |

TABLE 71

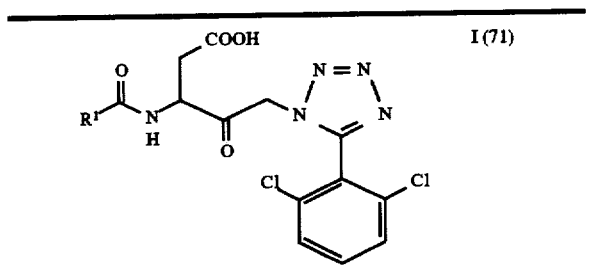

I(71)

| No. | R¹ | No. | R¹ |
|---|---|---|---|
| 1 | Me | 10 | 3-HO-C₆H₄- |
| 2 | 2-biphenyl | 11 | 2-(1H-tetrazol-5-yl)phenyl |
| 3 | 3-CH₃OOC-C₆H₄- | 12 | 3-HOOC-C₆H₄- |
| 4 | 2-Cl-C₆H₄- | 13 | 2-OCH₃-C₆H₄- |
| 5 | 2-CF₃-C₆H₄- | 14 | cyclohexyl |
| 6 | 2-naphthyl | 15 | 3-quinolyl |
| 7 | 1,2,3,4-tetrahydroquinolin-3-yl | 16 | 2-pyridyl |
| 8 | 2-thienyl | 17 | 2-furyl |
| 9 | pyrimidin-5-yl | 18 | t-BuO-C(CH₃)₂- |

TABLE 72

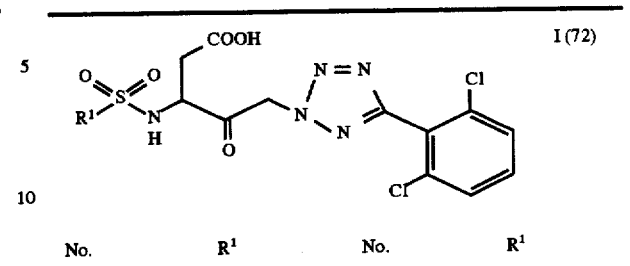

I(72)

| No. | R¹ | No. | R¹ |
|---|---|---|---|
| 1 | Me | 10 | 3-HO-C₆H₄- |
| 2 | 2-biphenyl | 11 | 2-(1H-tetrazol-5-yl)phenyl |
| 3 | 3-CH₃OOC-C₆H₄- | 12 | 3-HOOC-C₆H₄- |
| 4 | 2-Cl-C₆H₄- | 13 | 2-OCH₃-C₆H₄- |
| 5 | 2-CF₃-C₆H₄- | 14 | cyclohexyl |
| 6 | 2-naphthyl | 15 | 3-quinolyl |
| 7 | 1,2,3,4-tetrahydroquinolin-3-yl | 16 | 2-pyridyl |
| 8 | 2-thienyl | 17 | 2-furyl |
| 9 | pyrimidin-5-yl | 18 | t-BuO-C(CH₃)₂- |

TABLE 73
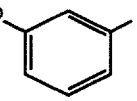
| No. | R¹ | No. | R¹ |
|---|---|---|---|
| 1 | Me | 10 | 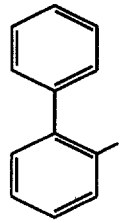 |
| 2 | 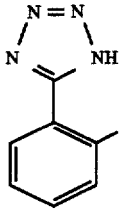 | 11 | 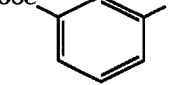 |
| 3 | 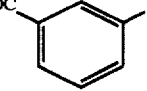 | 12 | 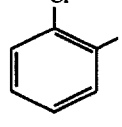 |
| 4 | 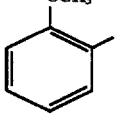 | 13 | 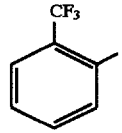 |
| 5 | 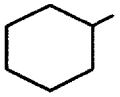 | 14 | (cyclohexyl) |
TABLE 73-continued
(same core structure)
| No. | R¹ | No. | R¹ |
|---|---|---|---|
| 6 | (2-naphthyl) | 15 | (3-quinolinyl) |
| 7 | (1,2,3,4-tetrahydroquinolin-3-yl) | 16 | (2-pyridyl) |
| 8 | (2-thienyl) | 17 | (2-furyl) |
| 9 | (imidazolyl) | 18 | (t-Bu-O-) |

TABLE 74
I (74)
| No. | R¹ | No. | R¹ |
|---|---|---|---|
| 1 | Me | 10 | 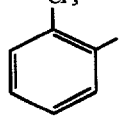 |
| 2 | 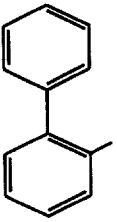 | 11 | 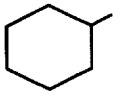 |
| 3 | 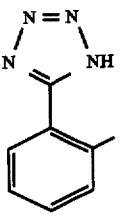 | 12 | 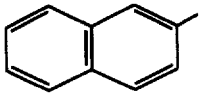 |
| 4 |  | 13 | 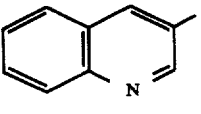 |
| 5 | 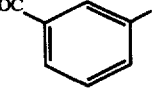 | 14 | 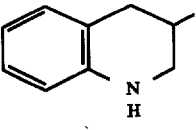 |
| 6 | 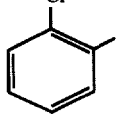 | 15 | 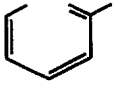 |
| 7 | 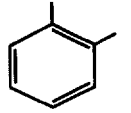 | 16 | 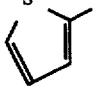 |
| 8 | 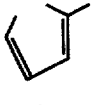 | 17 |  |
| 9 |  | 18 |  |

TABLE 75
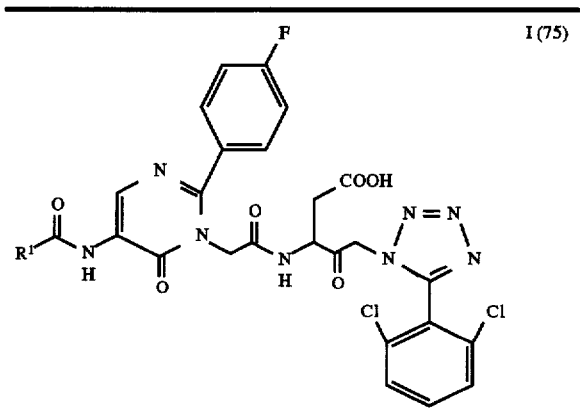
I (75)
| No. | R¹ | No. | R¹ |
|---|---|---|---|
| 1 | Me | 10 | 3-hydroxyphenyl |
| 2 | 2-biphenylyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |
| 5 | 2-(trifluoromethyl)phenyl | 14 | cyclohexyl |
TABLE 75-continued
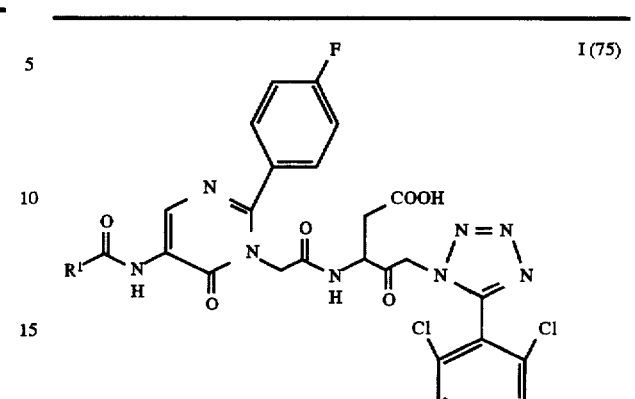
I (75)
| No. | R¹ | No. | R¹ |
|---|---|---|---|
| 6 | 2-naphthyl | 15 | 3-quinolyl |
| 7 | 1,2,3,4-tetrahydroquinolin-3-yl | 16 | 2-pyridyl |
| 8 | 2-thienyl | 17 | 2-furyl |
| 9 | pyrimidin-5-yl | 18 | tert-butoxy |

TABLE 76

I(76)

| No. | R¹ | No. | R¹ |
|---|---|---|---|
| 1 | Me | 10 | 3-hydroxyphenyl |
| 2 | 2-biphenylyl | 11 | 2-(1H-tetrazol-5-yl)phenyl |
| 3 | 3-(methoxycarbonyl)phenyl | 12 | 3-carboxyphenyl |
| 4 | 2-chlorophenyl | 13 | 2-methoxyphenyl |
| 5 | 2-(trifluoromethyl)phenyl | 14 | cyclohexyl |
| 6 | 2-naphthyl | 15 | quinolin-3-yl |
| 7 | 1,2,3,4-tetrahydroquinolin-3-yl | 16 | pyridin-2-yl |
| 8 | thiophen-2-yl | 17 | furan-2-yl |
| 9 | imidazol-4-yl | 18 | tert-butoxy |

TABLE 77

I(77)

[Structure: sulfonamide-containing peptide with 4-fluorophenyl imine, COOH-substituted amino acid, and tetrazole linked to 2,6-dichlorophenyl]

| No. | R¹ | No. | R¹ |
|---|---|---|---|
| 1 | Me | 10 | 3-hydroxyphenyl |
| 2 | biphenyl-2-yl | 11 | 2-(tetrazol-5-yl)phenyl |
| 3 | 2-(methoxycarbonyl)phenyl | 12 | 3-(carboxy)phenyl |
| 4 | 2-chlorophenyl | 13 | 2-methoxyphenyl |
| 5 | 2-trifluoromethylphenyl | 14 | cyclohexyl |
| 6 | 2-naphthyl | 15 | quinolin-3-yl |
| 7 | 1,2,3,4-tetrahydroquinolin-3-yl | 16 | pyridin-2-yl |
| 8 | thiophen-2-yl | 17 | furan-2-yl |

TABLE 77-continued

I(77)

[Structure: same as above]

| No. | R¹ | No. | R¹ |
|---|---|---|---|
| 9 | 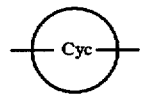 | 18 | 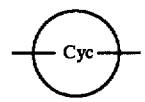 |

Processes for the Preparation

For compounds of formula (I) of the present invention, those in which R does not contain a COOH group, AA¹ does not contain a COOH group, AA² does not contain a COOH group and Y does not contain a COOH group, i.e., the compounds of formula (I-A)

$$R^A—AA^{1A}—AA^{2A}—N(H)—Y^A \qquad (I-A)$$

wherein $R^A$, $AA^{1A}$, $AA^{2A}$ and $Y^A$ have the same meaning as hereinbefore defined for R, $AA^1$, $AA^2$ and Y, respectively, provided that all of $R^A$, $AA^{1A}$, $AA^{2A}$ and $y^A$ do not contain a COOH group may be prepared by methods (a) to (c) as follows.

(a) For compounds of formula (I-A) of the present invention, those in which $R^A$ dord not contain an amino group, $AA^{1A}$ does not contain an amino group, $AA^{2A}$ does not contain an amino group, $Y^A$ does not contain an amino group and $$—(Cyc)—$$

is bonded directly to a carbon atom of tetrazole, i.e., the compounds of formula (I-A-a)

$$R^{A-a}—AA^{1A-a}—AA^{2A-a}—N(H)—Y^{A-a} \qquad (I-A-a)$$

wherein $R^{A-a}$, $AA^{1A-a}$, $AA^{2A-a}$ and $Y^{A-a}$ have the same meaning as hereinbefore defined for $R^A$, $AA^{1A}$, $AA^{2A}$ and $Y^A$, respectively, provided that all of $R^{A-a}$, $AA^{1A-a}$, $AA^{2A-a}$ and $Y^{A-a}$ do not contain an amino group and $$—(Cyc)—$$

is bonded directly to a carbon atom of tetrazole of $Y^{A-a}$ may be prepared by reacting a compound of formula (II-a)

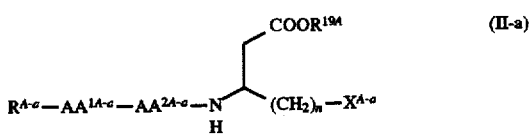

(II-a)

wherein $R^{19A}$ is C1–8 alkyl, phenyl or C1–4 alkyl substituted with phenyl, $X^{A-a}$ is a leaving group known per se (e.g., chlorine, bromine or iodine atom, mesyl, tosyl group etc.) and the other symbols have the same meaning as hereinbefore defined with a compound of formula (III-a)

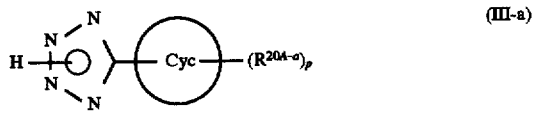

(III-a)

wherein $R^{20A-a}$ has the same meaning as hereinbefore defined for $R^{20}$, provided that $R^{20A-a}$ does not contain COOH and amino groups, the other symbols have the same meaning as hereinbefore defined.

This reaction is known per se, and may be carried out, for example, in an organic solvent (e.g., N,N-dimethylformamide etc.), in the presence of potassium fluoride etc., at a temperature of from 20° C. to 40° C.

(b) For compounds of formula (I-A-a) of the present invention, they may be prepared by reacting a compound of formula (II-b)

(II-b)

wherein $X^{A-b}$ is a leaving group (e.g., chlorine, bromine or iodine atom etc.) or a hydroxy group and the other symbols have the same meaning as hereinbefore defined with a compound of formula (III-b)

(III-b)

wherein all the symbols have the same meaning as hereinbefore defined.

The reaction can be carried out as an amidation reaction, sulfonamidation reaction and the like.

Amidation reactions are known per se and can be carried out by, for example:

(1) using an acid halide, (2) using a mixed acid anhydride, (3) using a condensing agent etc.

Each of those methods can be carried out, for example, as follows:

(1) the method using an acid halide may be carried out, for example, by reacting a carboxylic acid with an acid halide (e.g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with an amine in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C., (2) the method using a mixed acid anhydride may be carried out, for example, by reacting a carboxylic acid and an acid halide (e.g., pivaloyl chloride, tosyl chloride, mesyl chloride etc.) or an acid derivative (e.g., ethyl chloroformate, isobutyl chloroformate etc.) in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.) or without a solvent at a temperature of from 0° C. to 40° C., and then by reacting the mixture of acid anhydride obtained with an amine in an inert organic solvent (e.g., chloroform, methylene chloride, diethyl ether, tetrahydrofuran etc.), at a temperature of from 0° C. to 40° C., or (3) the method using a condensing agent (e.g., 1,3-dicyclohexyl carbodiimide (DCC), 1-ethyl-3-[3-(dimethylamino)propyl]carbodiimide (EDC), 2-chloro-1-methylpyridinium iodide etc.) may be carried out, for example, by reacting a carboxylic acid with an amine using a condensing agent in the presence or absence of a tertiary amine (e.g., pyridine, triethylamine, dimethylaniline, dimethylaminopyridine etc.) in an inert organic solvent (e.g., chloroform, methylene chloride, dimethyl formamide, diethyl ether etc.) Or without a solvent at a temperature of from 0° C. to 40° C.

The reactions (1), (2) and (3) hereinbefore described preferably may be carried out in an atmosphere of inert gas (e.g., argon, nitrogen etc.) under anhydrous conditions.

Sulfonamidation reactions are known pre se, and can be carried out, for example, by reacting a sulfonic acid with an acid halide (e.g., oxalyl chloride, thionyl chloride, phosphous trichloride, phosphous pentachloride etc.) in an inert organic solvent (e.g., chloroform, methylene chloride, diethyl ether, tetrahydrofuran etc.) or without a solvent at from −20° C. to the reflux temperature of the solvent, and then by reacting the sulfonyl halide obtained with an amine in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C.

(c) For compounds of formula (I-A) of the present invention, those in which at least one of $R^A$, $AA^{1A}$, $AA^{2A}$ and $Y^A$ contains an amino group, i.e., the compounds of formula (I-A-c)

(I-A-c)

wherein $R^{A-c}$, $AA^{1A-c}$, $AA^{2A-c}$ and $Y^{A-c}$ have the same meaning as hereinbefore defined for $R^A$, $AA^{1A}$, $AA^{2A}$ and $Y^A$, respectively, provided that at least one of $R^{A-c}$, $AA^{1A-c}$, $AA^{2A-c}$ and $Y^{A-c}$ contains an amino group may be prepared by subjecting the amino protecting group to elimination, the compound prepared by the same methods (a) or (b) above and protecting an amino group as known per se (e.g., t-butyloxycarbonyl, benzyloxycarbonyl, triphenylmethyl or 2-(trimethylsilyl)ethoxymethyl etc.), i.e., the compound of formula (II-c)

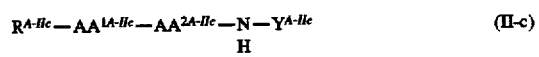

(II-c)

wherein $R^{A-IIc}$, $AA^{1A-IIc}$, $AA^{2A-IIc}$ and $Y^{A-IIc}$ have the same meaning as hereinbefore defined for $R^{A-c}$, $AA^{1A-c}$, $AA^{2A-c}$ and $Y^{A-c}$, respectively, provided that at least one of $R^{A-a-IIc}$, $AA^{1A-IIc}$, $AA^{A-IIc}$ and $Y^{A-IIc}$ contains a protected amino group with a known protecting group (e.g., t-butyloxycarbonyl, benzyloxycarbonyl, triphenylmethyl or 2-(trimethylsilyl) ethoxymethyl etc.).

The elimination of an amino protecting group may be carried out by methods known per se, and depends on the protecting group. For example, when the protecting group is t-butoxycarbonyl, triphenylmethyl or 2-(trimethylsilyl) ethoxymethyl, the reaction may be carried out in a water-miscible organic solvent (e.g., methanol, tetrahydrofuran, dioxane, acetone etc.) in the presence of aqueous solution of organic acid (e.g., acetic acid, trifluoroacetic acid etc.) or inorganic acid (hydrochloric acid, sulfuric acid etc.) or a mixture of them, at a temperature of from 0° C. to 100° C.

When the protecting group is a benzyloxycarbonyl group, the elimination of the protecting group can be carried out by hydrogenation. The hydrogenation reaction is known per se, and may be carried out, for example, in an inert solvent [ether (e.g., tetrahydrofuran, dioxane, diethoxyethane, diethyl ether etc.), alcohol (e.g., methanol, ethanol etc.), benzene analogues (e.g., benzene, toluene etc.), ketone (e.g., acetone, methyl ethyl ketone etc.), nitrile (e.g., acetonitrile etc.), amide (e.g., dimethylformamide etc.), water, ethyl acetate, acetic acid, mixture of two or more of them etc.], in the presence of a catalyst of hydrogenation (e.g., palladium on activated carbon, palladium black, palladium, palladium hydroxide on carbon, platinum oxide, nickel, Raney nickel (registered trade mark) etc.), in the presence or absence of an inorganic acid (e.g., hydrochloric acid, sulfuric acid, hypochlorous acid, boric acid, tetrafluoroboric acid etc.) or an organic acid (e.g., acetic acid, p-toluenesulfonic acid, oxalic acid, trifluoroacetic acid, formic acid etc.), at ordinary or additional pressure under an atmosphere of hydrogen, at a temperature of from 0° C. to 200° C. When using an acid, its salt may be used at the same time.

It should be easily understood by those skilled in the art, that other amino protecting groups that can be used in the present invention are available and the choices are not limited only to t-butyloxycarbonyl, benzyloxycarbonyl, triphenylmethyl or 2-(trimethylsilyl) ethoxymethyl groups. Any group which can be easily and selectively eliminated essentially can be used. For example, a protecting group may be one described in Protective Groups in Organic Synthesis (T. W. Greene, Wiley, New York (1991)). The proposed compounds of the present invention may be easily prepared with those protecting group practicing known methods.

For compounds of formula (I) of the present invention, those in which at least one of R, AA$^1$, AA$^2$ and Y contains a COOH group, i.e., the compounds of formula (I-B)

   (I-A-c)

wherein R$^B$, AA$^{1B}$, AA$^{2B}$ and Y$^B$ have the same meaning as hereinbefore defined for R, AA$^1$, AA$^2$ and Y, respectively, provided that at least one of R$^B$, AA$^{1B}$, AA$^{2B}$ and Y$^B$ contains a COOH group
may be prepared by, for example, hydrolysis of a t-butylester, hydrogenation, hydrolysis of an ester or a cleavage reaction of a 2,2,2-trichloroethylester group of a compound having at least one COOH group derivatized to contain a t-butylester, benzylester, alkylester or 2,2,2-trichloroethylester i.e., the compound of formula (I-A-1)

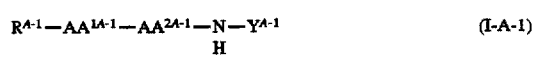   (I-A-1)

wherein R$^{A-1}$, AA$^{1A-1}$, AA$^{2A-1}$ and have the same meaning as hereinbefore defined for R$^A$, AA$^{1A}$, AA$^{2A}$ and Y$^A$, respectively, provided that at least one of R$^{A-1}$, AA$^{1A-1}$, AA$^{2A-1}$ and Y$^{A-1}$ contains a t-butylester, benzylester, alkylester or 2,2,2-trichloroethylester group.

Hydrolysis of t-butylester is known per se, and may be carried out, for example, in an inert organic solvent (e.g., dichloromethane, chloroform, methanol, dioxane, ethyl acetate, anisole etc.) in the presence of an organic acid (e.g., trifluoroacetic acid etc.), or inorganic acid (e.g., hydrochloric acid etc.) or a mixture of them, at a temperature of from 0° C. to 90° C.

Hydrogenation may be carried out by the same method as hereinbefore described.

Hydrolysis of an ester is known per se, and may be carried out, for example, by hydrolysis in acid or under alkaline conditions. Hydrolysis under alkaline conditions may be carried out, for example, in an appropriate organic solvent (e.g., methanol, dimethoxyethane etc.), using a hydroxide or a carbonate of an alkali metal or alkaline earth metal, at a temperature of from 0° C. to 40° C. Hydrolysis under acidic conditions may be carried out by the same method as for hydrolysis of a t-butylester.

Cleavage of 2,2,2-trichloroethylester is known per se, and may be carried out, for example, in an acidic solvent (e.g., acetic acid, buffer of pH4.2–7.2 or a mixture of organic solvent (e.g. tetrahydrofuran etc.) and solution thereof etc.), in the presence of zinc powder, sonicated or not sonicated, at a temperature of from 0° C. to 40° C.

It should be easily understood by those skilled in the art that the carboxyl protecting group of the present invention are not to only t-butylester, benzylester or 2,2,2-trichloroethylester but any group which can be easily and selectively eliminated can be used in the present invention. For example, a protecting group described in Protective Groups in Organic Synthesis (T. W. Greene, Wiley, New York (1991)) may be used. The proposed compounds of the present invention may be easily prepared using those protecting groups and practicing known methods.

For compounds of formula (I) of the present invention, those in which R does not contain COOH and amino groups, AA$^1$ does not contain a COOH and amino group, AA$^2$ does not contain a COOH and amino group and Y does not contain a CO OH and amino group, and R$^{20}$ of Y is an ester or amide group, i.e., the compounds of formula (I-C)

   (I-A-c)

wherein R$^C$, AA$^{1C}$, AA$^{2C}$ and Y$^C$ have the same meaning as hereinbefore defined for R, AA$^1$, AA$^2$ and Y, respectively, provided that at least one of R$^C$, AA$^{1C}$, AA$^{2C}$ and Y$^C$ does not contain a COOH and amino group and R$^{20}$ of Y$^C$ is an ester or amide may be prepared by subjecting to esterification or amidation a compound of formula (I-B), wherein R$^{20}$ contains a COOH group, i.e., a compound of formula (I-B-1)

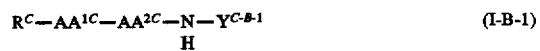   (I-B-1)

wherein Y$^{C-B-1}$ has the same meaning as hereinbefore defined for Y$^C$, provided that R$^{20}$ of Y$^C$ contains a COOH group with an amine compound of formula (III-C-1)

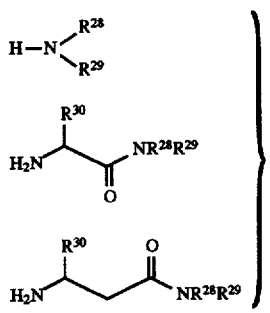 (III-C-1)

wherein all the symbols have the same meaning as hereinbefore defined or with an alcohol compound of formula (III-C-2)

 (III-C-2)

wherein $R^{26}$ has the same meaning as hereinbefore defined.

The amidation reaction may be carried out by the same methods hereinbefore described.

The esterification reaction is known pre se and can be carried out by known methods for example:

(1) using an acid halide, (2) using a mixed acid anhydride, (3) using a condensing agent etc.

Each of those methods can be carried out, for example, as follows:

(1) the method using an acid halide may be carried out, for example, by reacting a carboxylic acid with an acid halide (e.g., oxalyl chloride, thionyl chloride etc.) in an inert organic solvent (e.g., chloroform, methylene chloride, diethyl ether, tetrahydrofuran etc.) or without a solvent at from −20° C. to the reflux temperature of the solvent, and then by reacting the acid halide obtained with an alcohol in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.), at a temperature of from 0° C. to 40° C., (2) the method using a mixed acid anhydride may be carried out, for example, by reacting a carboxylic acid and an acid halide (e.g., pivaloyl chloride, tosyl chloride, mesyl chloride etc.) or an acid derivative (e.g., ethyl chloroformate, isobutyl chloroformate etc.) in the presence of a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.) or without a solvent at a temperature of from 0° C. to 40° C., and then by reacting the mixture of acid anhydride obtained with an alcohol in an inert organic solvent (e.g., chloroform, methylene chloride, diethyl ether, tetrahydrofuran etc.), at a temperature of from 0° C. to 40° C., or (3) the method using a condensing agent (e.g., 1,3-dicyclohexyl carbodiimide (DCC), 1-ethyl-3-[3-(dimethylamino)propyl]carbodiimide (EDC), 2-chloro-1-methylpyridinium iodide etc.) may be carried out, for example, by reacting a carboxylic acid with an alcohol using a condensing agent in the presence or absence of a tertiary amine (e.g., pyridine, triethylamine, dimethylaniline, dimethylaminopyridine etc.) in an inert organic solvent (e.g., chloroform, methylene chloride, dimethyl formamide, diethyl ether etc.) or without a solvent at a temperature of from 0° C. to 40° C.

The reactions (1), (2) and (3) hereinbefore described may be preferably carried out in an atmosphere of inert gas (e.g., argon, nitrogen etc.) under anhydrous conditions.

Further, for compounds of formula (I) of the present invention, those in which at least one of R, $AA^1$, $AA^2$ and Y contains a COOH and amino group, and $R^{20}$ of Y group is an ester or amide group, may be prepared by subjecting to elimination the amino protecting group or carboxyl protecting group hereinbefore described by using a compound of formula (I-C).

A compound of formula (11-a) may be prepared by methods known per se. For example, the compound may be produced by methods described in the literature of J. Med. Chem., 37, 563 (1994) or in EP 0623592.

The products of such synthesis reactions may be purified in a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

The starting materials and each reagents used in the process for the preparation of the present invention are known per se or may be easily prepared by known methods.

Effect

It has been confirmed that the compounds of formula (I) of the present invention have inhibitory activities on IL-1β converting enzyme. For example, in laboratory tests the following results were obtained.

Method (1) Assay for IL-1β converting enzyme

The reaction mixture contains, for example, 20 mM of HEPES-NaOH pH7.4, 10 mM of KOH, 1.5 mM of $MgCl_2$, 0.1 mM of EDTA and 10% glycerol. Various concentrations of test compounds (50 μl), human ICE solution (50 μl) and various concentrations of substrate (Ac-Tyr-Val-Ala-Asp-MCA) were mixed and incubated at 37° C. Fluorescence intensity was measured at En=355 nm and Ex=460 nm. The compounds of the present invention have ICE inhibitory values less than 1 μM (for example, in Example 2(1), the compound has an $IC_{50}$ of 0.03 μM).

In the aboved example method,

HEPES is 4-(2-Hydroxyethyl)-1-piperazineethane-sulfonic acid,

EDTA is Ethylenediamine tetraacetate, and

Ac-Tyr-Val-Ala-Asp-MCA is Acetyl-L-tyrosyl-L-valyl-L-alanyl-L-asparaginic acid 4-methyl-coumarinyl-7-amide.

Toxicity

The compounds of the present invention are substantially non-toxic. Therefore, the compounds of the present invention may be considered sufficiently safe and suitable for pharmaceutical use.

Application for Pharmaceuticals

Compounds of the present invention have an inhibitory activity on ICE in animals, including humans. Therefore the compounds are useful for prevention and/or treatment of insulin dependent diabetes (type I), multiple sclerosis, acute or delayed type hypersensitivity, infectious diseases, infection complications, septic shock, arthritis, colitis, glomerular nephritis, hepatitis, hepatic cirrhosis, pancreatitis, reperfusion injury, cholangeitis, encephalitis, endocarditis, myocarditis, vasculitis, Alzheimer's disease, Parkinson's disease, dementia, cerebral vascular disturbance, neuro-degenerative diseases, bone or cartilage-resorption diseases, AIDS, ARC (AIDS related complex), adult T cell leukemia, hairy cell (pilocytic) leukemia, myelosis, respiratory dysfunction, arthropathy, uveitis, neoplasm, diffuse collagen diseases such as systemic lupus erythematosis or rheumatoid arthritis, ulcerative colitis, Sjogren's syndrome, primary biliary cirrhosis, idiopathic thrombocytopnic purpura, autoimmonohaemolytic anemia, severe myasthenia, osteodisplasia syndrome, periodic thrombocytopenia, aplastic anemia, idiopathic thrombocytopenia, various diseases accompanied with thrombocytopenia such as disseminated intravascular coagulation, adult dyspnea syndrome, hyperplasia of the prostae gland, myoma of the uterus, asthma bronchiole, arteriosclerosis, various kinds of teratoma, nephritis, senile cataract, chronic fatigue syndrome, myodystrophy, peripheral nervous disturbance, Crohn's diseases and osteo arthritics etc. essentially disorders arising from or influenced by IL-1β activity.

For the purpose above described, the compounds of formula (I) of the present invention, non-toxic salts thereof, acid additional salts thereof and hydrates thereof may be normally administered systemically or partially, usually by oral or parenteral administration.

The doses to be administered are determined depending on age, body weight, symptom, the desired therapeutic effect, the route of administration, the duration of the treatment etc. In the human adult, the dose per person is generally between 1 mg and 1000 mg, by oral administration, up to several times per day, and between 0.1 mg and 100 mg, by parenteral administration, up to several times per day, or continuous administration between 1 and 24 hrs. per day intravenously.

As mentioned above, the doses to be used depend on various conditions. Therefore, there are cases in which doses lower than or greater than the ranges specified above may be used.

The compounds of the present invention can be administered as solid compositions, liquid compositions or other compositions for oral administration, as injections, liniments or suppositories etc. for parenteral administration.

Solid compositions for oral administration include compressed tablets, pills, capsules, dispersible powders and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate etc.). The compositions also may comprise, as is normal practice, additional substances other than inert diluents: e.g. lubricating agents (such as magnesium stearate etc.), disintegrating agents (such as cellulose calcium glycolate etc.), stabilizing agents (such as lactose etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phthalate etc.), or be coated with more than two films. Further, the coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (purified water, ethanol etc.). Besides inert diluents, such compositions also may comprise adjuvants (such as wetting agents, suspending agents etc.), sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid etc.). For preparation of such spray compositions, for example, the method described in the U.S. Pat. Nos. 2,868,691 or 3,095,355 (herein incorporated in their entirety by reference) may be used.

Injections for parenteral administration include sterile aqueous or nonaqueous solutions, suspensions and emulsions. In such compositions, one more of active compound (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark) etc.).

Injections may comprise other inert diluents: e.g. preserving agents, wetting agents, emulsifying agents, dispersing agents, stabilizing agent (lactose etc.), assisting agents, such as assisting agents for dissolving (glutamic acid, asparaginic acid etc.) etc.

They may be sterilized for example, by filtration through a bacteria-retaining filter, by incorporation of sterilizing agents in the compositions or by irradiation. They may also be manufactured in the form of sterile, solid compositions, for example, by freeze-drying, which may be dissolved in sterile water or some other sterile diluent(s) for injection immediately before use.

Other compositions for parenteral administration include liquids for external use, and endermic liniments, ointments, suppositories and pessaries which comprise one or more of the active compound(s) and may be prepared by per se known methods.

REFERENCE EXAMPLES AND EXAMPLES

The following reference examples and examples illustrate the present invention, but should not be construed to limit the present invention.

The solvents in the parentheses show the developing or eluting solvents and the ratios of the solvents used are by volume in chromatographic separations and TLC.

NMR in the parentheses show measured solvents. The TLC plate used was Merck 5715, and the HPTLC plate used was Merck 05642.

Reference Example 1

2,6-dichlorobenzamide

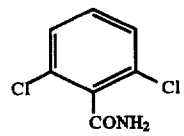

To a solution of 2,6-dichlorobenzoyl chloride(10 g) in dichloromethane (3 ml) was added 28 % aqueous solution of ammonia (25 ml) at 0° C. The reaction mixture was stirred at room temperature for 2 h. To the reaction mixture was added benzene, and the mixture was concentrated under reduced pressure. To the residue was added ethyl acetate, and the mixture was filtered. The filtrate was washed with a saturated aqueous solution of sodium hydrocarbonate and a saturated aqueous solution of sodium chloride, and dried over anhydrous magnesium sulfate and concentrated. The residue was washed with hexane, and dried to give the title compound (7.05 g) having the following physical data.

TLC: Rf 0.60 (hexane:ethyl acetate=1:1).

Reference Example 2

2,6-dichlorobenzonitrile

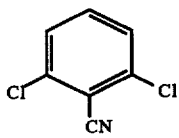

To the compound prepared in reference example 1 (5 g) was added thionyl chloride (8 ml), and the mixture was refluxed for 3 h. After the reaction mixture was concentrated under reduced pressure, the residue was dissolved in ethyl acetate. The ethyl acetate solution was washed with a saturated aqueous solution of sodium hydrocarbonate, water and a saturated aqueous solution of sodium chloride, dried over anhydrous magnesium sulfate and concentrated. The residue was recrystallized from ethyl acetate/hexane to give the title compound (3.56 g) having the following physical data.

TLC: Rf 0.70 (hexane:ethyl acetate=2:1).

Reference Example 3

5-(2,6-dichlorophenol)tetrazole

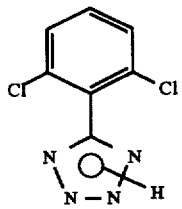

To a solution of the compound prepared in reference example 2 (1.2 g) in toluene (6 ml) was added azidotrimethyltin [$(CH_3)_3SnN_3$] (1.72 g), and the mixture was stirred for 2 days. After the reaction mixture was concentrated under reduced pressure, the residue was dissolved in methanol. To the thus obtained solution was added a 1N aqueous solution of hydrochloric acid (100 ml), and the mixture was stirred for 30 min at room temperature. To the reaction mixture was added a 1N aqueous solution of sodium hydroxide until a pH 3 or 4 was obtained, and the mixture was concentrated under reduced pressure. To the residue was added water, and the mixture was extracted with chloroform. The extract was dried over anhydrous magnesium sulfate and concentrated to give the title compound (1.06 g) having the following physical data.

TLC: Rf 0.11 (chloroform:methanol=10:1).

Example 1

N-((N-(3-phenylpropionyl)-L-valyl)-L-alanyl)-3-amino-4-oxo-5-(5-(2,6-dichlorophenyl)tetrazol-2-yl)pentanoic acid.t-butylester (1) and N-((N-(3-phenylpropionyl)-L-valyl)-L-alanyl)-3-amino-4-oxo-5-(5-(2,6-dichlorophenyl)tetrazol-1-yl)pentanoic acid.t-butylester(2)

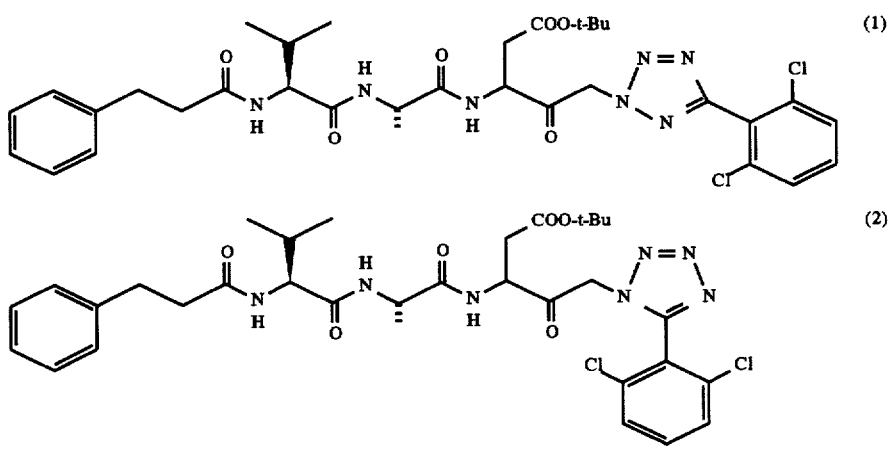

To a solution of N-((N-(3-phenylpropionyl)-L-valyl)-L-alanyl)-3-amino-4-oxo-5-bromopentanoic acid.t-butylester [The compound prepared by the method of J. Med. Chem., 37, 563 (1994)] (0.31 g) in dimethylformamide (7 ml) was successively added potassium fluoride (0.14 g) and the compound prepared in reference example 3 (0.22 g). The reaction mixture was stirred for 2 days at room temperature. The mixture was quenched by addition of water and extracted with ethyl acetate. The extract was washed with a saturated aqueous solution of sodium chloride, dried over anhydrous magnesium sulfate and concentrated. The residue was purified by column chromatography on Merck 7734 silica gel (Merck, registered trade mark) (chloroform:methanol=50:1) to give the title mixture compound (284 mg). The thus obtained mixture compound (110 mg) was purified by column chromatography on NAM-600M silica gel (Nam research institute, registered trade mark) (chloroform:methanol=50:1) to give the compounds of example 1 (1) (51 mg) and example 1 (2) (26 mg) having the following physical dataly.

Example 1(1)

TLC: Rf 0.25 (chloroform:methanol=10:1)

Example 1(2)

TLC: Rf 0.21 (chloroform:methanol=10:1)

Examples 1(3)–1(31)

By the same procedure as provided in example 1, using correspondings tetrazole compounds instead of the compound prepared in reference example 3, compounds of the present invention having the following physical data were obtained.

Example 1(3)

N-((N-(3-phenylpropionyl)-L-valyl)-L-alanyl)-3-amino-4-oxo-5-(5-(2,6-ditrifluoromethylphenyl)tetrazol-2-yl)pentanoic acid.t-butylester

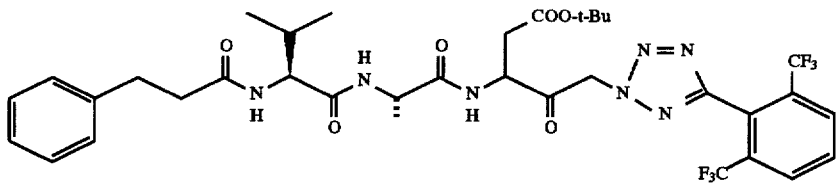

HPTLC: Rf 0.42 (chloroform:methanol=19:1);

NMR (CDCl₃+CD₃OD): δ8.10 (3H, m), 7.90–7.69 (2H, m), 7.34–7.13 (3H, m), 6.80–6.70 (1H, m), 5.98 and 5.74 (each 1H, d, J=17.5 Hz), 4.93–4.80 (1H, m), 4.47–4.28 (1H, m), 4.19–4.07 (1H, m), 2.95 (2H, t, J=7.0 Hz), 2.88–2.67 (2H, m), 2.56 (2H, t, J=7.0 Hz), 2.10–1.95 (1H, m), 1.43 (9H, s), 1.39 (3H, d, J=7.6 Hz), 0.88 and 0.82 (each 3H, d, J=6.8 Hz).

Example 1(4)

N-((N-(3-phenylpropionyl)-L-valyl)-L-alanyl)-3-amino-4-oxo-5-(5-(2,6-ditrifluoromethylphenyl)tetrazol-1-yl)pentanoic acid.t-butylester

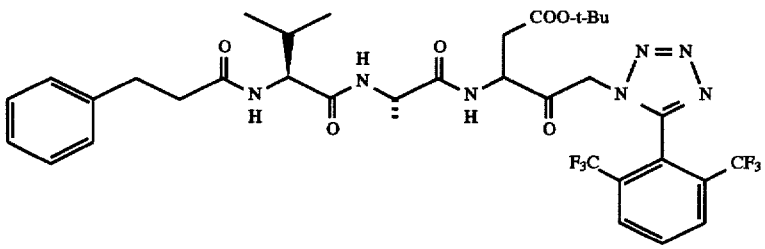

HPTLC: Rf 0.35 (chloroform:methanol=19:1);

NMR (CDCl₃+CD₃OD): δ8.15–8.03 (2H, m), 8.00–7.77 (2H, m), 7.62–7.52 (1H, m), 7.35–7.12 (5H, m), 6.75–6.65 (1H, m), 2.94 (2H, t, J=7.5 Hz), 2.85–2.67 (2H, m), 2.54 (2H, t, J=7.5 Hz), 2.10–1.90 (1H, m), 1.37 (9H, s), 1.27 (3H, d, J=7.2 Hz), 0.82 and 0.78 (each 3H, d, J=7.0 Hz).

Example 1(5)

N-((N-(3-phenylpropionyl)-L-valyl)-L-alanyl)-3-amino-4-oxo-5-(5-(2-chlorophenyl)tetrazol-2-yl)pentanoic acid.t-butylester

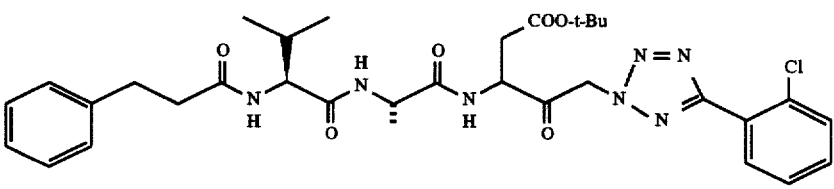

HPTLC: Rf 0.45 (chloroform:methanol=19:1);

NMR (d₆-DMSO): δ8.89 and 8.60 (total 1H, each d, J=7.5 Hz), 8.32 (1H, m), 7.88, 7.72–7.46 and 7.20 (total 10H, m), 6.15–5.83 (2H, m), 4.86 and 4.64 (total 1H, m), 4.20 (2H, m), 2.90–2.31 (6H, m), 1.91 (1H, m), 1.40 (9H, s), 1.25 (3H, m), 0.85 (6H, m).

Example 1(6)

N-((N-(3-phenylpropionyl)-L-valyl)-L-alanyl)-3-amino-4-oxo-5-(5-(2-chlorophenyl)tetrazol-1-yl)pentanoic acid.t-butylester

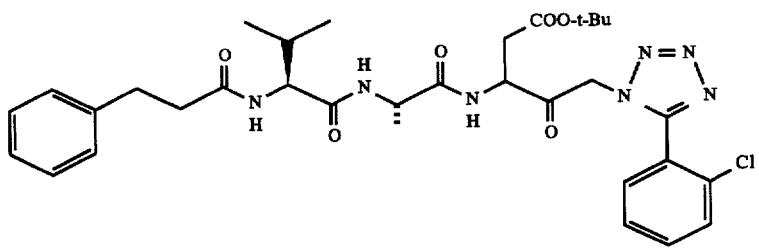

HPTLC: Rf 0.42 (chloroform:methanol=19:1).

Example 1(7)

N-((N-(3-phenylpropionyl)-L-valyl)-L-alanyl)-3-amino-4-oxo-5-(5-(3-chlorophenyl)tetrazol-2-yl)pentanoic acid.t-butylester

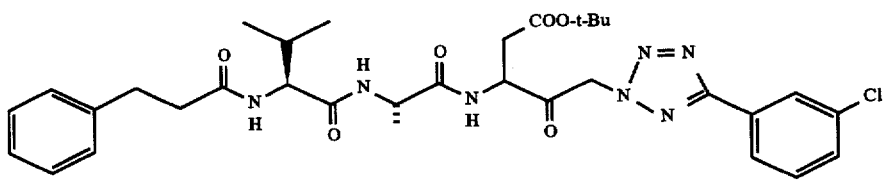

TLC: Rf 0.51 (ethyl acetate:diethyl ether=6:4);

NMR(CD$_3$OD): δ8.80–8.73 (1H, m), 8.44–8.34 (1H, m), 8.10–7.87 (3H, m), 7.60–7.45 (2H, m), 7.30–7.01 (5H, m), 6.11–5.71 (2H, m), 4.80–4.64 (1H, m), 4.39–4.20 (1H, m), 4.20–4.01 (1H, m), 3.01–2.62 (4H, m), 2.56 (2H, t, J=7.5 Hz) 2.11–1.86 (1H, m), 1.57–1.30 (12H, m), 1.06–0.78 (6H, m).

Example 1(8)

N-((N-(3-phenylpropionyl)-L-valyl)-L-alanyl)-3-amino-4-oxo-5-(5-(4-chlorophenyl)tetrazol-2-yl)pentanoic acid.t-butylester

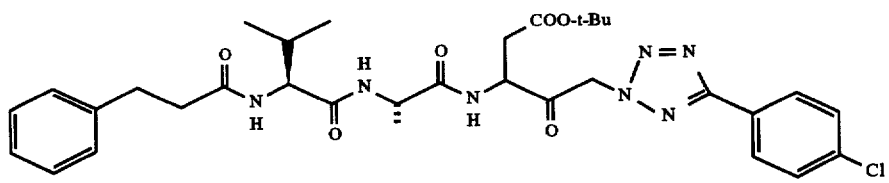

TLC: Rf 0.70 (ethyl acetate:diethyl ether=6:4);

NMR (CD$_3$OD): δ8.15–7.96 (2H, m), 7.57–7.45 (2H, m), 7.30–7.13 (5H, m), 6.00 (1H, d, J=18.0 Hz), 5.81 (1H, d, J=18.0 Hz), 4.75 (1H, t, J=6.0Hz), 4.37–4.24 (1H, m), 4.20–4.03 (1H, m), 3.03–2.71 (4H, m), 2.56 (2H, t, J=7.5 Hz), 2.14–1.90 (1H, m), 1.56–1.27 (12H, m), 1.03–0.76 (6H, m).

Example 1(9)

N-((N-(3-phenylpropionyl)-L-valyl)-L-alanyl)-3-amino-4-oxo-5-(5-(2,3-dichlorophenyl)tetrazol-2-yl)pentanoic acid.t-butylester

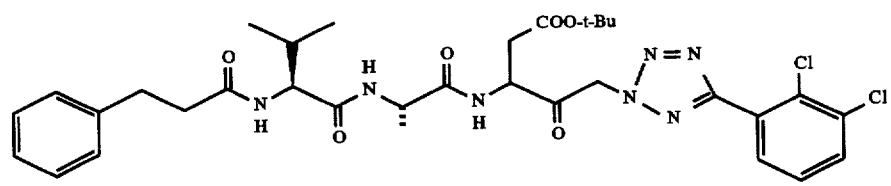

TLC: Rf 0.61 (chloroform:methanol=19:1);

NMR (CD$_3$OD): δ7.82(total 1H, each d, J=8.0 Hz), 7.71 (total 1H, each d, J=8.0 Hz), 7.45 (total 1H, each t, J=8.0

Hz), 7.35–7.13 (5H, m), 6.11 and 5.84 (total 1H, each d, J=18 Hz), 5.87 and 5.84 (total 1H, each d, J=18 Hz), 4.97 and 4.76 (total 1H, each t, J=7.0 Hz), 4.31 and 4.28 (total 1H, each q, J=6.5 Hz), 4.10 (total 1H, each d, J=7.5 Hz), 3.05–2.65 (4H, m), 2.65–48 (2H, m), 2.13–1.92 (1H, m), 1.60–1.28 (12H, m), 1.03–0.80 (6H, m).

Example 1(10)

N-((N-(3-phenylpropionyl)L-valyl)-L-alanyl)-3-amino-4-oxo-5-(5-(4-trifluoromethylphenyl)tetrazol-2-yl)pentanoic acid.t-butylester

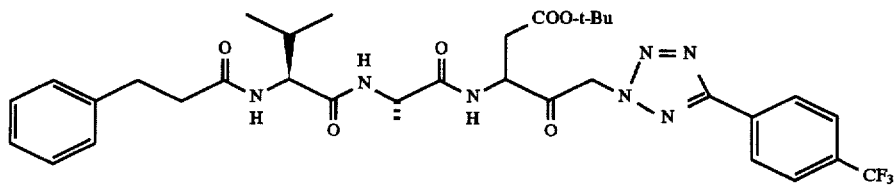

TLC: Rf 0.61 (chloroform:methanol=19:1);

NMR (CD₃OD): δ8.29 (2H, d, J=8.0 Hz), 7.82 (2H, d, J=8.0 Hz), 7.32–7.05 (5H, m), 6.03 (1H, d, J=18.0 Hz), 5.84 (1H, d, J=18.0 Hz), 4.75 (1H, t, J=6.4hz), 4.31 (1H, q, J=7.2 Hz), 4.11 (1H, d, J=7.0 Hz), 2.98–2.65 (4H, m), 2.56 (2H, t, J=8.0 Hz), 2.15–1.91 (1H, m), 1.55–1.20 (12H, m), 1.05–0.76 (6H, m).

Example 1(11)

N-((N-(3-phenylpropionyl)-L-valyl)-L-alanyl)-3-amino-4-oxo-5-(5-(4-nitrophenyl)tetrazol-2-yl)pentanoic acid.t-butylester

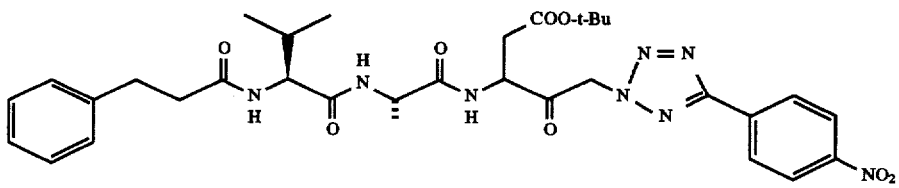

TLC: Rf 0.59 (chloroform:methanol=19:1);

NMR (CDCl₃): δ8.35 (4H, brs), 8.20 (1H, m), 7.54 (1H, m), 7.37–7.10 (5H, m), 6.06 (1H, d, J=18.0 Hz), 5.72 (1H, d, J=18.0 Hz), 4.95–4.80 (1H, m), 4.55–4.33 (1H, m), 4.30–4.12 (1H, m), 2.98 (2H, t, J=7.5 Hz), 2.83 (2H, d, J=6.0 Hz), 2.60 (2H, t, J=7.5 Hz), 2.17–1.98 (1H, m), 1.57–1.23 (12H, m), 1.05–0.77 (6H, m).

Example 1(12)

N-((N-(3-phenylpropionyl)-L-valyl)-L-alanyl)-3-amino-4-oxo-5-(5-phenyltetrazol-2-yl)pentanoic acid.t-butylester

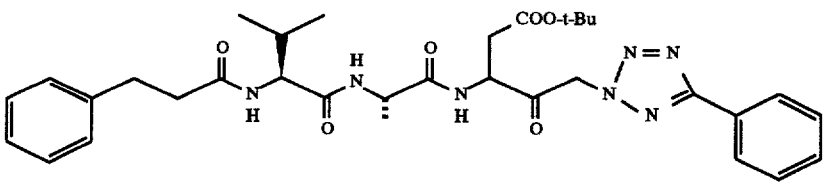

TLC: Rf 0.59 (ethyl acetate:diethyl ether=1:1);

NMR (d₇-DMF): δ8.84 (1H, d, J=8.0 Hz), 8.34 (1H, d, J=6.0 Hz), 8.23–7.87 (4H, m), 7.70–7.48 (2H, m), 7.40–7.11 (5H, m), 6.24–5.98 (2H, m), 4.92–4.77 (1H, m), 4.54–4.14 (1H, m), 3.11–2.82 (4H, m), 2.67–2.50 (2H, m), 2.18–1.95 (1H, m), 1.75–1.22 (12H, m), 1.04–0.77 (6H, m).

Example 1(13)

N-((N-(3-phenylpropionyl)-L-valyl)-L-alanyl)-3-amino-4-oxo-5-(5-(pyridin-2-yl)tetrazol-2-yl)pentanoic acid.t-butylester

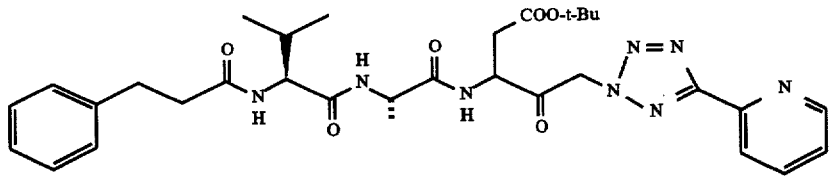

TLC: Rf 0.34 (chloroform:methanol=19:1);

NMR (CDCl₃): δ8.63 (1H, brs), 8.13 (1H, d, J=7.9 Hz), 7.86 (1H, t, J=7.9 Hz), 7.55–7.34 (1H, m), 7.33–6.97 (5H, m), 6.10–5.63 (2H, m), 4.88 and 4.75 (total 1H, each t, each J=6.0 Hz), 4.36–4.13 (1H, m), 4.10–3.95 (1H, m), 2.95–2.56 (4H, m), 2.55–2.40 (2H, m), 2.10–1.76 (1H, m), 1.46–1.08 (12H, m), 1.00–0.58 (6H, m).

Example 1(14)

N-((N-(3-phenylpropionyl)-L-valyl)-L-alanyl)-3-amino-4-oxo-5-(5-(pyridin-3-yl)tetrazol-2-yl)pentanoic acid.t-butylester

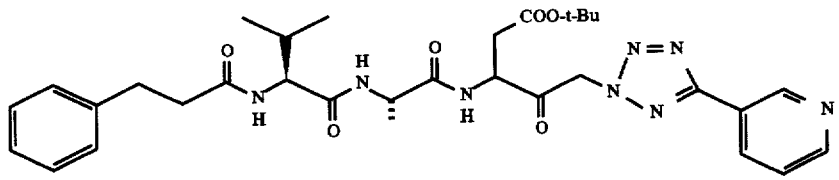

TLC: Rf 0.40 (chloroform:methanol=19:1);

NMR (CD₃OD): δ9.32 (1H, brs), 8.68 (1H, brs), 8.44 (1H, d, J=8.0 Hz), 8.04 (1H, d, J=8.0 Hz), 7.81 (1H, d, J=6.0 Hz), 7.58–7.40 (1H, m), 7.30–7.03 (5H, m), 6.82 (1H, d, J=8.6 Hz), 5.96 (1H, d, J=18.0 Hz), 5.71 (1H, d, J=18.0Hz), 4.95–4.82 (1H, m), 4.50–4.32 (1H, m), 4.28–4.10 (1H, m), 2.95 (2H, t, J=7.5 Hz), 2.88–2.70 (2H, m), 2.56 (2H, t, J=7.5 Hz), 2.15–1.85 (1H, m), 1.70–1.23 (12H, m) 1.05–0.73 (6H, m).

Example 1(15)

N-((N-(3-phenylpropionyl)-L-valyl)-L-alanyl)-3-amino-4-oxo-5-(5-(pyridin-4-yl)tetrazol-2-yl)pentanoic acid.t-butylester

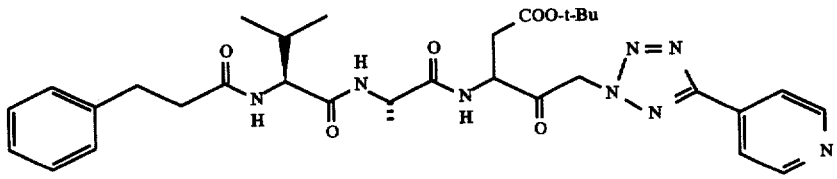

TLC: Rf 0.33 (chloroform:methanol=19:1);

NMR (CDCl₃+CD₃OD): δ8.71 (2H, d, J=6.0 Hz), 8.22 (1H, d, J=7.8 Hz), 8.06 (2H, d, J=8.0 Hz), 7.95 (1H, d, J=6.4 Hz), 7.35–7.13 (5H, m), 7.07 (1H, d, J=8.2 Hz), 6.00 (1H, d, J=18.0 Hz), 5.74 (1H, d, J=18.0 Hz), 4.93–4.77 (1H, m, 4.42–4.20 (1H, m), 4.20–4.06 (1H, m), 2.95 (2H, t, J=7.5 Hz), 2.85 (2H, d, J=5.8 Hz), 2.57 (2H, t, J=7.5Hz), 2.13–1.85 (1H, m), 1.55–1.28 (12H, m), 1.05–0.73 (6H, m).

Example 1(16)

N-((N-(3-phenylpropionyl)-L-valyl)-L-alanyl)-3-amino-4-oxo-5-(5-(2-methoxycarbonylphenyl)tetrazol-2-yl)pentanoic acid.t-butylester

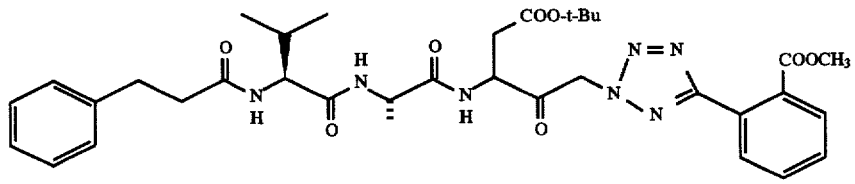

HPTLC: Rf 0.41 (chloroform:methanol=19:1);

NMR (CDCl₃+CD₃OD): δ7.95–7.77 (3H, m), 7.72–7.50 (3H, m), 7.32–7.09 (5H, m), 6.75–6.65 (1H, m), 5.87 and 5.66 (each 1H, d, J=18.0 Hz), 4.89–4.76 (1H, m), 4.47–4.27 (1H, m), 4.23–4.08 (1H, m), 3.76 (3H, s), 2.95 (2H, t, J=8.2 Hz), 2.81 (2H, d, J=6.0 Hz), 2.55 (2H, t, J=8.2 Hz), 2.09–1.88 (1H, m), 1.43 (9H, s), 1.41 (3H, d, J=9.6 Hz), 0.88 and 0.83 (each 3H, d, J=6.8 Hz).

Example 1(17)

N-((N-(3-phenylpropionyl)-L-valyl)-L-alanyl)-3-amino-4-oxo-5-(5-(2-methoxycarbonylphenyl)tetrazol-1-yl)pentanoic acid.t-butylester

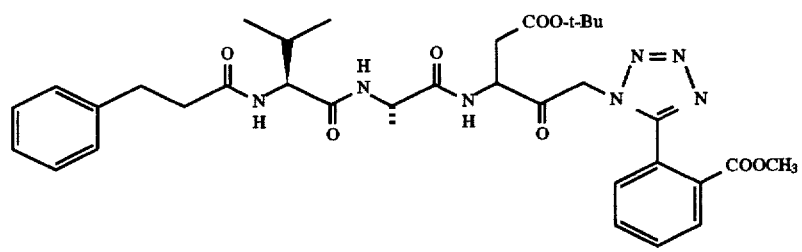

HPTLC: Rf 0.32 (chloroform:methanol=19:1);

NMR (CDCl₃): δ8.18–8.07 (1H, m), 7.66–7.36 (4H, m), 7.33–7.10 (5H, m), 6.95–6.85 (1H, m), 6.47–6.36 (1H, m), 5.46 and 5.23 (each 1H, d, J=18.5 Hz), 4.80–4.63 (1H, m), 4.47–4.22 (1H, m), 4.22–4.10 (1H, m), 3.71 (3H, s), 3.00–2.85 (2H, m), 2.76–2.50 (4H, m), 2.05–1.80 (1H, m), 1.35 (9H, s), 1.32 (3H, d, J=7.4 Hz), 0.83 and 0.79 (each 3H, d, J=7.0 Hz).

Example 1(18)

N-((N-(3-phenylpropionyl)-L-valyl)-L-alanyl)-3-amino-4-oxo-5-(5-(2,6-difluorophenyl)tetrazol-2-yl)pentanoic acid.t-butylester

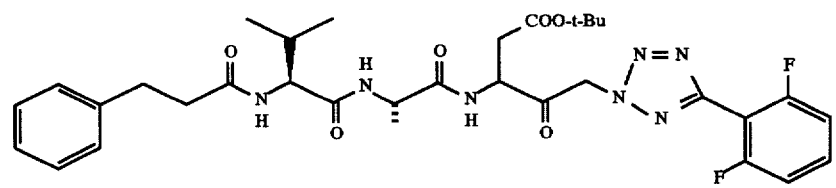

TLC: Rf 0.25 (chloroform:methanol=19:1);

NMR (CDCl₃): δ7.83 (1H, d, J=8.4 Hz), 7.58–7.33 and 7.30–6.97 (8H, m), 6.45 (1H, d, J=8.2 Hz), 5.95 and 5.70 (each 1H, d, J=17.8 Hz), 4.98–4.81 (1H, m), 4.63–4.45 (1H, m), 4.39–4.23 (1H, m), 2.96 (2H, t, J=7.4 Hz), 2.87–2.65 (2H, m), 2.58 (2H, t, J=7.4 Hz), 2.12–1.89 (1H, m), 1.42 (9H, s), 1.40 (3H, d, J=6.6 Hz), 0.88 and 0.82 (each 3H, d, J=6.8 Hz).

Example 1(19)

N-((N-(3-phenylpropionyl)-L-valyl)-L-alanyl)-3-amino-4-oxo-5-(5-(2,6-difluorophenyl)tetrazol-1-yl)pentanoic acid.t-butylester

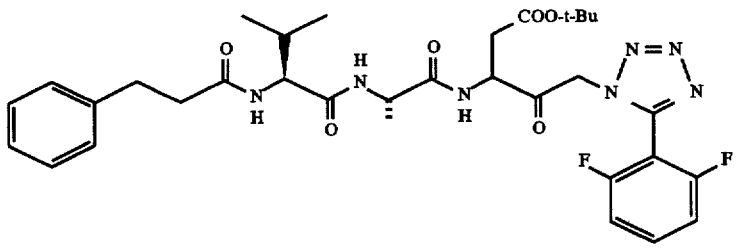

TLC: Rf 0.19 (chloroform:methanol=19:1);

NMR (CDCl₃): δ7.62–7.34 and 7.34–7.00 (9H, m), 6.50 (1H, d, J=7.0 Hz), 5.97 (1H, d, J=7.0 Hz), 5.66 and 5.40 (each 1H, d, J=18.0 Hz), 4.80–4.66 (1H, m), 4.44–4.27 (1H, m), 4.15–4.05 (1H, m), 2.97 (2H, t, J=7.8Hz), 2.95–2.64 (2H, m), 2.58 (2H, t, J=7.8 Hz), 2.10–1.93 (1H, m), 1.36 (3H, d, J=6.5 Hz), 1.33 (9H, s), 0.86 and 0.82 (each 3H, d, J=6.5Hz).

Example 1(20)

N-((N-(3-phenylpropionyl)-L-valyl)-L-alanyl)-3-amino-4-oxo-5-(5-(2,3,4,5,6-pentafluorophenyl)tetrazol-2-yl) pentanoic acid.t-butylester

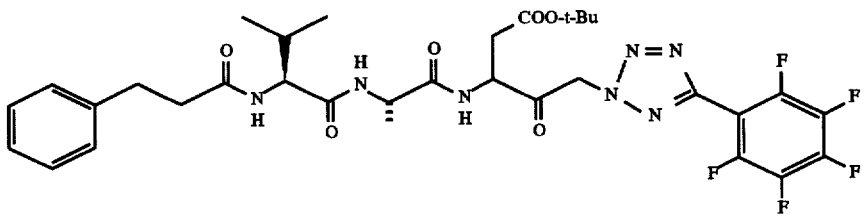

TLC: Rf 0.24 (chloroform:methanol=19:1);

NMR (CDCl₃): δ7.90–7.75 (1H, m), 7.33–6.97 (6H, m), 6.44–6.29 (1H, m), 6.00 and 5.71 (each 1H, d, J=17.8 Hz), 4.96–4.83 (1H, m), 4.63–4.35 (1H, m), 4.35–4.22 (1H, m), 2.96 (2H, t, J=7.4 Hz), 2.87–2.65 (2H, m), 2.59 (2H, t, J=7.4 Hz), 2.12–1.87 (1H, m), 1.43 (9H, s), 1.41 (3H, d, J=7.0 Hz), 0.89 and 0.84 (each 3H, d, J=6.8 Hz).

Example 1(21)

N-((N-(3-phenylpropionyl)-L-valyl)-L-alanyl)-3-amino-4-oxo-5-(5-(2,6-dimethylphenyl)tetrazol-2-yl)pentanoic acid.t-butylester

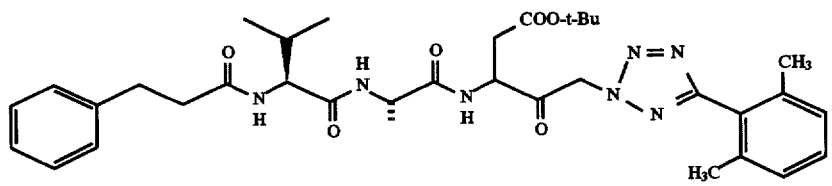

HPTLC: Rf 0.48 (chloroform:methanol=19:1);

NMR (CDCl₃): δ8.02 (1H, d, J=7.5 Hz), 7.37–7.06 (9H, m), 6.69 (1H, d, J=7.5 Hz), 6.01 and 5.69 (each 1H, d, J=18.5 Hz), 5.01–4.85 (1H, m), 4.58–4.35 (1H, m), 4.31–4.18 (1H, m), 3.03–2.88 (2H, m), 2.88–2.76 (2H, m), 2.63–2.49 (2H, m), 2.14 and 2.11 (total 6H, s), 2.20–1.96 (1H, m), 1.43 (9H, s), 1.42 (3H, d, J=6.4 Hz), 0.91 and 0.86 (each 3H, d, J=7.0 Hz).

Example 1(22)

N-((N-(3-phenylpropionyl)-L-valyl)-L-alanyl)-3-amino-4-oxo-5-(5-(2,6-dimethylphenyl)tetrazol-1-yl)pentanoic acid.t-butylester

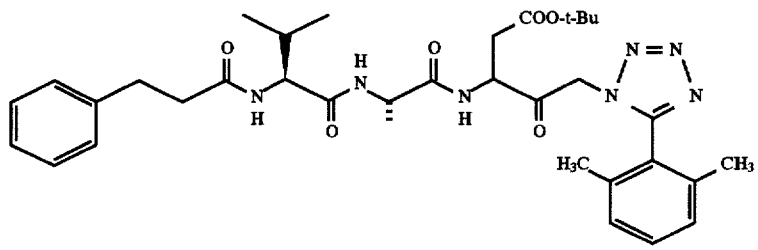

HPTLC: Rf 0.43 (chloroform:methanol=19:1);

NMR (CDCl₃): δ7.45–7.05 (9H, m), 6.72–6.65 and 6.65–6.55 (total 1H, m), 6.16–6.08 and 6.08–6.00 (1H, m), 5.47 and 5.33 (total 1H, each d, J=18.0 Hz), 5.10 and 5.03 (total 1H, each d, J=18.0 Hz), 4.82–4.67 (1H, m), 4.41–4.22 (1H, m), 4.13–3.95 (1H, m), 2.95 (2H, t, J=7.6 Hz), 2.80–2.47 (4H, m), 2.12–1.87 (1H, m), 2.02 and 2.00 (total 6H, each s), 1.36 (9H, s), 1.31 (3H, d, J=7.4 Hz), 0.83 and 0.80 (each 3H, d, J=6.6 Hz).

Example 1(23)

N -((N-(3-phenylpropionyl)-L-valyl)-L-alanyl)-3-amino-4-oxo-5-(5-(2-chloro-6-methoxycarbonylphenyl)tetrazol-2-yl)pentanoic acid.t-butylester

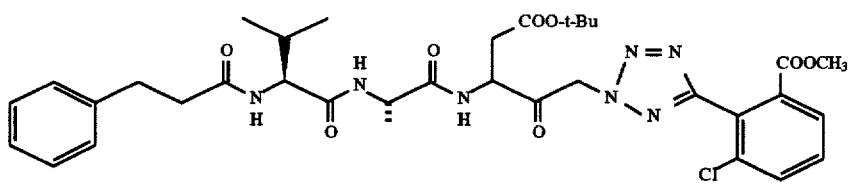

TLC: Rf 0.63 (chloroform:methanol=19:1);

NMR (d₆-DMSO): δ8.87 and 8.60 (total 1H, m), 8.32 (1H, m), 7.99–7.68 (4H, m), 7.32–7.08 (5H, m), 6.13–5.72 (2H, m), 4.85 and 4.63 (total 1H, m), 4.33–4.09 (2H, m), 3.60 (3H, s), 2.93–2.36 (6H, m), 1.89 (1H, m), 1.39 (9H, s), 1.26 (3H, m), 0.80 (6H, m).

Example 1(24)

N-((N-(3-phenylpropionyl)-L-valyl)-L-alanyl)-3-amino-4-oxo-5-(5-((2-phenyl)phenyl)tetrazol-2-yl)pentanoic acid.t-butyl ester

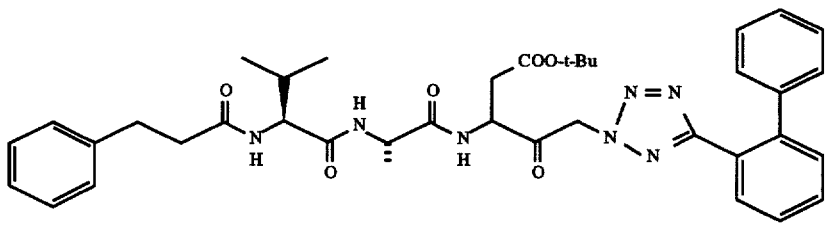

TLC: Rf 0.41 (chloroform:benzene:methanol=50:50:1);

NMR (d₆-DMSO): 8.81 and 8.56 (total 1H, each d, each J=7.0, 8.0 Hz) 8.40–7.93 (2H, m), 7.93–7.80 (1H, m), 7.72–7.43 (4H, m), 7.43–7.00 (9H, m), 6.00–5.64 (2H, m), 4.90–4.50 (1H, m), 4.35–4.06 (2H, m), 2.88–2.67 (2H, m), 2.67–2.22 (4H, m), 2.05–1.73 (1H, m), 1.38 (9H, s), 1.30–1.04 (3H, m), 0.95–0.58 (6H, m).

Example 1(25)

N-((N-(3-phenylpropionyl)-L-valyl)-L-alanyl)-3-amino-14-oxo-5-(5-((2-phenyl)phenyl)tetrazol-1-yl)pentanoic acid.t-butyl ester

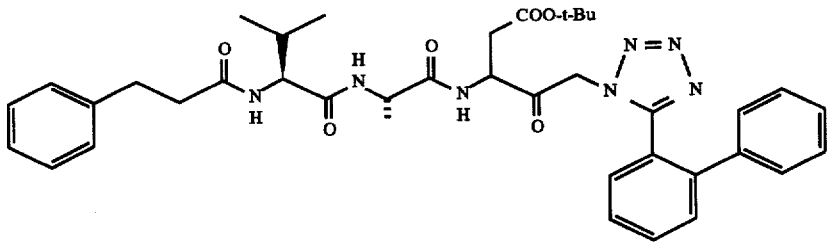

TLC: Rf 0.37(chloroform:benzene:methanol=50:50:1);

NMR (d$_6$-DMSO): δ8.50–8.35 (1H, m), 8.25–8.08 (1H, m), 7.98–7.80 (1H, d, J=7.5 Hz), 7.80–7.06 (14H, m), 5.50–4.95 (2H, m), 4.70–4.38 (1H, m), 4.35–4.04 (2H, m), 2.86–2.71 (2H, m), 2.70–2.30 (4H, m), 2.01–1.74 (1H, m), 1.30 (9H, s), 1.25–1.10 (3H, m), 0.95–0.55 (6H, m).

Example 1(26)

N-((N-(3-phenylpropionyl)-L-valyl)-L-alanyl)-3-amino-4-oxo-5-(5-(2,6-dimethoxyphenyl)tetrazol-2-yl)pentanoic acid.t-butyl ester

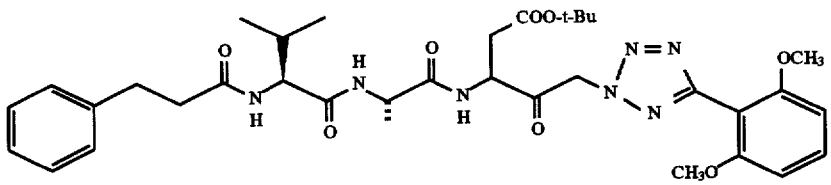

TLC: Rf 0.55 (chloroform:methanol=19:1);

NMR (d$_6$-DMSO): δ8.86 and 8.61 (total 1H, d, J=7.6 Hz), 8.32 (1H, m), 7.92 (1H, d, J=8.4 Hz), 7.48 (1H, t, J=8.6 Hz), 7.30–7.06 (5H, m), 6.78 (2H, d, J=8.6 Hz), 6.03–5.74 (2H, m), 4.90–4.53 (total 1H, m), 4.28–4.06 (2H, m), 3.67 (6H, s), 2.90–2.26 (6H, m), 2.03–1.75 (1H, m), 1.40 (9H, s), 1.24 (3H, d, J=6.8 Hz), 0.83 (3H, d, J=6.8 Hz), 0.77 (3H, d, J=6.8Hz).

Example 1(27)

N-((N-(3-phenylpropionyl)-L-valyl)-L-alanyl)-3amino 4-oxo-5-(5-(2,6-dimethoxyphenyl)tetrazol-1-yl)pentanoic acid.t-butyl ester

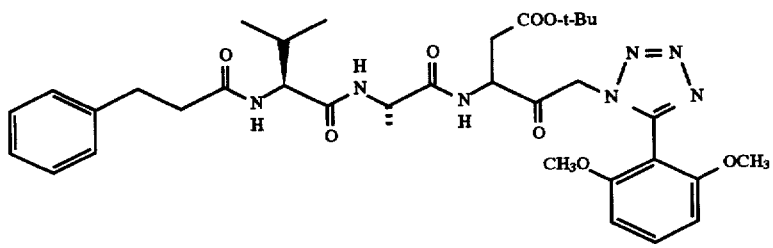

TLC: Rf 0.43 (chloroform:methanol=19:1);

NMR (d$_6$-DMSO): δ8.47 (1H, d, J=7.4 Hz), 8.17 (1H, d, J=6.4 Hz), 7.88 (1H, d, J=8.2 Hz), 7.54 (1H, t, J=8.4 Hz), 7.31–7.10 (5H, m), 6.81 (2H, d, J=8.4 Hz), 5.39 and 5.17 (total 2H, d, J=17.1 Hz), 4.50–4.37 (total 1H, m), 4.29–4.01 (2H, m), 3.68 (6H, s), 2.88–2.32 (6H, m), 2.01–1.78 (1H, m), 1.34 (9H, s), 1.16 (3H, d, J=7.0 Hz), 0.81 (3H, d, J=6.9 Hz), 0.77 (3H, d, J=6.9 Hz).

Example 1(28)

N-((N-(3-phenylpropionyl)-L-valyl)-L-alanyl)-3-amino-4-oxo-5-(5-(morpholin-1-yl)tetrazol-2-yl)pentanoic acid.t-butyl ester

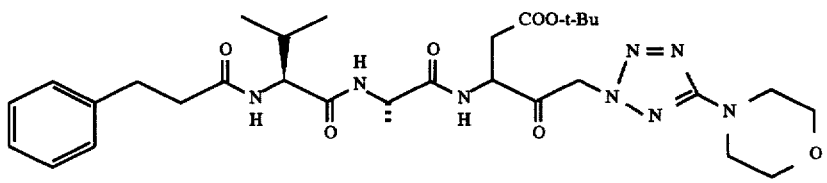

TLC: Rf 0.45 (chloroform:methanol=15:1);

NMR(d₆-DMSO): δ8.79 and 8.59 (total 1H, each d J=8 Hz), 8.28 (1H, m), 7.90 (1H, m), 7.20 (5H, m), 5.80–5.50 (2H, m), 4.78 and 4.58 (total 1H, each m), 4.18 (2H, m), 3.70 (4H, brs), 3.34 (4H, brs), 2.80 and 2.50 (total 6H, each m), 1.90 (1H, m), 1.40 (9H, s), 1.22 (3H, m), 0.82 (6H, m).

Example 1(29)

N-((N-(3-phenylpropionyl)-L-valyl)-L-alanyl)-3-amino-4-oxo-5-(5-(piperidin-1-yl)tetrazol-2-yl)pentanoic acid.t-butyl ester

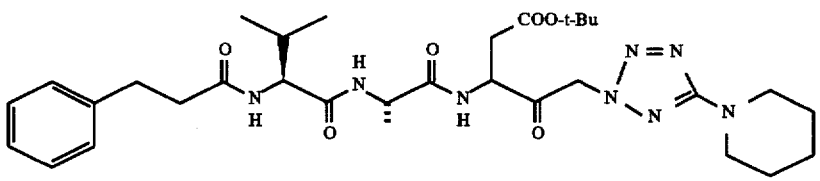

TLC: Rf 0.31 (chloroform:methanol=19:1);

NMR (CDCl₃): δ7.52 (1H, m), 7.30–7.10 (5H, m), 6.78 (1H, m), 6.20 (1H, m), 5.62–5.30 (2H, m), 4.84 (1H, m), 4.44 (1H, m), 4.20 (1H, m), 3.50–3.40 m), 3.00–2.84 (2H, m), 2.82–2.70 (2H, m), 2.66–2.50 (2H, m), 2.00 (1H, m), 1.76–1.56 (6H, m), 1.50–1.40 (12H, m), 0.96–0.90 (6H, m).

Example 1(30)

N-((N-(3-phenylpropionyl)-L-valyl)-L-alanyl)-3-amino-4-oxo-5-(5-(pyrrolidin-1-yl)tetrazol-2-yl)pentanoic acid.t-butyl ester

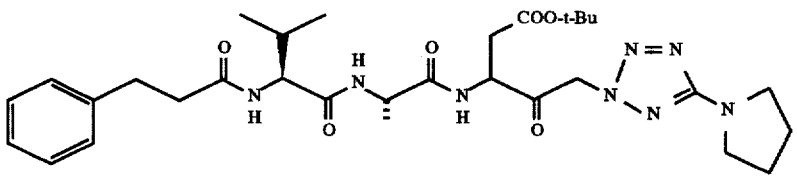

TLC: Rf 0.31 (chloroform:methanol=19:1);

NMR (CDCl₃): δ7.56 (1H, m), 7.26–7.10 (5H, m), 6.82 (1H, m), 6.24 (1H, m), 5.64–5.30 (2H, m), 4.88 (1H, m), 4.44 (1H, m), 4.22 (1H, m), 3.50–3.40 (4H, m), 3.00–2.84 (2H, m), 2.82–2.70 (2H, m), 2.60–2.50 (2H, m), 2.08–1.90 (4H, m), 1.44–1.36 (12H, m), 0.96–0.78 (6H, m).

Example 1(31)

N-((N-(3-phenylpropionyl)-L-valyl)-L-alanyl)-3-amino-4-oxo-5-(5-(pyridin-2-yl)tetrazol-1-yl)pentanoic acid.t-butyl ester

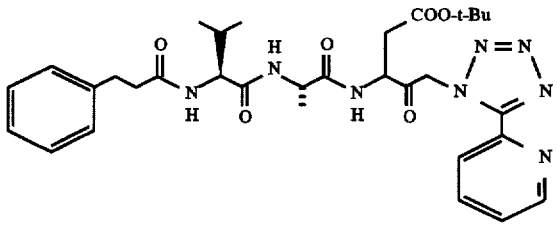

TLC: Rf 0.26 (chloroform:methanol:acetic acid=18:1:1);

NMR (d₆-DMSO): δ8.80–8.60 (2H, m), 8.35–8.20 (2H, m), 8.06 (1H, t, J=8.0 Hz), 7.93 (1H, d, J=8.0 Hz), 7.65–7.51 (1H, m), 7.36–7.03 (5H, m), 5.92 (2H, brs), 4.87–4.69 (1H, m), 4.36–4.04 (2H, m), 2.90–2.28 (6H, m), 2.07–1.80 (1H, m), 1.27 (3H, d, J=7.2 Hz), 0.97–0.63 (6H, m).

Example 2(1)

N-((N-(3-phenylpropionyl)-L-valyl)-L-alanyl)-3-amino-4-oxo-5-(5-(2,6-dichlorophenyl)tetrazol-2-yl)pentanoic acid

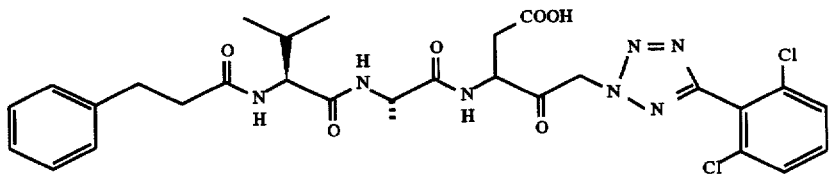

To a solution of compound (1) prepared in example 1 (51 mg) in thioanisole (0.34 ml) and m-cresole (0.31 ml) was added trifluoroacetic acid (3.5 ml). The reaction mixture was stirred for 2 h at room temperature. To the reaction mixture was added toluene, and then the mixture was concentrated. The residue was washed with diethyl ether, and dried over to give the compound of the present invention (28 mg) having the following physical data.

TLC: Rf 0.38 (chloroform:ethanol:acetic acid=18:1:1);

NMR (CD$_3$OD): δ8.86 and 8.62 (total 1H, m), 8.29 (1H, m), 7.85 (1H, m), 7.68 (3H, m), 7.20 (5H, m), 6.05 (2H, m), 4.60 (1H, m), 4.38–4.05 (2H, m), 2.90–2.20 (6H, m), 1.95 (1H, m), 1.25 (3H, m), 0.80 (6H, m).

Examples 2(2)–(31)

By the same procedure as provided in example 2(1), and if necessary, by known methods converted to accomodate the corresponding salts, using the compounds of examples 1(2)–1(31) instead of compound (1) prepared in example 1, compounds of the present invention having the following physical data were obtained.

Example 2(2)

N-((N-(3-phenylpropionyl)-L-valyl)-L-alanyl)-3-amino-4-oxo-5-(5-(2,6-dichlorophenyl)tetrazol-1-yl)pentanoic acid

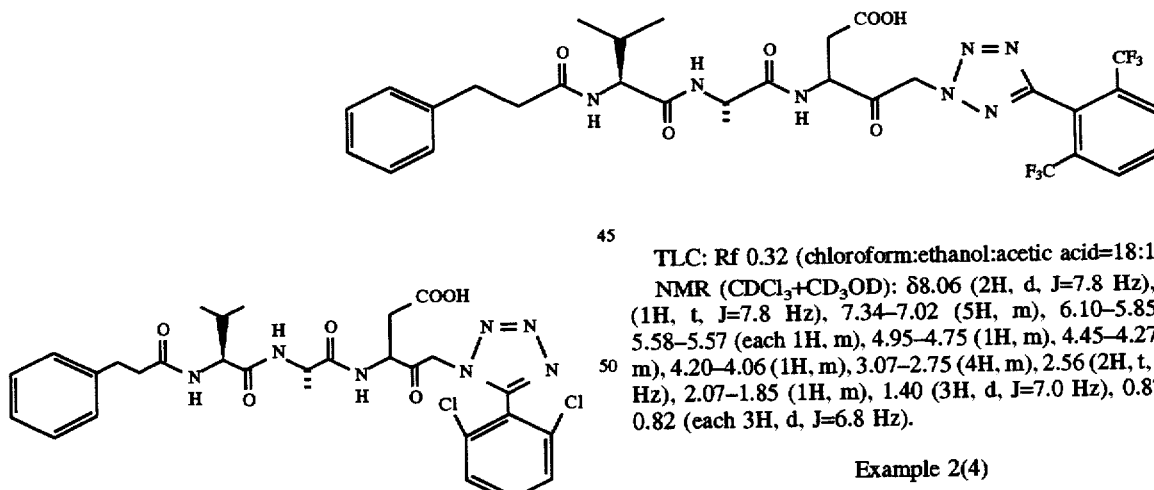

TLC: Rf 0.30 (chloroform:ethanol:acetic acid=18:1:1);

NMR (d$_6$-DMSO): δ8.50 (1H, m), 8.15 and 8.08 (total 1H, m), 7.84 (1H, m), 7.68 (3H, m), 7.21 (5H, m), 5.69–5.33 (2H, m), 4.56 (1H, m), 4.33–4.02 (2H, m), 2.90–2.30 (6H, m), 1.89 (1H, m), 1.17 (3H, m), 0.78 (6H, m).

Example 2(3)

N-((N-(3-phenylpropionyl)-L-valyl)-L-alanyl)-3-amino-4-oxo-5-(5-(2,6-ditrifluoromethylphenyl)tetrazol-2-yl)pentanoic acid TLC: Rf 0.32 (chloroform:ethanol:acetic acid=18:1:1);

NMR (CDCl$_3$+CD$_3$OD): δ8.06 (2H, d, J=7.8 Hz), 7.86 (1H, t, J=7.8 Hz), 7.34–7.02 (5H, m), 6.10–5.85 and 5.58–5.57 (each 1H, m), 4.95–4.75 (1H, m), 4.45–4.27 (1H, m), 4.20–4.06 (1H, m), 3.07–2.75 (4H, m), 2.56 (2H, t, J=8.0 Hz), 2.07–1.85 (1H, m), 1.40 (3H, d, J=7.0 Hz), 0.87 and 0.82 (each 3H, d, J=6.8 Hz).

Example 2(4)

N-((N-(3-phenylpropionyl)-L-valyl)-L-alanyl)-3-amino-4-oxo-5-(5-(2,6-ditrifluoromethylphenyl)tetrazol-1-yl)pentanoic acid

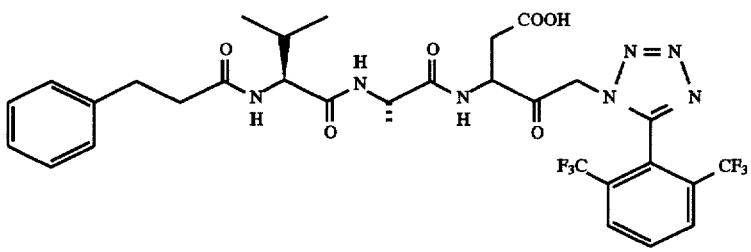

TLC: Rf 0.24 (chloroform:ethanol:acetic acid=18:1:1);

NMR (d$_6$-DMSO): δ8.50–8.26 (3H, m), 8.22–7.95 (2H, m), 7.87–7.74 (1H, m), 7.33–7.08 (5H, m), 5.47–5.32 (2H, m), 4.65–4.47 (1H, m), 4.26–3.95 (2H, m), 2.87–2.67 (2H, m), 2.67–2.35 (4H, m), 2.01–1.77 (1H, m), 1.30–1.03 (3H, m), 0.87–0.67 (6H, m).

Example 2(5)

N-((N-(3-phenylpropionyl)-L-valyl)-L-alanyl)-3-amino-4-oxo-5-(5-(2-chlorophenyl)tetrazol-2-yl)pentanoic acid

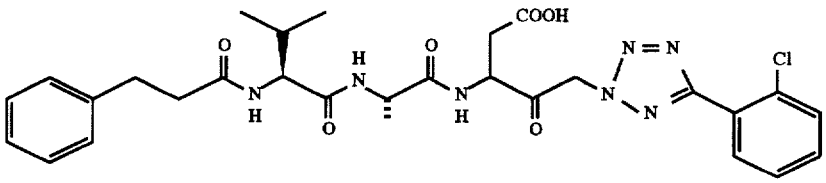

TLC: Rf 0.63, 0.60 (chloroform:ethanol:acetic acid= 18:1:1);

NMR (d$_6$-DMSO): δ8.83 and 8.63 (total 1H, m), 8.30 (1H, m), 7.95–7.45 (5H, m), 7.20 (5H, m), 6.15–5.77 (2H, m), 4.78 and 4.65 (total 1H, m), 4.35–4.08 (2H, m), 2.90–2.29 (6H, m), 1.92 (1H, m), 1.26 (3H, m), 0.80 (6H, m).

Example 2(6)

N-((N-(3-phenylpropionyl)-L-valyl)-L-alanyl)-3-amino-4-oxo-5-(5-(2-chlorophenyl)tetrazol-1-yl)pentanoic acid

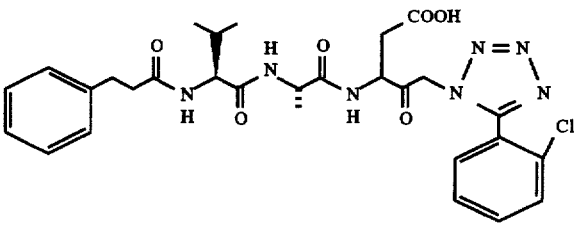

TLC: Rf 0.54, 0.53 (chloroform:ethanol:acetic acid= 18:1:1);

NMR (d$_6$-DMSO): δ12.5 (1H, brs), 8.51 (1H, m), 8.20 and 8.11(total 1H, m), 7.85 (1H, m), 7.76–7.36 (4H, m), 7.22 (5H, m), 5.78–5.34 (2H, m), 4.54 (1H, m), 4.16 (2H, m), 2.80 (2H, m), 2.70–2.26 (4H, m), 1.88 (1H, m), 1.17 (3H, m), 0.78 (6H, m).

Example 2(7)

N-((N-(3-phenylpropionyl)-L-valyl)-L-alanyl)-3-amino-4-oxo-5-(5-(3-chlorophenyl)tetrazol-2-yl)pentanoic acid

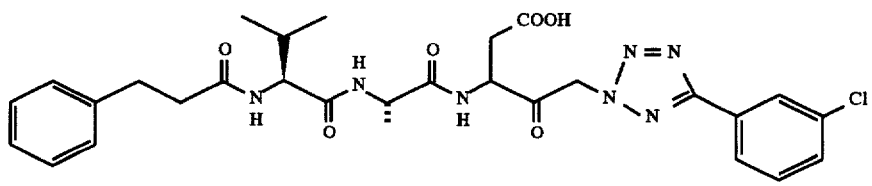

TLC: Rf 0.58 (chloroform:methanol:acetic acid=18:1:1);

231

NMR (CD₃OD): δ8.10–7.90 (2H, m), 7.54–7.45 (2H, m), 7.25–7.07 (5H, m), 6.09–5.80 (2H, m), 4.73 (1H, t, J=7.0 Hz), 4.31 (1H, q, J=7.0 Hz), 4.11 (1H, d, J=7.0 Hz), 3.07–2.76 (4H, m), 2.56 (2H, t, J=7.0 Hz), 2.10–1.95 (1H, m), 1.40 (3H, d, J=7.0 Hz), 0.96–0.88 (6H, m).

Example 2(8)

N-((N-(3-phenylpropionyl)-L-valyl)-L-alanyl)-3-amino-4-oxo-5-(5-(4-chlorophenyl)tetrazol-2-yl)pentanoic acid

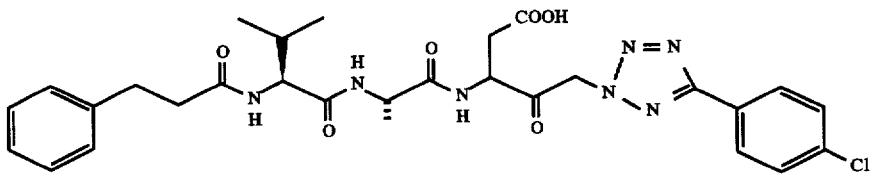

TLC: Rf 0.55, 0.42 (ethyl acetate:diethyl ether=6:4);

NMR (CD₃OD): δ8.08 (2H, d, J=8.8 Hz), 7.53 (2H, d, J=8.8 Hz), 7.30–7.08 (5H, m), 4.38–4.25 (1H, m), 4.17–4.08 (1H, m), 2.97–2.75 (4H, m), 2.60–2.56 (2H, m), 2.13–1.92 (1H, m), 1.42–1.23 (3H, m), 0.97–0.73 (6H, m).

Example 2(9)

N-((N-(3-phenylpropionyl)-L-valyl)-L-alanyl)-3-amino-4-oxo-5-(5-(2,3-dichlorophenyl)tetrazol-2-yl)pentanoic acid

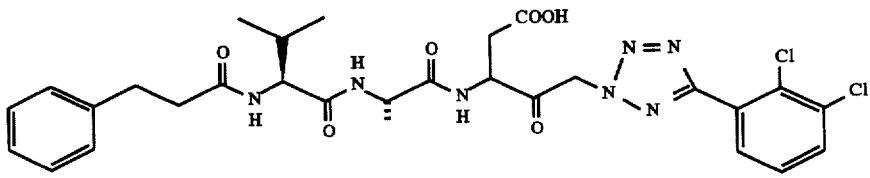

TLC: Rf 0.55, 0.42 (chloroform:methanol=19:1);

NMR (CD₃OD): δ7.89 and 7.80 (total 1H, each d, J=8.0 Hz), 7.75 (1H, d, J=8.0 Hz), 7.43 (1H, t, J=8.0 Hz), 7.30–7.07 (5H, m), 6.25–5.70 (2H, m), 4.93 and 4.78 (total 1H, each m), 4.46–4.20 (1H, m), 4.17–4.05 (1H, m), 3.10–2.68 (4H, m), 2.62–2.48 (2H, m), 2.11–1.87 (1H, m), 1.50–1.25 (3H, m), 1.00–0.73 (6H, m).

Example 2(10)

N-((N-(3-phenylpropionyl)-L-valyl)-L-alanyl)-3-amino-4-oxo-5-(5-(4-trifluoromethylphenyl)tetrazol-2-yl)pentanoic acid

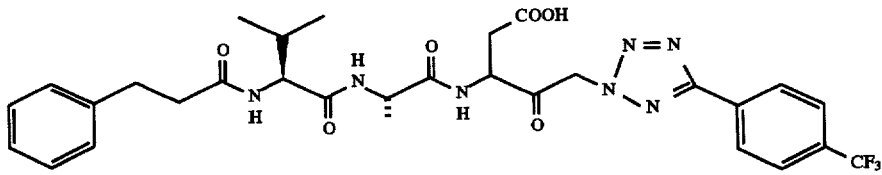

TLC: Rf 0.45 (chloroform:methanol=19:1);

NMR (CDCl₃+d₆-DMSO): δ8.26 (2H, d, J=8.0 Hz), 8.20–8.00 (1H, m), 7.75 (2H, d, J=8.0 Hz), 7.58–7.46 (1H, m), 7.33–7.09 (5H, m), 6.98–6.78 (1H, m), 6.20–5.52 (2H, m), 5.04–4.75 (1H, m), 4.55–4.38 (1H, m), 4.33–4.12 (1H, m), 3.12–2.75 (4H, m), 2.68–2.46 (2H, m), 2.21–1.91 (1H, m), 1.50–1.30 (3H, m), 1.02–0.78 (6H, m).

Example 2(11)

N-((N-(3-phenylpropionyl)-L-valyl)-L-alanyl)-3amino-4-oxo-5-(5-(4-nitrophenyl)tetrazolo-2-yl)pentanoic acid 233 234

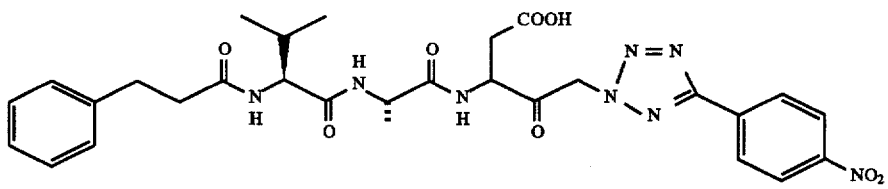

TLC: Rf 0.19 (chloroform:methanol=19:1);

NMR (CDCl$_3$+d$_6$-DMSO): δ8.42–8.38 (4H, brs), 8.20–8.06 (1H, m), 7.56 (1H, d, J=7.5 Hz), 7.35–7.10 (5H, m), 6.06–6.90 (1H, m), 6.17–5.64 (2H, m), 5.00–4.82 (1H, m), 4.57–4.35 (1H, m), 4.28–4.12 (1H, m)3.06–2.45 (4H, m), 2.20–1.92 (1H, m), 1.57–1.19 (3H, m), 1.04–0.70 (6H, m).

Example 2(12)

N-((N-(3-phenylpropionyl)-L-valyl)-L-alanyl)-3-amino-4-oxo-5-(5-phenyltetrazol-2-yl)pentanoic acid

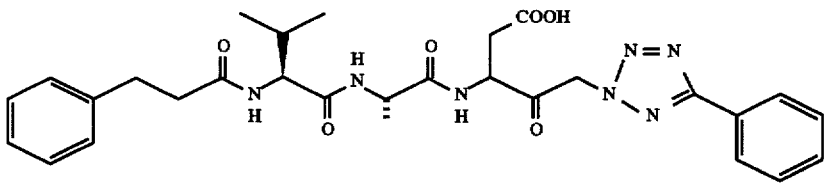

TLC: Rf 0.42 (chloroform:methanol:acetic acid=18:1:1);

NMR (d$_7$DMF): δ8.87–8.61 (2H, m), 8.49–8.34 (1H, m), 8.28–8.03 (2H, m), 7.62–7.47 (3H, m), 7.33–7.07 (5H, m), 6.32–5.82 (2H, m), 4.86–4.31 (3H, m), 3.05–2.45 (6H, m), 2.19–1.92 (1H, m), 1.49–1.22 (3H, m), 1.01–0.79 (6H, m).

Example 2(13)

N-((N-(3-phenylpropionyl)-L-valyl)-L-alanyl)-3-amino-4-oxo-5-(5-(pyridin-2-yl)tetrazol-2-yl)pentanoic acid.hydrochloride

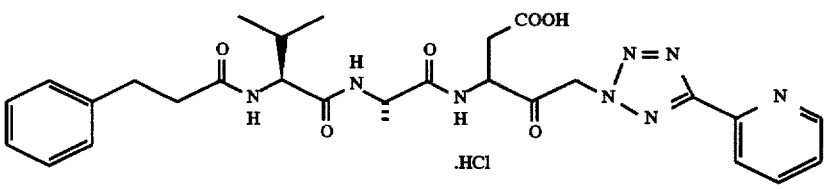

TLC: Rf 0.15 (chloroform:methanol:acetic acid=18:1:1);

NMR (d$_6$-DMSO): δ8.85 and 8.68 (total 1H, each d, J=8.0 Hz), 8.75 (1H, d, J=6.0 Hz), 8.38–8.22 (1H, m), 8.16–8.07 (1H, m), 8.02 (1H, t, J=6.0 Hz), 7.96–7.83 (1H, m), 7.62–7.50 (1H, m), 7.30–7.07 (5H, m), 6.07 (1H, d, J=14.0Hz), 5.91 (1H, d, J=14.0 Hz), 4.89–4.58 (total 1H, m), 4.40–4.10 (2H, m), 2.98–2.55 (4H, m), 2.00–1.78 (1H, m), 1.32–1.12 (2H, m), 2.45–2.28 (2H, m), 0.92–0. m).

Example 2(14)

N-((N-(3-phenylpropionyl)-L-valyl)-L-alanyl)-3-amino-4-oxo-5-(5-(pyridin-3-yl)tetrazol-2-yl)pentanoic acid.hydrochloride

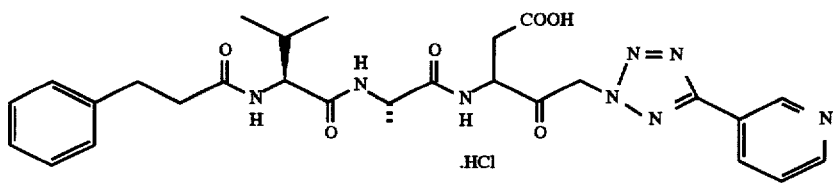

TLC: Rf 0.12 (chloroform:methanol:acetic acid=18:1:1);

NMR (CD₃OD): δ9.53 (1H, s), 9.24 (1H, d, J=8.4 Hz), 8.93 (1H, d, J=6.0 Hz), 8.26 (1H, dd, J=8.4, 6.0 Hz), 6.15 (1H, d, J=18.0 Hz), 5.95 (1H, d, J=18.0 Hz), 4.76 (1H, t, J=5.8 Hz), 4.32 (1H, q, J=7.8 Hz), 4.10 (1H, d, J=6.8 Hz), 3.06–2.78 (4H, m), 2.57 (2H, t, J=7.9 Hz), 2.08–1.94 (1H, m), 1.40 (3H, d, J=7.4 Hz), 0.95–0.81 (6H, m).

Example 2(15)

N-((N-(3-phenylpropionyl)-L-valyl)-L-alanyl)-3amino-4-oxo-5-(5-(pyridin-4-yl)tetrazol-2-yl)pentanoic acid.hydrochloride

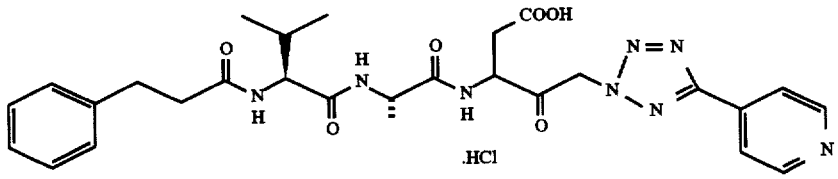

TLC: Rf 0.18(chloroform:methanol:acetic acid=18:1:1);

NMR (CDCl₃+CD₃OD): δ8.75 (2H, d, J=6.0 Hz), 8.04 (2H, d, J=6.0 Hz), 7.38–7.09 (5H, m), 6.08 (1H, d, J=18.0 Hz), 5.76 (1H, d, J=18.0 Hz), 4.83 (1H, t, J=8.0 Hz), 4.50–4.30 (1H, m), 4.17 (1H, d, J=6.0 Hz), 3.03–2.78 (3H, m), 2.66–2.47 (3H, m), 2.16–1.93 (1H, m), 1.41 (3H, d, J=6.0 Hz), 0.94–0.86 (6H, m).

Example 2(16)

N-((N-(3-phenylpropionyl)-L-valyl)-L-alanyl)-3-amino-4-oxo-5-(5-(2-methoxycarbonylphenyl)tetrazol-2-yl) pentanoic acid

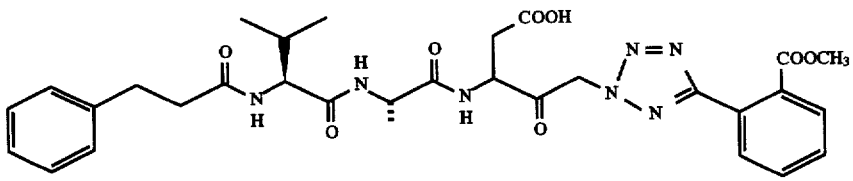

TLC: Rf 0.34(chloroform:methanol:acetic acid=18:1:1);

NMR (CDCl₃+CD₃OD): δ7.90–7.75 (2H, m), 7.71–7.52 (2H, m), 7.29–7.10 (5H, m), 6.05–5.80 and 5.80–5.57 (each 1H, m), 4.90–4.78 (1H, m), 4.55–4.25 (1H, m), 4.20–4.07 (1H, m), 3.77 and 3.76 (total 3H, d), 3.05–2.80 (4H, m), 2.58 (2H, t, J=7.5 Hz), 2.10–1.87 (1H, m), 1.40 (3H, d, J=6.8 Hz), 0.87 and 0.82 (each 3H, d, J=6.8 Hz).

Example 2(17)

N-((N-(3-phenylpropionyl)-L-valyl)-L-alanyl)-3-amino-4-oxo-5-(5-(2-methoxycarbonylphenyl)tetrazol-1-yl) pentanoic acid

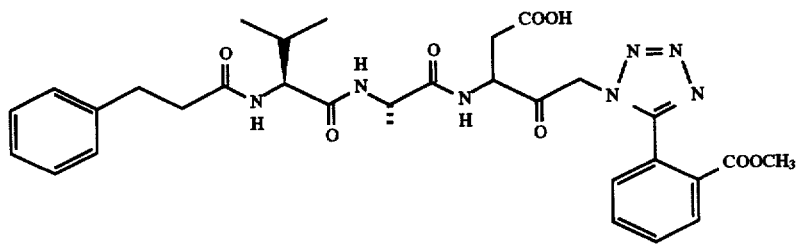

TLC: Rf 0.32 (chloroform:methanol:acetic acid=18:1:1);

NMR (d₆-DMSO): δ8.48–8.39 (1H, m), 8.21–8.05 and 7.90–7.70 (2H, m), 7.71–7.52 (2H, m), 7.41–7.07 (6H, m), 5.60–5.20 (2H, m), 4.58–4.35 (1H, m), 4.25–4.02 (1H, m), 3.67 and 3.66 (total 3H, d), 2.95–2.72 (2H, m), 2.62–2.35 (4H, m), 2.00–1.88 (1H, m), 1.27–1.05 (3H, m), 0.90–0.68 (each 3H, m).

Example 2(18)

N-((N-(3-phenylpropionyl)-L-valyl)-L-alanyl)-3-amino-4-oxo-5-(5-(2,6-difluorophenyl)tetrazol-2-yl)pentanoic acid

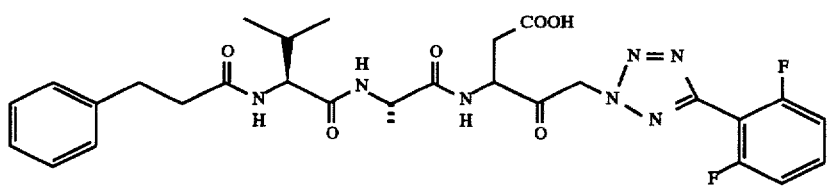

TLC: Rf 0.37 (chloroform:methanol:acetic acid=18:1:1);

NMR (d₆-DMSO): δ8.88 (1H, d, J=7.5 Hz), 8.28 (1H, d, J=6.0 Hz), 7.86 (1H, d, J=8.5Hz), 7.80–7.60 (1H, m), 7.45–7.07 (7H, m), 6.19–5.94 (2H, m), 4.72–4.55 (1H, m), 4.34–4.07 (2H, m), 2.93–2.30 (6H, m), 2.03–1.77 (1H, m), 1.25 (3H, d, J=7.2 Hz), 0.84 and 0.78 (each 3H, d, J=6.6 Hz).

Example 2(19)

N-((N-(3-phenylpropionyl)-L-valyl)-L-alanyl)-3-amino-4-oxo-5-(5-(2,6-difluorophenyl)tetrazol-1-yl)pentanoic acid

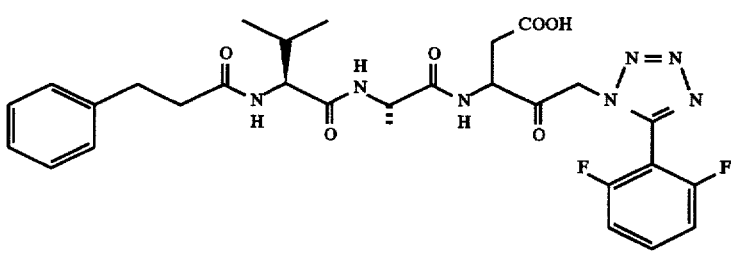

TLC: Rf 0.30 (chloroform:methanol:acetic acid=18:1:1);

NMR (d₆-DMSO): δ8.55 (1H, d, J=6.0 Hz), 8.14 (1H, d, J=5.5 Hz), 7.86 (1H, d, J=8.5 Hz), 7.92–7.66 (1H, m), 7.42–7.07 (7H, m), 5.71 and 5.54 (each 1H, d, J=16.5 Hz), 4.60–4.45 (1H, m), 4.30–4.05 (2H, m), 2.87–2.30 (6H, m), 2.02–1.80 (1H, m), 1.17 (3H, d, J=7.2 Hz), 0.82 and 0.78 (each 3H, d, J=6.8 Hz).

Example 2(20)

N-((N-(3-phenylpropionyl)-L-valyl)-L-alanyl)-3-amino-4-oxo-5-(5-(2,3,4,5,6-pentafluorophenyl)tetrazol-2-yl)pentanoic acid

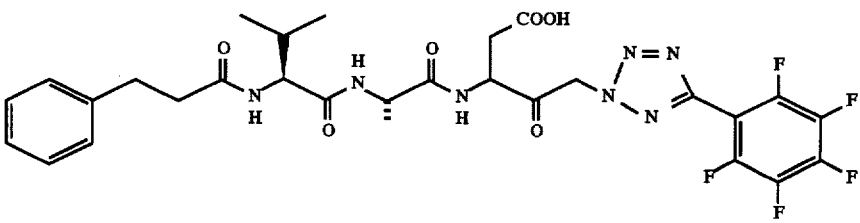

TLC: Rf 0.44 (chloroform:methanol:acetic acid=18:1:1);

NMR (d₆-DMSO): δ8.94–8.78 and 8.70–8.58 (total 1H, m), 8.35–8.15 (1H, m), 7.92–7.76 (1H, m), 7.32–7.07 (5H, m), 6.21–5.87 (2H, m), 4.85–4.53 (1H, m), 4.33–4.06 (2H, m), 2.92–2.30 (6H, m), 2.02–1.78 (1H, m), 1.35–1.13 (3H, m), 0.90–0.68 (each 3H, m).

Example 2(21)

N-((N-(3-phenylpropionyl)-L-valyl)-L-alanyl)-3-amino-4-oxo-5-(5-(2,6-dimethylphenyl)tetrazol-2-yl)pentanoic acid

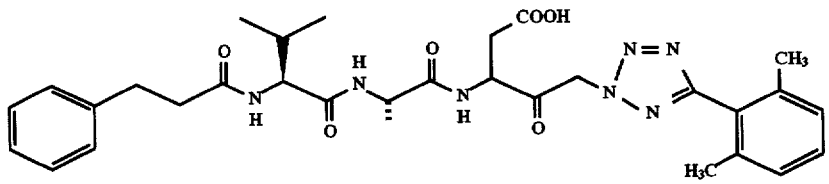

TLC: Rf 0.48 (chloroform:methanol:acetic acid=18:1:1);

NMR (d₆-DMSO): δ8.87–8.76 and 8.67–8.59 (total 1H, m), 8.36–8.22 (1H, m), 7.93–7.80 (1H, m), 7.40–7.07 (8H, m), 6.13–5.74 (2H, m), 4.83–4.70 and 4.70–4.54 (total 1H, m), 4.34–4.07 (2H, m), 2.92–2.61 and 2.61–2.30 (total 6H, s), 2.05 (6H, s), 2.00–1.80 (1H, m), 1.35–1.15 (3H, m), 1.87–0.67 (6H, m).

Example 2(22)

N-((N-(3-phenylpropionyl)-L-valyl)-L-alanyl)-3-amino-4-oxo-5-(5-(2,6-dimethylphenyl)tetrazol-1-yl)pentanoic acid

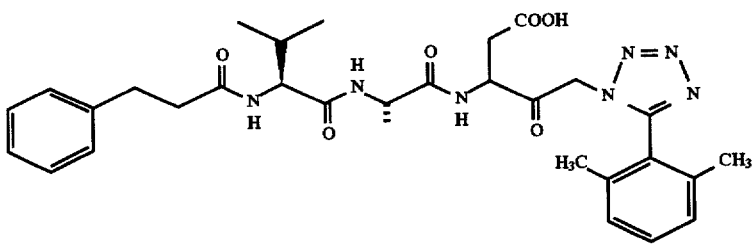

TLC: Rf 0.41 (chloroform:methanol:acetic acid=18:1:1);

NMR (d₆-DMSO): δ8.52–8.36 (1H, m), 8.21–8.00 (1H, m), 7.87–7.75 (1H, m), 7.42–7.07 (8H, m), 5.53–5.10 (2H, m), 4.60–4.42 (1H, m), 4.25–4.01 (2H, m), 2.85–2.74 (2H, m), 2.62–2.35 (4H, m), 2.00–1.80 (1H, m), 1.95 (6H, s), 1.20–1.06 (3H, m), 0.87–0.70 (6H, m).

Example 2(23)

N-((N-(3-phenylpropionyl)-L-valyl)-L-alanyl)-3-amino-4-oxo-5-(5-(2-chloro-6-methoxycarbonylphenyl)tetrazol-2-yl)pentanoic acid

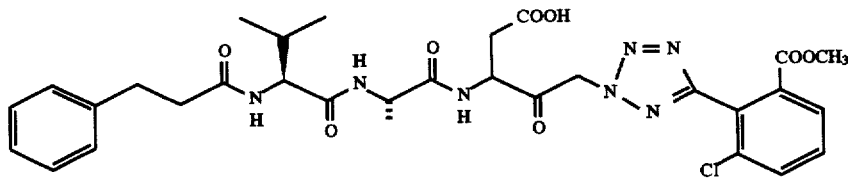

TLC: Rf 0.73 (chloroform:ethanol:acetic acid=18:1:1);

NMR (d₆-DMSO): δ8.83 and 8.63 (total 1H, m), 8.31 (1H, m), 8.05–7.66 (4H, m), 7.21 (5H, m), 6.14–5.80 (2H, m), 4.77 and 4.63 (total 1H, m), 4.34–4.05 (2H, m), 3.59 (3H, s), 2.93–2.27 (6H, m), 1.90 (1H, m), 1.26 (3H, m), 0.79 (6H, m).

Example 2(24)

N-((N-(3-phenylpropionyl)-L-valyl)-L-alanyl)-3-amino-4-oxo-5-(5-((2-phenyl)phenyl)tetrazol-2-yl)pentanoic acid

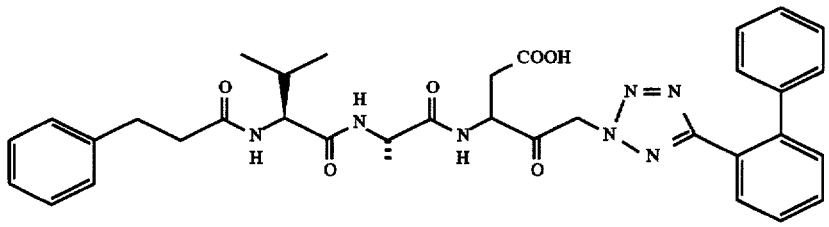

TLC: Rf 0.58, 0.54 (chloroform:methanol:acetic acid= 18:1:1);

NMR (d₆-DMSO): δ12.46 (1H, brs), 8.80–8.65 (total 1H, each m), 8.34–8.15 (1H, m), 7.95–7.80 (1H, m), 7.75–7.45 (4H, m), 7.35–6.90 (10H, m), 6.00–5.60 (2H, m), 4.72 and 4.56 (total 1H, each dt, each J=6.5, 6.5 Hz), 4.35–4.08 (2H, m), 2.90–2.28 (6H, m), 1.95–1.75 (1H, m), 1.32–1.10 (3H, m), 0.93–0.67 (6H, m).

Example 2(25)

N-((N-(3-phenylpropionyl)-L-valyl)-L-alanyl)-3-amino-4-oxo-5-(5-((2-phenyl)phenyl)tetrazol-1-yl)pentanoic acid TLC: Rf 0.35, 0.28 (chloroform:methanol:acetic acid= 18:1:1);

NMR (d₆-DMSO): δ12.50 (1H, brs), 8.83 and 8.63 (total 1H, each d, each J=7.4 Hz), 8.34 and 8.28 (total 1H, each d, each J=6.2 Hz), 7.90 (1H, d, J=7.6 Hz), 7.48 (1H, t, J=8.5 Hz), 7.32–7.05 (5H, m), 6.78 (2H; d, J=8.5 Hz), 6.06–5.75 (2H, m), 4.83–4.53 (total 1H, each m), 4.32–4.06 (2H, m), 2.94–2.30 (6H, m), 2.00–1.75 (1H, m), 1.24 (3H, d, J=7.2 Hz), 0.83 (3H, d, J=6.7 Hz), 0.77 (3H, d, J=6.7 Hz).

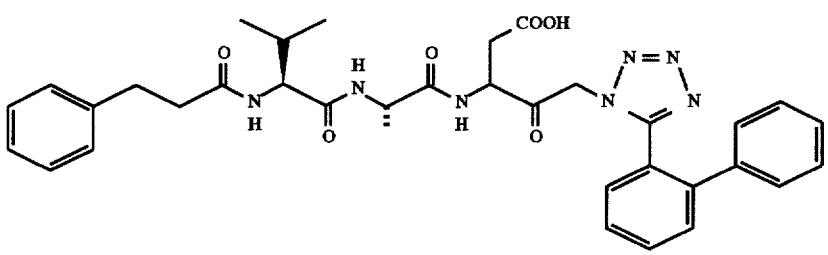

TLC: Rf 0.52, 0.49 (chloroform:methanol:acetic acid= 18:1:1);

NMR (d₆-DMSO): δ12.41 (1H, brs), 8.41 and 8.39 (total 1H, each d, each J=7.1 Hz), 8.15 and 8.08 (total 1H, each d, each J=6.6 Hz), 7.84 and 7.83 (total 1H, each d, each J=8.9 Hz), 7.70 (1H, t, J=7.4 Hz), 7.56 (1H, d, J=7.9 Hz), 7.54 (1H, m), 7.41 (1H, m), 7.32–7.06 (10H, m), 5.38 and 5.30 (total 1H, each d, each J=18 Hz), 5.08 and 5.05(total 1H, each d, each J=18 Hz), 4.54 and 4.45 (total 1H, each dt, each J=7.0, 6.6 Hz), 4.22 and 4.14 (1H, m), 4.12 (1H, dd, J=7.5, 7.5 Hz), 2.80 and 2.78 (total 2H, each, t, J=7.3 Hz), 2.63–2.32 (4H, m), 1.94–1.82 (1H, m), 1.18 and 1.15 (total 3H, each d, J=7.0 Hz), 0.79 and 0.77 (total 3H, each d, J=6.8 Hz), 0.76 and 0.74 (total 3H, each d, J=6.8 Hz).

Example 2(26)

N-((N-(3-phenylpropionyl)-L-valyl)-L-alanyl )-3-amino-4-oxo-5-(5-(2,6-dimethoxyphenyl)tetrazol-2-yl)pentanoic acid Example 2(27)

N-((N-(3-phenylpropionyl)-L-valyl)-L-alanyl)-3-amino-4-oxo-5-(5-(2, 6-dimethoxyphenyl)tetrazol-1-yl)pentanoic acid

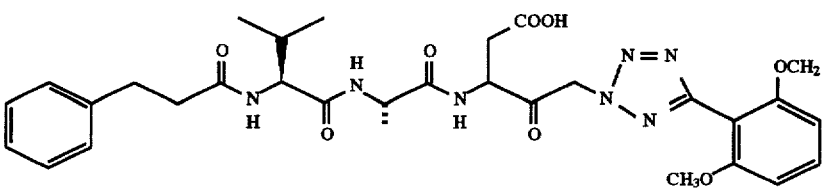

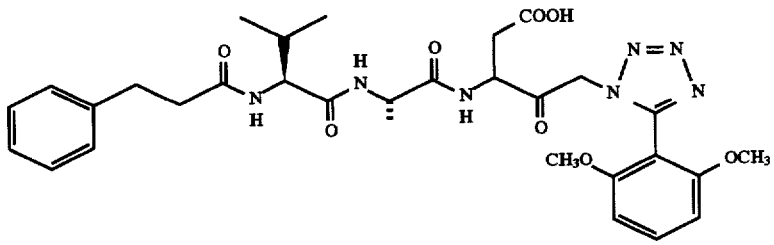

TLC: Rf 0.24, 0.21 (chloroform:methanol:acetic acid= 18:1:1);

NMR (d₆-DMSO): δ12.49 (1H, brs), 8.46 (1H, d, J=7.8 Hz), 8.12 (1H, d, J=6.4 Hz), 7.84 (1H, d, J=7.6 Hz), 7.54 (1H, t, J=8.4 Hz), 7.31–7.08 (5H, m), 6.80 (2H, d, J=8.4 Hz), 5.40 (1H, d, J=18.6 Hz), 5.19 (1H, d, J=18.6 Hz), 4.50–4.33 (1H, m), 4.25–4.00 (2H, m), 2.85–2.37 (6H, m), 2.00–1.78 (1H, m), 1.16 (3H, d, J=6.8 Hz), 0.80 (3H, d, J=6.7 Hz), 0.77 (3H, d, J=6.7 Hz).

Example 2(28)

N-((N-(3-phenylpropionyl)-L-valyl)-L-alanyl)-3-amino-4-oxo-5-(5-(morpholin-1-yl)tetrazol-2-yl)pentanoic acid.hydrochloride

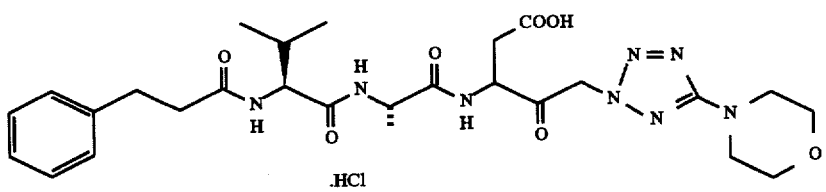

TLC: Rf 0.28(chloroform:methanol:acetic acid=15:1:1);

NMR (d₆-DMSO): δ8.79 and 8.59 (total 1H, each d, J=8 Hz), 8.28 (1H, m), 7.89 (1H, m), 720 (5H, m), 5.80–5.50 (2H, m), 4.70 and 4.56 (total 1H, each m), 4.20 (2H, m), 3.70 (4H, brs), 3.34 (4H, brs), 2.76 and 2.56 (total 6H, each m), 1.90 (1H, m), 1.25 (3H, m), 0.80 (6H, m).

Example 2(29)

N-((N-(3-phenylpropionyl)-L-valyl)-L-alanyl)-3-amino-4-oxo-5-(5-(piperidin-1-yl)tetrazol-2-yl)pentanoic acid.hydrochloride

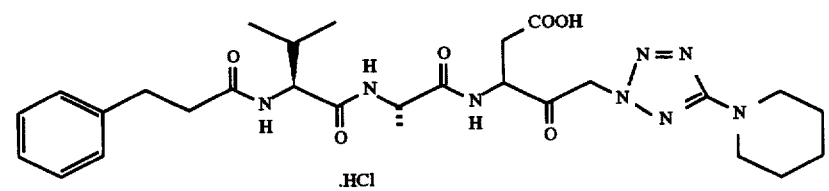

TLC: Rf 0.50 (chloroform:methanol:acetic acid=15:1:1);

NMR (d₆-DMSO): δ8.76 and 8.56 (total 1H, m), 8.24 (1H, m), 7.82 (1H, m), 7.30–7.10 (5H, m), 5.78–5.42 (2H, m), 4.72 and 4.56 (total 1H, m), 4.30–4.10 (2H, m), 3.40–3.20 (4H, m), 2.90–2.40 (6H, m), 1.90 (1H, m), 1.56 (6H, m), 1.24 (3H, m), 0.80 (6H, m).

Example 2(30)

N-((N-(3-phenylpropionyl)-L-valyl)-Ualanyl)-3-amino-4-oxo-5-(5-(pyrrolidin-1-yl)tetrazol-2-yl)pentanoic acid.hydrochloride

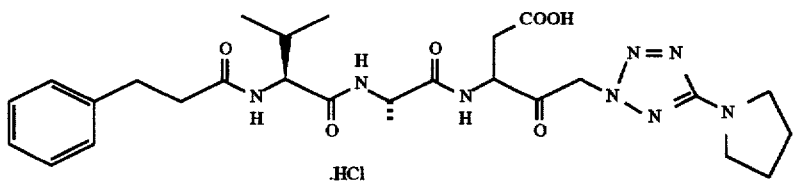

TLC: Rf 0.48(chloroform:methanol:acetic acid=15:1:1);

NMR (d₆-DMSO): δ8.72 and 8.56 (total 1H, m), 8.24 (1H, m), 7.82 (1H, m), 7.30–7.10 (5H, m), 5.76–5.40 (2H, m), 4.72 and 4.56 (total 1H, m), 4.30–4.10 (2H, m), 3.40–3.20 (4H, m), 2.88–2.38 (6H, m), 1.90 (5H, m), 1.24 (3H, m), 0.80 (6H, m).

Example 2(31)

N-((N-(3-phenylpropionyl)-L-valyl)-L-alanyl)-3-amino-4-oxo-5-(5-(pyridin-2-yl)tetrazol-1-yl)pentanoic acid.hydrochloride

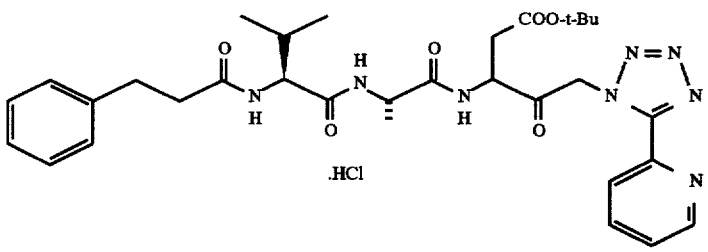

TLC: Rf 0.26 (chloroform:methanol:acetic acid=18:1:1);

NMR (d₆-DMSO): δ8.80–8.60 (2H, m), 8.35–8.20 (2H, m), 8.06 (1H, t, J=8.0 Hz), 7.93 (1H, t, J=8.0 Hz), 7.65–7.51 (1H, m), 7.36–7.03 (5H, m), 5.92 (2H, brs), 4.87–4.69 (1H, m), 4.36–4.04 (2H, m), 2.90–2.28 (6H, m), 2.07–1.80 (1H, m), 1.27 (3H, m), 0.97–0.63 (6H, m).

Reference Example 4

1-(4-methoxyphenylmethyl)-5-bromotetrazole

The mixture of 4-methoxybenzylamine (27 g), trimethylorthoformate (52.4 ml), sodium azide (19.2 g) and acetic acid (176 ml) was stirred at 80° C. for 14 h. The reaction mixture was concentrated under reduced pressure, the residue was dissolved in water and extracted with ethyl acetate. The extract was washed with a 1N aqueous solution of hydrochloric acid, water, a saturated aqueous solution of sodium hydrocarbonate and a saturated aqueous solution of sodium chloride, successively, dried over anhydrous sodium sulfate and concentrated. The residue was purified by column chromatography on silica gel (hexane:ethyl acetate= 1:1) to give 1-(4-methoxyphenylmethyl)tetrazole (17.6 g).

To a solution of the thus obtained 1-(4-methoxyphenylmethyl)tetrazole (12.0 g) in tetrahydrofuran (240 ml) was added N-bromosuccinimide (16.8 ml) under an atmosphere of argon. The reaction mixture was stirred at room temperature for 3 h. The mixture was quenched by adding a saturated aqueous solution of sodium thiosulfate and concentrated. To the residue was added water and then the mixture was extracted with ethyl acetate. The extract was washed with water and a saturated aqueous solution of sodium chloride, dried over anhydrous magnesium sulfate and concentrated. The residue was purified by column chromatography on silica gel (hexane:ethyl acetate=3:1) to give the title compound (15.6 g) having the following physical data.

TLC: Rf 0.63 (hexane:ethyl acetate=1:1);

NMR (CDCl₃): δ7.29 (2H, d, J=8.5 Hz), 6.87 (2H, d, J=8.5 Hz), 5.48 (2H, s), 3.80 (3H, s).

Reference Example 5

1-(4-methoxyphenylmethyl)-5-(2R-carboxypyrrolidin-1-yl)tetrazole

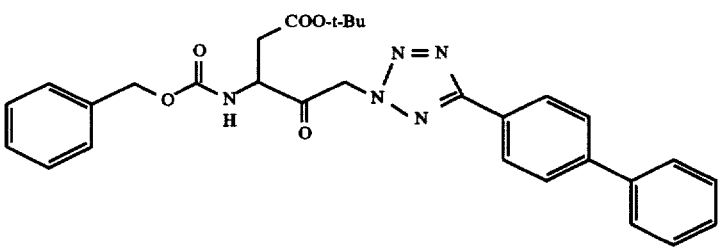

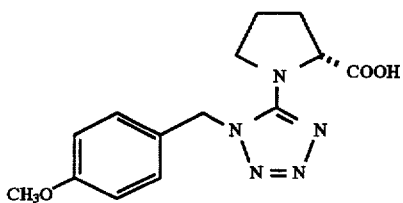

To a solution of the compound prepared in reference example 4 (2.15 g) in dimethylformamide (45 ml) were added D-proline (1.84 g) and potassium carbonate (4.42 g). The mixture was stirred at 70° C. for 42 h. The reaction mixture was quenched by adding ice water and 1N aqueous solution of hydrochloric acid and then extracted with ethyl acetate. The extract was washed with a saturated aqueous solution of sodium chloride, dried over anhydrous sodium sulfate and concentrated. The residue was purified by column chromatography on silica gel (chloroform:ethanol:acetic acid=18:1:1) to give the title compound (1.82 g) having the following physical data.

TLC: Rf 0.31 (chloroform:ethanol:acetic acid=18:1:1);

NMR (CDCl$_3$): δ7.54 (1H, brs), 7.07 and 6.88 (each 2H, each d, J=8.0Hz), 5.48 (2H, s), 4.58 (1H, m), 3.79 (3H, s), 3.74 and 3.50 (total 2H, m) 2.34–1.88 (4H, m).

[α]$_D^{26}$+52.32° (c=1.0, CHCl$_3$)

Reference Example 6

1-(4-methoxyphenylmethyl)-5-(2R-(2,2,2-trichloroethoxycarbonyl) pyrrolidin-1-yl)tetrazole

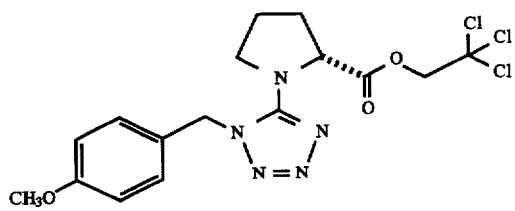

To a solution of the compound prepared in reference example 5 (1.68 g) in dichloromethane (23 ml) were added successively 2,2,2-trichloroethanol (1.24 g), N,N-dimethylaminopyridine (1.02 g) and 1-ethyl-3-[3-(dimethylamino) propyl]carbodiimide (1.59 g) at 0° C. The reaction mixture was stirred at room temperature for 9 h. The reaction mixture was quenched by adding water and then extracted with ethyl acetate. The extract was washed with a saturated aqueous solution of sodium hydrocarbonate, water and a saturated aqueous solution of sodium chloride, successively, dried over anhydrous sodium sulfate and concentrated. The residue was purified by column chromatography on silica gel (hexane:ethyl acetate=2:1) to give the title compound (1.98 g) having the following physical data.

TLC: Rf 0.49 (hexane:ethyl acetate=1:1).

Reference Example 7

5-(2R-(2,2,2-trichloroethoxycarbonyl)pyrrolidin-1-yl) tetrazole

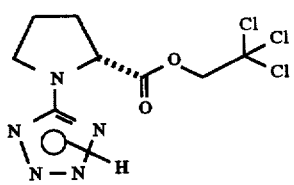

The compound prepared in reference example 6 (1.98 g) was dissolved into trifluoroacetic acid (100 ml) and the mixture was stirred at 45° C. for 3 h. The reaction mixture was concentrated under reduced pressure. To the residue was added diethyl ether and the precipitate was filtered to give the title compound having the following physical data.

TLC: Rf 0.49 (chloroform:methanol=4:1).

Example 3

N-benzyloxycarbonyl-3-amino-4-oxo-5-(5-(2-chlorophenyl)tetrazol-2-yl)pentanoic acid.t-butylester

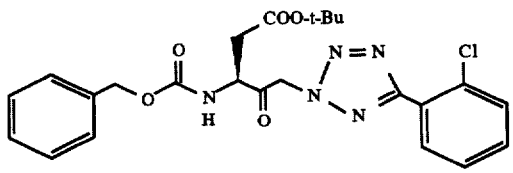

By the same procedure as example 1, using N-benzyloxycarbonyl-3-amino-4-oxo-5-bromopentanoic acid.t-butylester [see EP 0623592, Example 1] instead of N-((N-(3-phenylpropionyl)-L-valyl)-L-alanyl)-3-amino-4-oxo-5-bromopentanoic acid.t-butylester, the compound of the present invention having the following physical data was obtained.

TLC: Rf 0.35 (hexane:ethyl acetate=3:1);

NMR (CDCl$_3$): δ8.05–7.86 (1H, m), 7.62–7.15 (8H, m), 6.10–5.90 (1H, m), 5.93 (1H, d, J=18.0 Hz), 5.76 (1H, d, J=18.0 Hz), 5.19 (2H, s), 4.87–4.57 (1H, m), 3.05 (1H, dd, J=17, 4.5 Hz), 2.73 (1H, dd, J=17, 4.0 Hz), 1.43 (9H, s).

Examples 3(1)–3(38)

By the same procedure as provided in example 3, using N-benzyloxycarbonyl-3-amino-4-oxo-5-bromopentanoic acid.t-butyl ester and a corresponding tetrazole compound (for example, the compound prepared in reference Example 7), compounds of the present invention having the following physical data were obtained.

Example 3(1)

N-benzyloxycarbonyl-3-amino-4-oxo-5-(5-(2,6-dichlorophenyl) tetrazol-2-yl)pentanoic acid.t-butyl ester

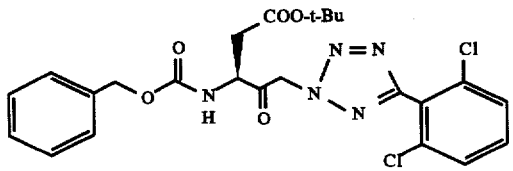

TLC: Rf 0.41 (hexane:ethyl acetate=2:1);

NMR (CDCl$_3$): δ7.48–7.28 (8H, m), 6.04–5.87 (1H, m), 5.96 and 5.79 (each 1H, d, J=17.6 Hz), 5.19 (2H, s), 4.77–4.62 (1H, m), 3.03 and 2.75 (each 1H, dd, J=18.5, 4.6 Hz), 1.43 (9H, s).

Example 3(2)

N-benzyloxycarbonyl-3-amino-4-oxo-5-(5-(2,6 (dichlorophenyl) tetrazol-1-yl)pentanoic acid.t-butyl ester

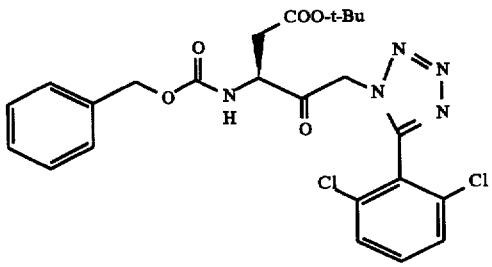

TLC: Rf 0.20 (hexane:ethyl acetate=2:1);

NMR (CDCl$_3$): δ7.46–7.27 (8H, m), 5.78–5.64 (1H, m), 5.51 and 5.40 (each 1H, d, J=17.6 Hz), 5.13 (2H, s), 4.56–4.40 (1H, m), 2.95 and 2.63 (each H, dd, 18.5, 4.6 Hz), 1.35 (9H, s).

Example 3(3)

N-benzyloxycarbonyl-3-amino-4-oxo-5-(5-((2-phenyl)phenyl)tetrazol-2-yl)pentanoic acid.t-butyl ester

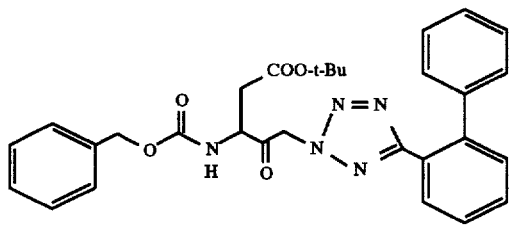

TLC: Rf 0.64 (hexane:ethyl acetate=3:2);

NMR (CDCl$_3$): δ7.86 (1H, d, J=6.2 Hz), 7.60–7.05 (13H, m), 5.86 (1H, d, J=8.2 Hz), 5.68 (1H, d, J=17.5 Hz), 5.53 (1H, d, J=17.5 Hz), 5.15 (2H, s), 4.65–4.46 (1H, m), 2.93 (1H, dd, J=17.5, 4.4 Hz), 2.68 (1H, dd, J=17.5, 5.1 Hz), 1.42 (9H, s).

Example 3(4)

N-benzyloxycarbonyl-3-amino-4-oxo-5-(5-((2-phenyl)phenyl)tetrazol-1-yl)pentanoic acid.t-butyl ester

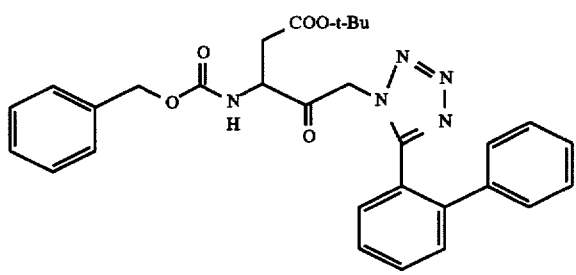

TLC: Rf 0.48 (hexane:ethyl acetate=3:2);

NMR (CDCl$_3$): δ7.63–7.06 (14H, m), 5.61 (1H, d, J=9.6 Hz), 5.14 (2H, s), 4.83 (1H, d, J=18.7 Hz), 4.69 (1H, d, J=18.7 Hz), 4.35–4.18 (1H, m), 2.81 (1H, dd, J=17.8, 4.1 Hz), 2.49 (1H, dd, J=17.8, 4.5 Hz), 1.32 (9H, s).

Example 3(5)

N-benzyloxycarbonyl-3-amino-4-oxo-5-(5-((4-phenyl)phenyl)tetrazol-2-yl)pentanoic acid.t-butyl ester

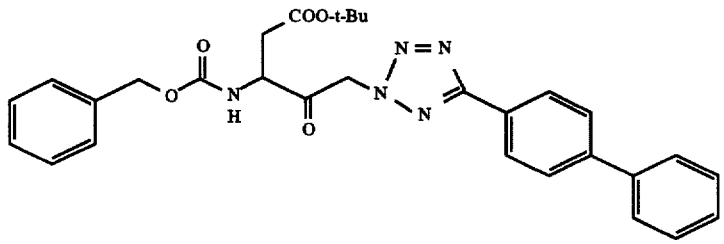

TLC: Rf 0.64 (hexane:ethyl acetate=3:2);
NMR (CDCl$_3$): δ8.21 (2H, d, J=8.5 Hz), 7.72 (2H, d, J=8.5 Hz), 7.65 (2H, d, J=6.8 Hz), 7.52–7.28 (8H, m), 6.00 (1H, d, J=8.8 Hz), 5.90 (1H, d, J=17.6 Hz), 5.72 (1H, d, J=17.6 Hz), 5.20 (2H, s), 4.73 (1H, dt, J=8.8, 4.6 Hz), 3.05 (1H, dd, J=17.4, 4.6 Hz), 2.74 (1H, dd, J=17.4, 4.6 Hz), 1.44 (9H, s).

Example 3(6)

N-benzyloxycarbonyl-3-amino-4-oxo-5-(5-((4-phenyl)phenyl)tetrazol-1-yl)pentanoic acid.t-butyl ester

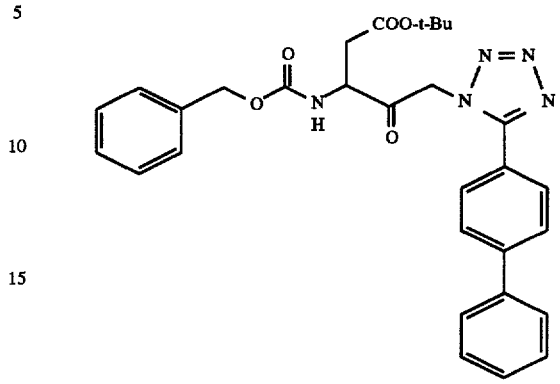

TLC: Rf 0.45 (hexane:ethyl acetate=3:2);

NMR (CDCl$_3$): δ7.75–7.55 (6H, m), 7.55–7.38 (3H, m), 7.38–7.27 (5H, m), 5.92 (1H, d, J=9.2 Hz), 5.69 (1H, d, J=18.3 Hz), 5.57 (1H, d, J=18.3Hz), 5.16 (2H, s), 4.68 (1H, dt, J=9.2, 4.6 Hz), 3.09 (1H, dd, J=17.2, 4.6 Hz), 2.73 (1H, dd, J=17.2, 4.6 Hz), 1.41 (9H, s).

Example 3(7)

N-benzyloxycarbonyl-3-amino-4-oxo-5-(5-(3-methoxycarbonylphenyl) tetrazol-2-yl)pentanoic acid.t-butyl ester

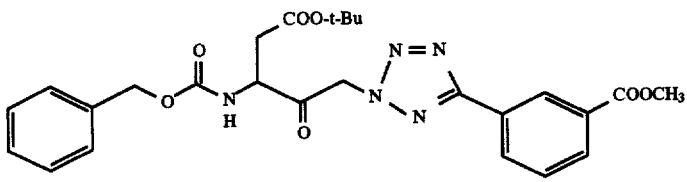

TLC: Rf 0.38 (hexane:ethyl acetate=2:1);

NMR (CDCl₃): δ8.81 (1H, s), 8.34 and 8.13 (each 1H, d, J=7.8 Hz), 7.57 (1H, t, J=7.8 Hz), 7.45–7.30 (5H, m), 6.06–5.95 (1H, m), 5.90 and 5.73 (each 1H, d, J=17.5 Hz), 5.19 (2H, s), 4.79–4.65 (1H, m), 3.96 (3H, s), 3.06 and 2.74 (each 1H, dd, J=17.0, 4.8 Hz), 1.44 (9H, s).

Example 3(8)

N-benzyloxycarbonyl-3-amino-4-oxo-5-(5-phenyltetrazol-2-yl)pentanoic acid.t-butyl ester

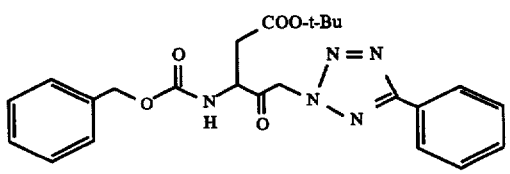

TLC: Rf 0.46 (hexane:ethyl acetate=7:3);

NMR (CDCl₃): δ8.20–8.07 (2H, m), 7.52–7.43 (3H, m), 7.43–7.28 (5H, m), 5.98 (1H, d, J=9.0 Hz), 5.88 (1H, d, J=17.7 Hz), 5.70 (1H, d, J=17.7 Hz), 5.19 (2H, s), 4.77–4.62 (1H, m), 3.04 (1H, dd, J=17.2, 4.6 Hz), 2.74 (1H, dd, J=17.2, 4.6 Hz), 1.43 (9H, s).

Example 3(9)

N-benzyloxycarbonyl-3-amino-4-oxo-5-(5-phenyltetrazol-1-yl)pentanoic acid.t-butyl ester

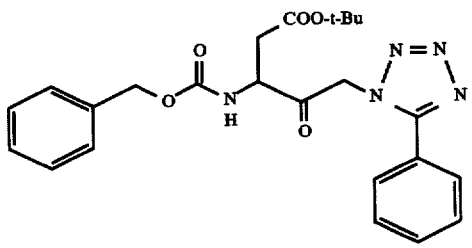

TLC: Rf 0.17 (hexane:ethyl acetate=3:1);

NMR (CDCl₃): δ7.65–7.42 (5H, m), 7.42–7.28 (5H, m), 5.88 (1H, d, J=9.0 Hz), 5.62 (1H, d, J=18 Hz), 5.52 (1H, d, J=18 Hz), 5.15 (2H, s), 4.75–4.58 (1H, m), 3.08 (1H, dd, J=17.4, 4.6 Hz), 2.71 (1H, dd, J=17.2, 4.8 Hz), 1.42 (9H, s).

Example 3(10)

N-benzyloxycarbonyl-3-amino-4-oxo-5-(5-(2,6-dimethoxyphenyl) tetrazol-2-yl)pentanoic acid.t-butyl ester

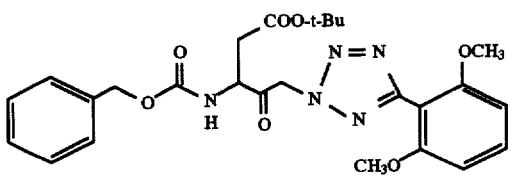

TLC: Rf 0.33 (hexane:ethyl acetate=3:2);

NMR (CDCl₃): δ7.45–7.30 (6H, m), 6.64 (2H, d, J=8.6 Hz), 5.94 (1H, d, J=9.0 Hz), 5.88 (1H, d, 17.7 Hz), 5.72 (1H, d, J=17.7 Hz), 5.17 (2H, s), 4.67 (1H, dt, J=9.0, 4.8 Hz), 3.76 (6H, s), 2.95 (1H, dd, J=17.5, 4.8 Hz), 2.75 (1H, dd, J=17.5, 4.8 Hz), 1.42 (9H, s).

Example 3(11)

N-benzyloxycarbonyl-3-amino-4-oxo-5-(5-(2,6-dimethoxyphenyl) tetrazol-1-yl)pentanoic acid.t-butyl ester

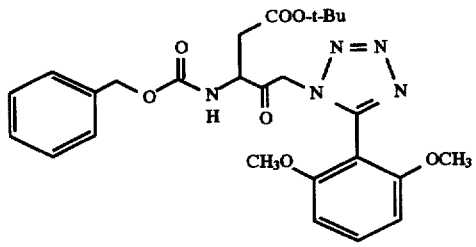

TLC: Rf 0.14 (hexane:ethyl acetate=3:2);

NMR (CDCl₃): δ7.46–7.30 (6H, m), 6.61 (2H, d, J=8.6 Hz), 5.81 (1H, d, J=9.0 Hz), 5.39 (1H, d, 17.8Hz), 5.23 (1H, d, J=17.8 Hz), 5.10 (2H, s), 4.42 (1H, dt, J=8.6, 4.3 Hz), 3.72 (6H, s), 2.87 (1H, dd, J=17.7, 4.3 Hz), 2.63 (1H, dd, J=17.7, 4.3 Hz), 1.37 (9H, s).

Example 3(12)

N-benzyloxycarbonyl-3-amino-4-oxo-5-(5-(2-methoxycarbonylphenyl) tetrazol-2-yl)pentanoic acid.t-butyl ester

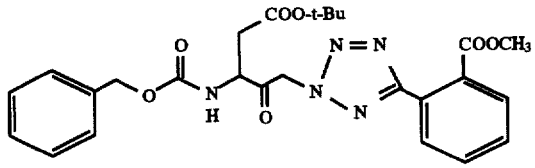

TLC: Rf 0.38 (hexane:ethyl acetate=3:2);

NMR (CDCl₃): δ7.82 (2H, m), 7.58 (2H, m), 7.38 (5H, m), 5.98 (1H, d, J=9 Hz), 5.85 (1H, d, J=19 Hz), 5.70 (1H, d, J=19 Hz), 5.20 (2H, s), 4.68 (1H, m), 3.78 (3H, s), 3.01 (1H, dd, J=17, 5Hz), 2.75 (1H, dd, J=17, 5Hz), 1.42 (9H, s).

Example 3(13)

N-benzyloxycarbonyl-3-amino-4-oxo-5-(5-(2-methoxycarbonylphenyl) tetrazol-1-yl)pentanoic acid.t-butyl ester

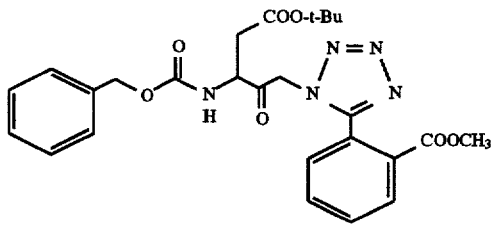

TLC: Rf 0.18 (hexane:ethyl acetate=3:2);

NMR (CDCl$_3$): δ8.10 (1H, m), 7.60 (2H, m), 7.35 (6H, m), 5.70 (1H, d, J=9Hz), 5.38 (2H, m), 5.10 (2H, s), 4.45 (1H, m), 3.74 (3H, s), 2.90 (1 H J=17, 5 Hz), 2.60 (1H, dd, J=17, 5 Hz), 1.35 (9H, s).

Example 3(14)

N-benzyloxycarbonyl-3-amino-4-oxo-5-(5-(4-methoxycarbonylphenyl) tetrazol-2-yl)pentanoic acid.t-butyl ester

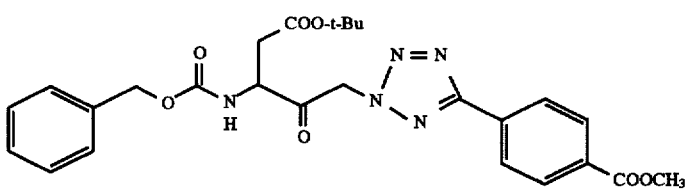

TLC: Rf 0.41 (hexane:ethyl acetate=2:1);

NMR (d$_6$-DMSO): δ8.21 (2H, d, J=8.4 Hz), 8.13 (2H, d, J=8.4 Hz), 8.03 (1H, d, J=8.1 Hz), 7.43–7.24 (5H, m), 6.08 (2H, s), 5.10 (2H, s), 4.76–4.63 (1H, m), 3.88 (3H, s), 2.81 (1H, dd, J=16.3, 5.9 Hz), 2.60 (1H, dd, J=16.3, 7.5 Hz), 1.36 (9H, s).

Example 3(15)

N-benzyloxycarbonyl-3-amino-4-oxo-5-(5-(4-methoxycarbonylphenyl) tetrazol-1-yl)pentanoic acid.t-butyl ester

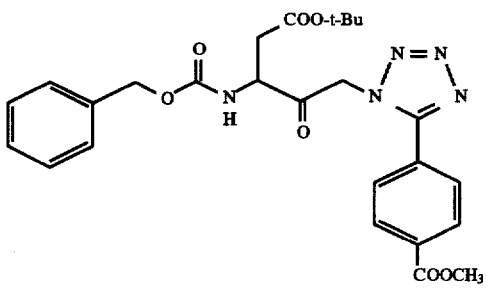

TLC: Rf 0.22 (hexane:ethyl acetate=2:1);

NMR (CDCl$_3$): δ8.16 (2H, d, J=8.4 Hz), 7.71 (2H, d, J=8.4 Hz), 7.50–7.15 (5H, m), 5.93 (1H, d, J=8.6 Hz), 5.68 (1H, d, J=18.7 Hz), 5.58 (1H, d, J=18.7 Hz), 5.16 (2H, s), 4.65 (1H, dt, J=8.6, 4.7 Hz), 3.96 (3H, s), 3.06 (1H, dd, J=17.7, 4.7 Hz), 2.60 (1H, dd, J=17.7, 4.7 Hz), 1.41 (9H, s).

Example 3(16)

N-benzyloxycarbonyl-3-amino-4-oxo-5-(5-cyclohexen-1-yltetrazol-2-yl)pentanoic acid.t-butyl ester TLC: Rf 0.51 (hexane:ethyl acetate=7:3);

NMR (CDCl$_3$): δ7.55–7.20 (5H, m), 7.03–6.87 (1H, m), 5.96 (1H, d, J=8.8 Hz), 5.78 (1H, d, J=17.6 Hz), 5.60 (1H, d, J=17.6 Hz), 5.18 (2H, s), 4.67 (1H, dt, J=8.8, 4.8 Hz), 3.00 (1H, dd, J=17.4, 4.6 Hz), 2.71 (1H, dd, J=17.4, 4.9 Hz), 2.57–2.42 (2H, m), 2.40–2.15 (2H, m), 1.90–1.55 (4H, m), 1.43 (9H, m). Example 3(17)

N-benzyloxycarbonyl-3-amino-4-oxo-5-(5-cyclohexen-1-yltetrazol-1-yl)pentanoic acid.t-butyl ester

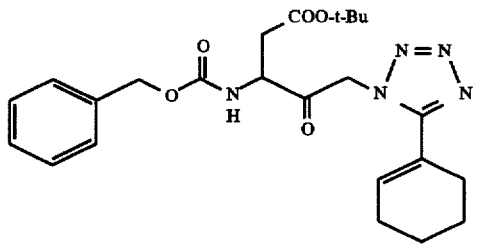

TLC: Rf 0.25 (hexane:ethyl acetate=7:3);

NMR (CDCl$_3$): δ7.55–7.23 (5H, m), 6.18–6.00 (1H, m), 6.00 (1H, d, J=9.0 Hz), 5.58 (1H, d, J=18.5 Hz), 5.47 (1H, d, J=18.5 Hz), 5.18 (2H, s), 465 (1H, dt, J=9.0, 4.8 Hz), 3.06 (1H, dd, J=17.6, 4.4 Hz), 2.74 (1H, dd, J=17.6, 5.1 Hz), 2.60–2.34 (2H, m), 2.34–2.10 (2H, m), 1.92–1.55 (4H, m), 1.42 (9H, m).

Example 3(18)

N-benzyloxycarbonyl-3-amino-4-oxo-5-(5-cyclohexyltetrazol-2-yl)pentanoic acid.t-butyl ester

255

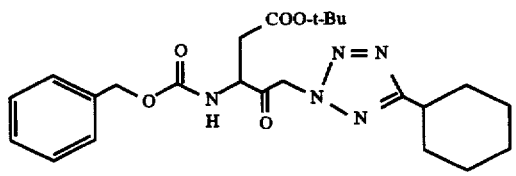

TLC: Rf 0.90 (hexane:ethyl acetate=7:3);

NMR (CDCl₃): δ7.60–7.15 (5H, m), 5.95 (1H, d, J=8.5 Hz), 5.77 (1H, d, J=17.6 Hz), 5.61 (1H, d, J=17.6 Hz), 5.18 (2H, s), 4.73–4.57 (1H, m), 3.08–2.86 (2H, m), 2.71 (1H, dd, J=17.4, 4.8 Hz), 2.20–2.00 (2H, m), 1.90–1.20 (17H, m).

Example 3(19)

N-benzyloxycarbonyl-3-amino-4-oxo-5-(5-cyclohexyltetrazol-1-yl)pentanoic acid.t-butyl ester

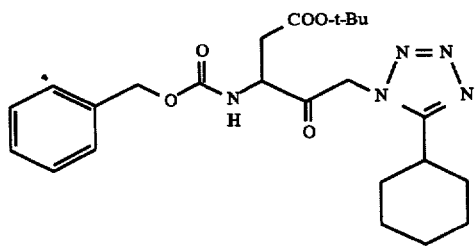

TLC: Rf 0.19 (hexane:ethyl acetate=7:3);

NMR (CDCl₃): δ7.60–7.40 (5H, m), 5.87 (1H, d, J=8.7 Hz), 5.49 (2H, s), 5.20 (2H, s), 4.64 (1H, dd, J=8.7, 4.7 Hz), 3.09 (1H, dd, J=17.6, 4.7 Hz), 2.76 (1H, dd, J=17.6, 4.7 Hz), 2.66–2.48 (1H, m), 1.95–1.00 (17H, m).

Example 3(20)

N-benzyloxycarbonyl-3-amino-4-oxo-5-(5-(4-(imidazol-1-yl)phenyl) tetrazol-2-yl)pentanoic acid.t-butyl ester

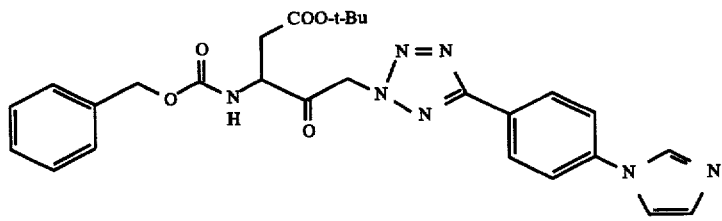

TLC: Rf 0.60 (chloroform:methanol:acetic acid=18:1:1);

NMR (d₆-DMSO): δ8.40 (1H, s), 8.18 (2H, d, J=8.8 Hz), 8.03 (1H, d, J=7.5 Hz), 7.89 (2H, d, J=8.8 Hz), 7.87 (1H, m), 7.45–7.25 (5H, m), 7.15 (1H, m), 6.07 (2H, m), 5.12 (2H, s), 4.80–4.62 (1H, m), 2.83 and 2.62 (each 1H, dd, J=16.0, 6.0 Hz), 1.39 (9H, s).

Example 3(21)

N-benzyloxycarbonyl-3-amino-4-oxo-5-(5-(naphthalen-1-yl)tetrazol-2-yl)pentanoic acid.t-butyl ester

256

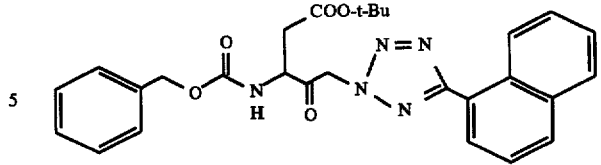

TLC: Rf 0.61 (hexane:ethyl acetate=3:2);

NMR (CDCl₃): δ8.90 (1H, m), 8.25 (1H, m), 7.95 (2H, m), 7.59 (3H, m), 7.40 (5H, m), 6.04 (1H, d, J=9 Hz), 5.99 (1H, d, J=19 Hz), 5.80 (1H, d, J=19 Hz), 5.18 (2H, s), 4.74 (1H, m), 3.08 (1H, dd, J=17, 5 Hz), 2.75 (1H, dd, J=17, 5 Hz), 1.42 (9H, s).

Example 3(22)

N-benzyloxycarbonyl-3-amino-4-oxo-5-(5-(naphthalen-1-yl)tetrazol-1-yl)pentanoic acid.t-butyl ester

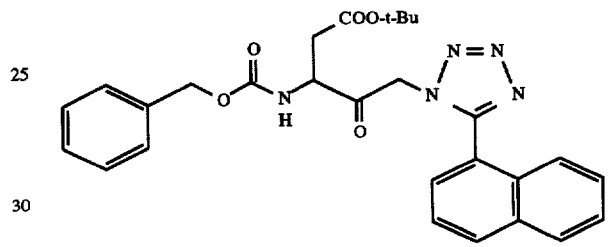

TLC: Rf 0.38 (hexane:ethyl acetate=3:2);

NMR (CDCl₃): δ8.04 (1H, m), 7.92 (1H, m), 7.70 (1H, m), 7.60–7.40 (4H, m), 7.30 (5H, m), 5.70 (1H, d, J=9 Hz), 5.48 (1H, d, J=19Hz), 5.35 (1H, d, J=19 Hz), 5.04 (2H, s), 4.50 (1H, m), 2.92 (1H, dd, J=17, 5 Hz), 2.59 (1H, dd, J=17, 5 Hz), 1.30 (9H, s).

Example 3(23)

N-benzyloxycarbonyl-3-amino-4-oxo-5-(5-(4-dimethylamino-3,5-difluorophenyl)tetrazol-2-yl)pentanoic acid.t-butyl ester

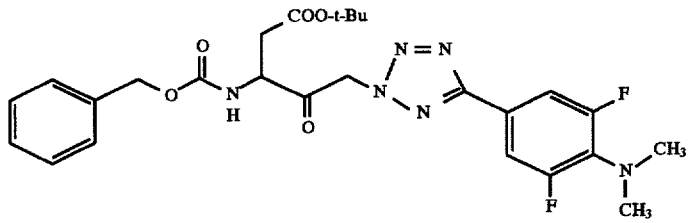

TLC: Rf 0.52 (hexane:ethyl acetate=2:1);

NMR (d₆-DMSO): δ7.70–7.50 (2H, m), 7.45–7.30 (5H, m), 6.03–5.92 (1H, m), 5.85 and 5.67 (each 1H, d, J=17.5 Hz), 5.19 (2H, s), 4.78–4.62 (1H, m), 3.04 (1H, dd, J=16.0, 5.0 Hz), 2.96 (6H, m), 2.72 (1H, dd, J=16.0, 5.0 Hz), 1.43 (9H, s).

Example 3(24)

N-benzyloxycarbonyl-3-amino-4-oxo-5-(5-(piperidin:1 -yl) tetrazol-2-yl)pentanoic acid.t-butyl ester

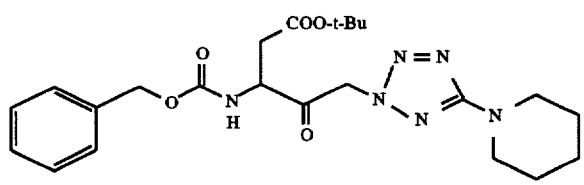

TLC: Rf 0.74 (hexane:ethyl acetate=1:1);

NMR (CDCl₃): δ7.45–7.24 (5H, m), 5.95 (1H, d, J=8.0 Hz), 5.59 (1H, d, J=17.6 Hz), 5.42 (1H, d, J=17.6 Hz), 5.17 (2H, s), 4.72–4.56 (1H, m), 3.57–3.34 (4H, m), 2.98 (1H, dd, J=17.0 and 4.4 Hz), 2.71 (1H, dd, J=17.4 and 5.0 Hz), 1.80–1.49 (6H, m), 1.42 (9H, s).

Example 3(25)

N-benzyloxycarbonyl-3-amino-4-oxo-5-(5-(piperidin-1-yl) tetrazol-1-yl)pentanoic acid.t-butyl ester

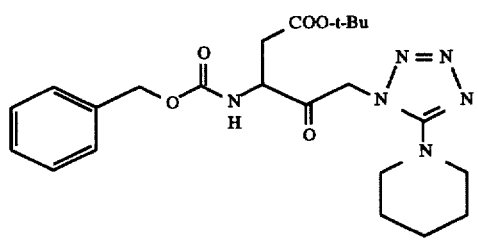

TLC: Rf 0.40 (hexane:ethyl acetate=1:1);

NMR (CDCl₃): δ7.48–7.26 (5H, m), 5.90 (1H, d, J=9.4 Hz), 5.30 (2H, s), 5.18 (2H, s), 4.72–4.54 (1H, m), 3.29–2.92 (5H, m), 2.73 (1H, dd, J=17.6 and 4.8 Hz), 1.82–1.50 (6H, m), 1.41 (9H, s).

Example 3(26)

N-benzyloxycarbonyl-3-amino-4-oxo-5-(5-(2-chloro-5-methylphenyl) tetrazol-2-yl)pentanoic acid.t-butyl ester

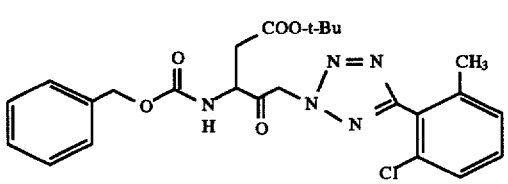

TLC: Rf 0.45 (hexane:ethyl acetate=7:3);

NMR (d₆-DMSO): δ8.03 (1H, d, J=8.1 Hz), 7.53–7.27 (8H, m), 6.11 (2H, s), 5.11 (2H, s), 4.79–4.60 (1H, m), 2.82 (1H, dd, J=16.4, 5.6 Hz), 2.62 (1H, dd, J=16.4, 7.5 Hz), 2.07 (3H, s), 1.38 (9H, s).

Example 3(27)

N-benzyloxycarbonyl-3-amino-4-oxo-5-(5-(2-chloro-5-methylphenyl) tetrazol-1-yl)pentanoic acid.t-butyl ester

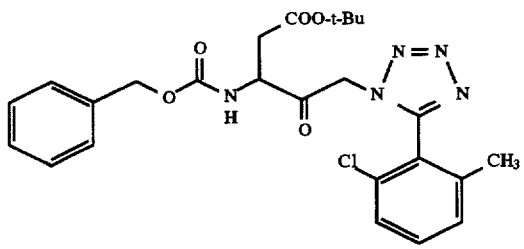

TLC: Rf 0.34 (hexane:ethyl acetate=7:3);

NMR (CDCl₃): δ7.95–7.82 (1H, m), 7.60–7.05 (8H, m), 5.84 and 5.79 (total 1H, each d, each J=18 Hz), 5.33 and 5.31 (total 1H, each d, each J=18 Hz), 5.04 and 4.95 (total 2H, each s), 4.55–4.38 (1H, m), 2.73–2.38 (2H, m 2.05 and 2.04 (total 3H, each s), 1.33 and 1.31 (total 9H, each s).

Example 3(28)

N-benzyloxycarbonyl-3-amino-4-oxo-5-(5-((3-phenyl) phenyl)tetrazol--yl)pentanoic acid.t-butyl ester

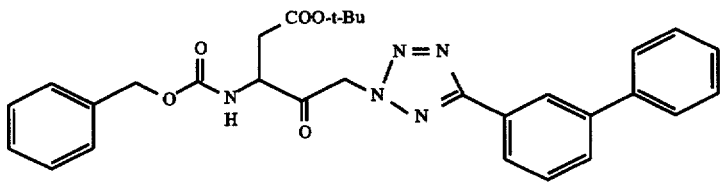

TLC: Rf 0.52 (hexane:ethyl acetate=2:1);

NMR (CDCl₃): δ8.40, 8.13 and 7.76–7.30 (total 14H, m), 5.98 (1H, m), 5.90 and 5.73 (each 1H, each d, J=17.0 Hz), 5.18 (2H, s), 4.71 (1H, m), 3.04 and 2.75 (each 1H, each dd, J=17.0, 4.0 Hz), 1.4.3 (9H, s).

Example 3(29)

N-benzyloxycarbonyl-3-amino-4-oxo-5-(5-((3-phenyl)phenyl)tetrazol-1-yl)pentanoic acid.t-butyl ester

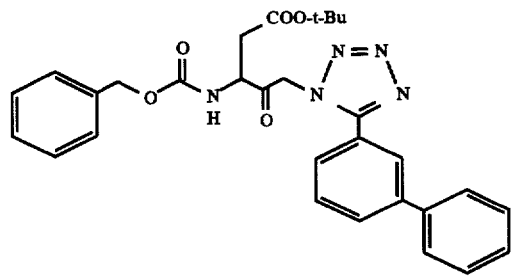

TLC: Rf 0.36 (hexane:ethyl acetate=2:1);

NMR (CDCl₃): δ7.92, 7.77 and 7.68–7.28 (total 14H, m), 5.88 (1H, m), 5.74–5.47 (2H, m), 5.12 (2H, s), 4.63 (1H, m), 3.03 and 2.72 (each 1H, each dd, J=18.0, 4.5 Hz), 1.37 (9H, s).

Example 3(30)

N-benzyloxycarbonyl-3-amino-4-oxo-5-(5-(benzocyclobuten-1-yl)tetrazol-2-yl)pentanoic acid.t-butyl ester

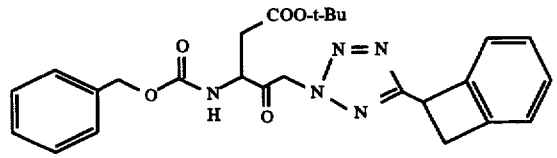

TLC: Rf 0.41 (hexane:ethyl acetate=2:1);

NMR (CDCl₃): δ7.41–7.10 (9H, m),5.95 (1H, d, J=8 Hz), 5.78 (1H, d, J=15 Hz), 5.63 (1H, d, J=15 Hz), 5.16 (2H, s), 4.97 (1H, dd, J=5 and 2 Hz), 4.63 (1H, m), 3.78 (1H, dd, J=13 and 5 Hz), 3.57 (1H, dd, J=13 and 2 Hz), 2.99 (1H, dd, J=14 and 5 Hz), 2.71 (1H, dd, J=15 and 5 Hz), 1.41 (9H, s).

Example 3(31)

N-benzyloxycarbonyl-3-amino-4-oxo-5-(5-(benzocyclobuten-1-yl)tetrazol-1-yl)pentanoic acid.t-butyl ester

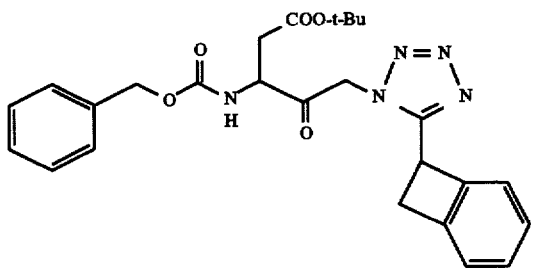

TLC: Rf 0.17 (hexane:ethyl acetate=2:1):

NMR (CDCl₃): δ7.41–7.08 (9H, m), 5.81 (1H, d, J=8 Hz), 5.63–5.30 (2H, m), 5.17 and 5.16 (2H, s each), 4.77 (1H, m), 4.49 (1H, m), 3.80–3.60 (1H, m), 3.50–3.35 (1H, m), 3.10–2.90 (1H, m), 2.80–2.60 (1H, m), 1.40 and 1.38 (9H, s each).

Example 3(32)

N-benzyloxycarbonyl-3-amino-4-oxo-5-(5-(2S-(2,2,2-trichloroethoxy-carbonyl)pyrrolidin-1-yl)tetrazol-2-yl)pentanoic acid.t-butyl ester

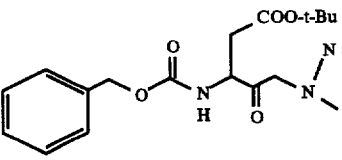

HPTLC: Rf 0.37 (hexane:ethyl acetate=2:1);

NMR (CDCl₃): δ7.38 (5H, m), 5.91 (1H, m), 5.57 and 5.44 (each 1H, each d, J=17.5 Hz), 5.16 (2H, s), 4.84 and 4.65 (each 1H, each d, J=12.5 Hz), 4.60 (2H, m), 3.84–3.54 (2H, m), 3.05–2.63 (2H, m), 2.51–2.00 (4H, m), 1.43 (9H, s).

Example 3(33)

N-benzyloxycarbonyl-3-amino-4-oxo-5-(5-(2R-(2,2,2-trichloroethoxycarbonyl)pyrrolidin-1-yl)tetrazol-2-yl)pentanoic acid.t-butyl ester

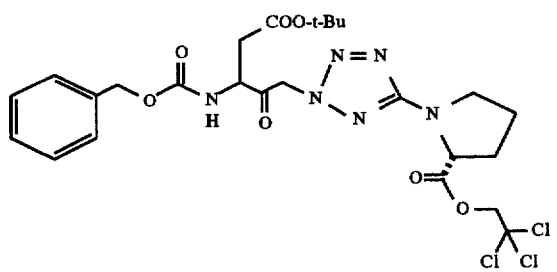

TLC: Rf 0.27 (hexane:ethyl acetate=2:1);

NMR (CDCl₃): δ7.38 (5H, m), 5.91 (1H, m), 5.57 and 5.42 (each 1H, each d, J=17.5 Hz), 5.17 (2H, s), 4.91–4.53 (4H, m), 3.85–3.53 (2H, m), 3.04–2.62 (2H, m), 2.53–2.00 (4H, m), 1.42 (9H, s).

Example 3(34)

N-benzyloxycarbonyl-3-amino-4-oxo-5-(5-(2-carboxyphenyl)tetrazol-2-yl)pentanoic acid.t-butyl ester

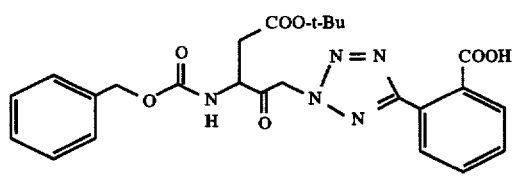

TLC: Rf 0.52 (chloroform:methanol=9:1).

Example 3(35)

N-benzyloxycarbonyl-3-amino-4-oxo-5-(5-(2-carboxyphenyl)tetrazol-1-yl)pentanoic acid.t-butyl ester

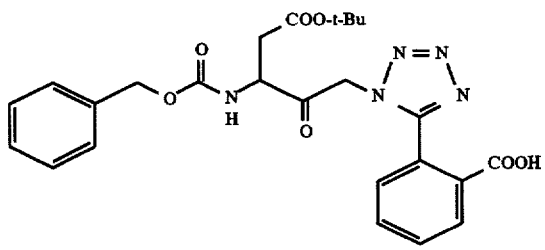

TLC: Rf 0.37 (chloroform:methanol:acetic acid=30:1:1);

NMR (CDCl₃): δ8.15 (1H, m), 7.62 (2H, m), 7.40 (1H, m), 7.32 (5H, m), 5.90 (1H, d, J=9 Hz), 5.38 (2H, s), 5.12 and 5.08 (total 2H, each d, J=18 Hz), 4.50 (1H, m), 2.89 (1H, dd, J=17, 5 Hz), 2.62 (1H, dd, J=17, 5 Hz), 1.32 (9H, s).

Example 3(36)

N-benzyloxycarbonyl-3-amino-4-oxo-5-(5-(3-carboxyphenyl)tetrazol-2-yl)pentanoic acid.t-butyl ester

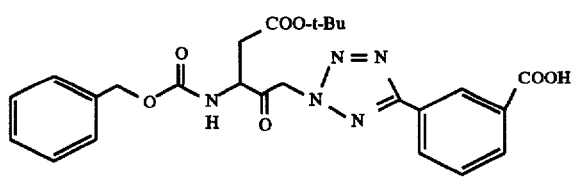

TLC: Rf 0.51 (chloroform:methanol=10:1);

NMR (d₆-DMSO): δ8.63 (1H, s), 8.25 and 8.10 (each 1H, d, J=7.5 Hz), 8.01 (1H, d, J=7.0 Hz), 7.68 (1H, t, J=7.5 Hz), 7.43–7.25 (5H, m), 6.13–5.99 (2H, m), 5.12 (2H, s), 4.78–4.61 (1H, m), 2.81 (1H, dd, J=16.5, 5.0 Hz), 2.60 (1H, dd, J=16.5, 7.5 Hz), 1.39 (9H, s).

Example 3(37)

N-benzyloxycarbonyl-3-amino-4-oxo-5-(5-(4-carboxyphenyl)tetrazol-2-yl)pentanoic acid.t-butyl ester

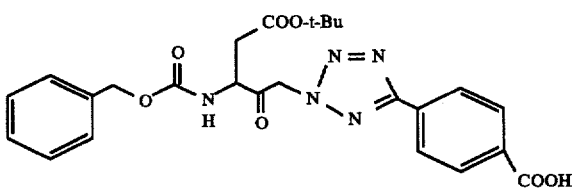

TLC: Rf 0.49 (chloroform:methanol=9:1);

NMR (CDCl₃): δ8.18 (2H, d, J=8.4 Hz), 7.11 (2H, d, J=8.4 Hz), 8.03 (1H, d, J=7.8 Hz), 7.50–7.23 (5H, m), 6.07 (2H, s), 5.10 (2H, s), 4.80–4.62 (1H, m), 2.80 (1H, dd, J=16.5, 5.9 Hz), 2.60 (1H, dd, J=16.5, 7.6 Hz), 1.36 (9H, s).

Example 3(38)

N-benzyloxycarbonyl-3-amino-4-oxo-5-(5-(2R-ethoxycarbonyl-pyrrolidin-1-yl)tetrazol-2-yl)pentanoic acid.t-butyl ester

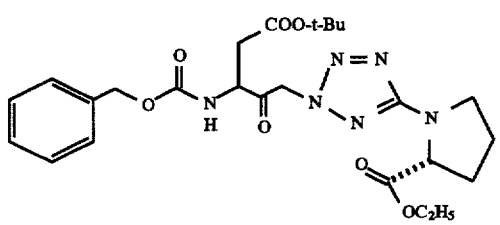

TLC: Rf 0.21 (hexane:ethyl acetate=2:1).

Example 4

N-benzyloxycarbonyl-3-amino-4-oxo-5-(5-(2-chlorophenyl)tetrazol-2-yl)pentanoic acid

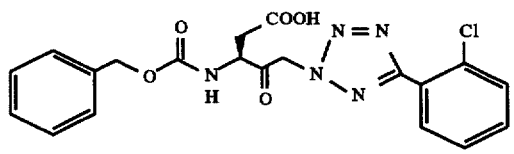

By the same procedure as provided in example 2(1), using the compound prepared in example 3, the compound of the present invention having the following physical data was obtained.

TLC: Rf 0.27 (chloroform:methanol=19:1);

NMR (CDCl₃+d₆-DMSO): δ8.05–7.83 (1H, brs), 7.58–7.18 (8H, m), 6.25–5.24 (2H, br), 5.15 (2H, s), 4.83–4.50 (1H, m), 3.24–2.60 (2H, m).

Examples 4(1)–4(38)

By the same procedure as provided in example 4, and if necessary, by known methods converting the same to a corresponding salt, using the compound of examples 3(1) –3(38) instead of the compound prepared in example 3, compounds of the present invention having the following physical data were obtained.

Example 4(1)

N-benzyloxycarbonyl-3-amino-4-oxo-5-(5-(2,6-dichlorophenyl) tetrazol-2-yl)pentanoic acid

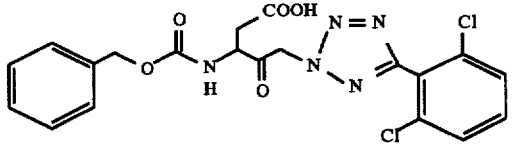

TLC: Rf 0.58 (chloroform:methanol:acetic acid=18:1:1);

NMR (d$_6$-DMSO): δ8.02 (1H, d, J=7.4 Hz), 7.75–7.57 (3H, m), 7.45–7.23 (5H, m), 6.14 (2H, s), 5.11 (2H, s), 4.76–4.60 (1H, m), 2.86 (1H, dd, J=18.5, 5.8 Hz), 2.68 (1H, dd, J=18.5, 7.0 Hz).

Example 4(2)

N-benzyloxycarbonyl-3-amino-4-oxo-5-(5-(2,6-dichlorophenyl) tetrazol-1-yl)pentanoic acid

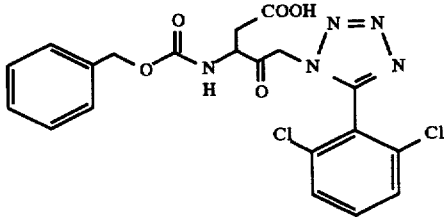

TLC: Rf 0.43 (chloroform:methanol:acetic acid=18:1:1);

NMR (d$_6$-DMSO): δ7.97–7.83 (1H, m), 7.72–7.64 (3H, m), 7.52–7.10 (5H, m), 5.78–5.46 (2H, m), 4.96 (2H, s), 4.53–4.35 (1H, m), 2:76–2.53 (2H, m).

Example 4(3)

N-benzyloxycarbonyl-3-amino-4-oxo-5-(5-((2-phenyl)phenyl)tetrazol-2-yl)pentanoic acid

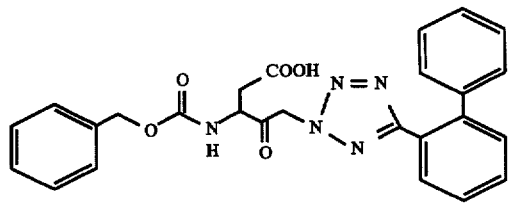

TLC: Rf 0.35 (chloroform:methanol:acetic acid=30:1:1);

NMR (d$_6$-DMSO): δ12.60 (1H, brs), 7.95 (1H, d, J=7.4 Hz), 7.80–6.90 (14H, m), 5.90 (2H, s), 5.07 (2H, s), 4.70–4.48 (1H, m), 2.80 (1H, dd, J=16.0, 6.0 Hz), 2.63 (1H, dd, J=16.0, 6.0 Hz).

Example 4(4)

N-benzyloxycarbonyl-3-amino-4-oxo-5-(5-((2-phenyl)phenyl)tetrazol-1-yl)pentanoic acid

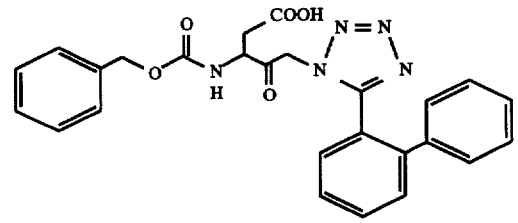

TLC: Rf 0.31 (chloroform:methanol:acetic acid=30:1:1);

NMR (d$_6$-DMSO): δ12.50 (1H, brs), 7.81 (1H, d, J=7.0 Hz), 7.68 (1H, t, J=7.5 Hz), 7.56 (1H, d, J=8.4 Hz), 7.54 (1H, t, J=8.4 Hz), 7.47 (1H, d, J=8.0 Hz), 7.39–7.00 (10H, m), 5.17 (2H, brs), 5.00 (2H, s), 4.46–4.25 (1H, m), 2.70–2.40 (2H, m).

Example 4(5)

N-benzyloxycarbonyl-3-amino-4-oxo-5-(5-((4-phenyl)phenyl)tetrazol-2-yl)pentanoic acid

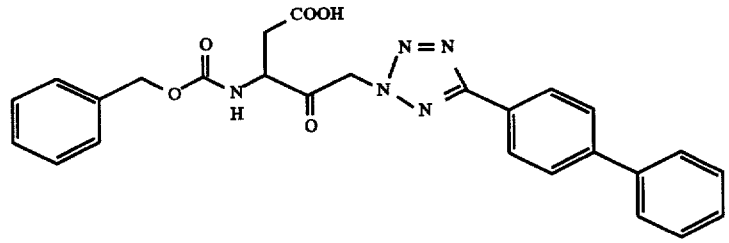

TLC: Rf 0.49 (chloroform:methanol:acetic acid=30:1:1);

NMR (d$_6$-DMSO): δ8.16 (2H, d, J=8.2 Hz), 8.06 (1H, d, J=7.0 Hz), 7.88(2H, d, J=8.2 Hz), 7.76 (2H, d, J=7.4 Hz), 7.60–7.25 (8H, m), 6.08 (2H, s), 5.12 (2H, s), 4.78–4.55 (1H, m), 2.86 (1H, dd, J=17.3, 5.2 Hz), 2.68 (1H, dd, J=17.3, 7.0 Hz).

Example 4(6)

N-benzyloxycarbonyl-3-amino-4-oxo-5-(5-((4-phenyl) phenyl)tetrazol-1-yl)pentanoic acid

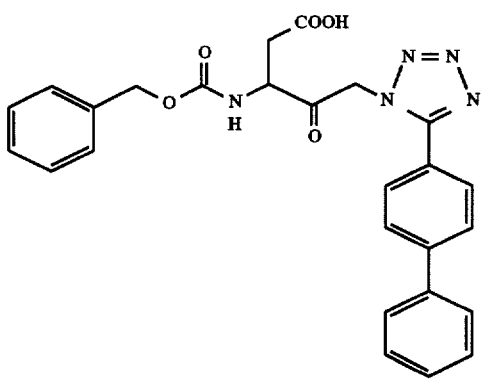

TLC: Rf 0.54 (chloroform:methanol:acetic acid=18:1:1);

NMR (d$_6$-DMSO): δ8.02 (1H, d, J=7.8 Hz), 7.95–7.66 (6H, m), 7.56–7.36 (3H, m), 7.36–7.25 (5H, m), 5.89 (2H, s), 5.06 (2H, s), 4.86–4.78 (1H, m), 2.79 (1H, dd, J=16.8, 6.3 Hz), 2.70 (1H, dd, J=16.8, 6.3 Hz).

Example 4(7)

N-benzyloxycarbonyl-3-amino-4-oxo-5-(5-(3-methoxycarbonylphenyl) tetrazol-2-yl)pentanoic acid

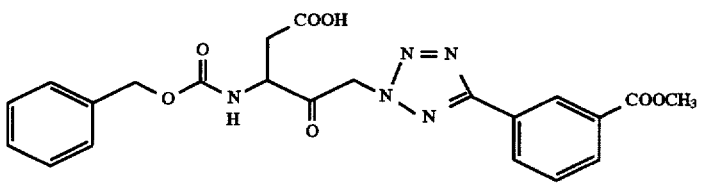

TLC: Rf 0.55 (chloroform:methanol:acetic acid=18:1:1);

NMR (d$_6$-DMSO): δ8.62 (1H, s), 8.31 and 8.26 (total 1H, each d, J=7.0 Hz), 8.10 (1H, d, J=7.0 Hz), 8.05–7.92 (1H, m), 7.71 (1H, t, J=7.0 Hz), 7.42–7.21 (5H, m), 6.12–5.87 (2H, m), 5.10 (2H, s), 4.75–4.59 (1H, m), 3.90 (3H, s), 2.72 and 2.67 (each 1H, dd, J=16.5, 7.0 Hz).

Example 4(8)

N-benzyloxycarbonyl-3-amino-4-oxo-5-(5-phenyltetrazol-2-yl) pentanoic acid

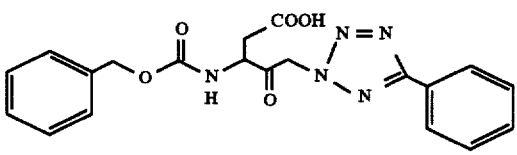

TLC: Rf 0.39 (chloroform:methanol:acetic acid=30:1:1);

NMR (d$_6$-DMSO): δ8.12–7.95 (3H, m), 7.62–7.52 (3H, m), 7.43–7.30 (5H, m), 6.04 (2H, brs), 5.11 (2H, s), 4.77–4.60 (1H, m), 2.84 (1H, dd, J=17.0, 5.8 Hz), 2.68 (1H, dd, J=17.0, 6.4 Hz).

Example 4(9)

N-benzyloxycarbonyl3-amino-4-oxo-5-(5-phenyltetrazol-1-yl) pentanoic acid

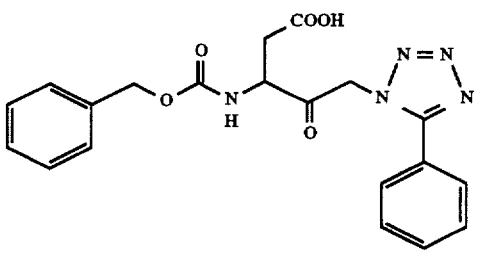

TLC: Rf 0.22 (chloroform:methanol:acetic acid=30:1:1);

NMR (d$_6$-DMSO): δ8.00 (1H, d, J=6.0 Hz), 7.72–7.46 (5H, m), 7.40–7.23 (5H, m), 5.82 (2H, brs), 5.06 (2H, s), 4.68–4.52 (1H, m), 2.76 (1H, dd, J=17.0, 5.7 Hz), 2.62 (1H, dd, J=17.0, 6.8 Hz).

Example 4(10)

N-benzyloxycarbonyl-3-amino-4-oxo-5-(5-(2,6-dimethoxyphenyl) tetrazol-2-yl)pentanoic acid

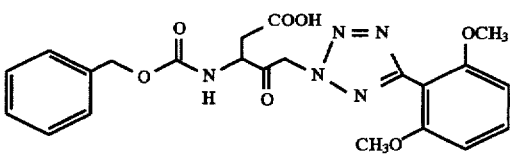

TLC: Rf 0.29 (chloroform:methanol:acetic acid=30:1:1);

NMR (d$_6$-DMSO): δ7.96 (1H, brs), 7.60–7.11 (6H, m), 6.99 (2H, d, J=7.5 Hz), 5.98 (2H, brs), 5.09 (2H, s), 4.64 (1H, brs), 3.68 (6H, s), 2.90–2.53 (2H, m).

Example 4(11)

N-benzyloxycarbonyl-3-amino-4-oxo-5-(5-(2,6-dimethoxyphenyl) tetrazol-1-yl)pentanoic acid

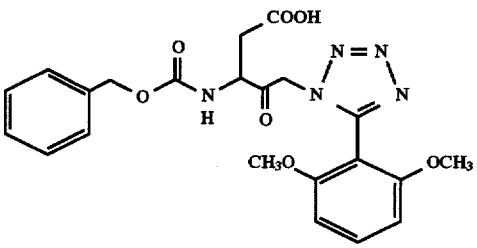

TLC: Rf 0.20 (chloroform:methanol:acetic acid=30:1:1);

NMR (d$_6$-DMSO): δ7.84 (1H, d, J=7.8 Hz), 7.53 (1H, t, J=8.5 Hz), 7.43–7.24 (5H, m), 6.79 (2H, d, J=8.5 Hz), 5.39 (2H, s), 4.99 (2H, s), 4.50–4.33 (1H, m), 3.67 (6H, s), 2.72–2.40 (2H, m).

Example 4(12)

N-benzyloxycarbonyl-3-amino-4-oxo-5-(5-(2-methoxycarbonylphenyl) tetrazol-2-yl)pentanoic acid

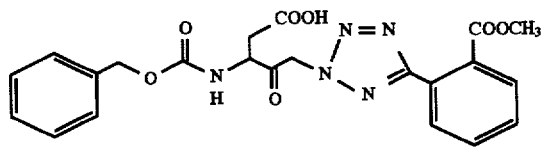

TLC: Rf 0.28 (chloroform:methanol:acetic acid=30:1:1);
NMR (d$_6$-DMSO): δ8.00 (1H, m), 7.88 (1H, m), 7.80–7.63 (3H, m), 7.36 (5H, m), 6.01 (2H, m), 5.10 (2H, s), 4.65 (1H, m), 3.65 (3H, s), 2.93–2.60 (2H, m).

Example 4(13)

N-benzyloxycarbonyl-3-amino-4-oxo-5-(5-(2-methoxycarbonylphenyl)tetrazol-1-yl)pentanoic acid

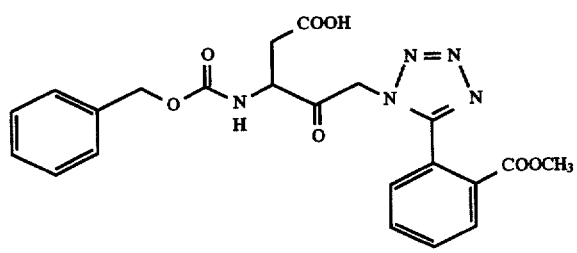

TLC: Rf 0.22 (chloroform:methanol:acetic acid=30:1:1);
NMR (CDCl$_3$): δ8.10 (1H, m), 7.60 (2H, m), 7.30 (6H, m), 6.00 (1H, br), 5.60–5.10 (2H, br), 5.04 (2H, s), 4.45 (1H, m), 3.70 (3H, s), 3.05–2.60 (2H, m).

Example 4(14)

N-benzyloxycarbonyl-3-amino-4-oxo-5-(5-(4-methoxycarbonylphenyl) tetrazol-2-yl)pentanoic acid

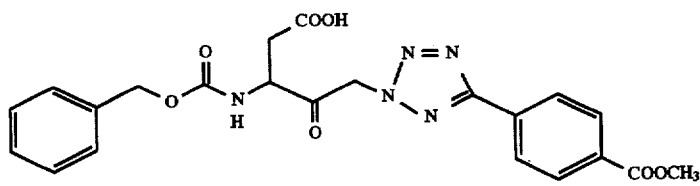

TLC: Rf 0.41 (chloroform:methanol:acetic acid=28:1:1);

NMR (d$_6$-DMSO): δ8.22 (2H, d, J=8.6 Hz), 8.14 (2H, d, J=8.6 Hz), 8.06–7.93 (1H, m), 7.45–7.25 (5H, m), 6.07 (2H, brs), 5.11 (2H, s), 4.74–4.60 (1H, m), 3.90 (3H, s), 2.83(1H, dd, J=16.9, 5.7 Hz), 2.68 (1H, dd, J=16.9, 6.5 Hz).

Example 4(15)

N-benzyloxycarbonyl-3-amino-4-oxo-5-(5-(4-methoxycarbonylphenyl)tetrazol-1-yl)pentanoic acid

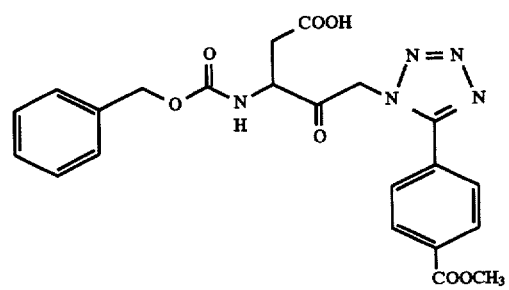

TLC: Rf 0.38 (chloroform:methanol:acetic acid=20:1:1);
NMR (CDCl$_3$): δ8.23–7.76 (2H, m), 7.73–7.39 (2H, m), 7.39–6.90 (5H, m), 6.70–6.38 (1H, m), 5.97–5.23 (2H, m), 5.00 (2H, s), 4.71–4.36 (1H, m), 3.87 (3H, brs), 3.21–2.60 (1H, m).

Example 4(16)

N-benzyloxycarbonyl-3-amino-4-oxo-5-(5-cyclohexen-1-yltetrazol-2-yl) pentanoic acid

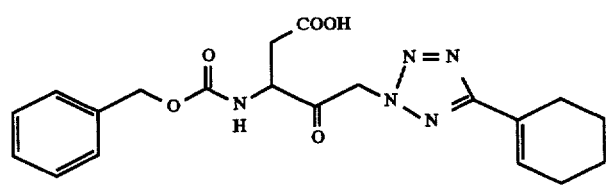

TLC: Rf 0.41 (chloroform:methanol:acetic acid=28:1:1);
NMR (CDCl$_3$): δ7.50–7.24 (5H, m), 7.05–6.83 (1H, m), 6.25–5.24 (3H, m), 5.16 (2H, s), 4.76–4.60 (1H, m), 3.24–2.92 (1H, m), 2.90–2.64 (1H, m), 2.54–2.32 (2H, m), 2.30–2.10 (2H, m), 1.86–1.55 (4H, m).

Example 4(17)

N-benzyloxycarbonyl-3-amino-4-oxo-5-(5-cyclohexen-1-yltetrazol-1-yl) pentanoic acid

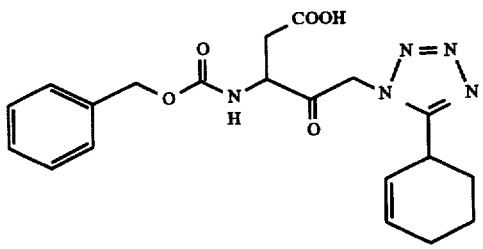

TLC: Rf 0.39 (chloroform:methanol:acetic acid=20:1:1);
NMR (CDCl$_3$): δ8.58 (1H, brs), 7.40–7.30 (5H, m), 6.54–6.30 (1H, m), 6.10–5.94 (1H, m), 5.57 (1H, d, J=18.0 Hz), 5.36 (1H, d, J=18.0 Hz), 5.11 (2H, s), 4.66–4.42 (1H, m), 3.17–2.92 (1H, m), 2.92–2.66 (1H, m), 2.39–2.24 (2H, m), 2.20–1.94 (2H, m), 1.79–1.40 (4H, m).

Example 4(18)

N-benzyloxycarbonyl-3-amino-4-oxo-5-(5-cyclohexyltetrazol-2-yl) pentanoic acid

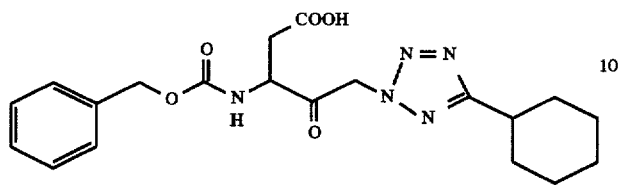

TLC: Rf 0.41 (chloroform:methanol:acetic acid=28:1:1);
NMR (CDCl$_3$): δ7.74 (1H, brs), 7.48–7.20 (5H, m), 6.27 (1H, m), 6.00–5.29 (2H, m), 5.12 (2H, s), 4.78–4.40 (1H, m), 3.20–2.63 (3H, m), 2.14–1.11 (10H, m).

Example 4(19)

N-benzyloxycarbonyl-3-amino-4-oxo-5-(5-cyclohexyltetrazol-1-yl)pentanoic acid

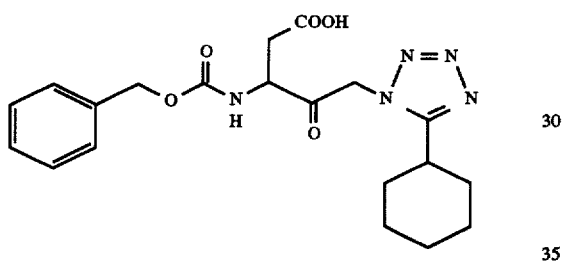

TLC: Rf 0.27 (chloroform:methanol:acetic acid=28:1:1);
NMR (CDCl$_3$): δ7.44–7.18 (5H, m), 6.25 (1H, m), 5.62–5.00 (4H, m), 4.69–4.48 (1H, m), 3.17–2.70 (2H, m), 2.70–2.48 (1H, m), 1.90–1.11 (10H, m).

Example 4(20)

N-benzyloxycarbonyl-3-amino-4-oxo-5-(5-(4-(imidazol-1-yl)phenyl) tetrazol-2-yl)pentanoic acid.hydrochloride

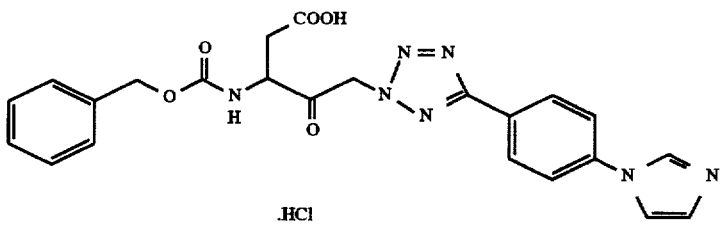

TLC: Rf 0.47 (chloroform:methanol:acetic acid=8:1:1);

NMR (d$_6$-DMSO): δ9.25–9.12 (1H, m), 8.21–7.83 (6H, m), 7.55–7.46 (1H, m), 7.35–7.12 (5H, m), 6.01 (2H, s), 5.00 (2H, s), 4.62–4.50 (1H, m), 2.85–2.45 (2H, m),

Example 4(21)

N-benzyloxycarbonyl-3-amino-4-oxo-5-(5-(naphthalen-1-yl)tetrazol-2-yl)pentanoic acid

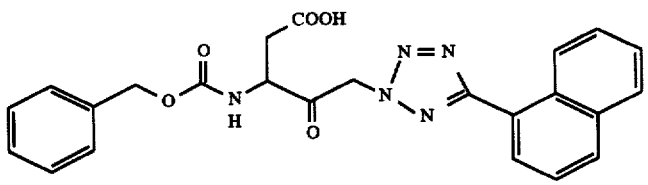

TLC: Rf 0.59 (chloroform:methanol:acetic acid=15:1:1);

NMR (d$_6$-DMSO): δ8.79 (1H, m), 8.10 (4H, m), 7.68 (3H, m), 7.35 (5H, m), 6.10 (2H, m), 5.12 (2H, s), 4.71 (1H, m), 2.80 (2H, m).

Example 4(22)

N-benzyloxycarbonyl-3-amino-4-oxo-5-(5-(naphthalen-1-yl)tetrazol-1-yl)pentanoic acid

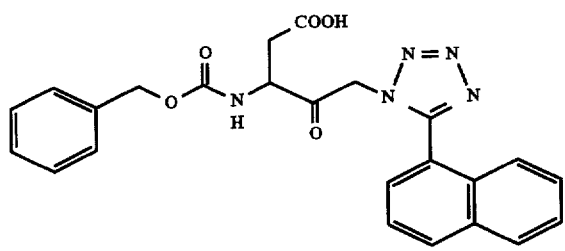

TLC: Rf 0.55 (chloroform:methanol:acetic acid=15:1:1);

NMR (d$_6$-DMSO): δ8.11 (2H, m), 7.61 (6H, m), 7.33 (5H, m), 5.65 (2H, m), 4.92 (2H, s), 4.40 (1H, m).

Example 4(23)

N-benzyloxycarbonyl-3-amino-4-oxo-5-(5-(4-dimethylamino-3,5-difluorophenyl)tetrazol-2-yl)pentanoic acid.hydrochloride

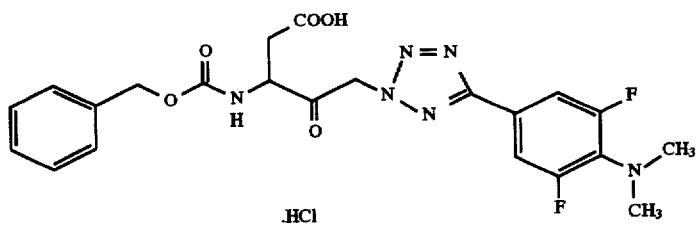

TLC: Rf 0.59 (chloroform:methanol:acetic acid=18:1:1);

NMR (d$_6$-DMSO): δ8.04 (1H, d, J=9.0 Hz), 7.61 (2H, d, J=10.0 Hz), 7.43–7.23 (5H, m), 6.07 (2H, s), 5.10 (2H, s), 4.75–4.59 (1H, m), 2.91 (6H, s), 2.93–2.59 (2H, m).

Example 4(24)

N-benzyloxycarbonyl-3-amino-4-oxo-5-(5-(piperidin-1-yl) tetrazol-2-yl) pentanoic acid.hydrochloride

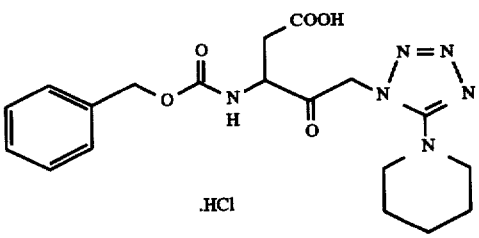

TLC: Rf 0.31 (chloroform:methanol:acetic acid=36:1:1);

NMR (d$_6$-DMSO): δ12.66–12.13 (1H, br), 7.96 (1H, d, J=8 Hz), 7.37 (5H, m), 5.71 (2H, s), 5.09 (2H, s), 4.69–4.51 (1H, m), 3.36 (4H, brs), 2.81 (1H, dd, J=17 and 7 Hz), 2.61 (1H, dd, J=17 and 7 Hz), 1.58 (6H, brs).

Example 4(25)

N-benzyloxycarbonyl-3-amino-4-oxo-5-(5-(piperidin-1-yl)tetrazol-1-yl)pentanoic acid.hydrochloride TLC: Rf 0.51 (chloroform:methanol:acetic acid=18:1:1);

NMR (d$_6$-DMSO): δ12.80–12.17 (1H, br), 8.03 (1H, d, J=7.4 Hz), 7.46–7.24 (5H, m), 5.58–5.40 (2H, m), 5.10 (2H, s), 4.70–4.50 (1H, m), 3.09 (4H, brs), 2.83 (1H, dd, J=16.8 and 6.0 Hz), 2.66 (1H, dd, J=16.8 and 6.8 Hz), 1.53 (6H, brs).

Example 4(26)

N-benzyloxycarbonyl-3-amino-4-oxo-5-(5-(2-chloro-5-methylphenyl) tetrazol-2-yl)pentanoic acid

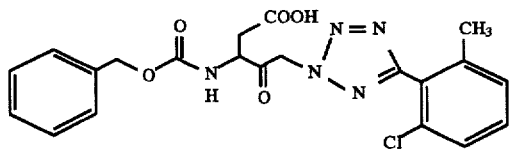

TLC: Rf 0.37 (chloroform:methanol:acetic acid=47:2:1);

NMR (d₆-DMSO): δ12.55 (1H, brs), 8.02 (1H, d, J=4.2 Hz), 7.53–7.22 (8H, m), 6.11 (2H, brs), 5.10 (2H, s),4.76–4.58 (1H, m), 2.85 (1H, dd, J=16.6, 5.8 Hz), 2.66 (1H, dd, J=16.6, 6.5 Hz), 2.08 (3H, s).

Example 4(27)

N-benzyloxycarbonyl-3-amino-4-oxo-5-(5-(2-chloro-5-methylphenyl)tetrazol-1-yl)pentanoic acid

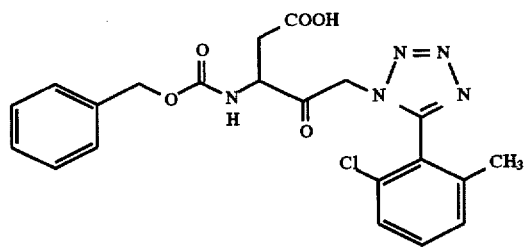

TLC: Rf 0.31 (chloroform:methanol:acetic acid=47:2:1);

NMR (d₆-DMSO): δ12.53 (1H, brs), 7.97–7.80 (1H, m), 7.58–7.18 (8H, m), 5.95–5.65 (1H, m), 5.88–5.17 (1H, m), 5.02 and 4.91 (total 2H, each s), 4.50–4.33 (1H, m),.2.74–2.36 (2H, m), 2.05 (3H, s).

Example 4(28)

N-benzyloxycarbonyl-3-amino-4-oxo-5-(5-((3-phenyl)phenyl)tetrazol-2-yl)pentanoic acid

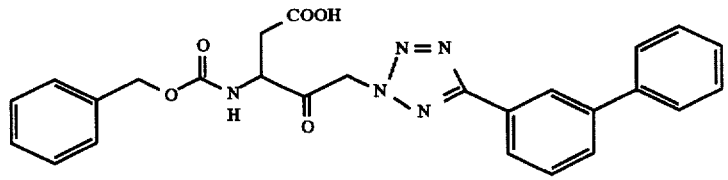

TLC: Rf 0.28 (chloroform:methanol=4:1);

NMR (d₆-DMSO): δ8.27 (1H, s), 8.03 (1H, d, J=6.5 Hz), 7.87–7.20 (13H, m), 6.10 (2H, br), 5.07 (2H, s), 4.55 (1H, m), 2.61 (2H, m).

Example 4(29)

N-benzyloxycarbonyl-3-amino-4-oxo-5-(5-((3-phenyl)phenyl)tetrazol-1-yl)pentanoic acid

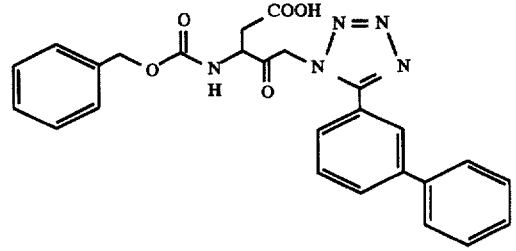

TLC: Rf 0.26 (chloroform:methanol=4:1);

NMR (d₆-DMSO): δ8.00–7.20 (15H, m), 5.92 (2H, brs), 4.96 (2H, s), 4.48 (1H, m).

Example 4(30)

N-benzyloxycarbonyl-3-amino-4-oxo-5-(5-(benzocyclobuten-1-yl) tetrazol-2-yl)pentanoic acid

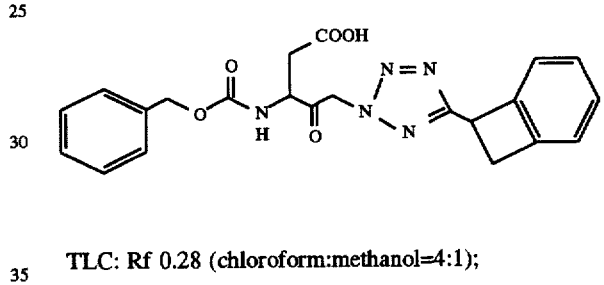

TLC: Rf 0.28 (chloroform:methanol=4:1);

NMR (d₆-DMSO): δ7.58 (1H, d, J=8 Hz), 7.40–7.10 (9H, m), 5.93 (1H, d, J=17 Hz), 5.89 (1H, d, J=17 Hz), 5.03 (2H, s), 4.97 (1H, m), 4.46 (1H, m), 3.70 (1H, dd, J=15 and 7 Hz), 2.70–2.40 (2H, m).

Example 4(31)

N-benzyloxycarbonyl-3-amino-4-oxo-5-(5-(benzocyclobuten-1-yl)tetrazol-1-yl)pentanoic acid

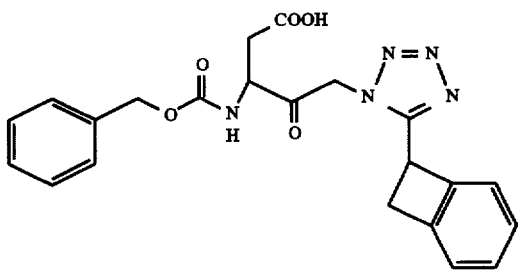

TLC: Rf 0.21 (chloroform:methanol=4:1);

NMR (d₆-DMSO): δ7.65 (1H, m), 7.42–7.06 (9H, m), 5.89 (2H, ABt, J=20Hz), 5.05 and 5.03 (2H, s each), 4.83 (1H, m), 4.50 (1H, m), 3.62 (1H, m) 2.70–2.50 (2H, m).

Example 4(32)

N-benzyloxycarbonyl-3-amino-4-oxo-5-(5-(2S-(2,2,2-trichloroethoxycarbonyl)pyrrolidin-1-yl)tetrazol-2-yl)pentanoic acid

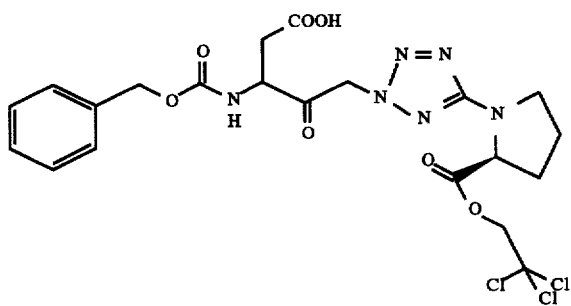

TLC: Rf 0.42 (chloroform:ethanol:acetic acid=18:1:1);

NMR (d₆-DMSO): δ7.59 (1H, m), 7.37 (5H, m), 5.73 (2H, br), 5.08 (2H, s), 4.95 and 4.88 (total 2H, each d, J=12.0 Hz), 4.53 (2H, m), 3.53 (2H, m), 2.59 (2H, m), 2.53–1.90 (4H, m).

Example 4(33)

N-benzyloxycarbonyl-3-amino-4-oxo-5-(5-(2R-(2,2,2-trichloroethoxycarbonyl)pyrrolidin-1-yl)tetrazol-2-yl)pentanoic acid

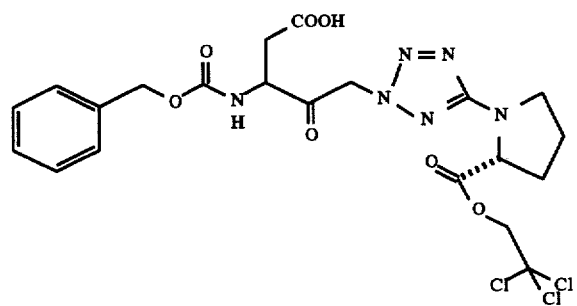

TLC: Rf 0.49 (chloroform:ethanol:acetic acid=18:1:1);

NMR (d₆-DMSO): δ7.91 (1H, m), 7.36 (5H, m), 5.69 (2H, m), 5.08 (2H, s), 4.93 and 4.87 (each 1H, each d, J=13.0 Hz), 4.57 (2H, m), 3.55 (2H, m), 2.87–2.54 (2H, m), 2.43 and 2.24–1.89 (4H, m).

Example 4(34)

N-benzyloxycarbonyl-3-amino-4-oxo-5-(5-(2-carboxyphenyl)tetrazol-2-yl)pentanoic acid

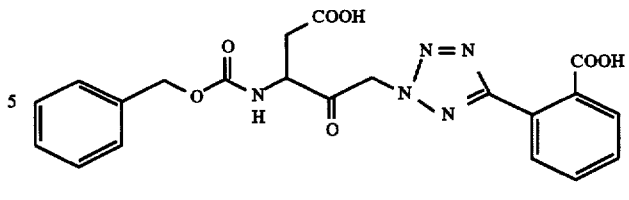

TLC: Rf 0.61 (chloroform:methanol:acetic acid=8:1:1);

NMR (CDCl₃): δ7.80 (1H, m), 7.68 (1H, m), 7.48 (2H, m), 7.24 (5H, m), 6.33 (1H, br), 5.88–5.30 (2H, br), 5.03 (2H, m), 4.66 (1H, m), 3.08–2.53 (2H, m).

Example 4(35)

N-benzyloxycarbonyl-3-amino-4-oxo-5-(5-(2-carboxyphenyl)tetrazol-1-yl)pentanoic acid

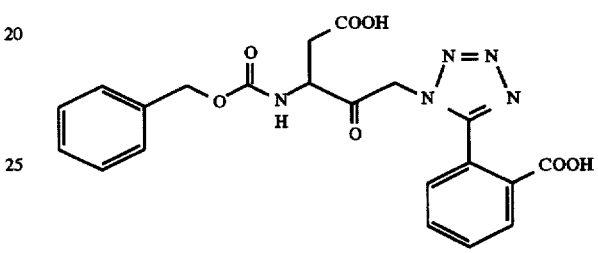

TLC: Rf 0.38(chloroform:methanol:acetic acid=8:1:1);

NMR (d₆-DMSO): δ8.00 (1H, m), 7.73 (1H, m), 7.51 (2H, m), 7.30 (6H, m), 5.45 (2H, br), 4.95 (2H, s), 4.38 (1H, m), 2.40 (2H, m).

Example 4(36)

N-benzyloxycarbonyl-3-amino-4-oxo-5-(5-(3-carboxyphenyl)tetrazol-2-yl)pentanoic acid

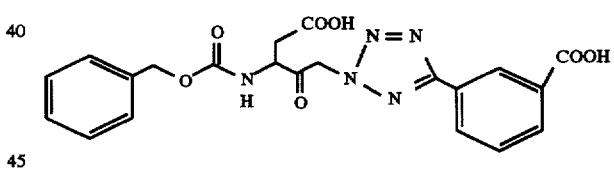

TLC: Rf 0.27 (chloroform:methanol:acetic acid=18:1:1);

NMR (d₆-DMSO): δ8.52 (1H, s), 8.05 (1H, d, J=7.0 Hz), 7.98 (1H, d, J=7.0 Hz), 7.87–7.73 (1H, m), 7.48 (1H, t, J=7.0 Hz), 7.32–7.12 (5H, m), 6.02–5.82 (2H, m), 4.98 (2H, s), 4.62–4.44 (1H, m), 2.78–2.45 (2H, m).

Example 4(37)

N-benzyloxycarbonyl-3-amino-4-oxo-5-(5-(4-carboxyphenyl)tetrazol-2-yl)pentanoic acid

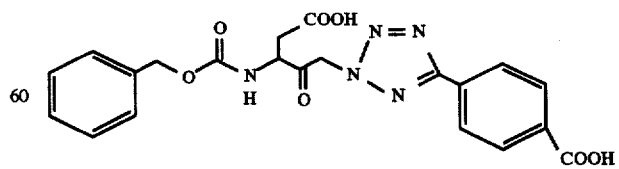

TLC: Rf 0.15 (chloroform:methanol:acetic acid=28:1:1);

NMR (d₆-DMSO): δ8.21 (2H, d, J=8.4 Hz), 8.13 (2H, d, J=8.4 Hz), 8.07–7.92 (1H, m), 7.70–7.20 (5H, m), 6.09 (2H, brs), 5.12 (2H, s), 4.82–4.54 (1H, m), 2.83(1H, dd, J=16.7, 6.0 Hz), 2.68 (1H, dd, J=16.7, 6.9 Hz).

Example 4(38)

N-benzyloxycarbonyl-3-amino-4-oxo-5-(5-(2R-ethoxycarbonylpyrrolidin-1-yl)tetrazol-2-yl)pentanoic acid

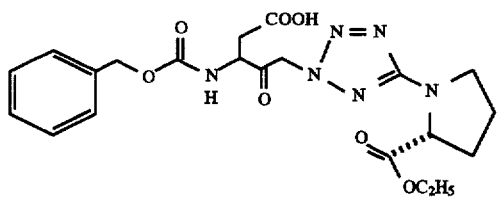

TLC: Rf 0.54 (chloroform:ethanol:acetic acid=8:1:1);

NMR (d$_6$-DMSO): δ7.78 (1H, m), 7.36 (5H, m), 5.69 (2H, brs), 5.07 (2H, s), 4.51 (1H, m), 4.34 (1H, m), 4.08 (2H, q, J=7.0 Hz), 2.62 (2H, m), 2.43–1.84 (4H, m), 1.16 (3H, t, J=7.0 Hz).

Examples 5(1)–5(4)

By the same procedure as provided in example 1, using a corresponding bromomethylketone [the compound prepared as described in J. Med. Chem., 37, 563(1994)] instead of N-((N-(3-phenylpropionyl)-L-valyl)-L-alanyl)-3-amino-4-oxo-5-bromopentanoic acid.t-butylester, compounds of the present invention having the following physical data were obtained.

Example 5(1)

3-(N-(2-(hexahydro-2-oxo-3S-(phenylcarbonylamino) azepin-1-yl))propionyl)amino-4-oxo-5-(5-(2,6-dichlorophenyl)tetrazol-2-yl)pentanoic acid.t-butylester

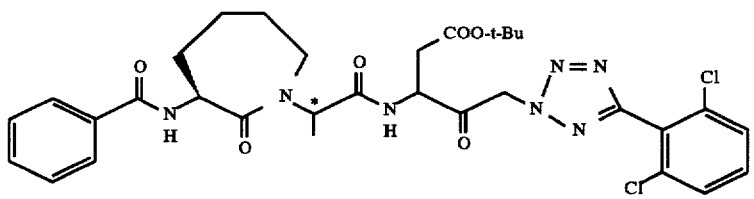

(wherein * represents R or S stereochemistry. The above compound has the opposite stereoconfiguration as the compound of Example 5(3))

HPTLC: Rf 0.53 (hexane:ethyl acetate=1:2);

NMR (CDCl$_3$): δ7.87–7.30 (10H, m), 5.96, 5.88, 5.75 and 5.70 (total 2H, each d, J=17.5 Hz), 5.25–5.00 (1H, m), 4.96–4.77 (2H, m), 3.74–3.30 (2H, m), 2.71 (2H, m), 2.28–1.20 (18H, m).

Example 5(2)

3-(N-(2-(hexahydro-2-oxo-3S-(phenylcarbonylamino) azepin-1-yl)) propionyl)amino-4-oxo-5-(5-(2,6-dichlorophenyl)tetrazol-1-yl)pentanoic acid.t-butylester

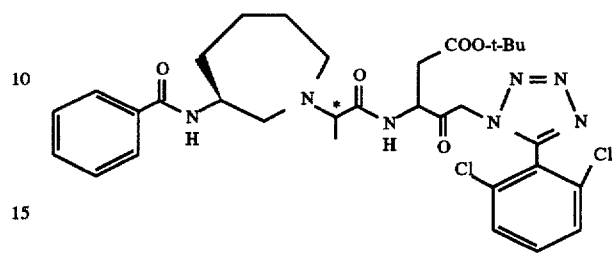

(wherein * represents R or S stereochemistry. The above Compound has the opposite stereoconfiguration as the compound of Example 5(4))

HPTLC: Rf 0.31 (hexane:ethyl acetate=1:2);

NMR (CDCl$_3$): δ7.85–7.31 (10H, m), 5.57, 5.55, 5.34 and 5.30 (total 2H, each d, J=17.5 Hz), 5.10 (1H, m), 4.88–4.60 (2H, m), 3.63–3.20 (2H, m), 2.65 (2H, m), 2.27–1.74 and 1.68–1.20 (total 18H, m).

Example 5(3)

3-(N-(2-(hexahydro-2-oxo-3S-(phenylcarbonylamino) azepin-1-yl)) propionyl)amino-4-oxo-5-(5-(2,6-dichlorophenyl)tetrazol-2-yl)pentanoic acid.t-butylester

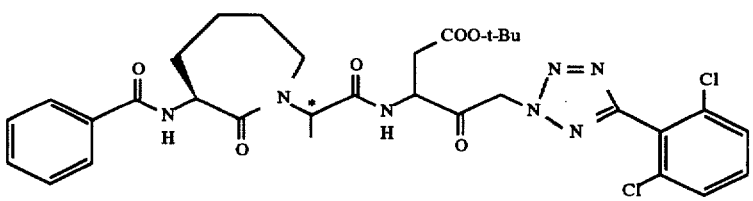

(wherein * represents R or S stereochemistry. The above compound has the opposite stereoconfiguration as the compound of Example 5(1))

HPTLC: Rf 0.38 (hexane:ethyl acetate=1:2);
NMR (CDCl₃): δ7.82 (2H, m), 7.65 (1H, m), 7.57–7.30 (7H, m), 6.01, 5.98, 5.82 and 5.78 (total 2H, each d, J=17.5 Hz), 5.14–4.75 (3H, m), 3.66–3.38 (2H, m), 3.08–2.58 (2H, m), 2.32–1.20 (18H, m).

Example 5(4)

3-(N-(2-(hexahydro-2-oxo-3S-(phenylcarbonylamino) azepin-1-yl))propionyl)amino-4-oxo-5-(5-(2,6-dichlorophenyl)tetrazol-1-yl)pentanoic acid.t-butylester

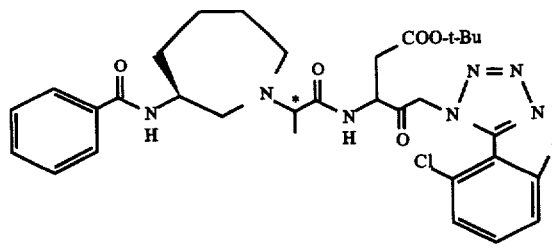

(wherein * represents R or S stereochemistry. The above compound has the opposite stereoconfiguration as the compound of Example 5(2))

HPTLC: Rf 0.22 (hexane:ethyl acetate=1:2);
NMR (CDCl₃): δ7.81 (2H, m), 7.65–7.38 (7H, m), 7.22 (1H, m), 5.63, 5.57, 5.37 and 5.36 (total 2H, each d, J=17.5 Hz), 5.00–4.64 (3H, m), 3.49 (2H, m), 2.95–2.50 (2H, m), 2.29–1.13 (18H, m).

Examples 6(1)–6(4)

By the same procedure as provided in example 2(1), using the compound of examples 5(1)–5(4) instead of compound (1) prepared in example 1, compounds of the present invention having the following physical data were obtained.

Example 6(1)

3-(N-(2-(hexahydro-2-oxo-3S-(phenylcarbonylamino) azepin-1-yl))propionyl)amino-4-oxo-5-(5-(2,6-dichlorophenyl)tetrazol-2-yl)Pentanoic acid

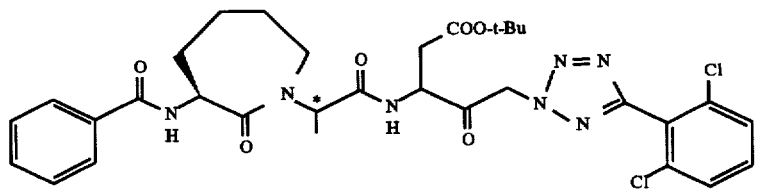

(wherein * represents R or S stereochemistry. The above compound has the opposite stereoconfiguration as the compound of Example 6(3))

TLC: Rf 0.40 (chloroform:methanol=4:1);
NMR (d₆-DMSO): δ8.45 (2H, m), 7.86 (2H, m), 7.73–7.36 (6H, m), 6.22–5.89 (2H, m), 5.11 (1H, m), 4.88 (1H, m), 4.68 (1H, m), 3.55 (2H, m), 2.66–2.85 (2H, m), 2.00–1.10 (9H, m).

Example 6(2)

3-(N-(2-(hexahydro-2-oxo-3S-(phenylcarbonylamino) azepin-1-yl)) propionyl)amino-4-oxo-5-(5-(2,6-dichlorophenyl)tetrazol-1-yl)pentanoic acid (wherein * represents R or S stereochemistry. The above compound has the opposite stereoconfiguration as the compound of Example 6(4))

TLC: Rf 0.33 (chloroform:methanol=4:1);

NMR (d₆-DMSO): δ8.42–8.21 (2H, m), 7.83 (2H, d, J=7.0 Hz), 7.70–7.33 (6H, m), 5.74–5.43 (2H, m), 4.96 (1H, m), 4.78 (1H, m), 4.40 (1H, m), 3.40 (2H, m), 2.38 (2H, m), 1.97–1.02 (9H, m).

Example 6(3)

3-(N-(2-(hexahydro-2-oxo-3S-(phenylcarbonylamino) azepin-1-yl))propionyl)amino-4-oxo-5-(5-(2,6-dichlorophenyl)tetrazol-2-yl)pentanoic acid

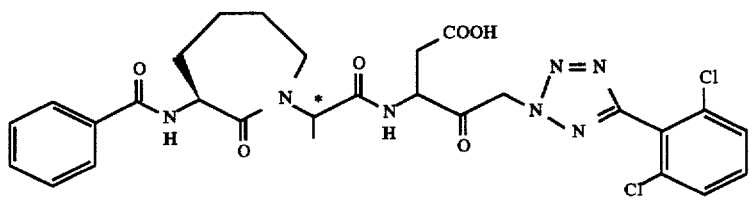

(wherein * represented R or S stereochemistry. The above compound has the opposite stereoconfiguration as the compound of Example 6(1))

TLC: Rf 0.40 (chloroform:methanol=4:1);

NMR (d$_6$-DMSO): δ8.59–8.30 (2H, m), 7.84 (2H, m), 7.67 (3H, m), 7.55–7.31 (3H, m), 6.28–5.85 (2H, m), 5.00–4.58 (3H, m), 3.51 (2H, m), 2.65–2.40 (2H, m), 2.00–1.10 (9H, m).

Example 6(4)

-(N-(2-(hexahydro-2-oxo-3S-(phenylcarbonylamino) azepin-1-yl)) propionyl)amino-4-oxo-5-(5-(2,6-dichlorophenyl)tetrazol-1-yl)pentanoic acid

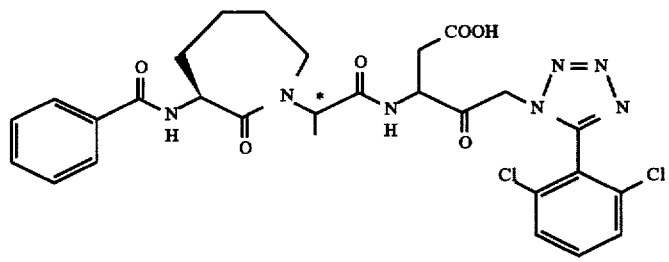

(wherein * represents R or S stereochemistry. The above compound has the opposite stereoconfiguration as the compound of Example 6(2))

TLC: Rf 0.33(chloroform:methanol=4:1);

NMR (d$_6$-DMSO): δ8.44 and 8.29 (total 2H, m), 7.82 (2H, m), 7.66 (3H, m), 7.58–7.38 (3H, m), 5.70–5.54 (2H, m), 4.82–4.64 (2H, m), 4.40 (1H, m), 3.40 (2H, m), 2.53–2.36 (2H, m), 1.94–1.08 (9H, m).

Example 7

N-((N-(3-phenylpropionyl)-L-valyl)-L-alanyl)-3-amino-4-oxo-5-(5-(2-chloro-6-carboxyphenyl)tetrazol-2-yl)pentanoic acid

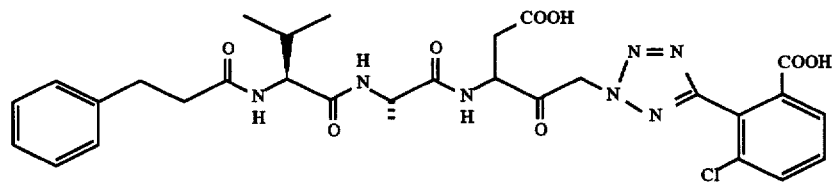

To a solution of the compound prepared in example 2(23) (35 mg) in dimethoxyethane (4 ml) was added a 1N aqueous solution of lithium hydroxide (2 ml) and the mixture was stirred for 1 h at room temperature. The reaction mixture was quenched by addition of a 1N aqueous solution of hydrochloric acid (6 ml) and extracted with ethyl acetate. The extract was washed with water and a saturated aqueous solution of sodium chloride, then dried over anhydrous magnesium sulfate and concentrated. The residue was washed with diethyl ether and dried to give the compound (30 mg) of the present invention having the following physical data.

TLC: Rf 0.42 (chloroform:ethanol:acetic acid=8:1:1);

NMR (CD$_3$OD): δ8.03 (1H, m), 7.66 and 7.64 (total 2H, m), 7.30–7.06 (5H, m), 6.04–5.65 (2H, m), 4.78 (1H, m), 4.32 (1H, m), 4.12 (1H, m), 3.02–2.75 (4H, m), 2.57 (2H, m), 1.99 (1H, m), 1.38 (3H, m), 0.87 (6H, m).

Examples 7(1)–(4)

By the same procedure as provided in example 7, using the compounds prepared in examples 4(7), 4(12), 4(13), or 4(14) instead of the compound prepared in example 2(23), compounds of the present invention having the following physical data were obtained.

Example 7(1)

N-benzyloxycarbonyl-3-amino-4-oxo-5-(5-(3-carboxyphenyl)tetrazol-2-yl)pentanoic acid

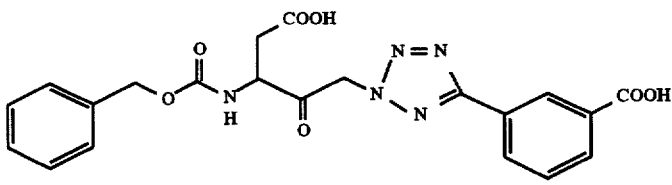

TLC: Rf 0.27 (chloroform:methanol:acetic acid=18:1:1);

NMR (d₆-DMSO): δ8.52 (1H, s), 8.05 (1H, d, J=7.0 Hz), 7.98 (1H, d, J=7.0 Hz), 7.87–7.73 (1H, m), 7.48 (1H, t, J=7.0 Hz), 7.32–7.12 (5H, m), 6.02–5.82 (2H, m), 4.98 (2H, s), 4.62–4.44 (1H, m), 2.78–2.45 (2H, m).

Example 7(2)

N-benzyloxycarbonyl-3-amino-4-oxo-5-(5-(2-carboxyphenyl)tetrazol-2-yl)pentanoic acid

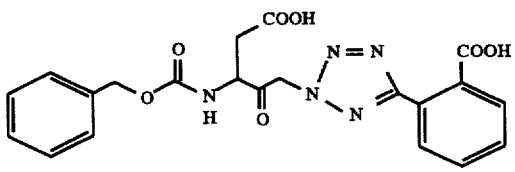

TLC: Rf 0.61 (chloroform:methanol:acetic acid=8:1:1);

NMR (CDCl₃): δ7.80 (1H, m), 7.68 (1H, m), 7.48 (2H, m), 7.24 (5H, m), 6.33 (1H, br), 5.88–5.30 (2H, br), 5.03 (2H, m), 4.66 (1H, m), 3.08–2.53 (2H, m).

Example 7(3)

N-benzyloxycarbonyl-3-amino-4-oxo-5-(5-(2-carboxyphenyl)tetrazol-1-yl)pentanoic acid

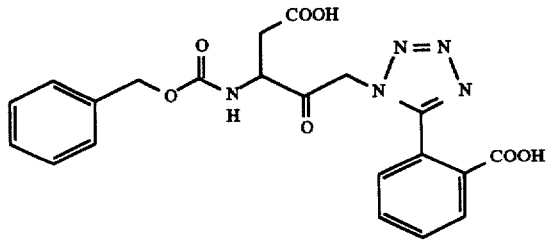

TLC: Rf 0.38(chloroform:methanol:acetic acid=8:1:1);

NMR (d₆-DMSO): δ8.00 (1H, m), 7.73 (1H, m), 7.51 (2H, m), 7.30 (6H, m), 5.45 (2H, br), 4.95 (2H, s), 4.38 (1H, m), 2.40 (2H, m).

Example 7(4) N-benzyloxycarbonyl-3-amino-4-oxo-5-(5-(4-carboxyphenyl)tetrazol-2-yl)pentanoic acid

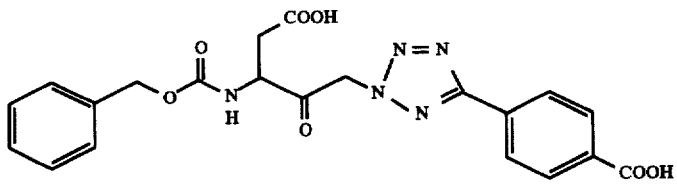

TLC: Rf 0.15 (chloroform:methanol:acetic acid=28:1:1);

NMR (d₆-DMSO): δ8.21 (2H, d, J=8.4 Hz), 8.13 (2H, d, J=8.4 Hz), 8.07–7.92 (1H, m), 7.70–7.20 (5H, m), 6.09 (2H, brs), 5.12 (2H, s), 4.82–4.54 (1H, m), 2.83 (1H, dd, J=16.7, 6.0 Hz), 2.68 (1H, dd, J=16.7, 6.9 Hz).

Example 8

N-benzyloxycarbonyl-3-amino-4-oxo-5-(5-(2S-carboxypyrrolidin-1-yl)tetrazol-2-yl)pentanoic acid.t-butyl ester

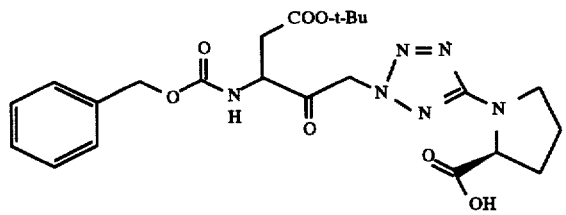

To a solution of the compound prepared in example 3(32) (1.47 g) in 99% acetic acid (119 ml) was added zinc (powder) (7.55 g). The reaction mixture was sonicated for 3 h. The mixture was filtered through Celite and the filtrate was concentrated. The residue was purified by column chromatography on silica gel (chloroform:ethanol:acetic acid=18:1:1) to give the compound (869 mg) of the present invention having the following physical data.

TLC: Rf 0.45 (chloroform:ethanol:acetic acid=18:1:1);

NMR (d₆-DMSO): δ7.93 (1H, d, J=7.5 Hz), 7.36 (5H, m), 5.71 (2H, brs), 5.08 (2H, s), 4.61 (1H, m), 4.25 (1H, m), 3.49 (2H, m), 2.85–2.48 (2H, m), 2.40–1.87 (4H, m), 1.38 (9H, s).

Example 8(1)

N-benzyloxycarbonyl-3-amino-4-oxo-5-(5-(2R-carboxypyrrolidin-1-yl)tetrazol-2-yl)pentanoic acid.t-butyl ester

285

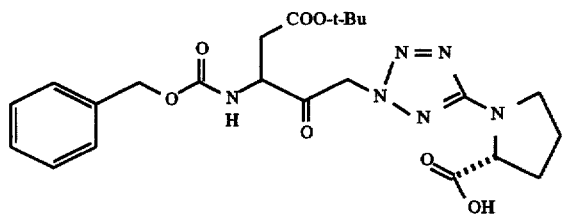

By the same procedure as set forth in example 8, using the compound prepared in example 3(33)instead of the compound prepared in example 3(32), the compound of the present invention having the following physical data was obtained.

TLC: Rf 0.50 (chloroform:ethanol:acetic acid=18:1:1).

Example 9

N-benzyloxycarbonyl-3-amino-4-oxo-5-(5-(2S-carboxypyrrolidin-1-yl)tetrazol-2-yl)pentanoic acid

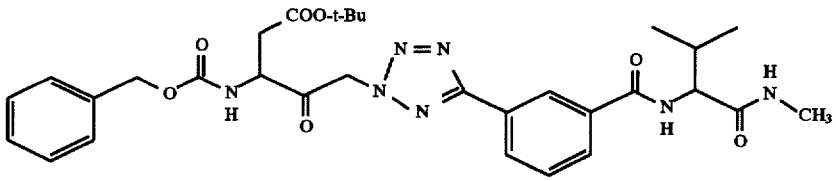

By the same procedure as provided in example 4, using the compound prepared in example 8 instead of the compound prepared in example 3, the compound of the present invention having the following physical data was obtained.

TLC: Rf 0.11 (chloroform:ethanol:acetic acid=18:1:1);

NMR (d$_6$-DMSO): δ7.78 (1H, m), 7.36 (5H, m), 5.66 (2H, br), 5.07 (2H, s), 4.54 (1H, m), 4.25 (1H, m), 4.22 (1H, m), 2.65 (2H, m), 2.40–1.85 (4H,

Example 9(1)

N-benzyloxycarbonyl-3-amino-4-oxo-5-(5-(2R-carboxypyrrolidin-1-yl)tetrazol-2-yl)pentanoic acid

286

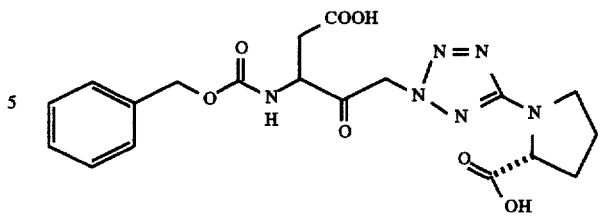

By the same procedure as provided in example 9, using the compound prepared in example 8(1) instead of the compound prepared in example 8, the compound of the present invention having the following physical data was obtained.

TLC: Rf 0.36 (chloroform:methanol:acetic acid=21:2:2);

NMR (d$_6$-DMSO): δ7.60–7.20 (6H, m), 5.62–5.35 (2H, m), 5.10–4.94 (2H, m), 4.56–4.24 (total 1H, m), 4.12–4.00 (1H, m), 3.65–3.49 (2H, m), 2.78–2.23 (2H, m), 2.22–1.75 (4H, m).

Example 10

N-benzyloxycarbonyl-3-amino-4-oxo-5-(5-(3-((1-(N-methylaminocarbonyl)-2-methylpropyl)aminocarbonyl)phenyl)tetrazol-2-yl)pentanoic acid.t-butyl ester To a solution of valylaminomethyl.hydrochloride (23 mg) in dimethylformamide (2 ml) were added the compound prepared in example 3(36) (40 mg), 1-hydroxybenzotriazole (16 mg) and 1-ethyl-3-[3-(dimethylamino)propyl] carbodiimide.hydrochloride (20 mg). The reaction mixture was stirred at room temperature for 4h. The reaction mixture was quenched by addition of a 1N aqueous solution of hydrochloric acid and extracted with ethyl acetate. The extract was washed with a saturated aqueous solution of sodium hydrocarbonate and a saturated aqueous solution of sodium chloride, dried over anhydrous sodium sulfate and concentrated to give the present invention compound (47 mg) having the following physical data.

TLC: Rf 0.66 (ethyl acetate);

NMR (CDCl$_3$): δ8.80–8.56 (0.5H, m), 8.50 and 8.39 (total 1H, m), 8.36–8.24 (1H, m), 8.00–7.88 (1H, m), 7.82–7.60 (0.5H, m), 7.60–7.30 (6H, m), 7.13–6.95 (0.5H, m), 6.38–6.12 (1.5H, m), 5.99, 5.90, 5.85–5.74, 5.57 and 5.47 (total 2H, m), 5.26–5.15 (2H, m), 5.06–4.77 (1H, m), 4.43–4.19 (1H, m), 3.00–2.82 (3H, m), 2.76–2.60 and 2.42–2.17 (total 3H, m), 1.50–1.39 (9H, m), 1.08–0.92 (6H, m).

Examples 10(1)–10(23)

By the same procedure as set forth in example 7, using We compounds prepared in examples 3(34), 3(35), 3(36), 3(37), 8 or 8(1) instead of the compound prepared in example 3(36), and the corresponding amine compound instead of valylaminomethyl.hydrochloride, compounds of the present invention having the following physical data were obtained.

Example 10(1)

N-benzyloxycarbonyl-3-amino-4-oxo-5-(5-(3-((1-aminocarbonyl-2-methylpropyl)aminocarbonyl)phenyl)tetrazol-2-yl)pentanoic acid.t-butyl ester

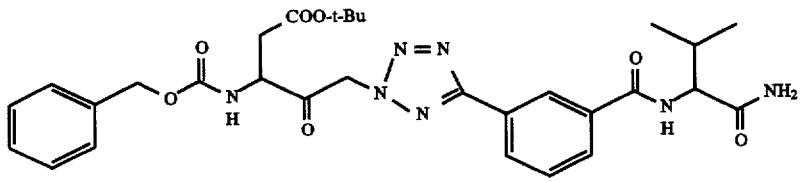

TLC: Rf 0.64 (ethyl acetate);

NMR (CDCl$_3$): δ8.54–8.43 (1H, m), 8.35–8.22 (1H, m), 8.20–7.88 (2H, m), 7.60–7.18 (6H, m), 6.75–6.60 and 6.30–6.10 (total 2H, m), 6.00–5.55 and 5.45–5.35 (total 3H, m), 5.25–5.15 (2H, m), 5.00–4.72 (1H, m), 4.60–4.47 (1H, m), 3.10–2.70 (2H, m), 2.40–2.15 (1H, m), 1.50–1.38 (9H, m), 1.10–0.99 (6H, m).

Example 10(2)

N-benzyloxycarbonyl-3-amino-4-oxo-5-(5-(3-(morpholin-1-ylcarbonyl)phenyl)tetrazol-2-yl)pentanoic acid.t-butyl ester

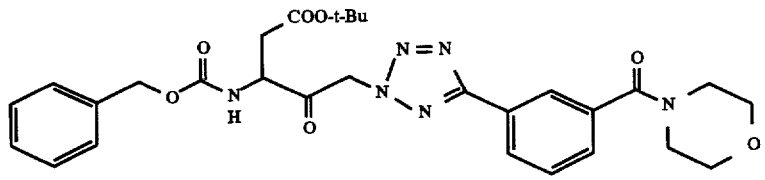

TLC: Rf 0.31 (hexane:ethyl acetate=2:1);

NMR (d$_6$-DMSO): δ8.25–8.15 (2H, m), 7.60–7.46 (2H, m), 7.46–7.30 (5H, m), 6.05–5.95 (1H, m), 5.89 and 5.71 (each 1H, d, J=17.5 Hz), 5.19 (2H, s), 4.79–4.63 (1H, m), 3.93–3.35 (8H, m), 3.05 and 2.72 (each 1H, dd, J=16.0, 5.0 Hz), 1.44 (9H, s).

Example 10(3)

N-benzyloxycarbonyl-3-amino-4-oxo-5-(5-(3-((1 S-(N-methylaminocarbonyl)-2-methylpropyl)aminocarbonyl)phenyl)tetrazol-2-yl)pentanoic acid.t-butyl ester

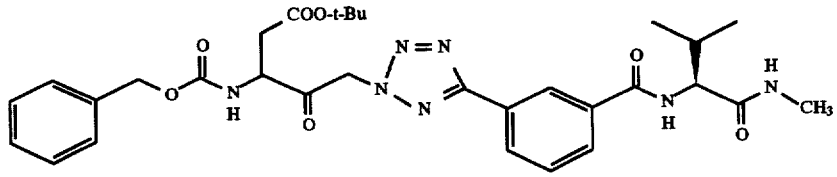

TLC: Rf 0.64 (ethyl acetate);

NMR (CDCl$_3$): δ9.30–9.14 (1H, m), 8.37 (1H, s), 8.29 (1H, d, J=7.8 Hz), 7.99 (1H, d, J=9.1 Hz), 7.95 (1H, d, J=7.8 Hz), 7.55–7.25 (6H, m), 6.35–6.14 (1H, m), 5.96 (1H, d, J=17.9 Hz), 5.46 (1H, d, J=17.9 Hz), 5.35–5.18 (2H, m), 5.12–4.90 (1H, m), 4.23 (1H, t, J=9.5 Hz), 3.08–2.76 (2H, m), 2.40–2.20 (1H, m), 2.20 (3H, d, J=4.5 Hz), 1.46 (9H, s), 1.03 (3H, d, J=6.6 Hz), 0.96 (3H, d, J=6.6 Hz).

Example 10(4)

N-benzyloxycarbonyl-3-amino-4-oxo-5-(5-(3-(N-methylaminocarbonyl)phenyl)tetrazol-2-yl)pentanoic acid.t-butyl ester

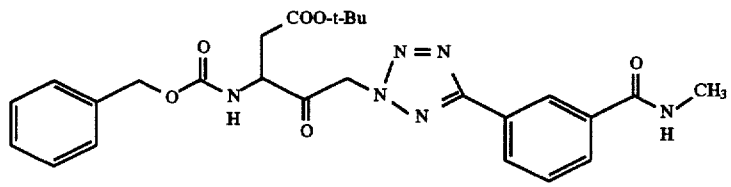

TLC: Rf 0.73 (ethyl acetate);

NMR (CDCl₃): δ8.45 (1H, s), 8.25 (1H, d, J=7.7 Hz), 7.97 (1H, d, J=7.7 Hz), 7.56 (1H, t, J=7.7 Hz), 7.45–7.30 (5H, m), 6.40 (1H, brs), 6.04 (1H, d, J=9.2 Hz), 5.88 (1H, d, J=17.8 Hz), 5.72 (1H, d, J=17.8Hz), 5.19 (2H, s), 4.80–4.65 (1H, m), 3.12–2.91 (4H, m), 2.75 (1H, dd, J=17.3, 5.0 Hz), 1.44 (9H, s).

Example 10(5)

N-benzyloxycarbonyl-3-amino-4-oxo-5-(5-(3-(hexahydro-2-azepinon-3-ylaminocarbonyl)phenyl)tetrazol-2-yl)pentanoic acid.t-butyl ester

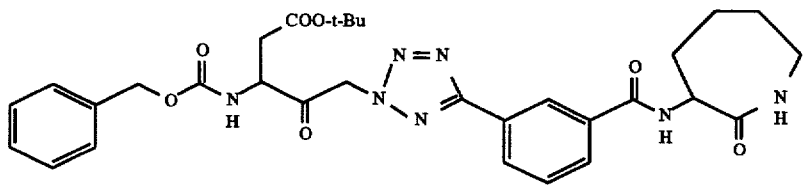

TLC: Rf 0.57 (ethyl acetate);

NMR (CDCl₃): δ8.57 (1H, s), 8.29 (1H, d, J=7.8 Hz), 7.96 (1H, d, J=7.8 Hz), 7.82–7.68 (1H, m), 7.56 (1H, t, J=7.8 Hz), 7.45–7.30 (5H, m), 6.12 (2H, brs) 5.89 (1H, d, J=17.8 Hz), 5.72 (1H, d, J=17.8 Hz), 5.19 (2H, s), 4.83–4.66 (2H, m), 3.40–3.15 (2H, m), 3.02 (1H, dd, J=17.4, 4.8 Hz), 2.75 (1H, dd, J=17.4, 4.7 Hz), 2.40–1.45 (6H, m), 1.44 (9H, s).

Example 10(6)

N-benzyloxycarbonyl-3-amino-4-oxo-5-(5-(3-((1 R-(N-methylaminocarbonyl)-2-methylpropyl)aminocarbonyl)phenyl)tetrazol-2-yl)pentanoic acid.t-butyl ester

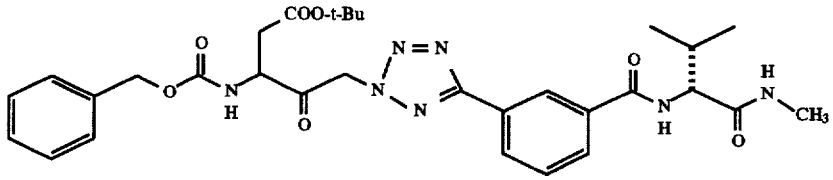

TLC: Rf 0.57 (ethyl acetate);

NMR (CDCl₃): δ8.44 (1H, s), 8.28 (1H, d, J=8.0 Hz), 7.94 (1H, d, J=8.0 Hz), 7.86 (1H, brs), 7.50 (1H, t, J=8.0 Hz), 7.44–7.24 (5H, m), 6.31 (2H, m), 5.79 (2H, s), 5.21 (2H, s), 4.97–4.80 (1H, m), 4.36 (1H, t, J=8.6 Hz), 3.05–2.75 (2H, m), 2.59 (3H, m), 2.35–2.20 (1H, m), 1.44 (9H, s), 1.15–0.92 (6H, m).

Example 10(7)

N-benzyloxycarbonyl-3-amino-4-oxo-5-(5-(3-((1-(N-methylaminocarbonyl)methyl)aminocarbonyl)phenyl)tetrazol-2-yl)Pentanoic acid.t-butyl ester

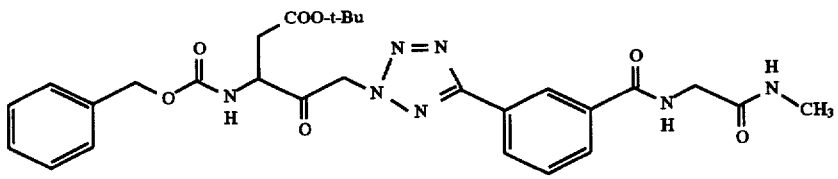

TLC: Rf 0.36 (ethyl acetate);

NMR (CDCl₃): δ8.50 (1H, s), 8.33–8.05 (2H, m), 7.93 (1H, d, J=7.6 Hz), 7.55–7.30 (6H, m), 6.65–6.20 (2H, m), 5.93 (1H, d, J=17.5 Hz), 5.65 (1H, J=17.5 Hz), 5.21 (2H, s), 4.92–4.72 (1H, m), 4.35–3.94 (2H, m), 3.08–2.58 (5H, m), 1.43 (9H, s).

Example 10(8)

N-benzyloxycarbonyl-3-amino-4-oxo-5-(5-(3-((2-(N-methylaminocarbonyl)ethyl)aminocarbonyl)phenyl) tetrazol-2-yl)Pentanoic acid.t-butyl ester

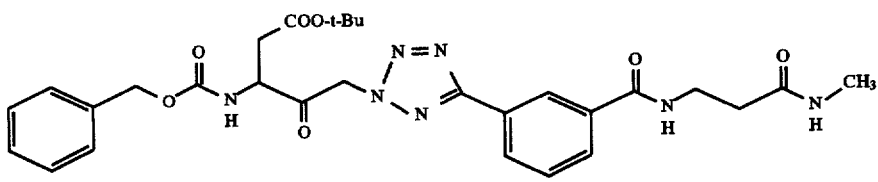

TLC: Rf 0.20 (ethyl acetate);

NMR (CDCl₃): δ8.32–8.28 (1H, m), 8.26–8.05 (1H, m), 7.80–7.20 (8H, m), 7.05–6.72 (1H, m), 6.70–6.38 (1H, m), 5.90–5.61 (2H, m), 5.21 (2H, s), 502–4.79 (1H, m), 3.95–3.57 (2H, m), 2.93 (2H, d, J=5.7 Hz), 2.80–2.30 (5H, m), 1.44 (9H, s).

Example 10(9)

N-benzyloxycarbonyl-3-amino-4-oxo-5-(5-(4-((1-aminocarbonyl-2-methylpropyl)aminocarbonyl)phenyl) tetrazol-2-yl)pentanoic acid. t-butyl ester

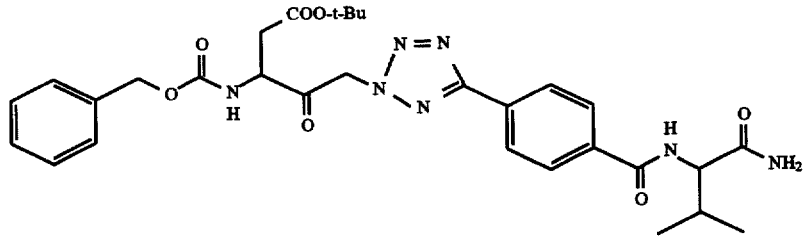

TLC: Rf 0.53 (ethyl acetate);

NMR (CDCl₃): δ8.22 (2H, d, J=8.5 Hz), 7.92 (2H, d, J=8.5 Hz), 7.60–7.44 (5H, m), 7.02 (1H, d, J=8.4Hz), 6.26 (1H, brs), 6.08 (1H, d, J=8.6Hz), 5.93 (1H, d, J=17.9 Hz), 5.74 (1H, d, J=17.9 Hz), 5.68 (1H, brs), 5.20 (2H, s), 4.85–4.65 (1H, m), 4.57 (1H, dd, J=8.4, 7.0 Hz), 3.10–2.65 (2H, m), 2.35–2.14 (1H, m), 1.43 (9H, s), 1.20–0.91 (6H, m).

Example 10(10)

N-benzyloxycarbonyl-3-amino-4-oxo-5-(5-(4-((1-(N-methylaminocarbonyl)-2-methylpropyl)aminocarbonyl) phenyl)tetrazol-2-yl)pentanoic acid.t-butyl ester

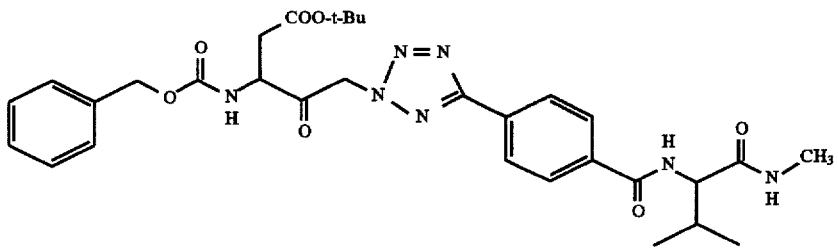

TLC: Rf 0.53 (ethyl acetate);

NMR (CDCl₃): δ8.22 (2H, d, J=8.5 Hz), 7.93 (2H, d, J=8.5 Hz), 7.55–7.31 (5H, m), 7.42 (1H, d, J=8.6 Hz), 6.30 (1H, q, J=4.8 Hz), 6.07 (1H, d, J=9.5 Hz), 5.92 (1H, d, J=19.8Hz), 5.73 (1H, d, J=19.8Hz), 5.20 (2H, s), 4.84–4.65 (1H, m), 4.43 (1H, dd, J=8.5, 7.7 Hz), 3.04 (1H, dd, J=17.2 Hz), 2.76 (1H, dd, J=17.2, 4.8 Hz), 2.30–2.10 (1H, m), 1.44 (9H, s), 1.10–0.90 (6H, m).

Example 10(11)

N-benzyloxycarbonyl-3-amino-4-oxo-5-(5-(4-(morpholin-1-ylcarbonyl)phenyl)tetrazol-2-yl)pentanoic acid.t-butyl ester

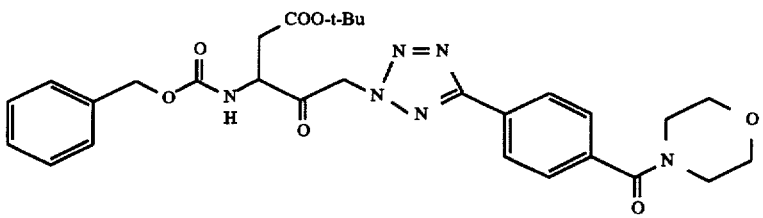

TLC: Rf 0.63 (ethyl acetate);

NMR (CDCl₃): δ8.21 (2H, d, d=8.0 Hz), 7.54 (2H, d, d=8.0 Hz), 7.48–7.34 (5H, m), 6.01 (1H, d, J=8.5Hz), 5.90 (1H, d, d=18.1 Hz), 5.73 (1H, d, J=18.1 Hz), 5.20 (2H, s), 4.82–4.65 (1H, m), 3.95–3.25 (8H, m), 3.05 (1H, dd, J=17.5, 4.2 Hz), 2.74 (1H, dd, d=17.5, 5.0 Hz), 1.44 (9H, s).

Example 10(12)

N-benzyloxycarbonyl-3-amino-4-oxo-5-(5-(4-((2-(N,N-dimethylamino)-ethyl)aminocarbonyl)phenyl)tetrazol-2-yl) pentanoic acid.t-butyl ester

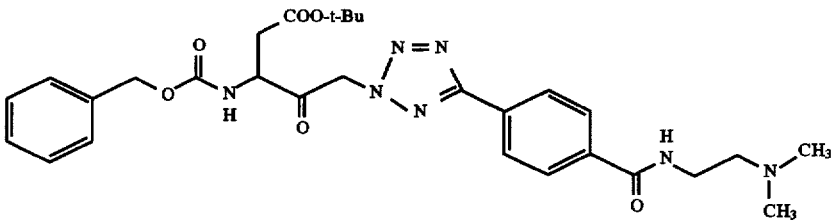

TLC: Rf 0.05 (ethyl acetate);

NMR (CDCl₃): δ8.22 (2H, d, J=8.3 Hz), 7.93 (2H, d, J=8.3 Hz), 7.55–7.25 (5H, m), 7.10–6.95 (1H, m), 6.02 (1H, d, J=8.9 Hz), 5.91 (1H, d, J=18.1 Hz), 5.73 (1H, d, J=18.1 Hz), 5.20 (2H, s), 4.80–4.65 (1H, m), 3.57 (2H, dt, J=5.5, 5.1 Hz), 3.05 (1H, dd, J=17.3, 5.1 Hz), 2.74 (1H, dd, J=17.3, 5.1 Hz), 2.59 (2H, t, J=5.5 Hz), 2.40–2.27 (6H, m), 1.44 (9H, s).

Example 10(13)

N-benzyloxycarbonyl-3-amino-4-oxo-5-(5-(4-(N-methylaminocarbonyl) phenyl)tetrazol-2-yl)pentanoic acid.t-butyl ester

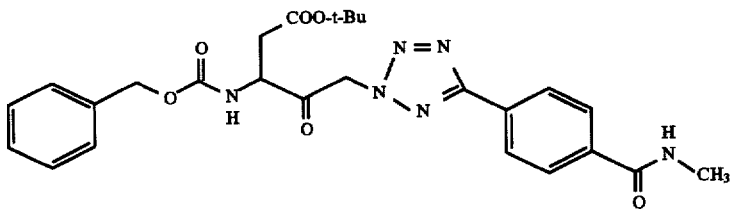

TLC: Rf 0.69 (ethyl acetate);

NMR (CDCl$_3$): δ8.21 (2H, d, J=8.4 Hz), 7.88 (2H, d, J=8.4 Hz), 7.5514 7.10 (5H, m), 6.30–6.15 (1H, m), 6.00 (1H, d, J=8.9 Hz), 5.90 (1H, d, J=17.7 Hz), 5.72 (1H, d, J=17.7 Hz), 5.19 (2H, s), 4.80–4.64 (1H, m), 3.13–2.94 (4H, m), 2.74 (1H, dd, J=17.4, 4.9 Hz), 1.44 (9H, s).

Example 10(14)

N-benzyloxycarbonyl-3-amino-4-oxo-5-(5-(4-(4-methylpiperazin-1-ylcarbonyl)phenyl)tetrazol-2-yl) pentanoic acid.t-butyl ester

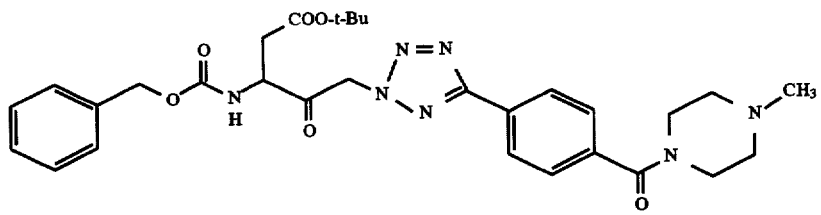

TLC: Rf 0.40 (chloroform:methanol:acetic acid=18:1:1);

NMR (CDCl$_3$): δ8.20 (2H, d, J=8.2 Hz), 7.53 (2H, d, J=8.2 Hz), 7.46–7.30 (5H, m), 6.10 (1H, d, J=9.1 Hz), 5.90 (1H, d, J=17.6 Hz), 5.78–5.64 (1H, m), 5.72 (1H, d, J=17.6 Hz), 5.20 (2H, s), 3.51 (4H, t, J=5.2Hz), 3.05 (1H, dd, J=17.2, 4.3 Hz), 2.74 (1H, dd, J=17.2, 4.6 Hz), 2.60–2.10 (2H, m), 1.44 (9H, s).

Example 10(15)

N-benzyloxycarbonyl-3-amino-4-oxo-5-(5-(4-((1-(N-methylamino-carbonyl)methyl)aminocarbonyl)phenyl) tetrazol-2-yl)pentanoic acid.t-butyl ester

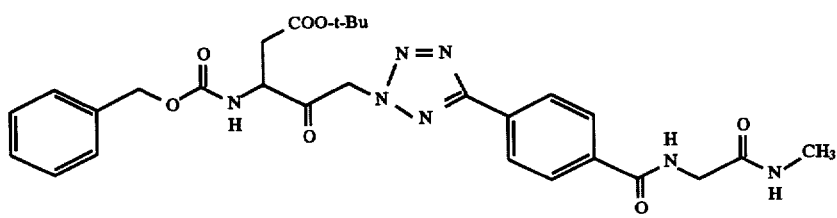

TLC: Rf 0.48 (chloroform:methanol=9:1);

NMR (CDCl$_3$): δ7.80–7.06 (10H, m), 6.91 (1H, d, J=3.4 Hz), 6.15 (1H, d, J=9.1 Hz), 5.60 (1H, d, J=18.7 Hz), 5.54 (1H, d, J=18.7 Hz), 5.08 (2H, s), 4.60–4.43 (1H, m), 4.05–3.75 (2H, m), 3.00–2.83 (2H, m), 2.79 (3H, d, J=4.4 Hz), 2.68 (1H, dd, J=17.5, 5.2 Hz), 1.36 (9H, s).

Example 10(16) N-benzyloxycarbonyl-3-amino-4-oxo-5-(5-(2-((1-aminocarbonyl-2-methylpropyl)aminocarbonyl)phenyl)tetrazol-2-yl)pentanoic acid.t-butyl ester

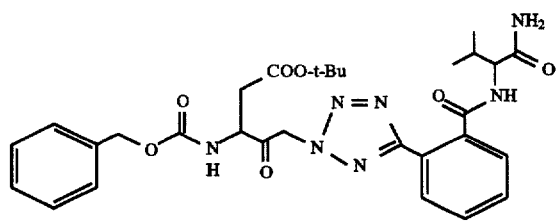

TLC: Rf 0.55 (chloroform:methanol=9:1);

NMR (CDCl₃): δ8.22–8.07 (1H, m), 7.70–7.46 (3H, m), 7.46–7.22 (5H, m), 7.02 (1H, d, J=16 Hz), 6.53–6.05 (3H, m), 5.76 and 5.71 (total 2H, each s), 5.16 and 5.14 (total 2H, each s), 4.74–4.68 (1H, m), 4.68–4.43 (1H, m), 3.02–2.65 (2H, m), 2.54–2.19 (1H, m), 1.42 and 1.41 (total 9H, each s), 1.13–0.80 (6H, m).

Example 10(17)

N-benzyloxycarbonyl-3-amino-4-oxo-5-(5-(2-((1-(N-methylaminocarbonyl)-2-methylpropyl)aminocarbonyl)phenyl)tetrazol-2-yl)pentanoic acid.t-butyl ester

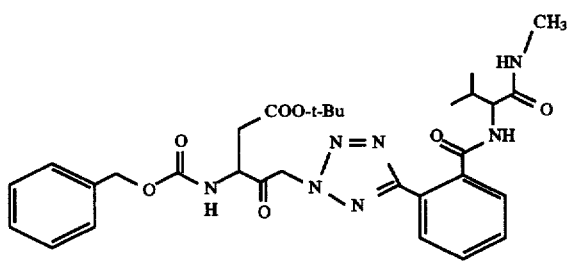

TLC: Rf 0.63 (chloroform:methanol=9:1);

NMR (CDCl₃): δ8.14–7.95 (1H, m), 7.81–7.18 (9H, m), 6.45–6.00 (2H, m), 5.92–5.55 (2H, m), 5.15 and 5.13 (total 2H, each s), 4.75–4.42 (2H, m), 3.10–2.67 (5H, m), 2.63–2.30 (1H, m), 1.45 and 1.43 (total 9H, each s), 1.16–0.77 (6H, m).

Example 10(18)

N-benzyloxycarbonyl-3-amino-4-oxo-5-(5-(2-(morpholin-1-ylcarbonyl)phenyl)tetrazol-2-yl)pentanoic acid.t-butyl ester

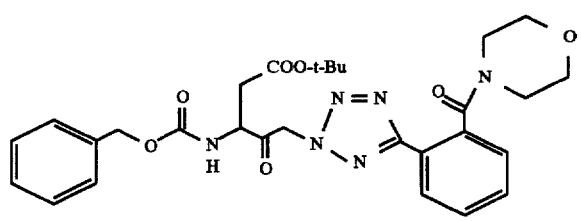

TLC: Rf 0.60 (ethyl acetate);

NMR (CDCl₃): δ8.30–8.10 (1H, m), 7.70–7.20 (8H, m), 6.10–5.60 (3H, m), 5.19 (2H, s), 4.78–4.54 (1H, m), 4.00–3.56 (4H, m), 3.56–3.34 (2H, m), 3.28–3.00 (2H, m), 3.01 (1H, dd, J=17.5, 4.4 Hz), 2.75 (1H, dd, J=17.5, 5.0 Hz), 1.43 (9H, s).

Example 10(19)

N-benzyloxycarbonyl-3-amino-4-oxo-5-(5-(2-((1-(N-methylaminocarbonyl)methyl)aminocarbonyl)phenyl)tetrazol-2-yl)pentanoic acid.t-butyl ester

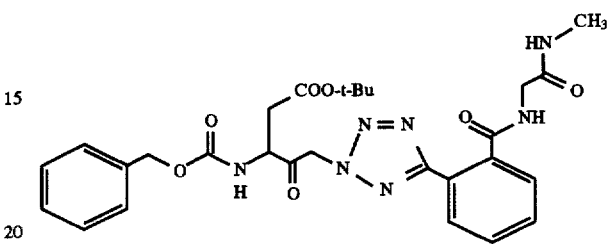

TLC: Rf 0.59 (chloroform:methanol=9:1);

NMR (CDCl₃): δ8.05–7.92 (1H, m), 7.90–7.75 (1H, m), 7.70–7.45 (3H, m), 7.45–7.10 (5H, m), 6.66 (1H, brs), 6.14 (1H, d, J=8.6 Hz), 5.84(1H, d, J=17.4 Hz), 5.70 (1H, d, J=17.7 Hz), 5.15 (2H, s), 4.75–4.58 (1H, m), 4.07 (2H, d, J=5.7 Hz), 3.10–2.65 (5H, m), 1.43 (9H, s).

Example 10(20)

N-benzyloxycarbonyl-3-amino-4-oxo-5-(5-(2-((1-(N-methylamino-carbonyl)methyl)aminocarbonyl)phenyl)tetrazol-1-yl)pentanoic acid.t-butyl ester

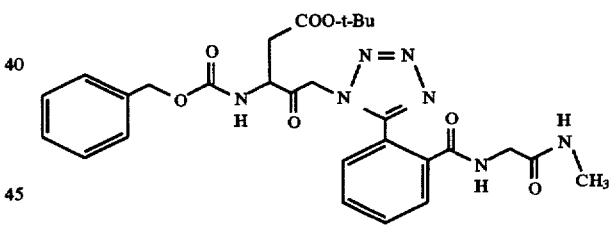

TLC: Rf 0.47 (chloroform:methanol=9:1);

NMR (CDCl₃): δ8.22 (2H, d, J=8.3 Hz), 7.94 (2H, d, J=8.3 Hz), 7.48–7.29 (5H, m), 7.21 (1H, brs), 6.25 (1H, brs), 6.04 (1H, d, J=9.0 Hz), 5.89(1H, d, J=17.7 Hz), 5.73 (1H, d, J=17.7 Hz), 5.15 (2H, s), 4.79–4.66 (1H, m), 4.13 (2H, d, J=5.1 Hz), 3.03 (1H, dd, J=17.4, 4.7 Hz), 2.79 (3H, d, J=5.6 Hz), 2.75 (1H, dd, J=17.4, 4.9 Hz), 1.48 (9H, s).

Example 10(21)

N-benzyloxycarbonyl-3-amino-4-oxo-5-(5-(2S-((1-(N-methylaminocarbonyl)-2-methylpropyl)aminocarbonyl)pyrrolidin-1-yl)tetrazol-2-yl)pentanoic acid.t-butyl ester

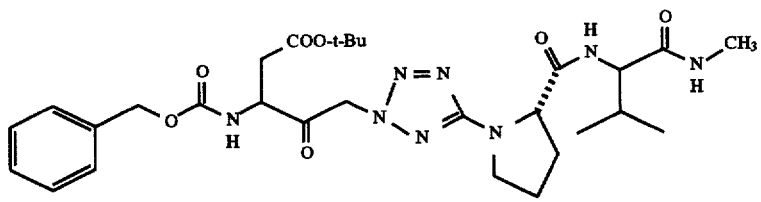

TLC: Rf 0.40, 0.37 (chloroform:methanol=10:1).

Example 10(22)

N-benzyloxycarbonyl-3-amino-4-oxo-5-(5-(2R-((1-(N-methylaminocarbonyl)-2-methylpropyl)aminocarbonyl)pyrrolidin-1-yl)tetrazol-2-yl)pentanoic acid.t-butyl ester By the same procedure as provided in example 2(1), using the compound prepared in example 10 instead of compound (1) prepared in example 1, the compound of the present invention having the following physical data was obtained.

TLC: Rf 0.48 (chloroform:methanol:acetic acid=18:1:1);

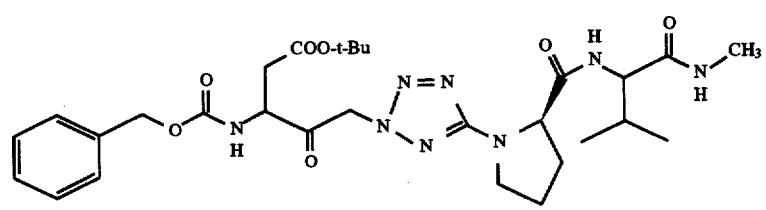

TLC: Rf 0.63 (chloroform:methanol=9:1);

NMR (CDCl$_3$): δ7.38 (5H, m), 6.90–6.36 (2H, m), 6.07 (1H, d, J=9.0 Hz), 5.75–5.38 (2H, m), 5.17 (2H, s), 4.71–4.56 (1H, m), 4.38–4.14 (2H, m), 3.85–3.40 (2H, m), 3.05–2.63 (5H, m), 2.52–1.81 (5H, m), 1.42 (9H, s), 0.95–0.69 (6H, m).

NMR (d$_6$-DMSO): δ8.71–8.60 (1H, m), 8.57 (1H, s), 8.19 (1H, d, J=7.0 Hz), 8.12–8.00 (2H, m), 7.83–7.71 (1H, m), 7.66 (1H, t, J=7.0 Hz), 7.44–7.25 (5H, m), 6.15–5.95 (2H, m), 5.09 (2H, s), 4.65–4.48 (1H, m), 4.35–4.18 (1H, m), 2.70–2.55 (2H, m), 2.62 and 2.60 (total 3H, each s), 2.24–2.03 (1H, m), 0.93 and 0.90 (each 3H, d, J=5.4 Hz).

Example 10(23)

N-benzyloxycarbonyl-3-amino-4-oxo-5-(5-(2R-(N-methylaminocarbonyl)pyrrolidin-1-yl)tetrazol-2-yl)pentanoic acid.t-butyl ester

Examples 11(1)–11(23)

By the same procedure as provided in example 11, using the compound prepared in examples 10(1)–10(23)instead of the compound prepared in example 10, compounds of the present invention having the following physical data were obtained.

Example 11(1)

N-benzyloxycarbonyl-3-amino-4-oxo-5-(5-(3-((1-aminocarbonyl-2-methylpropyl)aminocarbonyl)phenyl)tetrazol-2-yl)pentanoic acid

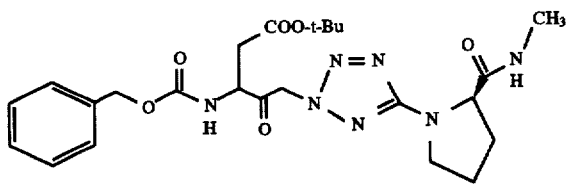

TLC: Rf 0.21 (chloroform:methanol=9:1).

Example 11

N-benzyloxycarbonyl-3-amino-4-oxo-5-(5-(3-((1-(N-methylaminocarbonyl)-2-methylpropyl)aminocarbonyl)phenyl)tetrazol-2-yl)pentanoic acid

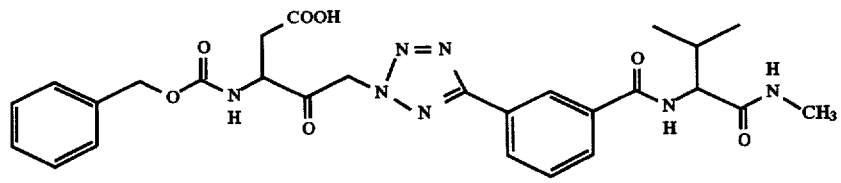

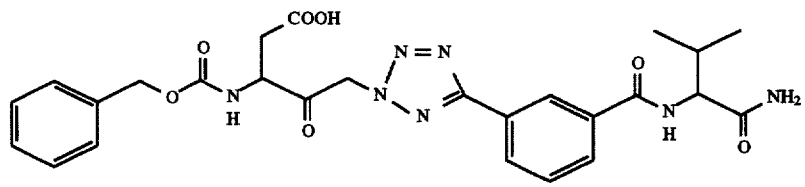

TLC: Rf 0.31 (chloroform:methanol:acetic acid=18:1:1);

NMR (d$_6$-DMSO): δ8.62–8.47 (2H, s), 8.20 (1H, d, J=7.0 Hz), 8.05 (1H, d, J=7.0 Hz), 7.75–7.59 (1H, m), 7.65 (1H, t, J=7.0 Hz), 7.42–7.22 (5H, m), 7.12–7.02 (1H, m), 6.22–5.92 (2H, m), 5.08 (2H, s), 4.58–4.42 (1H, m), 4.35–4.23 (1H, m), 2.72–2.37 (2H, m), 2.25–1.99 (1H, m), 1.00–0.95 (6H, m).

Example 11(2)

N-benzyloxycarbonyl-3-amino-4-oxo-5-(5-(3-(morpholin-1-ylcarbonyl)phenyl)tetrazol-2-yl)pentanoic acid

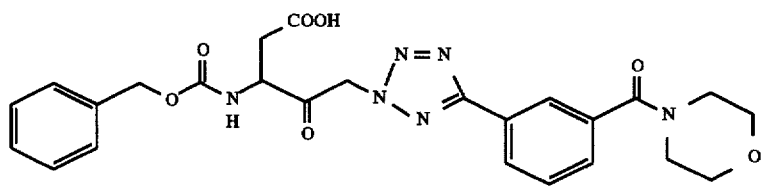

TLC: Rf 0.60 (chloroform:methanol:acetic acid=18:1:1);

NMR (d$_6$-DMSO): δ8.20–7.98 (2H, m), 7.98–7.82 (1H, m), 7.75–7.50 (2H, m), 7.50–7.22 (5H, m), 6.15–5.92 (2H, m), 5.09 (2H, s), 4.70–4.52 (1H, m), 3.80–3.51 and 3.51–2.90 (total 8H, m), 2.80–2.56 (2H, m).

Example 11(3)

N-benzyloxycarbonyl-3-amino-4-oxo-5-(5-(3-((1 S-(N-methylaminocarbonyl)-2-methylpropyl)aminocarbonyl) phenyl)tetrazol-2-yl)pentanoic acid

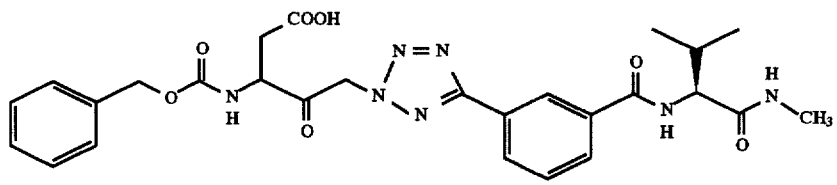

TLC: Rf 0.31 (chloroform:methanol:acetic acid=50:4:1);

NMR (d$_6$-DMSO): δ12.14 (1H, brs), 8.70–8.52 (2H, m), 8.20 (1H, d, J=8.2 Hz), 8.12–7.92 (3H, m), 7.65 (1H, t, J=8.2 Hz), 7.45–7.24 (5H, m), 6.09 (2H, s), 5.11 (2H, s), 4.76–4.59 (1H, m), 4.26 (1H, t, J=8.4 Hz), 2.92–2.52 (5H, m), 2.23–2.00 (1H, m), 1.00–0.84 (6H, m).

Example 11(4)

N-benzyloxycarbonyl-3-amino-4-oxo-5-(5-(3-(N-methylaminocarbonyl)phenyl)tetrazol-2-yl)pentanoic acid

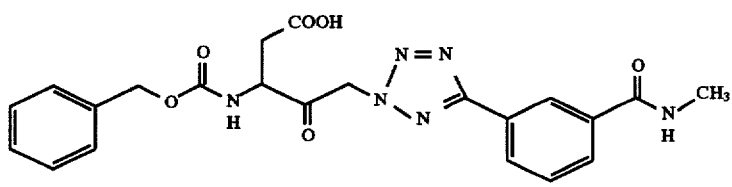

303

TLC: Rf 0.41 (chloroform:methanol:acetic acid=50:4:1);

NMR (d₆-DMSO): δ12.20 (1H, brs), 8.73–8.57 (1H, m), 8.53 (1H, s), 8.19 (1H, d, J=8.6 Hz), 8.10–7.91 (2H, m), 7.65 (1H, t, J=8.6 Hz), 7.47–7.25 (5H, m), 6.08 (2H, s), 5.11 (2H, s), 4.76–4.58 (1H, m), 2.92–2.53 (5H, m).

Example 11(5)

N-benzyloxycarbonyl-3-amino-4-oxo-5-(5-(3-(hexahydro-2-azepinon-3-ylaminocarbonyl)phenyl)tetrazol-2-yl)pentanoic acid

304

TLC: Rf 0.14 (chloroform:methanol:acetic acid=45:4:1);

NMR (d₆-DMSO): δ12.50 (1H, brs), 9.06–8.92 (1H, m), 8.59 (1H, s), 8.22 (1H, d, J=7.8 Hz), 8.10–7.98 (2H, m), 7.97–7.77 (1H, m), 7.68 (1H, t, J=7.8 Hz), 7.48–7.23 (5H, m), 6.08 (2H, s), 5.11 (2H, s), 4.80–4.60 (1H, m), 3.83 (2H, s), 2.96–2.54 (5H, m).

Example 11(8)

N-benzyloxycarbonyl-3-amino-4-oxo-5-(5-(3-((2-(N-methylamino-carbonyl)ethyl)aminocarbonyl)phenyl)tetrazol-2-yl)pentanoic acid

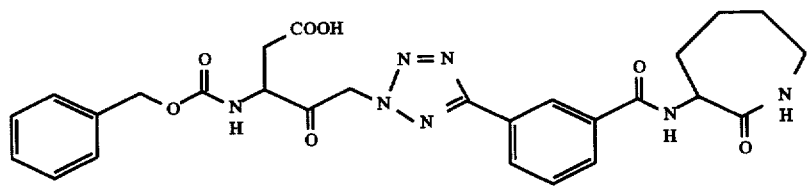

TLC: Rf 0.31 (chloroform:methanol:acetic acid=46:3:1);

NMR (d₆-DMSO): δ8.65–8.46 (2H, m), 8.21 (1H, d, J=7.7 Hz), 8.02 (1H, d, J=7.7 Hz), 7.94–7.76 (2H, m), 7.67 (1H, t, J=7.7 Hz), 7.47–7.24 (5H, m), 6.06 (2H, s), 5.10 (2H, s), 4.80–4.52 (2H, m), 3.25–3.00 (2H, m), 2.78–2.54 (2H, m) 2.06–1.20 (6H, m).

Example 11(6)

N-benzyloxycarbonyl-3-amino-4-oxo-5-(5-(3-((1 R-(N-methylaminocarbonyl)-2-methylpropyl)aminocarbonyl) Phenyl)tetrazol-2-yl)pentanoic acid

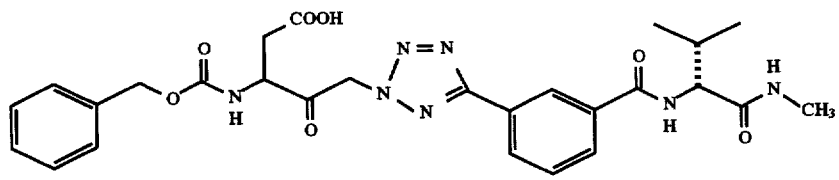

TLC: Rf 0.31 (chloroform:methanol:acetic acid=46:3:1);

NMR (d₆-DMSO): δ8.67–8.50 (2H, m), 8.20 (1H, d, J=8.0 Hz), 8.12–7.92 (3H, m), 7.72–7.56 (1H, m), 7.52–7.22 (5H, m), 6.09 (2H, brs), 5.11 (2H, s), 4.79–4.55 (1H, m), 4.26 (1H, t, J=8.8 Hz), 2.92–2.56 (5H, m), 2.22–2.00 (1H, m) 1.03–0.73 (6H, m).

Example 11(7)

N-benzyloxycarbonyl-3-amino-4-oxo-5-(5-(3-((1-(N-methylamino-carbonyl)methyl)aminocarbonyl)phenyl)tetrazol-2-yl)pentanoic acid

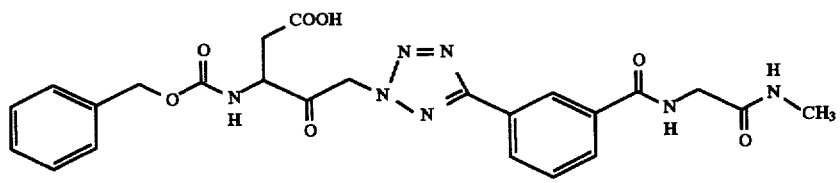

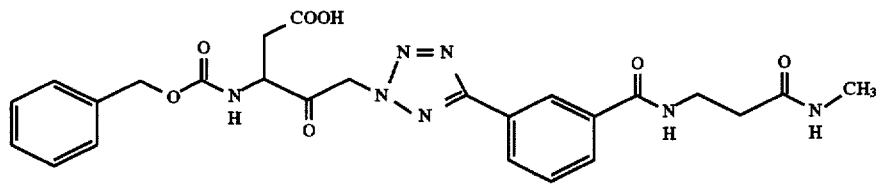

TLC: Rf 0.12 (chloroform:methanol:acetic acid=45:4:1);

NMR (d₆-DMSO): δ12.50 (1H, brs), 8.82–8.71 (1H, m), 8.53 (1H, s), 8.19 (1H, d, J=7.8 Hz), 8.10–7.94 (2H, m), 7.90–7.75 (1H, m), 7.65 (1H, t, J=7.8 Hz), 7.46–7.27 (5H, m), 6.07 (2H, s), 5.11 (2H, s), 4.74–4.57 (1H, m), 3.48 (2H, q, J=7.3 Hz), 2.92–2.53 (5H, m), 2.37 (2H, t, J=7.3 Hz).

Example 11(9)

N-benzyloxycarbonyl-3-amino-4-oxo-5-(5-(4-((1-aminocarbonyl-2-methylpropyl)aminocarbonyl)phenyl) tetrazol-2-yl)pentanoic acid TLC: Rf 0.29 (chloroform:methanol:acetic acid=18:1:1);

NMR (d₆-DMSO): δ12.46 (1H, brs), 8.33 (1H, d, J=8.8 Hz), 8.18–7.97 (5H, m), 7.49 (1H, brs), 7.43–7.24 (5H, m), 7.09 (1H, brs), 6.09 (2H, brs), 5.11 (2H, s), 4.78–4.59 (1H, m), 4.29 (1H, dd, J=8.4, 8.0 Hz), 2.94–2.57 (2H, m), 2.23–2.00 (1H, m), 0.94 (6H, d, J=6.6 Hz).

Example 11(10)

N-benzyloxycarbonyl-3-amino-4-oxo-5-(5-(4-((1-(N-methylaminocarbonyl)-2-methylpropyl)aminocarbonyl) phenyl)tetrazol-2-yl)pentanoic acid TLC: Rf 0.43 (chloroform:methanol:acetic acid=18:1:1);

NMR (d₆-DMSO): δ12.50 (1H, brs), 8.46 (1H, d, J=8.6 Hz), 8.28–7.93 (6H, m), 7.50–7.25 (5H, m), 6.09 (2H, brs), 5.11 (2H, s), 4.80–4.62 (1H, m), 4.32–4.18 (1H, m), 2.92–2.55 (5H, m), 2.24–2.00 (1H, m), 0.93 (3H, d, J=6.3 Hz), 0.90 (3H, d, J=6.3 Hz).

Example 11(11)

N-benzyloxycarbonyl-3-amino-4-oxo-5-(5-(2-(morpholin-1-ylcarbonyl) phenyl)tetrazol-2-yl)pentanoic acid

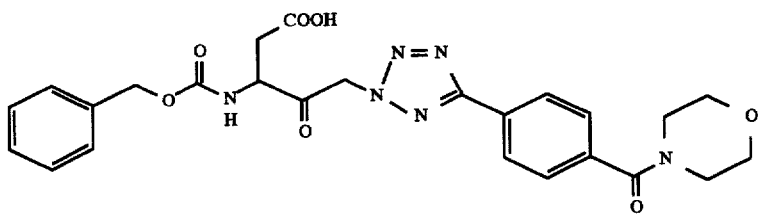

TLC: Rf 0.40 (chloroform:methanol=5:1);

NMR (d₆-DMSO): δ8.12 (2H, d, J=8.1 Hz), 7.90–7.74 (1H, m), 7.60 (2H, d, J=8.1 Hz), 7.45–7.25 (5H, m), 6.06 (2H, brs), 5.10 (2H, s), 4.73–4.54 (1H, m), 3.61 (8H, brs), 2.69 (2H, brs).

Example 11(12)

N-benzyloxycarbonyl-3-amino-4-oxo-5-(5-(4-((1-(N,N-dimethylamino) ethyl)aminocarbonyl)phenyl)tetrazol-2-yl)pentanoic acid.hydrochloride

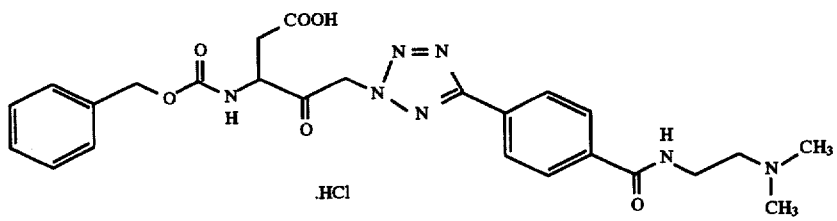

TLC: Rf 0.16 (chloroform:methanol:acetic acid=8:1:1);

NMR (d₆-DMSO): δ12.58 (1H, brs), 10.18 (1H, brs), 9.00 (1H, brs), 8.25–8.00 (5H, m), 7.57–7.10 (5H, m), 6.10 (2H, brs), 5.11 (2H, s), 4.80–4.55 (1H, m), 3.82–3.56 (2H, m), 3.50–3.10 (2H, m), 3.10–2.60 (8H, m).

Example 11(13)

N-benzyloxycarbonyl-3-amino-4-oxo-5-(5-(4-(N-methylaminocarbonyl) phenyl)tetrazol-2-yl)pentanoic acid

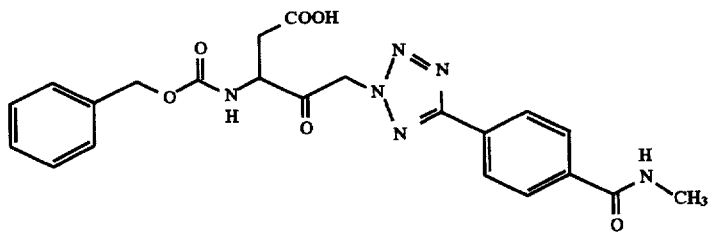

TLC: Rf 0.53 (chloroform:methanol:acetic acid=18:1:1);

NMR (d₆-DMSO): δ12.50 (1H, brs), 8.65–8.53 (1H, m), 8.13 (2H, d, J=8.4 Hz), 8.08–7.95 (3H, m), 7.50–7.24 (5H, m), 6.09 (2H, brs), 5.11 (2H, s), 4.78–4.55 (1H, m), 2.93–2.58 (5H, m).

Example 11(14)

N-benzyloxycarbonyl-3-amino-4-oxo-5-(5-(4-(4-methylpiperazin-1-ylcarbonyl)phenyl)tetrazol-2-yl) pentanoic acid.hydrochloride

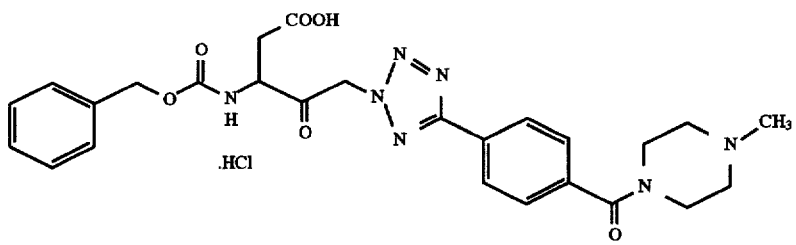

TLC: Rf 0.30 (chloroform:methanol:acetic acid=8:1:1);

NMR (d₆-DMSO): δ8.28–7.90 (3H, m), 7.66 (2H, d, J=8.0 Hz), 7.53–7.18 (5H, m), 6.10 (2H, brs), 5.11 (2H, s), 4.80–4.52 (1H, m), 3.50–3.00 (8H, m),2.95–2.54 (5H, m).

Example 11(15)

N-benzyloxycarbonyl-3-amino-4-oxo-5-(5-(4-((1-(N-methylamino-carbonyl)methyl)aminocarbonyl)phenyl)tetrazol-2-yl)pentanoic acid

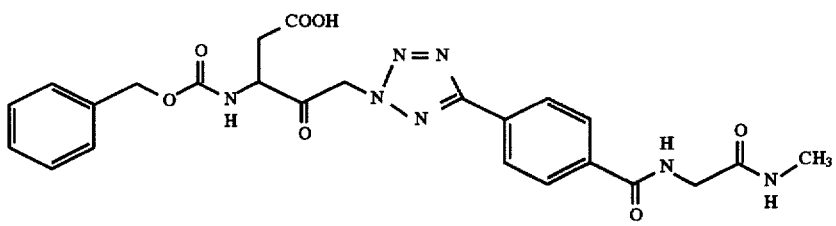

TLC: Rf 0.13 (chloroform:methanol:acetic acid=18:1:1);

NMR (d₆-DMSO): δ12.49 (1H, brs), 8.96–8.85 (1H, m), 8.22–8.00 (5H, m), 7.92–7.79 (1H, m), 7.44–7.23 (5H, m), 6.09 (2H, s), 5.11 (2H, s), 4.74–4.58 (1H, m), 3.90–3.74 (2H, m), 2.91–2.52 (5H, m).

Example 11(16)

N-benzyloxycarbonyl-3-amino-4-oxo-5-(5-(2-((1-aminocarbonyl-2-methylpropyl)aminocarbonyl)phenyl)tetrazol-2-yl)pentanoic acid

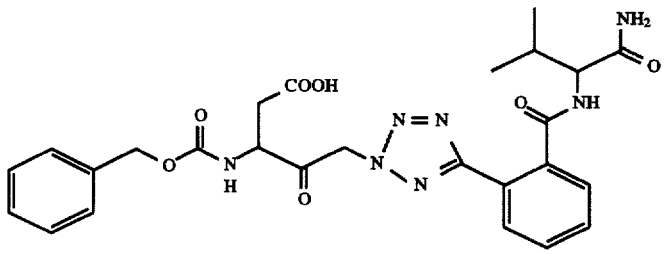

TLC: Rf 0.39, 0.34 (chloroform:methanol:acetic acid= 18:1:1);

NMR (d₆-DMSO): δ12.50 (1H, brs), 8.38 (1H, d, J=8.4 Hz), 8.04 (1H, d), 7.97–7.80 (1H, m), 7.73–7.45 (4H, m), 7.45–7.22 (5H, m), 7.12 (1H, brs), 6.09 (2H, brs), 5.11 (2H, s), 4.75–4.58 (1H, m), 4.21 (1H, dd, J=8.4, 6.1 Hz), 2.85 (1H, dd, J=16.3, 5.4 Hz), 2.67 (1H, d, J=16.3, 6.8 Hz), 2.20–1.95 (1H, m), 0.92 (3H, d J=6.9 Hz), 0.67 (3H, d, J=6.9 Hz).

Example 11(17)

N-benzyloxycarbonyl-3-amino-4-oxo-5-(5-(2-((1-(N-methylaminocarbonyl)-2-methylpropyl)aminocarbonyl)phenyl)tetrazol-2-yl)pentanoic acid

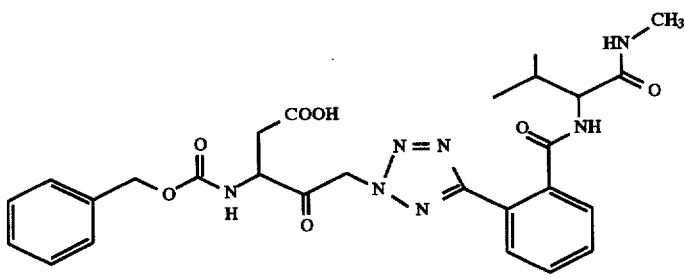

TLC: Rf 0.46, 0.41 (chloroform:methanol:acetic acid= 18:1:1);

NMR (d₆-DMSO): δ12.30 (1H, brs), 8.44 (1H, d, J=8.0 Hz), 8.10–7.80 (3H, m), 7.68–7.46 (3H, m), 7.44–7.20 (5H, m), 5.98 (2H, brs), 5.11 (2H, s), 4.66 (1H, brs), 4.26–4.12 (1H, m), 2.94–2.63 (5H, m), 2.23–2.00 (1H, m), 1.00–0.70 (6H, m).

Example 11(18)

N-benzyloxycarbonyl-3-amino-4-oxo-5-(5-(2-(morpholin-1-ylcarbonyl)phenyl)tetrazol-2-yl)pentanoic acid

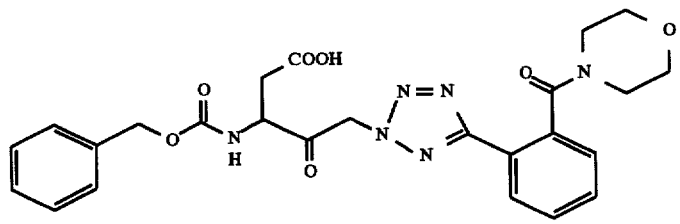

TLC: Rf 0.46 (chloroform:methanol:acetic acid=18:1:1);

NMR (d₆-DMSO): δ8.10–7.97 (1H, m), 7.90–7.78 (1H, m), 7.67–7.54 (2H, m), 7.47–7.22 (6H, m), 6.03 (2H, brs), 5.09 (2H, s), 4.65–4.46 (1H, m), 3.78–2.80 (8H, brs), 2.66 (2H, d, J=5.8 Hz).

Example 11(19)

N-benzyloxycarbonyl-3-amino-4-oxo-5-(5-(2-((1-(N-methylaminocarbonyl)methyl)aminocarbonyl)phenyl)tetrazol-2-yl)pentanoic acid

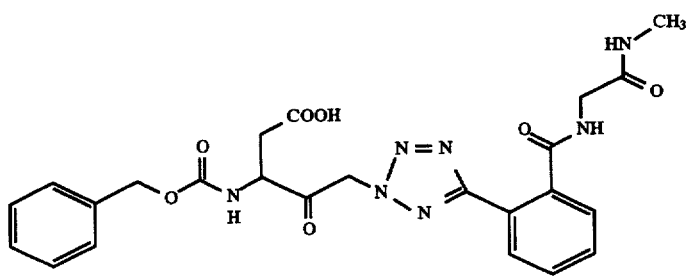

TLC: Rf 0.20 (chloroform:methanol:acetic acid=18:1:1);

NMR (d₆-DMSO): δ8.87–8.76 (1H, m), 8.09–7.83 (2H, m), 7.68–7.56 (3H, m), 7.44–7.26 (6H, m), 6.07 (2H, s), 5.11 (2H, s), 4.75–4.61 (1H, m), 3.81–3.71 (2H, m), 2.92–2.57 (5H, m).

Example 11(20)

N-benzyloxycarbonyl-3-amino-4-oxo-5-(5-(2-((1-(N-methylaminocarbonyl)methyl)aminocarbonyl)phenyl)tetrazol-1-yl)pentanoic acid

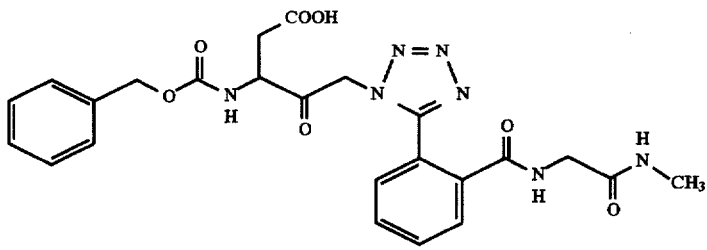

TLC: Rf 0.27 (chloroform:methanol:acetic acid=18:1:1);

NMR (d$_6$-DMSO): δ12.45 (1H, brs), 8.88–8.78 (1H, m), 7.98–7.50 (5H, m), 7.42–7.15 (6H, m), 5.56 (2H, brs), 4.98 (2H, s), 4.52–4.36 (1H, m), 3.74–3.60 (2H, m), 2.78–2.50 (5H, m).

Example 11(21)

N-benzyloxycarbonyl-3-amino-4-oxo-5-(5-(2S-((1-(N-methylaminocarbonyl)-2-methylpropyl)aminocarbonyl)pyrrolidin-1-yl)tetrazol-2-yl)pentanoic acid

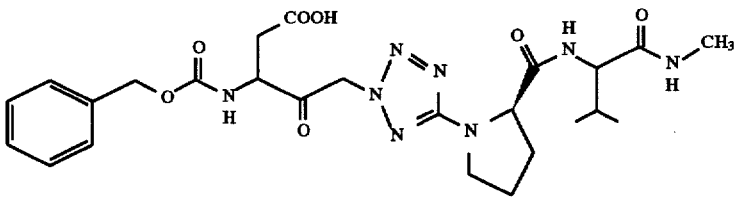

TLC: Rf 0.26 (chloroform:ethanol:acetic acid=18:1:1);

NMR (d$_6$-DMSO): δ7.82 and 7.50 (total 3H, m), 7.34 (5H, m), 5.72 (2H, m), 5.07 (2H, s), 4.50 (1H, m), 4.31 (1H, m), 4.08 (1H, m), 3.58 and 3.40 (total 2H, m), 2.63–1.80 (10H, m), 0.78 (6H, m).

Example 11(22)

N-benzyloxycarbonyl-3-amino-4-oxo-5-(5-(2R-((1-(N-methylaminocarbonyl)-2-methylpropyl)aminocarbonyl)pyrrolidin-1-yl)tetrazol-2-yl)pentanoic acid

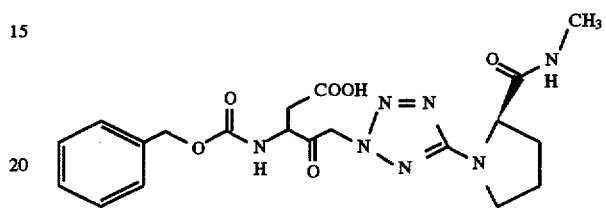

TLC: Rf 0.22 (chloroform:ethanol:acetic acid=8:1:1);

NMR (d$_6$-DMSO): δ7.98–7.78 (2H, m), 7.37 (5H, m), 5.71 (2H, br), 5.09 (2H, s), 4.59 (1H, m), 4.12 (1H, m), 3.70–3.40 (2H, m), 2.88–2.53 (2H, m), 2.58 and 2.55 (total 3H, each s), 2.30–1.80 (4H, m).

Example 12

N-benzyloxycarbonyl-3-amino-4-oxo-5-(5-(3-(thiazol-2-ylmethoxycarbonyl)phenyl)tetrazol-2-yl)pentanoic acid.t-butyl ester TLC: Rf 0.35 (chloroform:methanol:acetic acid=18:1:1);

NMR (d$_6$-DMSO): δ7.97–7.78 (2H, m), 7.55–7.50 (1H, m), 7.46–7.20 (5H, m), 5.69 (2H, brs), 5.06 (2H, s), 4.50–4.23 (2H, m), 4.14–3.94 (1H, m), 3.65–3.49 (1H, m), 2.87–2.57 (2H, m), 2.61–2.52 (3H, m), 2.40–1.78 (7H, m), 0.90–0.61 (6H, m).

Example 11(23)

N-benzyloxycarbonyl-3-amino-4-oxo-5-(5-(2R-(N-methylaminocarbonyl)pyrrolidin-1-yl)tetrazol-2-yl)pentanoic acid

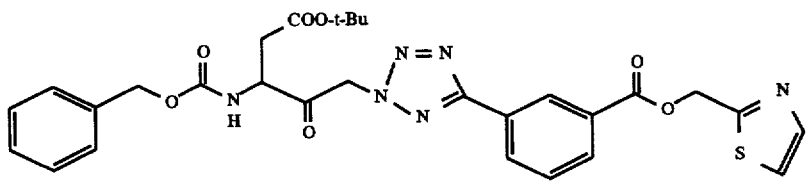

To a solution of the compound prepared in example 3(36) (255 mg) in dimethylformamide (10 ml) were successively added 1-ethyl-3-[3-(dimethylamino)propyl] carbodiimide.hydrochloride (115 mg) and a small amount of N,N-dimethylaminopyridine. The reaction mixture was stirred at room temperature. The reaction mixture was quenched by addition of water and the mixture extracted with ethyl acetate. The extract was washed with 1N aqueous solution of hydrochloric acid, a saturated aqueous solution of sodium hydrocarbonate and a saturated aqueous solution of sodium chloride, dried over anhydrous magnesium sulfate and concentrated. The residue was purified by column chromatography on silica gel (hexane: ethyl acetate=1:1) to give the present invention compound (107 mg) having the following physical data.

TLC: Rf 0.93 (ethyl acetate);

TLC: Rf 0.74 (chloroform:methanol=9:1);

NMR (CDCl₃): δ7.77 (1H, d, J=3.3 Hz), 7.43–7.32 (6H, m), 5.96 (1H, d, J=8.0 Hz), 5.66–5.35 (4H, m), 5.17 (2H, s), 4.70–4.52 (2H, m), 3.83–3.54 (2H, m), 3.04–2.88 (1H, m), 2.71 (1H, dd, J=17.2, 4.7 Hz), 2.50–1.95 (4H, m), 1.42 (9H, s).

Example 13

N-benzyloxycarbonyl-3-amino-4-oxo-5-(5-(3-(thiazol-2-ylmethoxycarbonyl)phenyl)tetrazol-2-yl)pentanoic acid

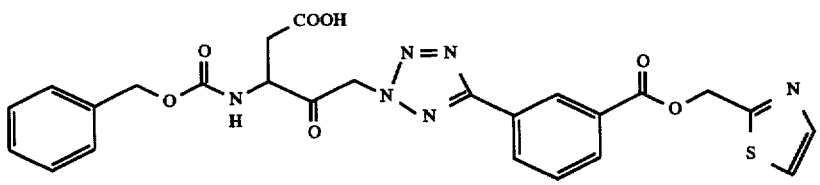

NMR (CDCl₃): δ8.87 (1H, s), 8.38 (1H, d, J=7.8 Hz), 8.20 (1H, d, J=7.8 Hz), 7.83 (1H, d, J=3.1 Hz), 7.60 (1H, t, J=7.8 Hz), 7.44–7.30 (6H, m), 6.01 (1H, d, J=9.1 Hz), 5.90 (1H, d, J=17.7 Hz), 5.73 (1H, d, J=17.7 Hz), 5.69 (2H, s), 5.19 (2H, s), 4.80–4.65 (1H, m), 3.05 (1H, dd, J=17.5, 4.3 Hz), 2.74 (1H, dd, 17.5, 4.5 Hz), 1.44 (9H, s).

Example 12(1)

N-benzyloxycarbonyl-3-amino-4-oxo-5-(5-(2R-(thiazol-2-ylmethoxycarbonyl)pyrrolidin-1-yl)tetrazol-2-yl)pentanoic acid.t-butyl ester By the same procedure as provided in example 2(1), using the compound prepared in example 12 instead of compound (1) prepared in example 1, the compound of the present invention having the following physical data was obtained.

TLC: Rf 0.63 (chloroform:methanol:acetic acid=18:1:1);

NMR (d₆-DMSO): δ12.50 (1H, brs), 8.66 (1H, s), 8.37 (1H, d, J=7.8 Hz), 8.27 (1H, d, J=7.8 Hz), 7.10–7.95 (1H, m), 7.86 (1H, d, J=3.3 Hz), 7.81 (1H, d, J=3.3 Hz), 7.78 (1H, t, J=7.8 Hz), 7.50–7.10 (5H, m), 6.08 (2H, s), 5.70 (2H, s), 5.10 (2H, s), 4.76–4.58 (1H, m), 2.90–2.55 (2H, m).

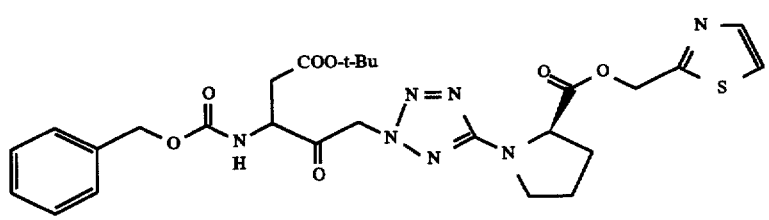

By the same procedure as set forth in example 12, using the compound prepared in example 8(1) instead of the compound prepared in example 3(36), the compound of the present invention having the following physical data was obtained.

Example 13(1)

N-benzyloxycarbonyl-3-amino-4-oxo-5-(5-(2R-(thiazol-2-ylmethoxycarbonyl)pyrrolidin-1-yl)tetrazol-2-yl)pentanoic acid

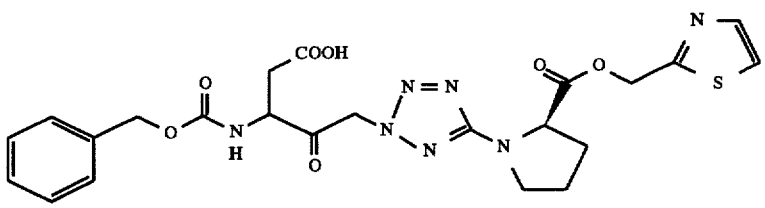

By the same procedure as provided in example 13, using the compound prepared in example 12(1) instead of the compound prepared in example 10, the compound of the present invention having the following physical data was obtained.

TLC: Rf 0.64 (chloroform:methanol:acetic acid=21:2:2);

NMR (d$_6$-DMSO): δ7.85–7.74 (2H, m), 7.70–7.53 (1H, m), 7.50–7.22 (5H, m), 5.71 (2H, brs), 5.42 (2H, m), 5.06 (2H, s), 4.55–4.39 (2H, m), 3.60–3.40 (2H, m), 2.50–1.85 (6H, m).

Reference Example 8

1-(2-trimethylsilyl)ethoxymethyl-2-formylimidazole

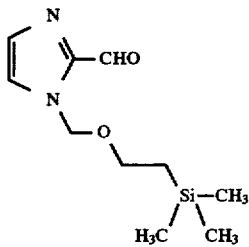

To a suspension of 2-formylimidazole (7.2 g) in dimethylformamide (150 ml) was added sodium hydride (3 g, 60% content) at 0° C. The reaction mixture was stirred at 0° C. for 30 min and at room temperature for 1 h. To the reaction mixture was added 2-(trimethylsilyl)ethoxymethyl chloride (13.3 ml) at 0° C. The reaction mixture was stirred at 0° C. for 30 min and at room temperature for 1 h. The reaction mixture was concentrated under reduced pressure and the residue was dissolved in ethyl acetate. The organic layer was washed with water and a saturated aqueous solution of sodium chloride, dried over anhydrous magnesium sulfate and concentrated. The residue was purified by column chromatography on silica gel (hexane:ethyl acetate =2:1) to give the title compound (14.96 g) having the following physical data.

TLC: Rf 0.50 (hexane:ethyl acetate=1:1);

NMR (CDCl$_3$): δ9.86 (1H, s), 7.39 (1H, s), 7.36 (1H, s), 5.80 (2H, s), 3.59 (2H, t, J=8.0 Hz), 0.94 (2H, t, J=8.0 Hz), 0.00 (9H, s).

Reference Example 9

1-(2-trimethylsilyl)ethoxymethyl-2-cyanoimidazole

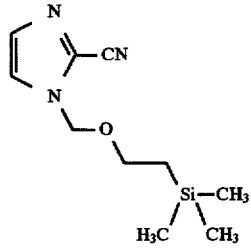

To a solution of hydroxylamine.hydrochloride (2.29 g) in water (7.5 ml) was added dropwise a solution of the compound prepared in reference example 8 (6.78 g) in pyridine (15 ml) at room temperature. The mixture was stirred at room temperature for 1 h. To the mixture was added copper sulfate pentahydrate (1.5 g) and then was added dropwise a solution of triethylamine (8.78 ml) in dichloromethane (15 ml). The reaction mixture was stirred at room temperature for 15 min. To the reaction mixture was added slowly a solution of 1,3-dicyclohexylcarbodiimide (7.43 g) in dichloromethane (60 ml). The reaction mixture was stirred at room temperature for 1 h. The reaction mixture was filtered and the filtrate was diluted with chloroform. The organic layer was washed with 1N aqueous solution of hydrochloric acid and with water, dried over anhydrous sodium sulfate and concentrated. The residue was purified by column chromatography on silica gel (hexane:ethyl acetate=4:1) to give the title compound (5.9 g) having the following physical data.

TLC: Rf 0.39 (hexane:ethyl acetate=2:1);

NMR (d$_6$-DMSO): δ7.82 (1H, d, J=1.2 Hz), 7.29 (1H, d, J=1.2 Hz), 5.56 (2H, s), 3.58 (2H, t, J=8.0 Hz), 0.90 (2H, t, J=8.0 Hz), 0.00 (9H, s).

Reference Example 10

5-(1-((2-trimethylsilyl)ethoxymethyl)imidazol-2-yl)tetrazole

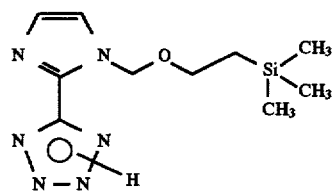

By the same procedure as provided in reference example 3, using the compound prepared in reference example 9, the title compound having the following physical data was obtained.

TLC: Rf 0.37 (chloroform:methanol:acetic acid=20:1:1);

NMR (d$_6$-DMSO): δ7.88 (1H, d, J=1.2 Hz), 7.58 (1H, d, J=1.2 Hz), 6.10 (2H, s), 3.66 (2H, t, J=8.0 Hz), 0.93 (2H, t, J=8.0 Hz), 0.00 (9H, s).

Reference Example 11

N-benzyloxycarbonyl-3-amino-4-oxo-5-(5-(1-((2-trimethylsilyl) ethoxymethyl)imidazol-2-yl)tetrazol-2-yl) pentanoic acid.t-butyl ester

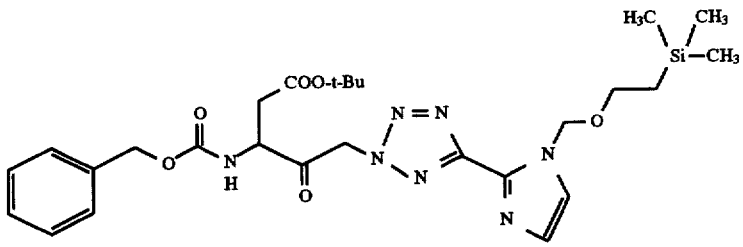

By the same procedure as as set forth in example 3, using N-benzyloxycarbonyl-3-amino-4-oxo-5-bromopentanoic acid.t-butyl ester and the compound prepared in reference example 10, the title compound having the following physical data was obtained.

TLC: Rf 0.39 (hexane:ethyl acetate=2:1);

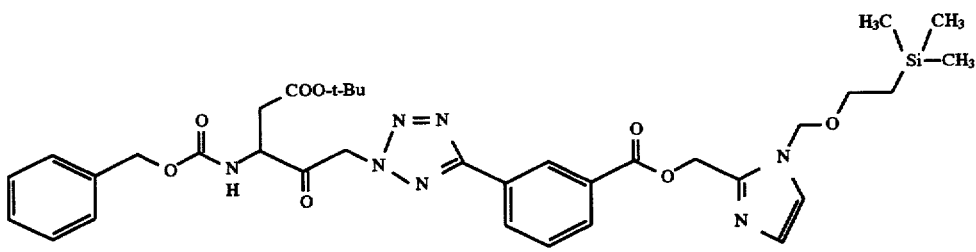

NMR (CDCl$_3$): δ7.38 (5H, m), 7.27 (1H, brs), 7.19 (1H, brs), 6.06 (1H, m), 6.01 (2H, s), 6.00 (2H, s), 5.19 (2H, s), 4.88 (1H, m), 3.57 (2H, t, J=8.2 Hz), 3.00–2.64 (2H, m), 1.40 (9H, s), 0.91 (2H, t, J=8.2 Hz), −0.05 (9H, s).

Example 14

N-benzyloxycarbonyl-3-amino-4-oxo-5-(5-(imidazol-2-yl) tetrazol-2-yl)pentanoic acid.hydrochloride

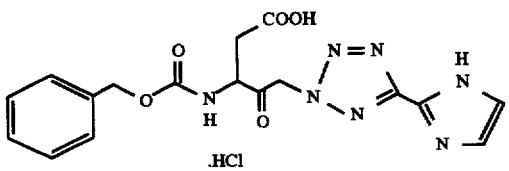

By the same procedure as provided in example 4 and by known methods for converting the same to corresponding salts, using the compound prepared in reference example 11, the compound of the present invention having the following physical data was obtained.

TLC: Rf 0.42 (chloroform:methanol:acetic acid=20:1:1);

NMR (d$_6$-DMSO): δ8.02 (1H, d, J=7.8 Hz), 7.40–7.20 (7H, m), 6.03 (2H, s), 5.11 (2H, s), 4.72 (1H, m), 2.87 (1H, dd, J=5.0, 17 Hz), 2.62 (1H, dd, J=7.6, 17 Hz).

Reference Example 12

N-benzyloxycarbonyl-3-amino-4-oxo-5-(5-(3-(1-((2-trimethylsilyl) ethoxymethyl)imidazol-2-ylmethoxycarbonyl)phenyl)tetrazol-2-yl)pentanoic acid.t-butyl ester By the same procedure as provided in example 12, using 1-((2-trimethylsilyl) ethoxymethyl)-2-hydroxymethylimidazole instead of 2-hydroxymethylthiazole, the title compound having the following physical data was obtained.

TLC: Rf 0.66 (ethyl acetate);

NMR (CDCl$_3$): δ8.77 (1H, s), 8.32 (1H, d, J=8.1 Hz), 8.12 (1H, d, J=8.1 Hz), 7.53 (1H, t, J=8.1 Hz), 7.42–7.25 (5H, m), 7.07 (1H, s), 7.05 (1H, s), 6.05–5.94 (1H, m), 5.87 (1H, d, J=17.8 Hz), 5.69 (1H, d, J=17.8 Hz), 5.50 (2H, s), 5.38 (2H, s), 5.17 (2H, s), 3.48 (1H, d, J=8.0 Hz), 3.44 (1H, d, J=8.4Hz), 3.02 (1H, dd, J=17.4, 4.6 Hz), 2.72 (1H, dd, J=17.4, 5.1 Hz), 1.41 (9H, s), 0.83 (1H, J=8.4 Hz), 0.89 (1H, d, J=8.0 Hz), −0.09 (9H, s).

Reference examples 12(1)–12(2)

By the same procedure as provided in reference example 12, using the compound prepared in example 8 or 8(1) instead of the compound prepared in example 3(36), the title compound having the following physical data were obtained.

Reference Example 12(1)

N-benzyloxycarbonyl-3-amino-4-oxo-5-(5-(2S-(1-((2-trimethylsilyl) ethoxymethyl)imidazol-2-ylmethoxycarbonyl)pyrrolidin-1-yl)tetrazol-2-yl) pentanoic acid.t-butyl ester

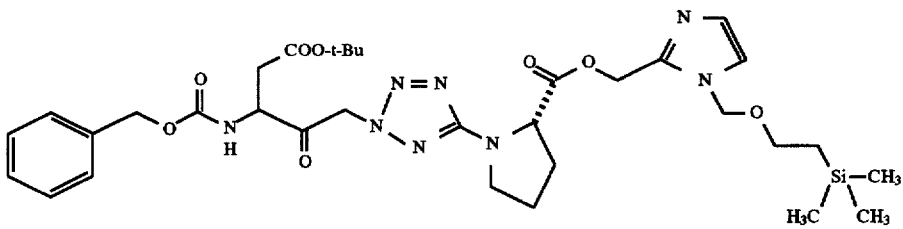

TLC: Rf 0.38 (chloroform:ethanol:acetic acid=18:1:1).

Reference Example 12(2)

N-benzyloxycarbonyl-3-amino-4-oxo-5-(5-(2R-(1-((2-trimethylsilyl)ethoxymethyl)imidazol-2-ylmethoxycarbonyl)pyrrolidin-1-yl)tetrazol-2-yl)-pentanoic acid.t-butyl ester

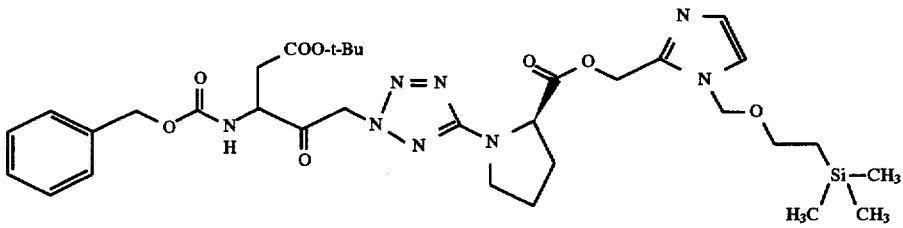

TLC: Rf 0.38 (chloroform:ethanol:acetic acid=18:1:1).

Example 15

N-benzyloxycarbonyl-3-amino-4-oxo-5-(5-(3-(imidazol-2-ylmethoxycarbonyl)phenyl)tetrazol-2-yl)pentanoic acid.hydrochloride

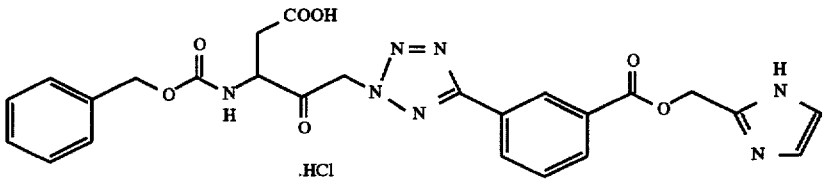

By the same procedure as described in example 14 and by known methods to obtain the corresponding salts, using the compound prepared in reference example 12 instead of the compound prepared in reference example 11, the compound of the present invention having the following physical data was obtained.

TLC: Rf 0.14 (chloroform:methanol:acetic acid=8:1:1);

NMR (d$_6$-DMSO): δ8.64 (1H, s), 8.35 (1H, d, J=8.0 Hz), 8.17 (1H, d, J=8.0 Hz), 8.11–7.98 (1H, m), 7.76 (1H, t, J=8.0 Hz), 7.50–7.24 (7H, m), 6.10 (2H, s), 5.51 (2H, s.), 5.09 (2H, s), 4.76–4.57 (1H, m), 2.92–2.53 (2H, m).

Examples 15(1)–15(2)

By the same procedure as provided in example 15 and by known methods for converting the same to corresponding salts, using the compounds prepared in reference examples 12(1) or 12(2) instead of the compound prepared in reference example 12, the compounds of the present invention having the following physical data were obtained.

Example 15(1)

N-benzyloxycarbonyl-3-amino-4-oxo-5-(5-(2S-(imidazol-2-ylmethoxycarbonyl)pyrrolidin-1-yl)tetrazol-2-yl)pentanoic acid.dihydrochloride

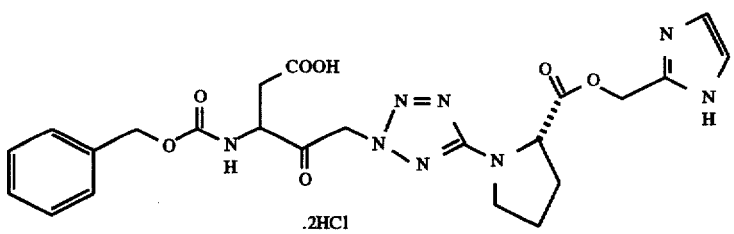

323

TLC: Rf 0.13 (chloroform:methanol=4:1);

NMR (d₆-DMSO): δ7.98 (1H, m), 7.58 (2H, s), 7.37 (5H, m), 5.71 (2H, m), 5.33 (2H, m), 5.09 (2H, s), 4.68–4.39 (2H, m), 2.90–2.55 (2H, m), 2.44–1.85 (4H, m).

Example 15(2)

N-benzyloxycarbonyl-3-amino-4-oxo-5-(5-(2R-(imidazol-2-ylmethoxycarbonyl)pyrrolidin-1-yl)tetrazol-2-yl)pentanoic acid.dihydrochloride

324

NMR (CDCl₃): δ7.31 (5H, m), 5.90 (1H, d, J=8.6 Hz), 5.46 (1H, d, J=17.9 Hz), 5.33 (1H, d, J=17.9 Hz), 5.08 (2H, s), 4.78–4.65 (1H, m), 4.58–4.44 (1H, m), 3.80–3.20 (10H, m), 2.85 (1H, dd, J=17.4, 4.5 Hz), 2.66 (1H, dd, J=17.4, 5.0 Hz), 2.25–1.80 (4H, m), 1.41 (9H, s), 1.35 (9H, s).

Example 16

N-benzyloxycarbonyl-3-amino-4-oxo-5-(5-(2R-(piperazin-1-yl) pyrrolidin-1-yl)tetrazol-2-ylcarbonyl)pentanoic acid.dihydrochloride

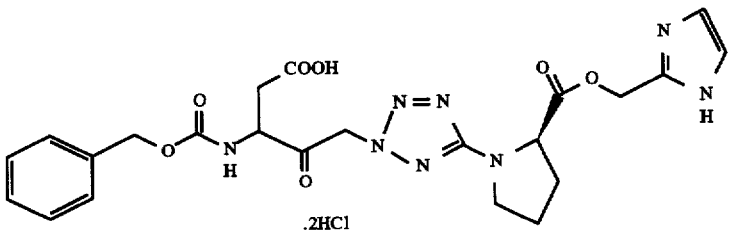

TLC: Rf 0.31 (chloroform:methanol:water=40:9:1);

NMR (d₆-DMSO): δ8.06–7.92 (1H, m), 7.68 (2H, s), 7.48–7.25 (5H, m), 5.71 (2H, brs), 5.36 (2H, brs), 5.09 (2H, s), 4.74–4.40 (2H, m), 3.57–3.40 (2H, m), 2.90–2.53 (2H, m), 2.23–1.81 (4H, m).

Reference Example 13

N-benzyloxycarbonyl-3-amino-4-oxo-5-(5-(2R-(4-t-butoxycarbonylpiperazin-1-yl)pyrrolidin-1-ylcarbonyl)tetrazol-2-yl)pentanoic acid.t-butyl ester

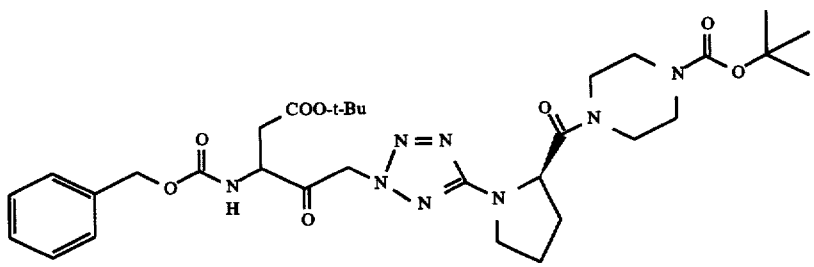

By the same procedure as provided in example 10, using the compound prepared in example 8(1) instead of the compound prepared in example 3(36) and 4-t-butoxycarbonylpiperazine instead of valylaminomethyl. hydrochloride, the title compound having the following physical data was obtained.

TLC: Rf 0.70 (chloroform:methanol=9:1);

By the same procedure as provided in example 14 and by known methods to obtain the corresponding salts, using the compound prepared in reference example 13 instead of the compound prepared in reference example 11, the compound of the present invention having the following physical data was obtained.

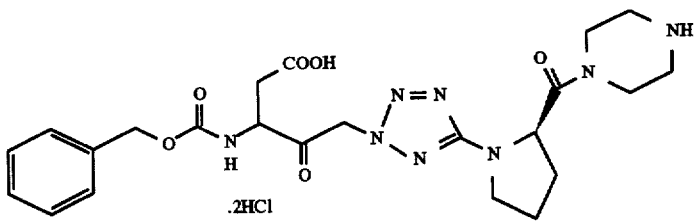

TLC: Rf 0.20 (chloroform:methanol:acetic acid=8:1:1);

NMR (d$_6$-DMSO): δ8.03–7.95 (1H, m), 7.50–7.26 (5H, m), 5.70 (2H, brs), 5.09 (2H, s), 4.90–4.76 (1H, m), 4.70–4.48 (1H, m), 4.20–2.86 (10H, m), 2.87–2.57 (2H, m), 2.40–1.74 (4H, m).

Reference Example 14

3-amino-4-oxo-5-(5-phenyltetrazol-2-yl)pentanoic acid.t-butyl ester hydrochloride

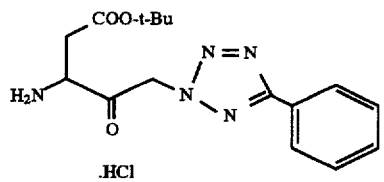

To a solution of the compound prepared in example 3(8) (0.407 g) in ethanol (40 ml) were added a 6N aqueous solution of hydrochloric acid and 10% palladium on activated carbon (40 mg) under an atmosphere of argon. The reaction mixture was stirred at room temperature for 1.5 h under an atmosphere of hydrogen gas. The reaction mixture was filtered through Celite and the filtrate was concentrated to give the title compound having the following physical data.

TLC: Rf 0.13 (hexane:ethyl acetate=1:1);

NMR (d$_6$-DMSO): δ8.90–8.25 (2H, br), 8.17–7.96 (2H, m), 7.67–7.46 (3H, m), 6.28 (1H, d, J=18.6Hz), 6.18 (1H, d, J=18.6 Hz), 4.66 (1H, t, J=4.8 Hz), 3.29–3.10 (2H, m), 1.47 (9H, s).

Example 17

N-(N-benzyloxycarbonyl-L-valyl)-3-amino-4-oxo-5-(5-phenyltetrazol-2-yl)pentanoic acid.t-butyl ester

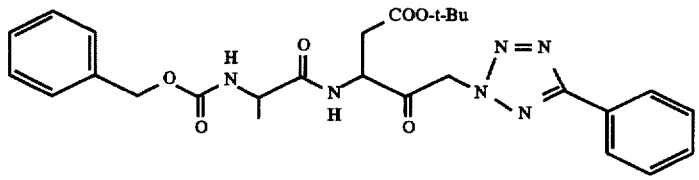

By the same procedure as set forth in example 10, using N-benzyloxycarbonyl-L-valine instead of the compound prepared in example 3(36) and the compound prepared in reference example 14, the compound of the present invention having the following physical data was obtained.

TLC: Rf 0.63 (hexane:ethyl acetate=1:1);

NMR (CDCl$_3$): δ8.26–8.02 (2H, m), 7.60–7.17 (9H, m), 6.03–5.44 (2H, m), 5.44–4.80 (4H, m), 4.19–3.92 (1H, m), 3.20–2.55 (2H, m), 2.36–2.04 (1H, m), 1.44 (9H, s), 1.22–0.83 (6H, m).

Examples 17(1)–17(2)

By the same procedure as set forth in example 17, using the corresponding carboxylic acid compound instead of N-benzyloxycarbonyl-L-valine, the compounds of the present invention having the following physical data were obtained.

Example 17(1)

N-(N-benzyloxycarbonyl-L-alanyl)-3-amino-4-oxo-5-(5-phenyltetrazol-2-yl)pentanoic acid.t-butyl ester

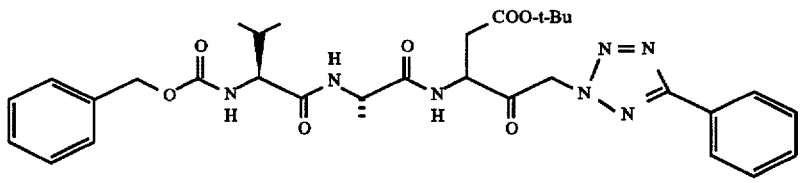

TLC: Rf 0.34 (hexane:ethyl acetate=1:1).

Example 17(2)

N-((N-benzyloxycarbonyl-L-valyl)-L-alanyl)-3-amino-4-oxo-5-(5-phenyltetrazol-2-yl)pentanoic acid.t-butyl ester TLC: Rf 0.54 (ethyl acetate:diethyl ether=1:1).

Example 18

N-(N-benzyloxycarbonyl-L-valyl)-3-amino-4-oxo-5-(5-phenyltetrazol-2-yl)pentanoic acid

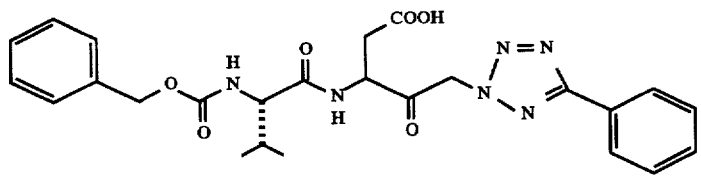

By the same procedure as set forth in example 2(1), using the compound prepared in example 17 instead of compound (1) prepared in example 1, the compound of the present invention having the following physical data was obtained.

TLC: Rf 0.45 (chloroform:methanol:acetic acid=18:1:1);

NMR (d$_6$-DMSO): δ13.12–11.40 (1H, br), 8.95–8.57 (1H, m), 8.16–7.93 (2H, m), 7.67–7.40 (4H, m), 7.40–7.08 (5H, m), 6.16–5.64 (2H, m), 5.04 (2H, brs), 4.95–4.62 (1H, m), 4.00–3.78 (1H, m), 2.96–2.56 (2H, m), 2.14–1.83 (1H, m), 1.03–0.75 (6H, m).

Examples 18(1)–18(2)

By the same procedure as provided in example 18, using the compound prepared in examples 17(1) or 17(2) instead of the compound prepared in example 17, the compounds of the present invention having the following physical data were obtained.

Example 18(1)

N-(N-benzyloxycarbonyl-L-alanyl)-3-amino-4-oxo-5-(5-phenyltetrazol-2-yl)pentanoic acid

Example 18(2)

N-((N-benzyloxycarbonyl-L-valyl)-L-alanyl)-3-amino-4-oxo-5-(5-phenyltetrazol-2-yl)pentanoic acid

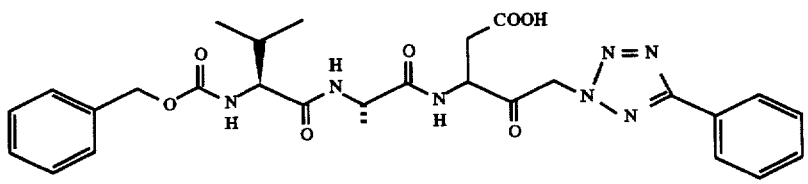

TLC: Rf 0.37 (chloroform:methanol:acetic acid=18:1:1);

NMR (d$_6$-DMSO): δ8.91–8.82 and 8.72–8.63 (total 1H, each m), 8.30–8.17 (1H, m), 8.10–7.95 (2H, m), 7.65–7.47 (3H, m), 7.40–7.17 (6H, m), 6.09–5.70 (2H, m), 5.01 (2H, brs), 4.87–4.70 and 4.70–4.56 (total 1H, each m), 4.40–4.08 (1H, m), 3.98–3.79 (1H, m), 2.91–2.60 (2H, m), 2.09–1.83 (1H, m), 1.33–1.12 (3H, m), 0.98–0.70 (6H, m).

Example 19

N-t-butoxycarbonyl-3-amino-4-oxo-5-(5-phenyltetrazol-2-yl)pentanoic acid.ethyl ester

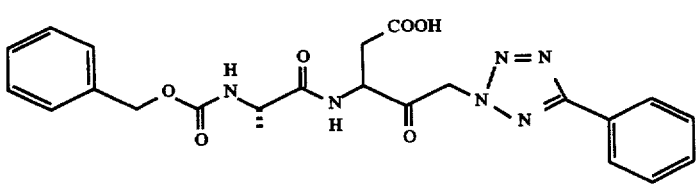

TLC: Rf 0.28 (chloroform:methanol:acetic acid=18:1:1);

NMR (d$_6$-DMSO): δ13.25–11.80 (1H, br), 8.92–8.58 (1H, m), 8.18–7.98 (2H, m), 7.80–7.45 (4H, m), 7.45–7.04 (5H, m), 6.24–5.55 (2H, m), 5.03 (2H, s), 4.90–4.63 (1H, m), 4.24–3.97 (1H, m), 2.99–2.52 (2H, m), 1.26 (3H, d, J=5.6 Hz).

329

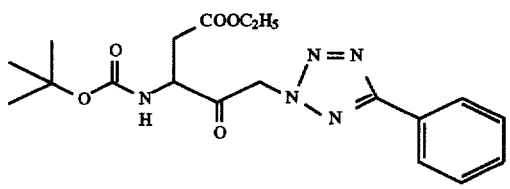

By the same procedure as provided in example 1, using N-t-butoxycarbonyl-3-amino-4-oxo-5-bromopentanoic acid.ethyl ester [the compound prepared as described in J. Med. Chem., 37, 563(1994)] instead of N-((N-(3-phenylpropionyl)-L-valyl)-L-alanyl)-3-amino-4-oxo-5-bromopentanoic acid.t-butyl ester, the compound of the present invention having the following physical data was obtained.

TLC: Rf 0.39 (hexane:ethyl acetate=2:1);

NMR (CDCl$_3$): δ8.24–8.06 (2H, m), 7.59–7.39 (3H, m), 5.93 (1H, d, J=17.8 Hz), 5.84–5.63 (2H, m), 4.81–4.58 (1H, m), 4.18 (2H, q, J=7.3 Hz), 3.12 (1H, dd, J=17.4 and 4.4 Hz), 2.80 (1H, dd, J=17.6 and 5.2 Hz), 1.50 (9H, s), 1.28 (3H, t, J=7.3 Hz).

Example 20

N-t-butoxycarbonyl-3-amino-4-oxo-5-(5-phenyltetrazol-2-yl)pentanoic acid

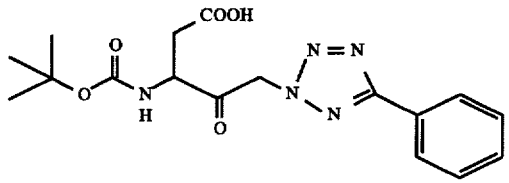

By the same procedure as set forth in example 7, using the compound prepared in example 19 instead of the compound prepared in example 2(23), the compound of the present invention having the following physical data was obtained.

TLC: Rf 0.61 (chloroform:methanol:acetic acid=18:1:1);

NMR (d$_6$-DMSO): δ13.56–11.05 (1H, br), 8.12–8.00 (2H, m), 7.67–7.46 (4H, m), 6.14–5.79 (2H, br), 4.71–4.42 (1H, m), 2.95–2.49 (2H, m), 1.44 (9H, s),

Example 21

N-(3-phenylpropylthio)carbonyl-3-amino-4-oxo-5-(5-(2-chlorophenyl) tetrazol-2-yl)pentanoic acid.t-butyl ester (1) and N-(3-phenylpropylthio)carbonyl-3-amino-4-oxo-5-(5-(2-chlorophenyl)tetrazol-1-yl)pentanoic acid.t-butyl ester (2)

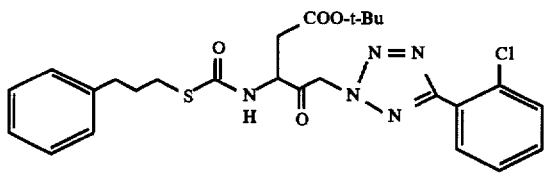

-continued

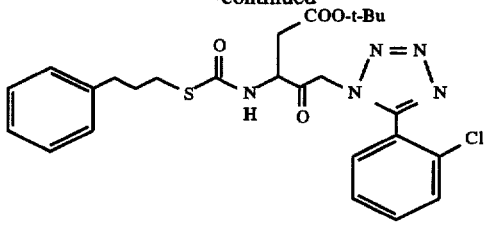

By the same procedure as provided in example 1, using N-(3-phenylpropylthio)carbonyl-3-amino-4-oxo-5-bromopentanoic acid.t-butyl ester instead of N-((N-(3-phenylpropionyl)-L-valyl)-L-alanyl)-3-amino-4-oxo-5-bromopentanoic acid.t-butyl ester, the compound of the present invention having the following physical data was obtained.

Example 21(1)

TLC: Rf 0.56 (hexane:ethyl acetate=2:1);

NMR (CDCl$_3$): δ8.01–7.95 (1H, m), 7.56–7.17 (9H, m), 6.66 (1H, m), 5.68 (2H, Abq, J=17.7 Hz), 5.01–4.91 (1H, m), 3.09–2.96 (3H, m), 2.78–2.67 (3H, m), 2.07–1.92 (2H, m), 1.45 (9H, s).

Example 21(2)

TLC: Rf 0.30 (hexane:ethyl acetate=2:1);

NMR (CDCl$_3$): δ7.51–7.17 (9H, m), 6.40 (1H, d, J=8.8 Hz), 5.48 (2H, Abq, J=18.4 Hz), 4.77–4.68 (1H, m), 2.98–2.84 (3H, m), 2.76–2.55 (3H, m), 2.07–1.92 (2H, m), 1.45 (9H, s).

Example 22(1)

N-(3-phenylpropylthio)carbonyl-3-amino-4-oxo-5-(5-(2-chlorophenyl)tetrazol-2-yl)pentanoic acid

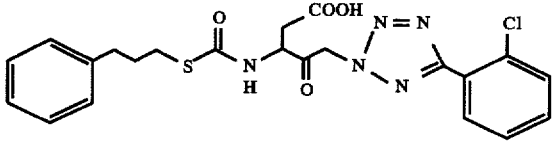

By the same procedure as set forth in example 2(1), using the compound (1) prepared in example 21 instead of the compound (1) prepared in example 1, the compound of the present invention having the following physical data was obtained.

TLC: Rf 0.51 (chloroform:methanol:acetic acid= 19:1:0.1);

NMR (d$_6$-DMSO): δ8.90 (1H, d, J=7.8 Hz), 7.89 (1H, m), 7.71–7.49 (3H, m), 7.29–7.15 (5H, m), 6.11–5.96 (2H, br), 4.91–4.80 (1H, m), 2.92–2.61 (6H, m), 1.92–1.77 (2H, m).

Example 22(2)

N-(3-phenylpropylthio)carbonyl-3-amino-4-oxo-5-(5-(2-chlorophenyl)tetrazol-1-yl)pentanoic acid

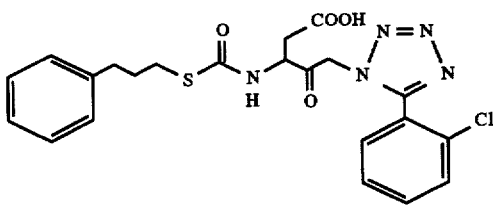

By the same procedure as provided in example 21(1), using the compound (2) prepared in example 21 instead of compound (1) prepared in example 21, the compound of the present invention having the following physical data was obtained.

TLC: Rf 0.43 (chloroform:methanol:acetic acid= 19:1:0.1);

NMR ($d_6$-DMSO): δ8.79 (1H, d, J=6.0 Hz), 7.64–7.18 (9H, m), 5.62 (2H, q, J=7.2 Hz), 4.68–4.58 (1H, m), 2.77–2.56 (6H, m), 1.86–1.71 (2H, m).

Reference Example 15

3-amino-4-oxo-5-(5-(2-chlorophenyl)tetrazol-2-yl)pentanoic acid.t-butyl ester.hydrochloride

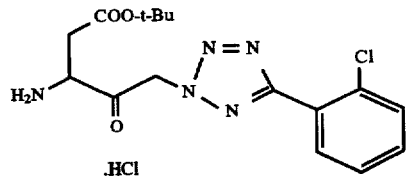

By the same procedure as provided in reference example 14, using the compound prepared in example 3 instead of the compound prepared in example 3(8), the title compound having the following physical data was obtained.

TLC: Rf 0.43 (hexane:ethyl acetate=1:1);

NMR ($d_6$-DMSO): δ8.67 (3H, brs), 7.96–7.91 (1H, m), 7.68–7.53 (3H, m), 6.27 (2H, s), 4.67 (1H, t, J=5.5 Hz), 3.36–3.09 (2H, m), 1.47 (9H, s).

Example 23

3-((2-fluorophenyl)sulfonylamino)-4-oxo-5-(5-(2-chlorophenyl)tetrazol-2-yl)pentanoic acid.t-butyl ester

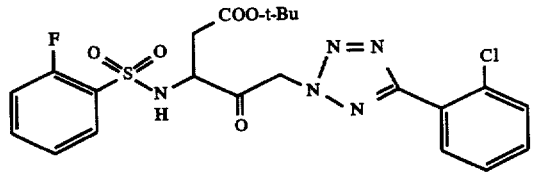

To a suspension of the compound prepared in reference example 15 (907 mg) in dichloromethane (7 ml) successively were added 2-fluorobenzenesulfonylchloride (660 mg), triethylamine (0.63 ml) and dimethylaminopyridine (277 mg) at 0° C. The reaction mixture was stirred at room temperature for 2 h. The reaction mixture was quenched by addition of ice water and a 1N aqueous solution of hydrochloric acid, and extracted with ethyl acetate. The extract was washed with a saturated aqueous solution of sodium hydrocarbonate and a saturated aqueous solution of sodium chloride, dried over anhydrous sodium sulfate and concentrated. The residue was purified by column chromatography on silica gel (hexane: ethyl acetate =3:1) to give the present invention compound (435 mg) having the following physical data.

TLC: Rf 0.51 (hexane:ethyl acetate=2:1);

NMR (CDCl₃): δ8.02–7.88 (2H, m), 7.73–7.20 (6H, m), 6.36 (1H, d, J=9.5 Hz), 6.09 and 5.92 (each 1H, d, J=18.0 Hz), 4.40–4.27 (1H, m), 2.99 (1H, dd, J=17.6 Hz, 3.5 Hz), 2.40 (1H, dd, J=17.6 Hz, 4.5 Hz), 1.43 (9H, s).

Example 24

3-((2-fluorophenyl)sulfonylamino)-4-oxo-5-(5-(2-chlorophenyl)tetrazol-2-yl)pentanoic acid

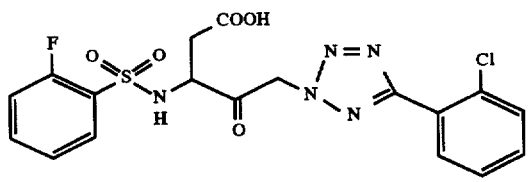

By the same procedure as provided in example 2(1), using the compound prepared in example 23 instead of compound (1) prepared in example 1, the compound of the present invention having the following physical data was obtained.

TLC: Rf 0.51 (chloroform:methanol:acetic acid=18:1:1);

NMR ($d_6$-DMSO): δ12.85–12.30 (1H, brs), 9.05–8.75 (1H, m), 8.15–7.32 (8H, m), 6.30–5.98 (2H, m), 4.62–4.46 (1H, m), 2.87–2.55 (2H, m).

Reference Example 16

3-phenylcarbonylamino-1-(1-ethoxycarbonyl)ethyl-2-pyridone

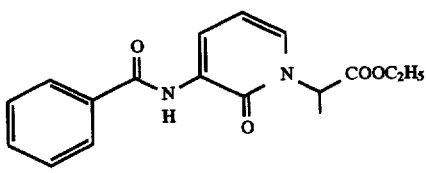

To a solution of 3-amino-1-(1-ethoxycarbonyl)ethyl-2-pyridone (650 mg) in pyridine (6 ml) was added benzoyl chloride (0.6 ml) at 0° C. The reaction mixture was stirred at room temperature for 30 min. The reaction mixture was concentrated under reduced pressure and the residue was diluted with ethyl acetate. The organic layer was washed with a 1N aqueous solution of hydrochloric acid, a saturated aqueous solution of sodium hydrocarbonate and a saturated aqueous solution of sodium chloride, dried over anhydrous sodium sulfate and concentrated. The residue was purified by column chromatography on silica gel (hexane:ethyl acetate=3:1) to give the title compound (721 mg) having the following physical data.

TLC: Rf 0.56 (hexane:ethyl acetate=1:1).

Reference example 17

3-phenylcarbonylamino-1-(1-carboxy)ethyl-2-pyridone

To a solution of the compound prepared in reference example 16 (710 mg) in dioxane (10 ml) was added a 1N aqueous solution of sodium hydroxide (2.7 ml) at 0° C. The reaction mixture was stirred at room temperature for 30 min. The reaction mixture was poured into ice water, a 1N aqueous solution of hydrochloric acid was added, and the mixture was extracted with ethyl acetate. The extract was washed with a saturated aqueous solution of sodium chloride, dried over anhydrous sodium sulfate and concentrated to give the title compound (450 mg) having the following physical data.

TLC: Rf 0.11 (chloroform:methanol=9:1).

Example 25

3-(N-(2-(2-oxo-3-(phenylcarbonylamino)pyridin-1-yl))propionyl)amino-4-oxo-5-(5-(2-chlorophenyl)tetrazol-2-yl)pentanoic acid.t-butyl ester

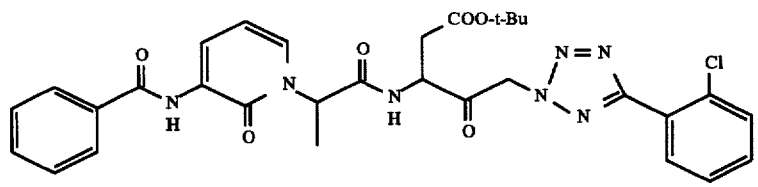

By the same procedure as provided in example 10, using the compound prepared in reference example 15 and the compound prepared in reference example 17 instead of the compound prepared in example 3(36), the compound of the present invention having the following physical data was obtained.

TLC: Rf 0.34 (hexane:ethyl acetate=1:1);

NMR (CDCl$_3$): δ9.15 (1H, brs), 8.61–8.57 (1H, m), 7.99–7.86 (3H, m), 7.68 (1H, d, J=8.4 Hz),7.64–7.34 (6H, m),7.24–7.16 (1H, m), 6.47–6.40 (1H, m),6.02–5.42 (3H, m), 4.96–4.89 (1H, m), 3.04–2.60 (2H, m), 1.75–1.69 (3H, m), 1.45–1.36 (9H, m).

Example 26

3-(N-(2-(2-oxo-3-(phenylcarbonylamino)pyridin-1-yl))propionyl)amino-4-oxo-5-(5-(2-chlorophenyl)tetrazol-2-yl)pentanoic acid

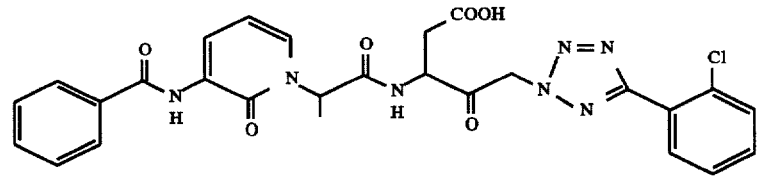

By the same procedure as set forth in example 2(1), using the compound prepared in example 25 instead of compound (1) prepared in example 1, the compound of the present invention having the following physical data was obtained.

TLC: Rf 0.36 (chloroform:methanol:acetic acid=36:1:1);

NMR (d$_6$-DMSO): δ9.28 (1H, s), 9.10–8.94 (1H, m), 8.38 (1H, d, J=6.2 Hz), 7.89–7.82 (3H, m), 7.65–7.45 (6H, m), 7.28–7.13 (1H, m), 6.43 (1H, t, J=7.0 Hz), 6.25–5.93 (2H, m), 5.53–5.37 (1H, m), 4.95–4.77 (1H, m), 2.92–2.64 (2H, m), 1.65 (3H, d, J=6.0 Hz).

FORMULATION EXAMPLE

Formulation Example 1

The following components were admixed in a conventional manner and punched out to obtain 100 tablets each containing 50 mg of active ingredient.

| | |
|---|---|
| N-((N-(3-phenylpropionyl)-L-valyl)-L-alanyl)-3-amino-4-oxo-5-(5-(2,6-dichlorophenyl)tetrazol-2-yl)pentanoic acid | 5.0 g |
| Carboxymethylcellulose calcium (disintegrating agent) | 0.2 g |
| Magnesium stearate (lubricating agent) | 0.1 g |
| Microcrystalline cellulose | 4.7 g |

Formulation example 2

The following components were admixed in a conventional manner. The solution was sterilized in a conventional manner, 5 ml portions were placed into ampules and freeze-dried to obtain 100 ampules each containing 20 mg of the active ingredient.

| | |
|---|---|
| N-((N-(3-phenylpropionyl)-L-valyl)-L-alanyl)-3-amino-4-oxo-5-(5-(2,6-dichlorophenyl)tetrazol-2-yl)pentanoic acid | 2.0 g |
| Mannitol | 20 g |
| Distilled water | 1000 ml |

References cited herein are incorporated herein in entirety. While the invention has been described with respect to certain specific embodiments, it will be clear to the artisan that various modifications can be implemented without departing from the spirit and scope of the invention.

What we claim is:

1. A tetrazole compound of formula (I):

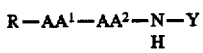    (I)

wherein R is a hydrogen atom,

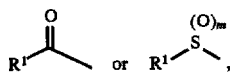

$R^1$ is

1) C1–8 alkyl,
2) C1–8 alkoxy,
3) C1–8 alkylamino,
4) C1–8 alkylthio,
5) $Cyc^1$, wherein $Cyc^1$ is a carbocyclic ring or hetero ring, and $Cyc^1$ is optionally substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, $-OR^2$, $-NR^2R^3$, $-SR^2$, $-COOR^2$ or $-COR^2$, wherein $R^2$ and $R^3$ each, independently, is a hydrogen atom, C1–4 alkyl, phenyl or C1–4 alkyl substituted by phenyl, or
6) C1–8 alkyl, C1–8 alkoxy, C1–8 alkylamino or C1–8 alkylthio substituted by $Cyc^1$, m is 0–2, with the proviso that, (1) when m is 0, $R^1$ is C1–8 alkyl or C1–8 alkoxy, each optionally substituted by $Cyc^1$, and
(2) when m is 1, $R^1$ is C1–8 alkyl, C1–8 alkoxy or C1–8 alkylamino, each optionally substituted by $Cyc^1$, $AA^1$ is
1) a bond
2)

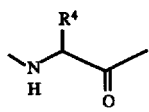

or 3) an amino acid, wherein $R^4$ is (1) a hydrogen atom,
(2) C1–8 alkyl,
(3) $Cyc^2$, wherein $Cyc^2$ is a carbocyclic ring or hetero ring, and $Cyc^2$ is optionally substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, $-OR^5$, $-NR^5R^6$, $-SR^5$, $-COOR^5$ or $-COR^5$, wherein $R^5$ and $R^6$ each, independently, is a hydrogen atom, C1–4 alkyl, phenyl or C1–4 alkyl substituted by phenyl, or
(4) C1–8 alkyl substituted by a substituent selected from $-OR^7$, $-NR^7R^8$, $-SR^7$, $-COOR^7$, $-COR^7$, $-CONH_2$, $-NR^7-CO-NR^7R^8$, guanidino or $Cyc^2$, wherein $R^7$ and $R^8$ each, independently, is a hydrogen atom, C1–4 alkyl, phenyl or C1–4 alkyl substituted by phenyl, $AA^2$ is
1) a bond
2)

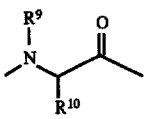

or 3) an amino acid, wherein $R^9$ and $R^{10}$ each, independently, is (1) a hydrogen atom,
(2) C1–8 alkyl,
(3) $Cyc^3$, wherein $Cyc^3$ is a carbocyclic ring or hetero ring, and $Cyc^3$ is optionally substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, $-OR^{11}$, $-NR^{11}R^{12}$, $-SR^{11}$, $-COOR^{11}$ or $-COR^{11}$, wherein $R^{11}$ and $R^{12}$ each, independently, is a hydrogen atom, C1–4 alkyl, phenyl or C1–4 alkyl substituted by phenyl,
(4) C1–8 alkyl substituted by a substituent selected from $-OR^{13}$, $-NR^{13}R^{14}$, $-SR^{13}$, $-COOR^{13}$, $-COR^{13}$, $-CONH_2$, $-NR^{13}-CO-NR^{13}R^{14}$, guanidino or $Cyc^3$, wherein $R^{13}$ and $R^{14}$ each, independently, is a hydrogen atom, C1–4 alkyl, phenyl or C1–4 alkyl substituted by phenyl, or
(5) $R^9$ and $R^{10}$, together, is a C1–6 alkylene or C2–6 alkenylene, $AA^1$ and $AA^2$, together, may have the formula:

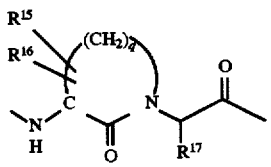

in which $R^{15}$ and $R^{16}$ each, independently, is a hydrogen atom, C1–4 alkyl, phenyl or C1–4 alkyl substituted by phenyl, with the proviso that, C1–4 alkyl or phenyl is optionally substituted by C1–4 alkyl, C1–4 alkoxy, a halogen atom, trifluoromethyl or phenyl, $R^7$ is (1) a hydrogen atom,
(2) C1–8 alkyl,
(3) $Cyc^3$, wherein $Cyc^3$ has the same meaning as hereinbefore defined, or
(4) C1–8 alkyl substituted by a substituent selected from $-OR^{13}$, $-NR^{13}R^{14}$, $-SR^{13}$, $-COOR^{13}$, $-COR^{13}$, $-CONH_2$, $-NR^{13}-CO-NR^{13}R^{14}$, guanidino or $Cyc^3$, wherein $R^{13}$ and $R^{14}$ have the same meaning as hereinbefore defined, q is 2–12, with the proviso that, a carbon atom in $-(CH_2)_q-$ is optionally replaced by an oxygen atom, sulfur atom or $-NR^{18}-$, wherein $R^{18}$ is a hydrogen atom, C1–4 alkyl, phenyl or C1–4 alkyl substituted by phenyl, or two hydrogen atom at ortho positions are replaced by a double bond and Y is

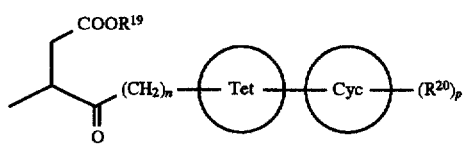

in which R¹⁹ is a hydrogen atom, C1–8 alkyl, phenyl or C1–4 alkyl substituted by phenyl, n is 1–4,

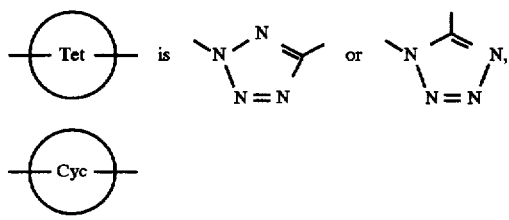

is a carbocyclic ring or hetero ring,
with the proviso that,

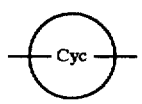

is bonded directly to the carbon atom on a tetrazole ring,

R²⁰ is
1) a hydrogen atom,
2) C1–4 alkyl,
3) a halogen atom,
4) nitro,
5) trifluoromethyl,
6) nitrile,
7) —OR²²,
8) —NR²²R²³,
9) —SR²²,
10) Cyc⁴, wherein Cyc⁴ is a carbocyclic ring or hetero ring, and Cyc⁴ is optionally substituted by 1 to 5 substituents selected from a hydrogen atom, C1–4 alkyl, phenyl, C1–4 alkyl substituted by phenyl, a halogen atom, nitro, trifluoromethyl, nitrile, tetrazole, —OR²⁴, —NR²⁴R²⁵, —SR²⁴, —COOR²⁴ or —COR²⁴, wherein R²⁴ and R²⁵ each, independently, is a hydrogen atom, C1–4 alkyl, phenyl or C1–4 alkyl substituted by phenyl,
11)—COOR²⁶ or
12)—COR²⁷, R²² and R²³ each, independently, is a hydrogen atom, C1–4 alkyl, phenyl or C1–4 alkyl substituted by phenyl, R²⁶ is a hydrogen atom, C1–4 alkyl, trihalomethyl, C1–4 alkyl substituted by trihalomethyl, Cyc⁴, wherein Cyc⁴ has the same meaning as hereinbefore defined, C 1–4 alkyl substituted by Cyc⁴, R²⁷ is
(1) a hydrogen atom,
(2) C1–4 alkyl,
(3) —NR²⁸R²⁹,
(4) phenyl, (5) C1–4 alkyl substituted by phenyl, (6) 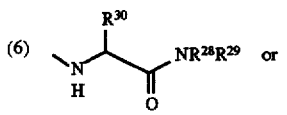 or (7) 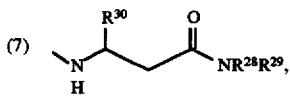

wherein R²⁸ and R²⁹ each, independently, is a hydrogen atom, C1–4 alkyl, phenyl or C1–4 alkyl substituted by phenyl, or
R²⁸ and R²⁹, together, is a hetero ring,
R³⁰ is a hydrogen atom, C1–8 alkyl, Cyc², wherein Cyc² has the same meaning as hereinbefore defined, or C1–8 alkyl substituted by a substituent selected from —OR⁷, —NR⁷R⁸, —SR⁷, —COOR⁷, —COR⁷, —CONH₂, —NR⁷—CO—NR⁷R⁸, guanidino or Cyc², wherein Cyc², R⁷ and R⁸ have the same meaning as hereinbefore defined, or
R³⁰ and one of R²⁸ or R²⁹, together, is —(CH₂)_q—, wherein —(CH₂)_q— has the same meaning as hereinbefore defined, and p is 1–5;
or a non-toxic salt thereof, an acid addition salt thereof or a hydrate thereof.

2. The compound of claim 1, wherein

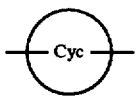

is a 3–10 membered mono-cyclic or bi-cyclic carbocyclic ring.

3. The compound of claim 1, wherein

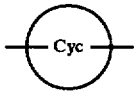

is a 5–15 membered mono-cyclic or bi-cyclic hetero ring containing one or two nitrogens, one oxygen or one sulfur.

4. The compound of any one of claims 1 to 3, wherein AA¹ is an α-amino acid residue and AA² is an α-amino acid group.

5. The compound of any one of claims 1 to 3, wherein AA¹ is a bond and AA² is an α-amino acid group.

6. The compound of any one of claims 1 to 3, wherein AA¹ is a bond and AA² is bond.

7. The compound of any one of claims 1 to 3, wherein AA¹ and AA², together, is

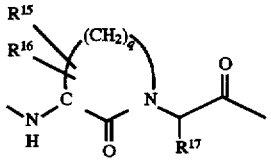

8. The compound of claim 1, which is selected from the group consisting of
N-((N-(3-phenylpropionyl)-L-valyl)-L-alanyl)-3-amino-4-oxo-5-(5-(pyridin-2-yl)tetrazol-2-yl)pentanoic acid, N-((N-(3-phenylpropionyl)-L-valyl)-L-alanyl)-3-amino-4-oxo-5-(5-(pyridin-3-yl)tetrazol-2-yl)pentanoic acid, N-((N-(3-phenylpropionyl)-L-valyl)-L-alanyl)-3-amino-4-oxo-5-(5-(pyridin-4-yl)tetrazol-2-yl)pentanoic acid, N-((N-(3-phenylpropionyl)-L-valyl)-L-alanyl)-3-amino-4-oxo-5-(5-(morpholin-1-yl)tetrazol-2-yl)pentanoic acid, N-((N-(3-phenylpropionyl)-L-valyl)-L-alanyl)-3-amino-4-oxo-5-(5-(piperidin-1-yl)tetrazol-2-yl)pentanoic acid, N-((N-(3-phenylpropionyl)-L-valyl)-L-alanyl)-3-amino-4-oxo-5-(5-(pyrrolidin-1-yl)tetrazol-2-yl)pentanoic acid, N-((N-(3-phenylpropionyl)-L-valyl)-L-alanyl)-3-amino-4-oxo-5-(5-(pyridin-2-yl)tetrazol-1-yl)pentanoic acid, N-benzyloxycarbonyl-3-amino-4-oxo-5-(5-(piperidin-1-yl)tetrazol-2-yl)pentanoic acid, N-benzyloxycarbonyl-3-amino-4-oxo-5-(5-(piperidin-1-yl)tetrazol-1-yl)pentanoic acid, N-benzyloxycarbonyl-3-amino-4-oxo-5-(5-(2S-(2,2,2-trichloroethoxycarbonyl)pyrrolidin-1-yl)tetrazol-2-yl)pentanoic acid, N-benzyloxycarbonyl-3-amino-4-oxo-5-(5-(2R-(2,2,2-trichloroethoxycarbonyl)pyrrolidin-1-yl)tetrazol-2-yl)pentanoic acid, N-benzyloxycarbonyl-3-amino-4-oxo-5-(5-(2R-ethoxycarbonylpyrrolidin-1-yl)tetrazol-2-yl)pentanoic acid, N-benzyloxycarbonyl-3-amino-4-oxo-5-(5-(2S-carboxypyrrolidin-1-yl)tetrazol-2-yl)pentanoic acid, N-benzyloxycarbonyl-3-amino-4-oxo-5-(5-(2R-carboxypyrrolidin-1-yl)tetrazol-2-yl)pentanoic acid, N-benzyloxycarbonyl-3-amino-4-oxo-5-(5-(2S-((1-(N-methylaminocarbonyl)-2-methylpropyl)aminocarbonyl)pyrrolidin-1-yl)tetrazol-2-yl)pentanoic acid, N-benzyloxycarbonyl-3-amino-4-oxo-5-(5-(2R-((1-(N-methylaminocarbonyl)-2-methylpropyl)aminocarbonyl)pyrrolidin-1-yl)tetrazol-2-yl)pentanoic acid, N-benzyloxycarbonyl-3-amino-4-oxo-5-(5-(2R-(N-methylaminocarbonyl)pyrrolidin-1-yl)tetrazol-2-yl)pentanoic acid, N-benzyloxycarbonyl-3-amino-4-oxo-5-(5-(2R-(thiazol-2-ylmethoxycarbonyl)pyrrolidin-1-yl)tetrazol-2-yl)pentanoic acid, N-benzyloxycarbonyl-3-amino-4-oxo-5-(5-(imidazol-2-yl)tetrazol-2-yl)pentanoic acid, N-benzyloxycarbonyl-3-amino-4-oxo-5-(5-(2S-(imidazol-2-ylmethoxycarbonyl)pyrrolidin-1-yl)tetrazol-2-yl)pentanoic acid, N-benzyloxycarbonyl-3-amino-4-oxo-5-(5-(2R-(imidazol-2-ylmethoxycarbonyl)pyrrolidin-1-yl)tetrazol-2-yl)pentanoic acid, and N-benzyloxycarbonyl-3-amino-4-oxo-5-(5-(2R-(piperazin-1-yl)pyrrolidin-1-ylcarbonyl)tetrazol-2-yl)pentanoic acid, an ester thereof, a non-toxic salt thereof, an acid addition salt thereof or a hydrate thereof.

9. The compound of claim 1, which is selected from the group consisting of

N-((N-(3-phenylpropionyl)-L-valyl)-L-alanyl)-3-amino-4-oxo-5-(5-(2,6-dichlorophenyl)tetrazol-2-yl)pentanoic acid, N-((N-(3-phenylpropionyl)-L-valyl)-L-alanyl)-3-amino-4-oxo-5-(5-(2,6-dichlorophenyl)tetrazol-1-yl)pentanoic acid, N-((N-(3-phenylpropionyl)-L-valyl)-L-alanyl)-3-amino-4-oxo-5-(5-(2,6-ditrifluoromethylphenyl)tetrazol-2-yl)pentanoic acid, N-((N-(3-phenylpropionyl)-L-valyl)-L-alanyl)-3amino-4-oxo-5-(5-(2,6-ditrifluoromethylphenyl)tetrazol-1-yl)pentanoic acid, N-((N-(3-phenylpropionyl)-L-valyl)-L-alanyl)-3-amino-4-oxo-5-(5-(2-chlorophenyl)tetrazol-2-yl)pentanoic acid, N-((N-(3-phenylpropionyl)-L-valyl)-L-alanyl)-3-amino-4-oxo-5-(5-(2-chlorophenyl)tetrazol-1-yl)pentanoic acid, N-((N-(3-phenylpropionyl)-L-valyl)-L-alanyl)-3-amino-4-oxo-5-(5-(3-chlorophenyl)tetrazol-2-yl)pentanoic acid, N-((N-(3-phenylpropionyl)-L-valyl)-L-alanyl)-3-amino-4-oxo-5-(5-(4-chlorophenyl)tetrazol-2-yl)pentanoic acid, N-((N-(3-phenylpropionyl)-L-valyl)-L-alanyl)-3-amino-4-oxo-5-(5-(2,3-dichlorophenyl)tetrazol-2-yl)pentanoic acid, N-((N-(3-phenylpropionyl)-L-valyl)-L-alanyl)-3-amino-4-oxo-5-(5-(4-trifluoromethylphenyl)tetrazol-2-yl)pentanoic acid, N-((N-(3-phenylpropionyl)-L-valyl)-L-alanyl)-3-amino-4-oxo-5-(5-(4-nitrophenyl)tetrazol-2-yl)pentanoic acid, N-((N-(3-phenylpropionyl)-L-valyl)-L-alanyl)-3-amino-4-oxo-5-(5-phenyltetrazol-2-yl)pentanoic acid, N-((N-(3-phenylpropionyl)-L-valyl)-L-alanyl)-3-amino-4-oxo-5-(5-(2-methoxycarbonylphenyl)tetrazol-2-yl)pentanoic acid, N-((N-(3-phenylpropionyl)-L-valyl)-L-alanyl)-3-amino-4-oxo-5-(5-(2-methoxycarbonylphenyl)tetrazol-1-yl)pentanoic acid, N-((N-(3-phenylpropionyl)-L-valyl)-L-alanyl)-3-amino-4-oxo-5-(5-(2,6-difluorophenyl)tetrazol-2-yl)pentanoic acid, N-((N-(3-phenylpropionyl)-L-valyl)-L-alanyl)-3-amino-4-oxo-5-(5-(2,6-difluorophenyl)tetrazol-1-yl)pentanoic acid, N-((N-(3-phenylpropionyl)-L-valyl)-L-alanyl)-3-amino-4-oxo-5-(5-(2,3,4,5,6-pentafluorophenyl)tetrazol-2-yl)pentanoic acid, N-((N-(3-phenylpropionyl)-L-valyl)-L-alanyl)-3-amino-4-oxo-5-(5-(2,6-dimethylphenyl)tetrazol-2-yl)pentanoic acid, N-((N-(3-phenylpropionyl)-L-valyl)-L-alanyl)-3-amino-4-oxo-5-(5-(2,6-dimethylphenyl)tetrazol-1-yl)pentanoic acid, N-((N-(3-phenylpropionyl)-L-valyl)-L-alanyl)-3-amino-4-oxo-5-(5-(2-chloro-6-methoxycarbonylphenyl)tetrazol-2-yl)pentanoic acid, N-((N-(3-phenylpropionyl)-L-valyl)-L-alanyl)-3-amino-4-oxo-5-(5-((2-phenyl)phenyl)tetrazol-2-yl)pentanoic acid, N-((N-(3-phenylpropionyl)-L-valyl)-L-alanyl)-3-amino-4-oxo-5-(5-((2-phenyl)phenyl)tetrazol-1-yl)pentanoic acid, N-((N-(3-phenylpropionyl)-L-valyl)-L-alanyl)-3-amino-4-oxo-5-(5-(2,6-dimethoxyphenyl)tetrazol-2-yl)pentanoic acid, N-((N-(3-phenylpropionyl)-L-valyl)-L-alanyl)-3-amino-4-oxo-5-(5-(2,6-dimethoxyphenyl)tetrazol-1-yl) pentanoic acid, N-((N-(3-phenylpropionyl)-L-valyl)-L-alanyl)-3-amino-4-oxo-5-(5-(2-chloro-6-carboxyphenyl)tetrazol-2-yl) pentanoic acid, N-((N-benzyloxycarbonyl-L-valyl)-L-alanyl)-3-amino-4-oxo-5-(5-phenyltetrazol-2-yl)pentanoic acid, N-(N-benzyloxycarbonyl-L-valyl)-3-amino-4-oxo-5-(5-phenyltetrazol-2-yl)pentanoic acid, N-(N-benzyloxycarbonyl-L-alanyl)-3-amino-4-oxo-5-(5-phenyltetrazol-2-yl)pentanoic acid N-benzyloxycarbonyl-3-amino-4-oxo-5-(5-(2-chlorophenyl)tetrazol-2-yl)pentanoic acid, N-benzyloxycarbonyl-3-amino-4-oxo-5-(5-(2,6-dichlorophenyl)tetrazol-2-yl)pentanoic acid, N-benzyloxycarbonyl-3-amino-4-oxo-5-(5-(2,6-dichlorophenyl)tetrazol-1-yl)pentanoic acid, N-benzyloxycarbonyl-3-amino-4-oxo-5-(5-((2-phenyl) phenyl)tetrazol-2-yl)pentanoic acid, N-benzyloxycarbonyl-3-amino-4-oxo-5-(5-((2-phenyl) phenyl)tetrazol-1-yl)pentanoic acid, N-benzyloxycarbonyl-3-amino-4-oxo-5-(5-((4-phenyl) phenyl)tetrazol-2-yl)pentanoic acid, N-benzyloxycarbonyl-3-amino-4-oxo-5-(5-((4-phenyl) phenyl)tetrazol-1-yl)pentanoic acid, N-benzyloxycarbonyl-3-amino-4-oxo-5-(5-(3-methoxycarbonylphenyl)tetrazol-2-yl)pentanoic acid, N-benzyloxycarbonyl-3-amino-4-oxo-5-(5-phenyltetrazol-2-yl)pentanoic acid, N-benzyloxycarbonyl-3-amino-4-oxo-5-(5-phenyltetrazol-1-yl)pentanoic acid, N-benzyloxycarbonyl-3-amino-4-oxo-5-(5-(2,6-dimethoxyphenyl)tetrazol-2-yl)pentanoic acid, N-benzyloxycarbonyl-3-amino-4-oxo-5-(5-(2,6-dimethoxyphenyl)tetrazol-1-yl)pentanoic acid, N-benzyloxycarbonyl-3-amino-4-oxo-5-(5-(2-methoxycarbonylphenyl)tetrazol-2-yl)pentanoic acid, N-benzyloxycarbonyl-3-amino-4-oxo-5-(5-(2-methoxycarbonylphenyl)tetrazol-1-yl)pentanoic acid, N-benzyloxycarbonyl-3-amino-4-oxo-5-(5-(4-methoxycarbonylphenyl)tetrazol-2-yl)pentanoic acid, N-benzyloxycarbonyl-3-amino-4-oxo-5-(5-(4-methoxycarbonylphenyl) tetrazol-1-yl)pentanoic acid, N-benzyloxycarbonyl-3-amino-4-oxo-5-(5-cyclohexen-1-yltetrazol-2-yl) pentanoic acid, N-benzyloxycarbonyl-3-amino-4-oxo-5-(5-cyclohexen-1-yltetrazol-1-yl) pentanoic acid, N-benzyloxycarbonyl-3-amino-4-oxo-5-(5-cyclohexyltetrazol-2-yl)pentanoic acid, N-benzyloxycarbonyl-3-amino-4-oxo-5-(5ocyclohexyltetrazol-1-yl)pentanoic acid, N-benzyloxycarbonyl-3-amino-4-oxo-5-(5-(4-(imidazol-1-yl)phenyl)tetrazol-2-yl)pentanoic acid, N-benzyloxycarbonyl-3-amino-4-oxo-5-(5-(naphthalen-1-yl)tetrazol-2-yl)pentanoic acid, N-benzyloxycarbonyl-3-amino-4-oxo-5-(5-(naphthalen-1-yl)tetrazol-1-yl)pentanoic acid, N-benzyloxycarbonyl-3-amino-4-oxo-5-(5-(4-dimethylamino-3,5-difluorophenyl)tetrazol-2-yl) pentanoic acid, N-benzyloxycarbonyl-3-amino-4-oxo-5-(5-(2-chloro-5-methylphenyl) tetrazol-2-yl)pentanoic acid, N-benzyloxycarbonyl-3-amino-4-oxo-5-(5-(2-chloro-5-methylphenyl) tetrazol-1-yl)pentanoic acid, N-benzyloxycarbonyl-3-amino-4-oxo-5-(5-((3-phenyl) phenyl)tetrazol-2-yl)pentanoic acid, N-benzyloxycarbonyl-3-amino-4-oxo-5-(5-((3-phenyl) phenyl)tetrazol-1-yl)pentanoic acid, N-benzyloxycarbonyl-3-amino-4-oxo-5-(5-(benzocyclobuten-1-yl)-tetrazol-2-yl)pentanoic acid, N-benzyloxycarbonyl-3-amino-4-oxo-5-(5-(benzocyclobuten-1-yl)tetrazol-1-yl)pentanoic acid, N-benzyloxycarbonyl-3-amino-4-oxo-5-(5-(2-carboxyphenyl)tetrazol-2-yl)pentanoic acid, N-benzyloxycarbonyl-3-amino-4-oxo-5-(5-(2-carboxyphenyl)tetrazol-1-yl)pentanoic acid, N-benzyloxycarbonyl-3-amino-4-oxo-5-(5-(3-carboxyphenyl)tetrazol-2-yl)pentanoic acid, N-benzyloxycarbonyl-3-amino-4-oxo-5-(5-(4-carboxyphenyl)tetrazol-2-yl)pentanoic acid, N-benzyloxycarbonyl-b 3-amino-4-oxo-5-(5-(3-((1-(N-methylaminocarbonyl)-2-methylpropyl) aminocarbonyl)phenyl)tetrazol-2-yl)pentanoic acid, N-benzyloxycarbonyl-3-amino-4-oxo-5-(5-(3-((1-aminocarbonyl-2-methylpropyl)aminocarbonyl) phenyl)tetrazol-2-yl)pentanoic acid, N-benzyloxycarbonyl-3-amino-4-oxo-5-(5-(3-(morpholin-1-ylcarbonyl)phenyl)tetrazol-2-yl) pentanoic acid, N-benzyloxycarbonyl-3-amino-4-oxo-5-(5-(3-((1 S-(N-methylaminocarbonyl)-2-methylpropyl) aminocarbonyl)phenyl)tetrazol-2-yl)pentanoic acid, N-benzyloxycarbonyl-3-amino-4-oxo-5-(5-(3-(N-methylaminocarbonyl)phenyl)tetrazol-2-yl)pentanoic acid, N-benzyloxycarbonyl-3-amino-4-oxo-5-(5-(3-(hexahydro-2-azepinon-3-ylaminocarbonyl)phenyl) tetrazol-2-yl)pentanoic acid, N-benzyloxycarbonyl-3-amino-4-oxo-5-(5-(3-((1 R-(N-methylaminocarbonyl)-2-methylpropyl) aminocarbonyl)phenyl)tetrazol-2-yl)pentanoic acid, N-benzyloxycarbonyl-3-amino-4-oxo-5-(5-(3-((1-(N-methylaminocarbonyl)methyl)aminocarbonyl)phenyl) tetrazol-2-yl)pentanoic acid, N-benzyloxycarbonyl-3-amino-4-oxo-5-(5-(3-((2-(N-methylaminocarbonyl)ethyl)aminocarbonyl)phenyl) tetrazol-2-yl)pentanoic acid, N-benzyloxycarbonyl-3-amino-4-oxo-5-(5-(4-((1-aminocarbonyl-2-methylpropyl)aminocarbonyl) phenyl)tetrazol-2-yl)pentanoic acid, N-benzyloxycarbonyl-3-amino-4-oxo-5-(5-(4-((1-(N-methylaminocarbonyl)-2-methylpropyl) aminocarbonyl)phenyl)tetrazol-2-yl)pentanoic acid, N-benzyloxycarbonyl-3-amino-4-oxo-5-(5-(4-(morpholin-1-ylcarbonyl)phenyl)tetrazol-2-yl) pentanoic acid, N-benzyloxycarbonyl-3-amino-4-oxo-5-(5-(4-((2-(N,N-dimethylamino)-ethyl)aminocarbonyl)phenyl)tetrazol-2-yl)pentanoic acid, N-benzyloxycarbonyl-3-amino-4-oxo-5-(5-(4-(N-methylaminocarbonyl)phenyl)tetrazol-2-yl)pentanoic acid, N-benzyloxycarbonyl-3-amino-4-oxo-5-(5-(4-(4-methylpiperazin-1-ylcarbonyl)phenyl)tetrazol-2-yl) pentanoic acid, N-benzyloxycarbonyl-3-amino-4-oxo-5-(5-(4-((1-(N-methylaminocarbonyl)methyl)aminocarbonyl)phenyl) tetrazol-2-yl)pentanoic acid, N-benzyloxycarbonyl-3-amino-4-oxo-5-(5-(2-((1-aminocarbonyl-2-methylpropyl)aminocarbonyl) phenyl)tetrazol-2-yl)pentanoic acid, N-benzyloxycarbonyl-3-amino-4-oxo-5-(5-(2-((1-(N-methylaminocarbonyl)-2-methylpropyl) aminocarbonyl)phenyl)tetrazol-2-yl)pentanoic acid, N-benzyloxycarbonyl-3-amino-4-oxo-5-(5-(2-(morpholin-1-ylcarbonyl)phenyl)tetrazol-2-yl) pentanoic acid, N-benzyloxycarbonyl-3-amino-4-oxo-5-(5-(2-((1-(N-methylamino-carbonyl)methyl)aminocarbonyl)phenyl) tetrazol-2-yl)pentanoic acid, N-benzyloxycarbonyl-3-amino-4-oxo-5-(5-(2-((1-(N-methylamino-carbonyl)methyl)aminocarbonyl)phenyl) tetrazol-1-yl)pentanoic acid, N-benzyloxycarbonyl-3-amino-4-oxo-5-(5-(3-(thiazol-2-ylmethoxycarbonyl)phenyl)tetrazol-2-yl)pentanoic acid, N-benzyloxycarbonyl-3-amino-4-oxo-5-(5-(3-(imidazol-2-ylmethoxycarbonyl)phenyl)tetrazol-2-yl)pentanoic acid, N-t-butoxycarbonyl-3-amino-4-oxo-5-(5-phenyltetrazol-2-yl)pentanoic acid, N-(3-phenylpropyl)thiocarbonyl-3-amino-4-oxo-5-(5-(2-chlorophenyl)tetrazol-2-yl)pentanoic acid, N-(3-phenylpropyl)thiocarbonyl-3-amino-4-oxo-5-(5-(2-chlorophenyl)tetrazol-1-yl)pentanoic acid, 3-((2-fluorophenyl)sulfonylamino)-4-oxo-5-(5-(2-chlorophenyl)tetrazol-2-yl)pentanoic acid, 3-(N-(2-(hexahydro-2-oxo-3S-(phenylcarbonylamino) azepin-1-yl))propionyl)amino-4-oxo-5-(5-(2,6-dichlorophenyl)tetrazol-2-yl)pentanoic acid, 3-(N-(2-(hexahydro-2-oxo-3S-(phenylcarbonylamino) azepin-1-yl))propionyl)amino-4-oxo-5-(5-(2,6-dichlorophenyl)tetrazol-1-yl)pentanoic acid, 3-(N-(2-(2-oxo-3-(phenylcarbonylamino)pyridin-1-yl)) propionyl)amino-4-oxo-5-(5-(2-chlorophenyl)tetrazol-2-yl)pentanoic acid, an ester thereof, a non-toxic salt thereof, an acid addition salt thereof or a hydrate thereof.

10. A pharmaceutical composition which comprises, as an active ingredient, an effective amount of the compound of claim 1, a non-toxic salt thereof, an acid addition salt thereof or a hydrate thereof, with a carrier or coating.

11. A method for treatment in animals, of diseases induced by interleukin-1β converting enzyme, which comprises the administration to a patient of an effective amount of the compound of claim 1, a non-toxic salt thereof, a non-toxic acid addition salt thereof or a hydrate thereof.

12. The method of claim 11, wherein said disease is insulin dependent diabetes, multiple sclerosis, acute or delayed type hypersensitivity, infectious diseases, infectious complications, septic shock, arthritis, colitis, glomelular nephritis, hepatitis, hepatic cirrhosis, pancreatitis, reperfusion injury, cholangeitis, encephalitis, endocarditis, myocarditis, vasculitis, Alzheimer's disease, Parkinson's disease, dementia, cerebral vascular disturbance, neurodegenerative diseases, bone or cartilage-resorption diseases, AIDS, AIDS related complex, adult T cell leukemia, hairy cell leukemia, myelosis, respiratory dysfunction, arthropathy, uveitis, systemic lupus, erythematosis, rheumatoid arthritis, ulcerative colitis, Sjogren's syndrome, primary biliary cirrhosis, idiopathic thrombocytopnic purpura, autoimmonohaemolytic anemia, severe myasthenia, osteodisplasia syndrome, periodic thrombocytopenia, aplastic anemia, idiopathic thrombocytopenia, disseminated intravascular coagulation, adult dyspnea syndrome, hyperplasia of the prostatic gland, myoma of the uterus, asthma bronchiole, arteriosclerosis, various kind of congenital teratoma, nephritis, senile cataract, chronic fatigue syndrome, myodystrophy, peripheral nervous disturbance, Crohn's disease and osteo arthritis.

* * * * *